(12) United States Patent
Xia et al.

(10) Patent No.: US 12,287,331 B2
(45) Date of Patent: *Apr. 29, 2025

(54) COMPOSITIONS, METHODS AND SYSTEMS FOR PROTEIN CORONA ANALYSIS AND USES THEREOF

(71) Applicant: Seer, Inc., Redwood City, CA (US)

(72) Inventors: Hongwei Xia, Fremont, CA (US); Lyndal Hesterberg, Loveland, CO (US); Michael Figa, San Mateo, CA (US); Xiaoyan Zhao, Foster City, CA (US); Gregory Troiano, Pembroke, MA (US); William Manning, Redwood City, CA (US); John Blume, Bellingham, WA (US); Omid Farokhzad, Waban, MA (US); Matthew McLean, Redwood City, CA (US); Craig Stolarczyk, San Mateo, CA (US); Marwin Ko, Redwood City, CA (US); Theodore Platt, Danville, CA (US)

(73) Assignee: Seer, Inc., Redwood City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/460,474

(22) Filed: Sep. 1, 2023

(65) Prior Publication Data

US 2023/0417744 A1 Dec. 28, 2023

Related U.S. Application Data

(63) Continuation of application No. 17/216,514, filed on Mar. 29, 2021, which is a continuation of application No. PCT/US2019/000061, filed on Nov. 7, 2019.

(Continued)

(51) Int. Cl.
*G01N 33/543* (2006.01)
*G01N 33/551* (2006.01)
*G01N 33/68* (2006.01)

(52) U.S. Cl.
CPC . *G01N 33/54326* (2013.01); *G01N 33/54346* (2013.01); *G01N 33/551* (2013.01); *G01N 33/6848* (2013.01)

(58) Field of Classification Search
None
See application file for complete search history.

(56) References Cited

U.S. PATENT DOCUMENTS 4,444,879 A 4/1984 Foster et al.
4,863,873 A 9/1989 Matson
(Continued)

FOREIGN PATENT DOCUMENTS

CN 1811406 A 8/2006
CN 1997284 A 7/2007
(Continued)

OTHER PUBLICATIONS

Sigdel, T.K. et al. Optimization for peptide sample preparation for urine peptidomics, Clinical Proteomics 2014, 11:7 (Year: 2014).*
(Continued)

*Primary Examiner* — Xiaoyun R Xu
(74) *Attorney, Agent, or Firm* — Wilson Sonsini Goodrich & Rosati

(57) ABSTRACT

Compositions, methods, and systems for analyzing the protein corona are described herein, as well as its application in the discovery of advanced diagnostic tools as well as therapeutic targets.

28 Claims, 47 Drawing Sheets

Related U.S. Application Data

(60) Provisional application No. 62/874,862, filed on Jul. 16, 2019, provisional application No. 62/824,278, filed on Mar. 26, 2019, provisional application No. 62/756,960, filed on Nov. 7, 2018.

(56) References Cited

U.S. PATENT DOCUMENTS

| | | |
|---|---|---|
| 5,366,140 A | 11/1994 | Koskenmaki et al. |
| 5,498,545 A | 3/1996 | Vestal |
| 5,900,481 A | 5/1999 | Lough et al. |
| 5,928,952 A | 7/1999 | Hutchins et al. |
| 5,952,653 A | 9/1999 | Covey et al. |
| 6,291,183 B1 | 9/2001 | Pirrung et al. |
| 6,327,410 B1 | 12/2001 | Walt et al. |
| 6,329,209 B1 | 12/2001 | Wagner et al. |
| 6,361,944 B1 | 3/2002 | Mirkin et al. |
| 6,413,780 B1 | 7/2002 | Bach et al. |
| 6,514,416 B1 | 2/2003 | Harradine et al. |
| 6,649,419 B1 | 11/2003 | Anderson |
| 6,730,517 B1 | 5/2004 | Koster et al. |
| 6,759,010 B2 | 7/2004 | Lewis et al. |
| 6,942,968 B1 | 9/2005 | Dickinson et al. |
| 6,969,615 B2 | 11/2005 | Knezevic et al. |
| 7,348,184 B2 | 3/2008 | Rich et al. |
| 7,375,234 B2 | 5/2008 | Sharpless et al. |
| 7,442,921 B2 | 10/2008 | Franzen |
| 7,754,861 B2 | 7/2010 | Boschetti et al. |
| 7,960,184 B2 | 6/2011 | Morozov et al. |
| 8,021,891 B2 | 9/2011 | Rotello et al. |
| 8,268,264 B2 | 9/2012 | Lenz |
| 8,304,187 B2 | 11/2012 | Fernando |
| 8,357,537 B2 | 1/2013 | Blecka et al. |
| 8,586,306 B2 | 11/2013 | Fernando |
| 8,795,960 B2 | 8/2014 | Seul et al. |
| 8,906,608 B2 | 12/2014 | Boschetti et al. |
| 9,005,994 B2 | 4/2015 | Huo |
| 9,234,895 B2 | 1/2016 | Hood et al. |
| 9,549,901 B2 | 1/2017 | Shi et al. |
| 9,657,227 B2 | 5/2017 | Fernando |
| 9,689,039 B2 | 6/2017 | Wong et al. |
| 9,758,811 B2 | 9/2017 | Brown et al. |
| 9,926,590 B2 | 3/2018 | Fernando |
| 9,945,994 B2 | 4/2018 | Hebrink et al. |
| 10,022,334 B2 | 7/2018 | Farokhzad et al. |
| 10,144,955 B2 | 12/2018 | Fernando |
| 10,294,513 B2 | 5/2019 | Fernando |
| 10,525,013 B2 | 1/2020 | Farokhzad et al. |
| 10,866,242 B2 | 12/2020 | Farokhzad et al. |
| 11,408,898 B2 | 8/2022 | Farokhzad et al. |
| 11,428,688 B2 | 8/2022 | Xia et al. |
| 11,435,242 B2 | 9/2022 | Sheng et al. |
| 11,435,360 B2 | 9/2022 | Farokhzad et al. |
| 11,567,086 B2 | 1/2023 | Farokhzad et al. |
| 11,630,112 B2 | 4/2023 | Manning et al. |
| 11,850,309 B2 | 12/2023 | Farokhzad et al. |
| 11,906,526 B2 | 2/2024 | Manning et al. |
| 12,000,827 B2 | 6/2024 | Farokhzad et al. |
| 2002/0009394 A1 | 1/2002 | Koster et al. |
| 2002/0094533 A1 | 7/2002 | Hess et al. |
| 2002/0102578 A1 | 8/2002 | Dickinson et al. |
| 2002/0127727 A1 | 9/2002 | Bach et al. |
| 2004/0106131 A1 | 6/2004 | Roy et al. |
| 2004/0132122 A1 | 7/2004 | Banerjee et al. |
| 2004/0147040 A1 | 7/2004 | Bluggel et al. |
| 2004/0153249 A1 | 8/2004 | Zhang et al. |
| 2005/0053999 A1 | 3/2005 | Gough et al. |
| 2005/0130240 A1 | 6/2005 | Lin et al. |
| 2005/0148101 A1 | 7/2005 | Bamdad et al. |
| 2005/0272049 A1 | 12/2005 | Banerjee et al. |
| 2006/0081539 A1 | 4/2006 | Safar et al. |
| 2007/0072250 A1 | 3/2007 | Kim et al. |
| 2007/0178504 A1 | 8/2007 | Colpitts et al. |
| 2007/0184456 A1 | 8/2007 | Chee et al. |
| 2007/0224644 A1 | 9/2007 | Liotta et al. |
| 2008/0160546 A1 | 7/2008 | Colpitts et al. |
| 2008/0277578 A1 | 11/2008 | Ferrari et al. |
| 2009/0004687 A1 | 1/2009 | Mansfield et al. |
| 2009/0054222 A1 | 2/2009 | Zhang et al. |
| 2009/0090855 A1 | 4/2009 | Kobold et al. |
| 2009/0182120 A1 | 7/2009 | Utermohlen et al. |
| 2009/0253181 A1 | 10/2009 | Vangbo et al. |
| 2009/0291454 A1 | 11/2009 | Sim et al. |
| 2009/0298710 A1 | 12/2009 | Farokhzad et al. |
| 2009/0305392 A1 | 12/2009 | Alfredsson et al. |
| 2009/0326614 A1 | 12/2009 | El-Sayed et al. |
| 2010/0267108 A1 | 10/2010 | Jordaan et al. |
| 2010/0291224 A1 | 11/2010 | Tong et al. |
| 2011/0027894 A1 | 2/2011 | Farias-Eisner et al. |
| 2011/0076735 A1 | 3/2011 | Jovanovich et al. |
| 2011/0111443 A1 | 5/2011 | Nishimura et al. |
| 2011/0111978 A1 | 5/2011 | Boschetti et al. |
| 2011/0306514 A1 | 12/2011 | Hewitt et al. |
| 2012/0043208 A1 | 2/2012 | Jin et al. |
| 2012/0046184 A1 | 2/2012 | Dawson et al. |
| 2012/0088249 A1 | 4/2012 | Jovanovich et al. |
| 2012/0156135 A1 | 6/2012 | Farokhzad et al. |
| 2012/0171291 A1 | 7/2012 | Rademacher et al. |
| 2012/0171694 A1 | 7/2012 | Mansfield et al. |
| 2012/0328594 A1 | 12/2012 | McKenna et al. |
| 2013/0058923 A1 | 3/2013 | Huo |
| 2013/0084561 A1 | 4/2013 | Coull et al. |
| 2014/0080119 A1 | 3/2014 | Stein et al. |
| 2014/0323330 A1 | 10/2014 | Bergo |
| 2015/0376678 A1 | 12/2015 | Krizman et al. |
| 2016/0327554 A1 | 11/2016 | Hung et al. |
| 2017/0007725 A1 | 1/2017 | Khoury et al. |
| 2017/0010283 A1 | 1/2017 | Karl et al. |
| 2017/0074869 A1 | 3/2017 | Krijgsveld et al. |
| 2017/0131276 A1 | 5/2017 | Johnston |
| 2017/0146527 A1 | 5/2017 | Kelly et al. |
| 2017/0216218 A1 | 8/2017 | Farokhzad et al. |
| 2018/0074049 A1 | 3/2018 | Loke et al. |
| 2018/0136231 A1 | 5/2018 | Borrebaeck et al. |
| 2018/0172694 A1* | 6/2018 | Farokhzad ......... G01N 33/6803 |
| 2018/0356414 A1 | 12/2018 | Strano et al. |
| 2018/0361000 A1 | 12/2018 | Weissleder et al. |
| 2019/0117799 A1 | 4/2019 | Xu et al. |
| 2019/0195903 A1 | 6/2019 | Leboudec |
| 2019/0301985 A1 | 10/2019 | Tao et al. |
| 2020/0033357 A1 | 1/2020 | Tavernier et al. |
| 2020/0085758 A1 | 3/2020 | Farokhzad et al. |
| 2020/0138728 A1 | 5/2020 | Farokhzad et al. |
| 2021/0072255 A1 | 3/2021 | Farokhzad et al. |
| 2021/0098083 A1 | 4/2021 | Ma et al. |
| 2021/0132071 A1 | 5/2021 | Kostarelos et al. |
| 2021/0215685 A1 | 7/2021 | Xia et al. |
| 2021/0215709 A1 | 7/2021 | Zhao et al. |
| 2021/0293801 A1 | 9/2021 | Farokhzad et al. |
| 2021/0299060 A1 | 9/2021 | Farokhzad et al. |
| 2021/0311064 A1 | 10/2021 | Farokhzad et al. |
| 2022/0226510 A1 | 7/2022 | Xu et al. |
| 2022/0260559 A1 | 8/2022 | Blume et al. |
| 2022/0334123 A1 | 10/2022 | Farokhzad et al. |
| 2022/0365096 A1 | 11/2022 | Farokhzad et al. |
| 2023/0076807 A1 | 3/2023 | Zhao et al. |
| 2023/0076840 A1 | 3/2023 | Farokhzad et al. |
| 2023/0160882 A1 | 5/2023 | Siddiqui et al. |
| 2023/0204596 A1 | 6/2023 | Manning et al. |
| 2023/0212647 A1 | 7/2023 | Farokhzad et al. |
| 2023/0213504 A1 | 7/2023 | Farokhzad et al. |
| 2023/0253113 A1 | 8/2023 | Guturu et al. |
| 2023/0324401 A1 | 10/2023 | Farokhzad et al. |
| 2023/0384317 A1 | 11/2023 | Manning et al. |
| 2023/0408503 A1 | 12/2023 | Hornburg et al. |
| 2024/0044884 A1 | 2/2024 | Farokhzad et al. |
| 2024/0044885 A1 | 2/2024 | Farokhzad et al. |

FOREIGN PATENT DOCUMENTS

| | | |
|---|---|---|
| CN | 102798658 A | 11/2012 |
| CN | 103703143 A | 4/2014 |
| CN | 105126736 A | 12/2015 |
| CN | 105771942 A | 7/2016 |

(56) References Cited

FOREIGN PATENT DOCUMENTS

| | | |
|---|---|---|
| CN | 106268707 A | 1/2017 |
| CN | 106432644 A | 2/2017 |
| CN | 107991277 A | 5/2018 |
| DE | 202017107858 U1 | 5/2018 |
| DE | 202017007363 U1 | 2/2021 |
| EP | 1308520 A2 | 5/2003 |
| EP | 2209893 A1 | 7/2010 |
| EP | 3510402 A1 | 7/2019 |
| EP | 3548652 A1 | 10/2019 |
| EP | 3554681 A1 | 10/2019 |
| EP | 3877400 A2 | 9/2021 |
| EP | 3554681 B1 | 2/2022 |
| EP | 4056263 A1 | 9/2022 |
| JP | H06500358 A | 1/1994 |
| JP | 2003517998 A | 6/2003 |
| JP | 2009509132 A | 3/2009 |
| JP | 2009524828 A | 7/2009 |
| WO | WO-0244327 A2 | 6/2002 |
| WO | WO-2007010252 A1 | 1/2007 |
| WO | WO-2007089731 A2 | 8/2007 |
| WO | WO-2007091077 A1 | 8/2007 |
| WO | WO-2009047526 A1 | 4/2009 |
| WO | WO-2010097785 A1 | 9/2010 |
| WO | WO-2010148365 A2 | 12/2010 |
| WO | WO-2010148365 A3 | 5/2011 |
| WO | WO-2011088128 A2 | 7/2011 |
| WO | WO-2012006385 A2 | 1/2012 |
| WO | WO-2012068226 A3 | 8/2012 |
| WO | WO-2012106385 A2 | 8/2012 |
| WO | WO-2012170711 A1 | 12/2012 |
| WO | WO-2013022995 A2 | 2/2013 |
| WO | WO-2015118152 A1 | 8/2015 |
| WO | WO-2018046542 A1 | 3/2018 |
| WO | WO-2018112460 A1 | 6/2018 |
| WO | WO-2019083856 A1 | 5/2019 |
| WO | WO-2019133892 A1 | 7/2019 |
| WO | WO-2020096631 A2 | 5/2020 |
| WO | WO-2020198209 A1 | 10/2020 |
| WO | WO-2021026172 A1 | 2/2021 |
| WO | WO-2021087407 A1 | 5/2021 |
| WO | WO-2022020272 A1 | 1/2022 |

OTHER PUBLICATIONS

Promega, Trypsin/Lys-C protease mix for enhanced protein mass spectrometry analysis, nature methods | Nov. 2013 (Year: 2013).*

Li, J. et al. Block copolymer conjugated Au-coated Fe3O4 nanoparticles as vectors for enhancing colloidal stability and cellular uptake, Journal of Nanobiotechnology, (2017) 15:56 (Year: 2017).*

Aebersold, R., et al. How many human proteoforms are there? Nat Chem Biol 14, 206-214 (2018).

Agasti et al. (Adv. Drug Deliv Rev. Mar. 8, 2010; 62(3):316-328) (Year: 2010).

Aggarwal, P., Hall, J.B., Mcleland, C.B., Dobrovolskaia, M.A. & McNeil, S.E. Nanoparticle interaction with plasma proteins as it relates to particle biodistribution, biocompatibility and therapeutic efficacy. Advanced drug delivery reviews 61, 428-437 (2009).

Ahn, J.-M. & Cho, J.-Y. Current serum lung cancer biomarkers. Journal of Molecular Biomarkers & Diagnosis 2013 (2013).

Aksoy-Sagirli, P., et al. Paraoxonase-1 192/55 polymorphisms and the risk of lung cancer in a Turkish population. Anticancer Res 31, 2225-2229 (2011).

Alavi et al.: Applying Automated Machine Learning to Accelerate Large-Scale Proteomics Data Analysis. Seer, Inc., Redwood City, CA; and Massachusetts General Hospital, Boston, MA. poster 1 page (2023).

Alavi et al.: Applying Automated ML for Classification and Regression in Large-Scale Clinical Proteomics Datasets. Seer, Inc., Redwood City, CA, poster 1 page (2023).

Alavi et al.: Challenges in Large Scale Proteomics Data Analysis: A Survey of Characterization and Correction Solutions for Batch Effects. Seer, Inc., Redwood City, CA, online video available at https://seer.bio/resources/video-gallery/?tx_category=publications &wchannelid=dfl89n6go7&wmediaid=d4eyac11ff (2022).

Alavi et al.: Challenges in Large Scale Proteomics Data Analysis: A Survey of Characterization and Correction Solutions for Batch Effects. Seer, Inc., Redwood City, CA, poster 1 page (2022).

Aldonza, M.B.D., et al. Paraoxonase-1 (PON1) induces metastatic potential and apoptosis escape via its antioxidative function in lung cancer cells. Oncotarget 8, 42817-42835 (2017).

Alexopoulos, C., Blatsios, B. & Avgerinos, A. Serum lipids and lipoprotein disorders in cancer patients. Cancer 60, 3065-3070 (1987).

Alexopoulos, C., Pournaras, S., Vaslamatzis, M., Avgerinos, A. & Raptis, S. Changes in serum lipids and lipoproteins in cancer patients during chemotherapy. Cancer chemotherapy and pharmacology 30, 412-416 (1992).

Ali, et al. "Erlotinib-Conjugated Iron Oxide Nanoparticles as a Smart Cancer-Targeted Theranostic Probe for MRI." Scientific reports vol. 6 36650. Nov. 11, 2016, doi:10.1038/srep36650.

Altomare, et al., An in depth proteomic analysis based on ProteoMiner, affinity chromatography and nano-HPLC-MS/MS to explain the potential health benefits of bovine colostrum. Journal of pharmaceutical and biomedical analysis, Mar. 2016; 121:297-306.

Amici, A. et al. In vivo protein corona patterns of lipid nanoparticles. RSC Advances 7, 1137-1145 (2017).

Andersen, J.D. et al. Identification of candidate biomarkers in ovarian cancer serum by depletion of highly abundant proteins and differential in-gel electrophoresis. Electrophoresis 31, 599-610(2010).

Anderson, et al. The Human Plasma Proteome, Molecular & Cellular Proteomics, 2002, 845-867.

Anderson, L. Candidate-Based Proteomics in the Search for Biomarkers of Cardiovascular Disease. The Journal of physiology 2005, 563, 23-60.

ANDERSON: The clinical plasma proteome: a survey of clinical assays for proteins in plasma and serum. Clin Chem 56(2):177-185 (2010).

Andriole et al.: Mortality results from a randomized prostate-cancer screening trial. N Engl J Med. 360(13):1310-1319 doi:10.1056/NEJMoa0810696 (2009).

Angel, T.E. et al. Mass spectrometry-based proteomics: existing capabilities and future directions. Chemical Society Reviews 41, 3912-3928 (2012).

Arvizo et al.: Identifying new therapeutic targets via modulation of protein corona formation by engineered nanoparticles. PLoS One 7(3):e33650, pp. 1-8 doi:10.1371/journal.pone.0033650 (2012).

Ashby et al., Size and surface functionalization of iron oxide nanoparticles influence the composition and dynamic nature of their protein corona. ACS Appl. Mater. Interfaces 2014, 6, p. 15412-15419.

Askim, J. R., Mahmoudi, M. & Suslick, K. S. Optical sensor arrays for chemical sensing: the optoelectronic nose. Chemical Society Reviews 42, 8649-8682 (2013).

Auluck et al.: A Cloud-Scalable Software Suite for Large-Scale Proteogenomics Data Analysis and Visualization. Seer, Inc., Redwood City, CA, poster 1 page (2022).

Bagalkot, V. et al. Quantum dot-aptamer conjugates for synchronous cancer imaging, therapy, and sensing of drug delivery based on bi-fluorescence resonance energy transfer. Nano letters 7, 3065-3070 (2007).

Bakhtiary, Z. et al. Targeted superparamagnetic iron oxide nanoparticles for early detection of cancer: Possibilities and challenges. Nanomedicine: Nanotechnology, Biology and Medicine 12, 287-307 (2016).

Bally, M., et al. "Liposome and lipid bilayer arrays towards biosensing applications." Small 6.22 (2010): 2481-2497.

Barkman et al.: Fabricated micro-nano devices for in vivo and in vitro biomedical applications. Wiley Interdiscip Rev Nanomed Nanobiotechnol 5(6):544-568 doi:10.1002/wnan.1236 (2013).

Barran-Berdon, et al., Time Evolution of Nanoparticle-Protein corona in Human Plasma: Relevance for targeted drug delivery. Langmuir, 2013, 29, 6485-6494.

(56) References Cited

OTHER PUBLICATIONS

Batth, Tanveer S et al. Protein Aggregation Capture on Microparticles Enables Multipurpose Proteomics Sample Preparation. Molecular & cellular proteomics : MCP vol. 18,5 (2019): 1027-1035. doi:10.1074/mcp.TIR118.001270.

Baumann et al.: Standardized approach to proteome profiling of human serum based on magnetic bead separation and matrix-assisted laser desorption/ionization time-of-flight mass spectrometry. Clin Chem. 51(6):973-980 doi: 10.1373/clinchem.2004.047308 (2005).

Beck, H.C., Overgaard, M. & Rasmussen, L.M. Plasma proteomics to identify biomarkers-application to cardiovascular diseases. Translational Proteomics 7, 40-48 (2015).

BEECKMANS: Chromatographic methods to study protein-protein interactions. Methods, Oct. 1999; 19(2):278-305.

Benz et al.: Deep Plasma Proteomics at Scale with Proteograph™ Product Suite: A Performance Evaluation with Label-free and TMT Multiplexing Methods. Seer, Inc., Redwood City, CA; Sanford Burnham Prebys Medical Discovery Institute, La Jolla, CA 92037, USA, poster 1 page (2022).

Beri, J., Rosenblatt, M.M., Strauss, E., Urh, M. & Bereman, M.S. Reagent for Evaluating Liquid Chromatography-Tandem Mass Spectrometry (LC-MS/MS) Performance in Bottom-Up Proteomic Experiments. Analytical chemistry 87, 11635-11640 (2015).

Bertrand, N., et al. Mechanistic understanding of in vivo protein corona formation on polymeric nanoparticles and impact on pharmacokinetics. Nat Commun 8, 777 (2017).

Bigbee et al.: Tumor Markers and Immunodiagnosis. Holland-Frei Cancer Medicine, 6th edition Hamilton (ON):BC Decker; Chapter 13, pp. 209-220 (2003).

Bigdeli et al. "Exploring cellular interactions in liposomes using protein corona fingerprints and physicochemical properties", ACS Nano, 10(3): 3723-3737 (2016).

Bio-Rad, ProteoMinerTM Protein Enrichment Technology [Online] Available at: http://wolfson.huji.ac.il/purification/PDF/AlbuminRemoval/BIORAD_ProteoMiner.pdf. [Accessed Sep. 17, 2020].

Bisker, et al. Protein-targeted corona phase molecular recognition. Nat Commun 7, 10241 (2016). https://doi.org/10.1038/ncomms10241.

Bloom, D., Cafiero, E., Jane-Llopis, E., et al. The Global Economic Burden of Noncommunicable Diseases. Program on the Global Demography of Aging;2012.

Bloomston, M. et al. Fibrinogen y overexpression in pancreatic cancer identified by large-scale proteomic analysis of serum samples. Cancer research 66, 2592-2599 (2006).

Blume, et al., Analytical validation of the multi-nanoparticle proteograph platform for rapid and deep proteomic profiling. Seer, Inc. Apr. 2020. 1 Page.

Blume, et al., Efficient and scalable profiling of a median of 1,779 plasma proteins in 288 subjects with multi-nanoparticle (NP) proteograph platform enables robust detection of early-stage non-small cell lung cancer (NSCLC) and classification vs. healthy and co-morbid subjects. Seer, Inc. Apr. 2020. 1 Page.

Blume, et al., Proteograph, a novel multi-nanoparticle platform, enables rapid and deep proteomics profiling, significantly improving coverage, throughput, and scalability versus existing methods. Seer, Inc. Jun. 2020. 1 Page.

Blume, et al. Rapid, deep and precise profiling of the plasma proteome with multi-nanoparticle protein corona. Nat Commun 11, 3662; 1-14 (2020). https://doi.org/10.1038/s41467-020-17033-7.

Boca Scientific. Magtivio. MagSi-Tools 600, 1.0, 3.0 Product Description: pp. 1-2. Aug. 2018.

Bodansky, O. & Mcinnes, G. F. Thermal coagulation of serum proteins in cancer, in the postoperative phase of surgery, and in the administration of adrenocorticotropic hormone. Cancer 3, 1-14 (1950).

Bolstad, et al. A comparison of normalization methods for high density oligonucleotide array data based on variance and bias. Bioinformatics. Jan. 22, 2003;19(2):185-93.

Boschetti, et al., Hexapeptide combinatorial ligand libraries: the march for the detection of the low-abundance proteome continues. BioTechniques, 2008; 44(5): 663-665.

Boschetti, et al., The ProteoMiner in the proteomic arena: a non-depleting tool for discovering low-abundance species. J Proteomics, Aug. 2008. 71(3): 255-264.

Brede et al., Applications of Nanoparticles in the Detection and Treatment of Kidney Diseases, Advances in Chronic kidney disease, vol. 20, Issue 6, Nov. 2013, pp. 454-465.

Breiman, L. Random forests. Machine learning 45, 5-32 (2001).

Brenner, et al., Gene Expression analysis by massively parallel signature sequencing (MPSS) on microbead arrays. Nature Biotechnology 18.6 (Jun. 2000): 630-634, doi:10.1038/76469.

Burgess, et al., Nanoparticle-Based Method Identifies 2200 Proteins In A Cardiovascular Disease Study Covering Known Biomarkers Among Other Differentially Expressed Proteins. Seer, Inc. Nov. 2021. 1 Page.

Buys et al.: Effect of screening on ovarian cancer mortality: the Prostate, Lung, Colorectal and Ovarian (PLCO) Cancer Screening Randomized Controlled Trial. JAMA 305(22):2295-2303 doi:10.1001/jama.2011.766 (2011).

Byrne, J.C. et al. 2D-DIGE as a strategy to identify serum markers for the progression of prostate cancer. Journal of proteome research 8, 942-957 (2008).

Calvo et al.: Clinical proteomics: from biomarker discovery and cell signaling profiles to individualized personal therapy. Biosci Rep. 25(1-2):107-125 doi:10.1007/s10540-005-2851-3 (2005).

Campos, et al., In-Depth Plasma Proteomics Profiling With Nanoparticle-Based Proteograph Workflow: A Performance Evaluation Of Label-Free And TMT Multiplexing Approaches. Seer, Inc. Nov. 2021. 1 Page.

Canchola, J.A., Tang, S., Hemyari, P., Paxinos, E. & Marins, E. Correct use of percent coefficient of variation (%CV) formula for log-transformed data. MOJPB 6, 316-317 (2017).

Canovi et al.: Applications of surface plasmon resonance (SPR) for the characterization of nanoparticles developed for biomedical purposes. Sensors (Basel). 12(12):16420-16432 doi:10.3390/s121216420 (2012).

Cao, Z., Tang, H.-Y., Wang, H., Liu, Q. & Speicher, D.W. Systematic comparison of fractionation methods for in-depth analysis of plasma proteomes. J Proteome Res 11, 3090-3100 (2012).

Capriotti, A.L. et al. Label-free quantitative analysis for studying the interactions between nanoparticles and plasma proteins. Analytical and bioanalytical chemistry 405, 635-645 (2013).

Capriotti et al.: Analytical methods for characterizing the nanoparticle-protein corona. Chromatographia 77(11-12):755-769 DOI:10.1007/s10337-014-2677-x (2014).

Capriotti et al., Shotgun proteomic analytical approach for studying proteins adsorbed onto liposome surface, Anal Bioanal Chem, 2011, 401, 1195-1202.

Caputo, et al. A protein corona-enabled blood test for early cancer detection. Nanoscale 9.1 (Jan. 7, 2017): 349-354.

Caracciolo, et al., Evolution of the protein corona of lipid gene vectors as a function of plasma concentration. Langmuir, 2011, 27, 15048-15053.

Caracciolo, G., Caputo, D., Pozzi, D., Colapicchioni, V. & Coppola, R. Size and charge of nanoparticles following incubation with human plasma of healthy and pancreatic cancer patients. Colloids and Surfaces B: Biointerfaces 123, 673-678 (2014).

Caracciolo, G., et al. Lipid composition: a "key factor" for the rational manipulation of the liposome-protein corona by liposome design. RSC Adv 5, 5967-5975 (2015).

Caracciolo, G., Farokhzad, O.C. & Mahmoudi, M. Biological Identity of Nanoparticles In Vivo: Clinical Implications of the Protein Corona. Trends in Biotechnology 35, 257-264 (2017).

Carey, J. R. et al. Rapid identification of bacteria with a disposable colorimetric sensing array. Journal of the American Chemical Society 133, 7571-7576 (2011).

Carter, A. M. Complement Activation: An Emerging Player in the Pathogenesis of Cardiovascular Disease. Scientifica 2012, 2012.

Carter, H. B. et al. Early detection of prostate cancer: AUA Guideline. The Journal of urology 190, 419-426 (2013).

(56) References Cited

OTHER PUBLICATIONS

Casals et al. Time evolution of the nanoparticle protein corona. ACS Nano. 4(7):3623-32. doi:10.1021/nn901372t (2010).

Cedervall, T., et al. Understanding the nanoparticle-protein corona using methods to quantify exchange rates and affinities of proteins for nanoparticles. Proc Natl Acad Sci U S A 104, 2050-2055 (2007).

Cerasoli, E. et al. MiS-MALDI: microgel-selected detection of protein biomarkers by MALDI-ToF mass spectrometry. Molecular Biosystems 6, 2214-2217 (2010).

Chang, et al., Proteomic Profiling Of Prostate Cancer Plasma Specimens Using Proteograph And TIMS Technology. Seer, Inc. Nov. 2021. 1 Page.

Chen et al.: Balancing deep proteome coverage with limited sample amounts using Seer's ProteographTM Product Suite. Application Note, Seer, Inc., Redwood City, CA, pp. 1-6 (2023).

Chen et al.: Balancing deep proteome coverage with limited sample amounts using Seer's ProteographTM Product Suite. Seer, Inc., Redwood City, CA, poster 1 page (2023).

Chintamaneni et al.: Biomarkers in Alzheimer's disease: a review. ISRN Pharmacol. 2012:984786:1-6 doi:10.5402/2012/984786 (2012).

Choi, Y.-E., Kwak, J.-W. & Park, J. W. Nanotechnology for early cancer detection. Sensors 10, 428-455 (2010).

Chung et al.: Novel serum protein biomarker panel revealed by mass spectrometry and its prognostic value in breast cancer. Breast Cancer Res. 16(3):R63:1-12 doi:10.1186/bcr3676 (2014).

Clarke et al.: Characterization of renal allograft rejection by urinary proteomic analysis. Ann Surg. 237(5):660-664; discussion 664-665. doi:10.1097/01.SLA.0000064293.57770.42 (2003).

Clemments, A. M. et al., Protein Adsorption From Biofluids on Silica Nanoparticles: Corona Analysis as a Function of Particle Diameter and Porosity, ACS Applied Materials & Interfaces 2015, 7, 21682-21689, with 5 pages of supporting information.

Colapicchioni, V. et al. Personalized liposome-protein corona in the blood of breast, gastric and pancreatic cancer patients. International Journal of Biochemistry and Cell Biology, 2015,75(11): 180-187.

Consortium, E.P. Europe PMC: a full-text literature database for the life sciences and platform for innovation. Nucleic acids research, gku1061 (2014).

Corbo, C. et al., Biomarker discovery by proteomics-based approaches for early detection and personalized medicine in colorectal cancer, Proteomics—Clinical Applications, 2017, 11, 5-6, paper 1600072, 19 pages.

Corbo, C. et al. Unveiling the in Vivo Protein Corona of Circulating Leukocyte-like Carriers. ACS Nano (2017).

Corbo, C., Molinaro, R., Parodi, A., Furman, N. E. T., Salvatore, F., Tasciotti, E. The Impact of Nanoparticle Protein Corona on Cytotoxicity, Immunotoxicity and Target Drug Delivery. Nanomedicine 2016, 11, 81-100.

Corbo, C., Molinaro, R., Tabatabaei, M., Farokhzad, O.C. & Mahmoudi, M. Personalized protein corona on nanoparticles and its clinical implications. Biomater Sci 5, 378-387 (2017).

Corbo, et al. Effects of the protein corona on liposome-liposome and liposome-cell interactions. Int J Nanomedicine. 2016; 11: 3049-3063. Published online Jul. 4, 2016. doi: 10.2147/IJN.S109059.

Craig, R. & Beavis, R.C. Tandem: matching proteins with tandem mass spectra. Bioinformatics 20, 1466-1467 (2004).

Cramer et al.: Ovarian cancer biomarker performance in prostate, lung, colorectal, and ovarian cancer screening trial specimens. Cancer Prev Res (Phila) 4(3):365-374 doi:10.1158/1940-6207.CAPR-10-0195 (2011).

Croft, D. et al. The Reactome pathway knowledgebase. Nucleic acids research 42, D472-D477 (2013).

Crutchfield, C.A., Thomas, S.N., Sokoll, L.J. & Chan, D.W. Advances in mass spectrometry-based clinical biomarker discovery. Clin Proteomics 13, 1 (2016).

Cruz, J.A. & Wishart, D.S. Applications of machine learning in cancer prediction and prognosis. Cancer informatics 2, 59 (2006).

Cuenca, A.G. et al. Emerging implications of nanotechnology on cancer diagnostics and therapeutics. Cancer 107, 459-466 (2006).

Cuzick, J. et al. Prevention and early detection of prostate cancer. The Lancet Oncology 15, e484-e492, doi: 10.1016/ S1470-2045(2014)70211-6.

Dai et al.: Combining proteograph technology with zeno swath dia acquisition enables the potential for deep, unbiased discovery of biomarkers in blood. PrognomiQ Inc., 1900 Alameda de las Pulgas, Suite 100, San Mateo, California, USA, poster 1 page (2022).

De Las Rivas, et al., Protein-Protein Interactions Essentials: Key Concepts to Building and Analyzing Interactome Networks. Plos computational biology, Jun. 2010; 6(6): e1000807, 1-8 Pages.

Del Pilar et al.: Proteomic analysis of the bio-corona formed on the surface of (Au, Ag, Pt)-nanoparticles in human serum. Colloids and Surfaces B: Biointerfaces 177:141-148 doi:10.1016/j.colsurfb.2019.01.056 (2019).

Del Pino, et al. Protein corona formation around nanoparticles—from the past to the future. Maler Horiz, 2014, 1, 301.

Deng, Y., Qi, D., Deng, C., Zhang, X. & Zhao, D. Superparamagnetic high-magnetization microspheres with an $Fe_3O_4@SiO_2$ core and perpendicularly aligned mesoporous $SiO_2$ shell for removal of microcystins. J Am Chem Soc 130, 28-29 (2008).

Deng, Z.J., Liang, M., Monteiro, M., Toth, I. & Minchin, R.F. Nanoparticle-induced unfolding of fibrinogen promotes Mac-1 receptor activation and inflammation. Nature nanotechnology 6, 39-44 (2011).

Deng, Z.J., Liang, M., Toth, I., Monteiro, M.J. & Minchin, R.F. Molecular interaction of poly (acrylic acid) gold nanoparticles with human fibrinogen. ACS nano 6, 8962-8969 (2012).

Di Domenico, M. et al., Nanoparticle-biomolecular corona: A new approach for the early detection of non-small-cell lung cancer. Journal of Cellular Physiology 2019, 234, 9378-9386.

Di Silvio, D. et al., Technical tip: high-resolution isolation of nanoparticle-protein corona complexes from physiological fluids, Nanoscale, 2015, 7, 11980-11990, with 7 pages of supplementary information.

Digiacomo, L. et al., A protein corona sensor array detects breast and prostate cancers, Nanoscale 2020, 12, 16697-16704.

Dobrovolskaia et al., Protein corona composition does not accurately predict hematocompatibility of colloidal gold nanoparticles, Nanomedicine: Nanotechnology, Biology, and Medicine, 2014, 10:1453-1463.

Docter, D., et al. Quantitative profiling of the protein coronas that form around nanoparticles. Nat Protoc 9, 2030-2044 (2014).

Docter, et al. The nanoparticle biomolecule corona: lessons learned-challenge accepted?. Chemical Society Reviews 44.17 (2015): 6094-6121.

Donovan, et al., Deep, Rapid and Unbiased Plasma Proteomics with the Proteograph™ Product Suite Enables Proteogenomic Studies with Differential Analysis of Proteoforms. Seer, Inc. Sep. 2021. 5 Pages.

Donovan et al.: Functionally distinct BMP1 isoforms show an opposite pattern of abundance in plasma from non-small cell lung cancer subjects and controls. PLoS One. 18(3):e0282821, pp. 1-11. doi:10.1371/journal.pone.0282821 (2023).

Donovan et al.: Peptide-centric analyses of human plasma enable increased resolution of biological insights into non-small cell lung cancer relative to protein-centric analysis. Seer, Inc. Biorxiv 2022.01.07.475393, pp. 1-21 doi:10.1101/2022.01.07.475393 (2022).

Donovan et al.: Proteoform inference using a proteogenomic approach in non-small cell lung cancer and healthy control plasma proteomes reveals disease-associated protein isoforms. Seer Inc., Redwood City, CA USA, poster 1 page (2022).

Dyna beads Products & Technology. ThennoFisher Scientific, Website accessed Dec. 15, 2021 at https://www.thermofisher.com/US/en/home/brands/product-brand/dynal/dynabeads-technology.html.

Einav, S. et al. Early postoperative serum S10013 levels predict ongoing brain damage after meningioma surgery: a prospective observational study. Critical Care 10, 1 (2006).

Elechalawar, C. K. et al, Analysing the nanoparticle-protein corona for potential molecular target identification, Journal of Controlled Release Jun. 10, 2020, 322, 122-136.

Ellenberger et al.: Robust, high throughput and deep plasma proteomics workflow with engineered nanoparticle panels. Seer, Inc., Redwood City, CA, poster 1 page (2022).

(56) References Cited

OTHER PUBLICATIONS

Ellenberger et al.: Robust in-depth label-free plasma proteomics with engineered nanoparticle panels: An evaluation of micro-pillar array cols. and FAIMS peptide separation. Seer, Inc., Redwood City, CA, poster 1 page (2022).

Enroth, S., Hallmans, G., Grankvist, K. & Gyllensten, U. Effects of long-term storage time and original sampling month on biobank plasma protein concentrations. EBioMedicine 12, 309-314 (2016).

Enten, A. et al., A Liquid-Handling Robot for Automated Attachment of Biomolecules to Microbeads, Journal of Laboratory Automation 2016, 21, 526-532.

EP17881767.2 Extended European Search Report dated Jul. 22, 2020.

Espina et al.: Use of proteomic analysis to monitor responses to biological therapies. Expert Opin Biol Ther. 4(1):83-93 doi:10.1517/14712598.4.1.83 (2004).

Etzioni, R. et al. The case for early detection. Nature Reviews Cancer 3, 243-252 (2003).

Everley, et al., Proteograph: Efficient and automated multi-nanoparticle platform for Deep, Unbiased Plasma protein profiling and protein-protein interaction biological insight. Seer, Inc. Mar. 2020.

Faca, V. M. et al. A mouse to human search for plasma proteome changes associated with pancreatic tumor development. PLoS Med 5, e123 (2008).

Farokhzad, O. C. et al. Targeted nanoparticle-aptamer bioconjugates for cancer chemotherapy in vivo. Proceedings of the National Academy of Sciences 103, 6315-6320 (2006).

Farrah, T., et al. A high-confidence human plasma proteome reference set with estimated concentrations in PeptideAtlas. Mol Cell Proteomics 10, M110 006353 (2011).

Faunce et al.: Integrated research into the nanoparticle-protein corona: a new focus for safe, sustainable and equitable development of nanomedicines. Nanomedicine (Lond). 3(6):859-866 doi:10.2217/17435889.3.6.859 (2008).

Feldman, E. B. & Carter, A. C. Circulating lipids and lipoproteins in women with metastatic breast carcinoma. The Journal of Clinical Endocrinology & Metabolism 33, 8-13 (1971 ).

Fengming et al.: Biomarkers of inflammatory bowel disease. Dis Markers 2014:710915:1-11 doi:10.1155/2014/710915 (2014).

Ferdosi et al.: Engineered nanoparticles enable deep proteomics studies at scale by leveraging tunable nano-bio interactions. PNAS USA 119(11): e2106053119, pp. 1-11 doi:10.1073/pnas.2106053119 (2022).

Ferdosi et al.: Enhanced Competition at the Nano-Bio Interface Enables Comprehensive Characterization of Protein Corona Dynamics and Deep Coverage of Proteomes. Adv Mater. e2206008, pp. 1-11 doi:10.1002/adma.202206008 (2022).

Ferdosi et al.: Multi-nanoparticle Workflow Enables Deep Plasma Proteomics at Scale, with Enhanced Precision, and Depths of Coverage. Seer, Inc. (Mar. 2022).

Ferdosi, et al., Proteograph™ multi-nanoparticle proteins coronas enable deep plasma proteomics studies at scale with unmatched sensitivity in combination with trapped ion mobility. Seer, Inc. Mar. 2021. 1 Page.

Ferdosi et al.: The Nanoparticle-Based Plasma Proteomics Workflow enables the Investigation of Glycoproteome. Seer, Inc., Redwood City, CA, poster 1 page (2022).

Ferdosi et al.: The Nanoparticle-Based Plasma Proteomics Workflow enables the Investigation of Glycoproteome. Seer, Inc., Redwood City, CA, poster 1 page (2023).

Ferdosi, et al., Unlocking Plasma Proteomics at Scale: A multi nanoparticle approach to improve the depth of coverage. Seer, Inc. Oct. 2021. 1 Page.

Ferguson, M. K. et al. Sex-associated differences in survival of patients undergoing resection for lung cancer. The Annals of thoracic surgery 69, 245-249 (2000).

Ferrari, M. Cancer nanotechnology: opportunities and challenges. Nature Reviews Cancer 5, 161-171 (2005).

Findeisen et al.: Preanalytical impact of sample handling on proteome profiling experiments with matrix-assisted laser desorption/ionization time-of-flight mass spectrometry. Clin Chem. 51(12):2409-2411 doi:10.1373/clinchem.2005.054585 (2005).

Flory et al.: A Highly Scaled Proteomic Discovery Study for Prostate Cancer Diagnostic Signatures Using ProteographTM Workflow with Trapped Ion Mobility Mass Spectrometry. Oregon Health and Science University, Knight Cancer Institute, Cancer Early Detection Advanced Research Center; University of Texas Health Science Center at San Antonio Health; Fred Hutchinson Cancer Research Center; Bruker Daltonics, Billerica; Seer Inc., poster 1 page (2022).

Fodor, S.P. et al., Light-directed, spatially addressable parallel chemical synthesis. Science, 251 (4995), 767-773 (1991).

Fontana, R. S. et al. Early Lung Cancer Detection: Results of the Initial (Prevalence) Radiologic and Cytologic Screening in the Mayo Clinic Study 1, 2. American Review of Respiratory Disease 130, 561-565 (1984).

Forbes, et al. COSMIC: exploring the world's knowledge of somatic mutations in human cancer. Nucleic Acids Res. Jan. 2015;43 (Database issue):D805-D811. Epub Oct. 29, 2014.

Foroozandeh et al.: Merging worlds of nanomaterials and biological environment: factors governing protein corona formation on nanoparticles and its biological consequences. Nanoscale Res Lett. 10(221):1-12 doi:10.1186/s11671-015-0922-3 (2015).

Fortunato, J. E., Bassiouny, H. S., Song, R.H., et al. Apolipoprotein (a) Fragments in Relation to Human Carotid Plaque Instability. Journal of vascular surgery 2000, 32, 555-563.

Gabizon, A. et al. Cancer nanomedicines: closing the translational gap. The Lancet 384, 2175-2176 (2014).

Gajadhar et al.: An integrated data processing and visualization suite leveraging cloud scalable architecture for large-cohort proteogenomics data analysis and interpretation. Seer, Inc., Redwood City, CA, poster 1 page (Jun. 2022).

Gajadhar et al.: Unbiased human biofluids analysis using a scalable, deep, automated, multi-nanoparticle-based proteomics workflow. Seer, Inc., Redwood City, CA, poster 1 page (2023).

Gao, W.-M. et al. Distinctive serum protein profiles involving abundant proteins in lung cancer patients based upon antibody microarray analysis. BMC cancer 5, 1 (2005).

Garcia et al.: A high-throughput and robust nanoparticle-based label-free mass spectrometry workflow for deep plasma proteomics at scale. Seer, Inc., Redwood City, CA, poster 1 page (2023).

Gautam, P. et al. Proteins with altered levels in plasma from glioblastoma patients as revealed by iTRAQ-based quantitative proteomic analysis. PloS one 7, e46153 (2012).

Geyer et al.: Revisiting biomarker discovery by plasma proteomics. Mol Syst Biol 13(942):1-15 (2017).

Geyer, P.E., et al., Plasma proteome profiling to assess human health and disease. Cell systems, 2016;2: 185-195.

Ghasemi, F., Hormozi-Nezhad, M. R. & Mahmoudi, M. Identification of catecholamine neurotransmitters using fluorescence sensor array. Analytica Chimica Acta 917, 85-92 (2016).

Ghavami, M. et al. Plasma concentration gradient influences the protein corona decoration on nanoparticles. Rsc Advances 3, 1119-1126 (2013).

Giulio Caracciolo et al: "Disease-specific protein corona sensor arrays may have disease detection capacity", Nanoscale Horizons, vol. 4, No. 5, Jan. 1, 2019 (Jan. 1, 2019), pp. 1063-1076,XP55681766,ISSN: 2055-6756, DOI: 10.1039/C9NH00097F.

Go from data to insight with the proteograph analysis suite. Seer. bio. Aug. 2021. Available at: https://seer.bio/resources/document-library/.

Gocheva, V., et al. Quantitative proteomics identify Tenascin-C as a promoter of lung cancer progression and contributor to a signature prognostic of patient survival. Proc Natl Acad Sci U S A 114, E5625-E5634 (2017).

Gopal, K., Grossi, E., Paoletti, P. & Usardi, M. Lipid composition of human intracranial tumors: A biochemical study. Acta neurochirurgica 11, 333-34 7 (1963).

Gossmann, R. et al., Comparative examination of adsorption of serum proteins on HSA- and PLGA-based nanoparticles using

(56) References Cited

OTHER PUBLICATIONS

SDS-PAGE and LC-MS, European Journal of Pharmaceutics and Biopharmaceutics 2015, 93, 80-87.
Guerrier et al.: A simplified monobuffer multidimensional chromatography for high-throughput proteome fractionation. J Chromatogr A. 1073(1-2):25-33 doi:10.1016/j.chroma.2004.10.002 (2005).
Guo, D. et al. An LXR agonist promotes glioblastoma cell death through inhibition of an EGFR/AKT/SREBP-1/LDLR-dependent pathway. Cancer discovery (2011 ).
Guo, D. et al. EGFR signaling through an Akt-SREBP-1-dependent, rapamycin-resistant pathway sensitizes glioblastomas to antilipogenic therapy. Science signaling 2, ra82 (2009).
Guo, D. et al. The AMPK agonist AICAR inhibits the growth of EGFRvlll-expressing glioblastomas by inhibiting lipogenesis. Proceedings of the National Academy of Sciences 106, 12932-12937 (2009).
Guo, Q. et al. Elevated levels of plasma fibrinogen in patients with pancreatic cancer: possible role of a distant metastasis predictor. Pancreas 38, e75-e79 (2009).
Gupta, A. et al. Synergistic antimicrobial therapy using nanoparticles and antibiotics for the treatment of multidrug-resistant bacterial infection. Nano Futures 1, 015004 (2017).
Guturu et al.: High-throughput plasma proteomics to identify diabetes associated protein biomarkers and pQTLs. 1. Seer, Inc., Redwood City, CA; and 2. Weill Cornell Medicine-Qatar, Doha, State of Qatar, poster 1 page (2023).
Guturu et al.: Systematic analysis of DIA LC-MS protein rollup strategies and their impact on phenotype association and proteogenomic applications. Seer, Inc., Redwood City, CA; and Massachusetts General Hospital, Boston, MA. poster 1 page (2023).
Hadjidemetriou, et al., A novel scavenging tool for cancer biomarker discovery based on the blood-circulating nanoparticle protein corona. Biomaterials. Jan. 2019; vol. 188: pp. 118-129.
Hadjidemetriou, et al., In Vivo Biomolecule Corona around Blood-Circulating, Clinically Used and Antibody-Targeted Lipid Bilayer Nanoscale Vesicles. ACS Nano, 2015; 9(8): pp. 8142-8156.
Hadjidemetriou, et al., The Human In Vivo Biomolecule Corona onto PEGylated Liposomes: A Proof-of-Concept Clinical Study. Advanced Materials. Nov. 28, 2018:e1803335. doi: 10.1002/adma. 201803335. [Epub ahead of print].
Hadjidemetriou, M., Al-Ahmady, Z. & Kostarelos, K. Time-evolution of in vivo protein corona onto blood-circulating PEGylated liposomal doxorubicin (DOXIL) nanoparticles. Nanoscale 8, 6948-6957 (2016).
Hajipour et al., Personalized disease-specific protein corona influences the therapeutic impact of graphene oxide, Nanoscale. 7(19):8978-8994 (2015) (pre-print).
Hajipour, et al., Personalized protein coronas: a "key" factor at the nanobiointerface. Biomate Sci. 2014; 2: 1210-1221.
Hajipour, M. J. et al. Personalized disease-specific protein corona influences the therapeutic impact of graphene oxide. Nanoscale, 2015, 7(19): 8978-8994.
Hajipour, M. J. et al., Sensing of Alzheimer's Disease and Multiple Sclerosis Using Nano-Bio Interfaces, Journal of Alzheimer's Disease 2017, 59, 1187-1202.
Hakimi et al.: Robust and Deep Plasma Proteomics using a Multi Nanoparticle-based Workflow coupled with an Orbitrap Exploris 480 Mass Spectrometry and FAIMS Pro Interface. ThermoFisher Scientific, San Jose, CA; and Seer, Inc., Redwood City, CA, poster 1 page (2023).
Hanash, S. M., Pitteri, S. J. & Faca, V. M. Mining the plasma proteome for cancer biomarkers. Nature 452, 571-579 (2008).
Hansson, G. K., Hermansson, A. The Immune System in Atherosclerosis. Nature immunology 2011, 12, 204-212.
Hasija, K. & Bagga, H. K. Alterations of serum cholesterol and serum lipoprotein in breast cancer of women. Indian Journal of Clinical Biochemistry 20, 61-66 (2005).
Hassanein, M. et al. The state of molecular biomarkers for the early detection of lung cancer. Cancer prevention research 5, 992-1006 (2012).
Havugimana et al., A census of human soluble protein complexes, Cell, 150(5): 1068-1081, 2012.
Heath, J. R. & Davis, M. E. Nanotechnology and cancer. Annual review of medicine 59, 251 (2008).
Henschke, C. I. et al. Early Lung Cancer Action Project: overall design and findings from baseline screening. The Lancet 354, 99-105 (1999).
Hirsch, F. R., Franklin, W. A., Gazdar, A. F. & Bunn, P. A. Early detection of lung cancer: clinical perspectives of recent advances in biology and radiology. Clinical Cancer Research 7, 5-22 (2001).
Honda, K. et al. Plasma biomarker for detection of early stage pancreatic cancer and risk factors for pancreatic malignancy using antibodies for apolipoprotein-AI I isoforms. Scientific reports 5 (2015).
Hong et al.: Discrimination Analysis of Mass Spectrometry Proteomics for Lung Adenocarcinoma Detection. Laboratory Medicine 42(6):6, pp. 344-349. doi:10.1309/LMXWEJV3FFDR0DHH (2011).
Hornburg, et al., Deep Plasma Proteomics at Scale: A machine learning enhanced multi nanoparticle approach to improve the depth of plasma proteome coverage. Seer, Inc. Nov. 2021. 1 Page.
Hornburg et al.: Enhanced Competition at the Nano-Bio Interface Enables Comprehensive Characterization of Protein Corona Dynamics and Deep Coverage of Proteomes. Seer Inc., Redwood City, CA USA, poster 1 page (2022).
Hornburg, et al., Enhanced competitive protein exchange at the nano-bio interface enables ultra-deep coverage of the human plasma proteome. Seer, Inc. Jan. 2022. pp. 1-18.
Hornburg et al.: Evaluation of an unbiased, deep, and scalable nanoparticle-based proteomics workflow for limited plasma sample vol. from model organisms. Seer, Inc., Redwood City, CA, poster 1 page (2022).
Houerbi et al.: Deep Profiling of the Spaceflight Plasma Proteome reveals Changes in Reactive Oxygen Species, Extracellular Matrix and Lipid Metabolism. Weill Cornell Medicine, New York, NY; Seer, Inc., Redwood City, CA; Colorado State University, Fort Collins, CO; and SpaceX, Hawthorne, CA, poster 1 page (2022).
Howlader N et al. SEER Cancer Statistics Review, 1975-2014, National Cancer Institute. Bethesda, MD, https://seer. cancer.gov/csr/1975_2014/, based on Nov. 2016 SEER data submission, posted to the SEER web site, Apr. 2017. (2017).
Huang et al.: Deep, Rapid and Unbiased Plasma Proteomics with Differential Analysis of Proteoforms Enabling Proteogenomic Studies in a NSCLC Lung Cancer Study. Seer, Inc. (Mar. 2022).
Huang et al.: Deep, Rapid and Unbiased Plasma Proteomics with Peptide Correlation Analysis Enabling Proteoform Inference and Differential analysis in a NSCLC Lung Cancer Study. Seer, Inc., Redwood City, CA, poster 1 page (2022).
Huang et al.: Deep, unbiased and quantitative mass spectrometry-based plasma proteome analyses of adaptive response to COVID-19 vaccine. 1. Seer, Inc., Redwood City, CA, USA; 2. Plexium, San Diego, CA, USA; 3. Federal University of Rio Grande do Sul, Porto Alegre, Brazil; and 4. Sanford Burnham Prebys, La Jolla, CA, USA, poster 1 page (2023).
Huang et al.: Deep, Unbiased and Quantitative mass spectrometry-based plasma proteome analyses of adaptive response to COVID-19 vaccine. Seer, Inc., Redwood City, CA, poster 1 page (2023).
Huang et al.: Proteoform detection in deep plasma proteomics through peptide expression correlation. Seer, Inc., Redwood City, CA, poster 1 page (2023).
Huang, et al. "Superparamagnetic iron oxide nanoparticles conjugated with folic acid for dual target-specific drug delivery and MRI in cancer theranostics" Mater Sci Eng C Mater Biol Appl. Jan. 1, 2017 ;70(Pt1) 763-771. doi: 10.1016/j.msec.2016.09.052.
Huggins, C., Miller, G. M. & Jensen, E. V. Thermal Coagulation of Serum Proteins II. Deficient Coagulation in Cancer and the Iodoacetate Index. Cancer Research 9, 177-182 (1949).
Hughes, Christopher S et al. Single-pot, solid-phase-enhanced sample preparation for proteomics experiments. Nature protocols vol. 14,1 (2019): 68-85. doi:10.1038/s41596-018-0082-x.
Hughes, Christopher S et al. Ultrasensitive proteome analysis using paramagnetic bead technology. Molecular systems biology vol. 10,10 (2014): 757. doi:10.15252/msb.20145625.

(56) References Cited

OTHER PUBLICATIONS

Huo et al.: Developing a nanoparticle test for prostate cancer scoring. J Transl Med. 10(44):1-8 doi:10.1186/1479-5876-10-44 (2012).
Huo, Q. et al., A facile nanoparticle immunoassay for cancer biomarker discovery. Journal of Nanobiotechnology 2011, 9, paper 20, 12 pages.
Hwang, T. L., Liang, Y., Chien, K. Y. & Yu, J. S. Overexpression and elevated serum levels of phosphoglycerate kinase 1 in pancreatic ductal adenocarcinoma. Proteomics 6, 2259-2272 (2006).
Jaffe, A. S., Babuin, L., Apple, F. S. Biomarkers in Acute Cardiac Disease. Journal of the American College of Cardiology 2006, 48, 1-11.
Jager et al., Investigation of Arsenic-Stressed Yeast (Saccharomyces cerevisiae) as a Bioassay in Homeopathic Basic Research, Scientific World Journal; 2011; vol. 11, pp. 568-583,Published online Mar. 7, 2011.
Jankovska, et al. Affinity depletion versus relative protein enrichment: a side-by-side comparison of two major strategies for increasing human cerebrospinal fluid proteome coverage. Clin Proteom, 2019; 16(9):1-10. https://doi.org/10.1186/s12014-019-9229-1.
Jansch et al.: Adsorption kinetics of plasma proteins on ultrasmall superparamagnetic iron oxide (USPIO) nanoparticles. Int J Pharm. 428(1-2):125-133 doi:10.1016/j.ijpharm.2012.01.060 (2012).
Jayaram, S., Gupta, M. K., Polisetty, R. V., Cho, W. C. & Sirdeshmukh, R. Towards developing biomarkers for glioblastoma multiforme: a proteomics view. Expert review of proteomics 11, 621-639 (2014).
Jerant, A. F., Johnson, J. T., Sheridan, C. & Caffrey, T. J. Early detection and treatment of skin cancer. American family physician 62, 357-386 (2000).
Jung, et al., Specific colorimetric detection of proteins using bidentate aptamer-conjugated polydiacetylene (PDA) liposomes, Adv Funct. Mater, 2010, vol. 20, No. 8 pp. 3092-3097.
Just et al.: A novel cloud-native pipeline enabling deep, unbiased proteomics at extreme scale. Seer, Inc., Redwood City, CA, poster 1 page (2023).
Just et al.: Matrix-Matched Calibration Curves Provide Verification of Quantitative Data-Independent Acquisition Techniques for Deep Plasma Proteomics. Seer, Inc., Redwood City, CA, poster 1 page (2022).
Karna, E. et al. Serum and tissue level of insulin-like growth factor-I (IGF-1) and IGF-1 binding proteins as an index of pancreatitis and pancreatic cancer. International journal of experimental pathology 83, 239-246 (2002).
Kashiwagi, K., et al. Differences of molecular expression mechanisms among neural cell adhesion molecule 1, synaptophysin, and chromogranin A in lung cancer cells. Pathol Int 62, 232-245 (2012).
Kawasaki, E. S. & Player, A. Nanotechnology, nanomedicine, and the development of new, effective therapies for cancer. Nanomedicine: Nanotechnology, Biology and Medicine 1, 101-109 (2005).
Ke, P.C., Lin, S., Parak, W.J., Davis, T.P. & Caruso, F. A Decade of the Protein Corona. ACS Nano 11, 11773-11776 (2017).
Keshishian, et al., Quantitative, multiplexed workflow for deep analysis of human blood plasma and biomarker discovery by mass spectrometry, Nat Protoc, 2017 12, 8, 1683-1701.
Keshishian, H., Addona, T., Burgess, M., Kuhn, E. & Carr, S.A. Quantitative, multiplexed assays for low abundance proteins in plasma by targeted mass spectrometry and stable isotope dilution. Molecular & Cellular Proteomics 6, 2212-2229 (2007).
Keshishian, H. et al. Quantification of cardiovascular biomarkers in patient plasma by targeted mass spectrometry and stable isotope dilution. Molecular & cellular proteomics 8, 2339-2349 (2009).
Khadka et al.: An unbiased multi-omics approach for the detection of pancreatic cancer biomarkers utilizing ion-mobility mass spectrometry and nanoparticle-based proteograph technology. PrognomiQ Inc., 1900 Alameda de las Pulgas, Suite 100, San Mateo, CA, USA, poster 1 page (2022).
Kharya, S., Dubey, D. & Soni, S. Predictive Machine Learning Techniques for Breast Cancer Detection. (IJCSIT) International Journal of Computer Science and Information Technologies 4, 1023-1028 (2013).
Kiehntopf et al.: Use of SELDI-TOF mass spectrometry for identification of new biomarkers: potential and limitations. Clin Chem Lab Med. 45(11):1435-1449 doi:10.1515/CCLM.2007.351 (2007).
Kitano, et al., Cloud scalable omics data analysis pipeline using serverless task infrastructure. Seer, Inc. Nov. 2021. 1 Page.
Kleine, A. et al. The polymerisation of oligo(ethylene glycol methyl ether) methacrylate from a multifunctional poly(ethylene imine)derived amide: a stabiliser for the synthesis and dispersion of magnetite, Polymer Chemistry, 5, 524-534 (Year: 2014).
Kluger et al.: Ultra-high coverage of the serum proteome using a multi-nanoparticle based workflow. Seer Evotec poster, 1 page (2022).
Koene et al.: Serum protein profiles as potential biomarkers for infectious disease status in pigs. BMC Vet Res. 8(32):1-14 doi:10.1186/1746-6148-8-32 (2012).
Kojima et al.: Detection of elevated proteins in peritoneal dissemination of gastric cancer by analyzing mass spectra data of serum proteins. J Surg Res. 155(1):13-17 doi:10.1016/j.jss.2008.07.024 (2009).
Konduru et al., Protein Corona: Implications for Nanoparticle Interactions with Pulmonary Cells, Particle and Fibre Toxicology, 2017, 14:42, pp. 1-12.
Koo et al.: Liquid flow in microchannels: experimental observations and computational analyses of microfluidics effects. Journal of Micromechanics and Microengineering 13(5):568-579 (2003).
Korbelik, M. & Cooper, P. Potentiation of photodynamic therapy of cancer by complement: the effect of y-inulin. British journal of cancer 96, 67-72 (2007).
Koscielny, G. et al. Open Targets: a platform for therapeutic target identification and validation. Nucleic acids research 45, D985-D994 (2016).
Kourou, K., Exarchos, T.P., Exarchos, K.P., Karamouzis, M.V. & Fotiadis, D.I. Machine learning applications in cancer prognosis and prediction. Computational and structural biotechnology journal 13, 8-17 (2015).
Kozak et al.: Identification of biomarkers for ovarian cancer using strong anion-exchange ProteinChips: potential use in diagnosis and prognosis. Proc Natl Acad Sci USA 100(21):12343-12348 doi:10.1073/pnas.2033602100 (2003).
Kroeck, et al., Native Cell Membrane Nanoparticles System for Membrane Protein-Protein Interaction Analysis. J. Vis. Exp. 2020; (161), e61298, doi:10.3791/61298.
Kugler, K.G. et al. The impact of sample storage time on estimates of association in biomarker discovery studies. Journal of clinical bioinformatics 1, 1 (2011).
Lacar et al.: Accelerating throughput with the ProteographTM XT Assay. Seer, Inc., Application Note (CF-1059 REV A), pp. 1-8 (2023).
Lacerda, S.H.D.P., et al. Interaction of gold nanoparticles with common human blood proteins. ACS Nano 4, 365-379 (2009).
Laurent, S. et al. Corona protein composition and cytotoxicity evaluation of ultra-small zeolites synthesized from template free precursor suspensions. Toxicology Research 2, 270-279 (2013).
Laurent, S. et al., Superparamagnetic iron oxide nanoparticles: promises for diagnosis and treatment of cancer. Int J Mol Epidemiol Genet. 2011; 2(4): 367-390. Published online Nov. 25, 2011.
Le, N. D., Yazdani, M., Rotello, V. M. Array-Based Sensing Using Nanoparticles: An Alternative Approach for Cancer Diagnostics. Nanomedicine 2014, 9, 1487-1498.
Lebrecht et al.: Surface-enhanced Laser Desorption/Ionisation Time-of-flight Mass Spectrometry to Detect Breast Cancer Markers in Tears and Serum. Cancer Genomics Proteomics. 6(2):75-83 (2009).
Lee et al., Recognition of Volatile Organic Compounds Using SnO2 Sensor Array and Pattern Recognition Analysis. Sensors and Actuators B: Chemical, Jun. 2001, 77, 228-236.
Lee et al.: Revealing urologic diseases by proteomic techniques. J Chromatogr B Analyt Technol Biomed Life Sci. 815(1-2):203-213 doi:10.1016/j.jchromb.2004.11.008 (2005).

(56) References Cited

OTHER PUBLICATIONS

Lee, G. Cancerous immunoglobulins in cancer immunology. Journal of Clinical & Cellular Immunology 2014.
Leong et al.: Profiling of apoptotic changes in human breast cancer cells using SELDI-TOF mass spectrometry. Cell Physiol Biochem. 20(5):579-590 doi:10.1159/000107541 (2007).
Levandowsky, M. & Winter, D. Distance between Sets. Nature 234, 34-35 (1971).
Levin, B. et al. Screening and surveillance for the early detection of colorectal cancer and adenomatous polyps, 2008: a joint guideline from the American Cancer Society, the US Multi-Society Task Force on Colorectal Cancer, and the American College of Radiology*t. CA: a cancer journal for clinicians 58, 130-160 (2008).
Levitan et al.: Evaluation of engineered multi-nanoparticle-based proteomics analysis for unbiased, deep, and rapid analysis of fetal bovine serum derived cell culture media. Seer, Inc., Redwood City, CA, poster 1 page (2022).
Li et al.: A high-throughput and robust multi nanoparticle-based label-free mass spectrometry workflow for deep plasma proteomics at scale. Seer, Inc., Redwood City, CA, poster 1 page (2023).
Li et al. A review on phospholipids and their main applications in drug delivery systems. Asian Journal of Pharmaceutical Sciences 10:81-98 (2015).
Li, et al., Digging More Missing Proteins Using an Enrichment Approach with ProteoMiner. J. Proteome Res. Sep. 2017; 16(12): 4330-4339.
Li et al.: LC-MS MS1 image map classification enables real-time sample quality control for nanoparticle-based deep untargeted proteomics. Seer, Inc., Redwood City, CA, poster 1 page (2023).
Li, J. et al. Block copolymer conjugated Au-coated Fe3O4 nanoparticles as vectors for enhancing colloidal stability and cellularuptake, Journal of Nanobiotechnology, 15(56) 1-11 (Year: 2017).
Li, Lei., Dynamic range compression with ProteoMiner™: principles and examples. Methods Mol Biol, 2015;1295:99-107.
Lilien et al.: Probabilistic disease classification of expression-dependent proteomic data from mass spectrometry of human serum. J Comput Biol. 10(6):925-946 doi:10.1089/106652703322756159 (2003).
Lim, S. H., Feng, L., Kemling, J. W., Musto, C. J. & Suslick, K. S. An optoelectronic nose for the detection of toxic gases. Nature chemistry 1, 562-567 (2009).
Lin, et al. A chemically functionalized magnetic nanoplatform for rapid and specific biomolecular recognition and separation Biomacromolecules 2013, 14, 1, 160-168.
Lin et al.: Plasma proteomic pattern as biomarkers for ovarian cancer. Int J Gynecol Cancer 16 Suppl 1:139-146 doi:10.1111/j.1525-1438.2006.00475.x (2006).
Lin Jiang et al.: "Patterning of Plasmonic Nanoparticles into Multiplexed One-Dimensional Arrays Based on Spatially Modulated Electrostatic Potential",ACS Nano, vol. 5, No. 10, Oct. 25, 2011 (Oct. 25, 2011), pp. 8288-8294.
Little, D.P. et al., MALDI on a Chip: Analysis of Arrays of Low-Femtomole to Subfemtomole Quantities of Synthetic Oligonucleotides and DNA Diagnostic Products Dispensed by a Piezoelectric Pipet. Analytical Chemistry, 69 (22), 4540-4546 (1997).
Liu et al.: MALDI-TOF MS combined with magnetic beads for detecting serum protein biomarkers and establishment of boosting decision tree model for diagnosis of hepatocellular carcinoma. Am J Clin Pathol. 134(2):235-241 doi:10.1309/AJCPA6C6NOGFLYIR (2010).
Liu et al.: Proteomic profiling of hepatitis B virus-related hepatocellular carcinoma with magnetic bead-based matrix-assisted laser desorption/ionization time-of-flight mass spectrometry. Acta Biochim Biophys Sin (Shanghai) 43(7):542-550 doi:10.1093/abbs/gmr044 (2011).
Liu, J., et al. Highly water-dispersible biocompatible magnetite particles with low cytotoxicity stabilized by citrate groups. Angew Chem Int Ed Engl 48, 5875-5879 (2009).
Liu, J.Z. et al. Association analyses identify 38 susceptibility loci for inflammatory bowel disease and highlight shared genetic risk across populations. Nature genetics 47, 979-986 (2015).
Liu, Y. et al., Theranostic near-infrared fluorescent nanoplatform for imaging and systemic SiRNA delivery to metastatic anaplastic thyroid cancer, Proceedings of the National Academy of Sciences of the United States of America Jul. 12, 2016, 113, 7750-7755.
Longo, C. et al. Core-shell hydrogel particles harvest, concentrate and preserve labile low abundance biomarkers. PLoS one 4, e4763 (2009).
Lu, et al., Tailoring the component of protein corona via simple chemistry. Nature Communications, 2019; 10(4520):1-14.
Luchini, A. et al. Smart hydrogel particles: biomarker harvesting: one-step affinity purification, size exclusion, and protection against degradation. Nano letters 8, 350-361 (2008).
Ludwig, J. A. & Weinstein, J. N. Biomarkers in cancer staging, prognosis and treatment selection. Nature Reviews Cancer 5, 845-856 (2005).
Lundqvist, et al. The nanoparticle protein corona formed in human blood or human blood fractions. PloS one 12.4 (Apr. 17, 2017): e0175871. 15 Pages.
Lundqvist, M., et al. Nanoparticle size and surface properties determine the protein corona with possible implications for biological impacts. Proc Natl Acad Sci U S A 105, 14265-14270 (2008).
Lundqvist, M., et al. The evolution of the protein corona around nanoparticles: a test study. ACS Nano 5, 7503-7509 (2011).
Machado, R. F., Laskowski, D., Deffenderfer, 0., et al. Detection of Lung Cancer by Sensor Array Analyses of Exhaled Breath. American journal of respiratory and critical care medicine 2005, 171, 1286-1291.
Maciel, C. M. et al. Differential proteomic serum pattern of low molecular weight proteins expressed by adenocarcinoma lung cancer patients. Journal of experimental therapeutics & oncology 5 (2005).
Magni et al.: Biomarkers discovery by peptide and protein profiling in biological fluids based on functionalized magnetic beads purification and mass spectrometry. Blood Transfus. 8 Suppl 3(Suppl 3):s92-s97 doi:10.2450/2010.015S (2010).
Magtivio B.V. MagSiMUS and MagSi Product Catalog. Magnetic Separation Solutions (2018).
Mahmoudi, M., Bertrand, N., Zope, H. & Farokhzad, O.C. Emerging understanding of the protein corona at the nano-bio interfaces. Nano Today 11, 817-832 (2016).
Mahmoudi, M. et al. Protein-nanoparticle interactions: opportunities and challenges. Chemical reviews 111, 5610-5637 (2011).
Mahmoudi, M. et al. Variation of protein corona composition of gold nanoparticles following plasmonic heating. Nano letters 14, 6-12 (2013).
Mahmoudi, M., Lohse, S., Murphy, C. J. & Suslick, K. S. Identification of Nanoparticles with a Colorimetric Sensor Array. ACS Sensors 1, 17-21 (2016).
Mahmoudi, M., Saeedi-Eslami, S. N., Shokrgozar, M.A., et al. Cell "Vision": Complementary Factor of Protein Corona in Nanotoxicology. Nanoscale 2012, 4, 5461-5468.
Majek, P., Reicheltova, Z., Suttnar, J., et al. Plasma Proteome Changes in Cardiovascular Disease Patients: Novel Isoforms of Apolipoprotein A 1. Journal of translational medicine 2011, 9, 84.
Malik, G. et al. Serum levels of an isoform of apolipoprotein A-II as a potential marker for prostate cancer. Clinical Cancer Research 11, 1073-1085 (2005).
Mani et al.: Data mining strategies to improve multiplex microbead immunoassay tolerance in a mouse model of infectious diseases. PLoS One 10(1):e0116262:1-19. doi:10.1371/journal.pone.0116262 (2015).
Mani, et al., Magnetic particles in ultrasensitive biomarker protein measurements for cancer detection and monitoring. Expert Opin Med Diagn. Sep. 1, 2011; 5(5): 381-391.
Matuszak, et al. "Drug delivery to atherosclerotic plaques using superparamagnetic iron oxide nanoparticles." International journal of nanomedicine vol. 13 8443-8460. Dec. 11, 2018, doi:10.2147/IJN.S179273.
May: Digging Deep to Release the Power of the Proteome. Inside Precision Medicine, pp. 1-11 [retrieved online from https://www.

(56) References Cited

OTHER PUBLICATIONS insideprecisionmedicine.com/topics/translational-research/proteomics/digging-deep-to-release-the-power-of-the-proteome/] (2023).
McDonald, W.H. & Yates, J.R., 3rd. Shotgun proteomics and biomarker discovery. Dis Markers 18, 99-105 (2002).
Mehan et al.: Chapter 20. Highly Multiplexed Proteomic Platform for Biomarker Discovery, Diagnostics, and Therapeutics. Complement Therapeutics, Advances in Experimental Medicine and Biology, Lambris, J. D. et al. (eds.), Springer Science+Business Media, New York, pp. 283-300. doi:10.1007/978-1-4614-4118-2 (2013).
Mertens et al.: On the use of double cross-validation for the combination of proteomic mass spectral data for enhanced diagnosis and prediction. Statistics & Probability Letters 81(7):759-766 (2011).
Micallef, J. et al. Applying mass spectrometry based proteomic technology to advance the understanding of multiple myeloma. Journal of hematology & oncology 3, 1 (2010).
Milani et al.: Reversible versus irreversible binding of transferrin to polystyrene nanoparticles: soft and hard corona. ACS Nano. 6(3):2532-2541 doi:10.1021/nn204951s (2012).
Miller, A., Hoogstraten, B., Staquet, M. & Winkler, A. Reporting results of cancer treatment. cancer 4 7, 207-214 (1981).
Millioni et al., High Abundance Proteins Depletion vs Low Abundance Proteins Enrichment: Comparison of Methods to Reduce the Plasma Proteome Complexity, PloS One, 2011, 6, 5, e19603.
Minelli et al. Measuring the size and density of nanoparticles by centrifugal sedimentation and flotation. Anal. Methods, 2018, 10, 1725-1732. DOI: 10.1039/C8AY00237A.
Miotto G, et al. Protein corona as a proteome fingerprint: The example of hidden biomarkers for cow mastitis. Colloids Surf B Biointerfaces. 2016;140:40-49. doi:10.1016/j.colsurfb.2015.11.043.
Mirshafiee, et al., Protein corona significantly reduces active targeting yield. Chemical communications vol. 49,25(2013): 2557-9. doi:10.1039/c3cc37307j.
Mirshafiee, V. et al., The importance of selecting a proper biological milieu for protein corona analysis in vitro: Human plasma versus human serum. Int J Biochem Cell Biol. Jun. 2016;75:188-95. doi: 10.1016/j.biocel.2015.11.019. Epub Nov. 28, 2015.
Mirshafiee, V., Kim, R., Park, S., Mahmoudi, M. & Kraft, M.L. Impact of protein pre-coating on the protein corona composition and nanoparticle cellular uptake. Biomaterials 75, 295-304 (2016).
Misek, D. E., Patwa, T. H., Lubman, D. M. & Simeone, D. M. Early detection and biomarkers in pancreatic cancer. Journal of the National Comprehensive Cancer Network 5, 1034-1041 (2007).
Müller, et al., Light-mediated discovery of surfaceome nanoscale organization and intercellular receptor interaction networks. bioRxiv, Aug. 2020; https://doi.org/10.1101/2020.08.11.246652.
Mody, et al. Introduction to metallic nanoparticles. Journal of Pharmacy and Bioallied Sciences 2.4 (2010): 282-289.
Mohtashemi et al.: Improving LC-MS Data Analysis Pipelines to Leverage Distributed Compute Engines. Seer, Inc., Redwood City, CA, poster 1 page (2022).
Mohtashemi, et al., Mass spectrometry data acquisition with machine learning methods for deep plasma protein characterization. Seer, Inc. Nov. 2021. 1 Page.
Monopoli, et al. Nanoparticle coronas take shape. Nature Nanotechnology, Jan. 2011. vol. 6; 11-12.
Monopoli, M.P., Aberg, C., Salvati, A. & Dawson, K.A. Biomolecular coronas provide the biological identity of nanosized materials. Nat Nanotechnol 7, 779-786 (2012).
Monopoli, M.P., et al. Physical-chemical aspects of protein corona: relevance to in vitro and in vivo biological impacts of nanoparticles. J Am Chem Soc 133, 2525-2534 (2011).
Mortensen, N. P.; Hurst, G. B.; Wang, W.; Foster, C. M.; Nallathamby, P. D.; Retterer, S. T., Dynamic development of the protein corona on silica nanoparticles: composition and role in toxicity. Nanoscale 2013, 5 (14), 6372-6380.
Moss et al.: Integrated Plasma Multi-Omics Using Nanoparticle Technology and Single Shot Capillary MS. University of Wisconsin-Madison, Madison, WI, 53706, USA; Morgridge Institute for Research, Madison, WI ,53715, USA; and Seer, Redwood City, CA, poster 1 page (2022).
Motamedchaboki et al.: Deep plasma protein profiling in Alzheimer's disease (AD) with a novel unbiased and scalable proteogenomics approach. Seer, Inc., Redwood City, CA, poster 1 page (2022).
Muntoni, S. et al. Serum lipoproteins and cancer. Nutrition, Metabolism and Cardiovascular Diseases 19, 218-225 (2009).
Nakamura et al.: Differential profiling analysis of proteins involved in anti-proliferative effect of interferon-alpha on renal cell carcinoma cell lines by protein biochip technology. Int J Oncol. 28(4):965-970 (2006).
Nanjappa, V., et al. Plasma Proteome Database as a resource for proteomics research: 2014 update. Nucleic Acids Res 42, D959-965 (2014).
Nanni et al.: Serum protein profiling in patients with inflammatory bowel diseases using selective solid-phase bulk extraction, matrix-assisted laser desorption/ionization time-of-flight mass spectrometry and chemometric data analysis. Rapid Commun Mass Spectrom. 21(24):4142-4148 doi:10.1002/rcm.3323 (2007).
NanoComposix: Silica Physical Properties. 2021. Retrieved Oct. 14, 2021; Available at: https://nanocomposix.com/pages/silica-physical-properties#target.
Nel, A.E. et al. Understanding biophysicochemical interactions at the nano-bio interface. Nature materials 8, 543 2009.
Nesvizhskii, A.I. Proteogenomics: concepts, applications and computational strategies. Nat Methods 11, 1114-1125 (2014).
Nibbe, et al., Discovery and Scoring of Protein Interaction Subnetworks Discriminative of Late Stage Human Colon Cancer. Mol Cell Proteomics. Apr. 2009; 8(4): 827-845. doi: 10.1074/mcp.M800428-MCP200.
Nie, S. et al. Glycoprotein biomarker panel for pancreatic cancer discovered by quantitative proteomics analysis. Journal of proteome research 13, 1873-1884 (2014).
O'Connell, et al., Characterization of the bionano interface and mapping extrinsic interactions of the corona of nanomaterials. Nanoscale, Aug. 26, 2015; 37(7): 15268-15276.
Oka, Amita R et al. Functional Proteomic Profiling of Phosphodiesterases Using SeraFILE Separations Platform. International journal of proteomics vol. 2012 (2012): 515372. doi:10.1155/2012/515372.
Omenn, G.S., et al. Overview of the HUPO Plasma Proteome Project: results from the pilot phase with 35 collaborating laboratories and multiple analytical groups, generating a core dataset of 3020 proteins and a publicly-available database. Proteomics 5, 3226-3245 (2005).
Ono, M. et al. Prolyl 4-Hydroxylation of α-Fibrinogen: A Novel Protein Modification Revealed by Plasma Proteomics. Journal of Biological Chemistry 284, 29041-29049 (2009).
O'Rourke, N. & Edwards, R. Lung cancer treatment waiting times and tumour growth. Clinical Oncology 12, 141-144 (2000).
Orr, W. S., Sandoval, J. A., Malkas, L. H. & Hickey, R. J. Acute Phase Proteins as Cancer Biomarkers. (INTECH Open Access Publisher, 2011).
Ostrand-Rosenberg, S., Cancer and complement. Nature biotechnology vol. 26, No. 12, Dec. 2008;1348-1349.
Paez, J. G. et al. EGFR mutations in lung cancer: correlation with clinical response to gefitinib therapy. Science 304, 1497-1500 (2004).
Page et al.: A Cloud-Scalable Software Suite for Large-Scale Proteogenomics Data Analysis and Visualization. Seer, Inc., Redwood City, CA, poster 1 page (2023).
Palchetti, et al. Exploitation of nanoparticle-protein corona for emerging therapeutic and diagnostic applications. Journal of Materials Chemistry B 4.25 (May 23, 2016): 4376-4381.
Palchetti, S.; Colapicchioni, V.; Digiacomo, L.; Caracciolo, G.; Pozzi, D.; Capriotti, A. L.; La Barbera, G.; Lagana, A., The protein corona of circulating PEGylated liposomes. Biochimica et Biophysica Acta (BBA)-Biomembranes 2016, 1858 (2), 189-196.
Palchetti, S. et al. Nanoparticles-cell association predicted by protein corona fingerprints. Nanoscale 8(25):12755-12763 doi:10.1039/C6NR03898K (2016).

(56) References Cited

OTHER PUBLICATIONS

Palmieri, V. et al. Dynamic light scattering for the characterization and counting of extracellular vesicles: a powerful noninvasive tool. Journal of Nanoparticle Research 16, 1-8 (2014).

Pan, S., Brentnall, T. A. & Chen, R. Proteomics analysis of bodily fluids in pancreatic cancer. Proteomics 15, 2705-2715 (2015).

Pan, S. et al. Multiplex targeted proteomic assay for biomarker detection in plasma: a pancreatic cancer biomarker case study. Journal of proteome research 11, 1937-1948 (2012).

Pan, S. et al. Protein alterations associated with pancreatic cancer and chronic pancreatitis found in human plasma using global quantitative proteomics profiling. Journal of proteome research 10, 2359-2376 (2011).

Panda, et al., Affinity Pulldown of Biotinylated RNA for Detection of Protein-RNA Complexes. Bio Protoc. Dec. 20, 2016; 6(24): e2062, pp. 1-10.

Pang, W.W., Abdul-Rahman, P. S., Izlina Wan-Ibrahim, W. & Haji Hashim, 0. Can the acute-phase reactant proteins be used as cancer biomarkers? International Journal of Biological Markers 25, 1 (2010).

Papi, M. et al., Exploitation of nanoparticle-protein interactions for early disease detection. Applied Physics Letters 2019, 114, paper 163702, 5 pages.

Pardo, et al., Resolving Affinity Purified Protein Complexes by Blue Native PAGE and Protein Correlation Profiling. J Vis Exp. 2017; 122:55498, pp. 1-11.

Patra, et al., Component-Specific Analysis of Plasma Protein Corona Formation on Gold Nanoparticles Using Multiplexed Surface Plasmon Resonance. Small, 2016; 12(9): 1174-1182.

Patwa, T. H. et al. The identification of phosphoglycerate kinase-1 and histone H4 autoantibodies in pancreatic cancer patient serum using a natural protein microarray. Electrophoresis 30, 2215-2226 (2009).

PCT/US2017/067013 International Search Report dated May 1, 2018.

PCT/US2017/067013 Written Opinion of the International Searching Authority dated May 1, 2018.

PCT/US2019/000061 International Search Report and Written Opinion dated May 20, 2020.

PCT/US2020/024426 International Search Report and Written Opinion dated Jul. 31, 2020.

PCT/US2020/044908 International Search Report and Written Opinion dated Jan. 12, 2021.

PCT/US2020/058422 International Search Report and Written Opinion dated Mar. 16, 2021.

PCT/US2021/042254 International Search Report and Written Opinion dated Dec. 20, 2021.

Pease et al.: Deep and unbiased proteomics analysis reveals differences between serum and plasma proteome in matched donors. Seer, Inc., Redwood City, CA, poster 1 page (2022).

Pease et al.: Evaluation of blood-based sample types for deep plasma proteomics. Application Note, Seer, Inc., Redwood City, CA, pp. 1-4 (2023).

Peer, D. et al. Nanocarriers as an emerging platform for cancer therapy. Nature nanotechnology 2, 751-760 (2007).

Pena et al.: Evaluation of deep plasma proteomic analysis with the ProteographTM workflow and TMT sample labeling. 1. Proteomics Shared Resource at Sanford Burnham Prebys, La Jolla, CA; and 2. Seer, Inc., Redwood City, CA, pp. 1-5 (2023).

Pepe, M. S. et al. Phases of biomarker development for early detection of cancer. Journal of the National Cancer Institute 93, 1054-1061 (2001).

Petricoin, E. F. & Liotta, L.A. SELDI-TOF-based serum proteomic pattern diagnostics for early detection of cancer. Current Opinion in Biotechnology 15, 24-30 (2004).

Pichler, M. et al. High plasma fibrinogen level represents an independent negative prognostic factor regarding cancer-specific, metastasis-free, as well as overall survival in a European cohort of non-metastatic renal cell carcinoma patients. British journal of cancer 109, 1123 (2013).

Pio, R., Ajona, D. & Lambris, J. D. Complement inhibition in cancer therapy. Seminars in Immunology 25, 54-64, doi: http://dx.doi.org/10.1016/j.smim.2013.04.001 (2013).

Pio, R., Corrales, L. & Lambris, J. D. The Role of Complement in Tumor Growth, Adv Exp Med Biol., 229-262 (Springer, 2014).

Platt et al.: A Cloud-scalable Software Suite for Large-Scale Proteogenomics Data Analysis and Visualization. Seer, Inc., Redwood City, CA, poster 1 page (2022).

Polanski, et al., A list of candidate cancer biomarkers for targeted proteomics. Biomark Insights, 2006; 1: 1-48.

Popescu, I. D. et al. Potential serum biomarkers for glioblastoma diagnostic assessed by proteomic approaches. Proteome science 12, 1 (2014).

Pourshams, A. et al. Cohort profile: the Golestan Cohort Study-a prospective study of oesophageal cancer in northern Iran. International journal of epidemiology 39, 52-59 (2010).

Pozzi, et al., Surface chemistry and serum type both determine the nanoparticle-protein corona. Journal of Proteomics, 2015, 119, 209-217.

Puri et al.: Lipid-based nanoparticles as pharmaceutical drug carriers: from concepts to clinic. Critical Reviews™ in Therapeutic Drug Carrier Systems. 26(6):523-580 (2009).

Qian, W.-J. et al. Enhanced detection of low abundance human plasma proteins using a tandem IgY12-SuperMix immunoaffinity separation strategy. Molecular & Cellular Proteomics 7, 1963-1973 (2008).

Qu, Yinsheng, et al., "Boosted decision tree analysis of surface-enhanced laser desorption/ionization mass spectral serum profiles discriminates prostate cancer from noncancer patients". Clinical Chemistry (2002), 48(10): 1835-1843.

Rahimi, M. et al. Zeolite Nanoparticles for Selective Sorption of Plasma Proteins. Scientific reports 5, 17259-17259 (2015).

Rahman et al., Nanoparticle and Protein Corona, Chapter 2 in Protein-Nanoparticle Interactions, Springer Series in Biophysics 15, pp. 21-44 (Springer Science & Business Media, 2013).

Rahman M et al.: Disease specific protein corona, Progress in Biomedical Optics and Imaging, SPIE-International Society for Optical Engineering, Bellingham, WA, US, vol. 9338, Mar. 11, 2015 (Mar. 11, 2015), pp. 93380V-93380V,XP060049391,ISSN: 1605-7422, DOI: 10.1117 /12.2079771ISBN: 978-1-5106-0027-0.

Rakow, N. A., Suslick, K. S. A Colorimetric Sensor Array for Odour Visualization. Nature 2000, 406, 710-713.

Resyn Biosciences (Pty) Ltd. MagReSyn® SAX Strong anion exchange magnetic microparticles: pp. 1-2. Retrieved online on Jun. 4, 2023 available at https://resynbio.com/wp-content/uploads/2020/IFU_SAX.pdf.

Ridker, P. M., Hennekens, C. H., Suring, J. E., Rifai, N. C-Reactive Protein and Other Markers of Inflammation in the Prediction of Cardiovascular Disease in Women. New England Journal of Medicine 2000, 342, 836-843.

Riley et al.: A Cloud-Scalable Software Suite for Large-Scale Proteogenomics Data Analysis and Visualization. Seer, Inc., Redwood City, CA, poster 1 page (2023).

Ritz, S. et al., Protein Corona of Nanoparticles: Distinct Proteins Regulate the Cellular Uptake, Biomacromolecules 2015, 16, 1311-1321, with 11 pages of supporting information.

RNA (ribonucleic acid), 1988. Illustrated Dictionary of Science, Andromeda. Retrieved online on Feb. 8, 2012 http://www.credoreference.com/etry/andidsci/rna_ribonucleic_acid.

Rost, H.L., et al. OpenMS: a flexible open-source software platform for mass spectrometry data analysis. Nat Methods 13, 741-748 (2016).

Rubio-Perez, C. et al. In silico prescription of anticancer drugs to cohorts of 28 tumor types reveals targeting opportunities. Cancer cell 27, 382-396 (2015).

Sacanna et al.: Thermodynamically stable pickering emulsions. Phys Rev Lett. 98(15):158301 doi:10.1103/PhysRevLett.98.158301 (2007).

Safarik, et al., Magnetic techniques for the isolation and purification of proteins and peptides. Biomagn Res Technol. 2004; 2(7): 1-17.

Saha, K. et al. Regulation of Macrophage Recognition through the Interplay of Nanoparticle Surface Functionality and Protein Corona. ACS nano 10, 4421-4430 (2016).

(56) References Cited

OTHER PUBLICATIONS

Sakulkhu et al., Ex situ evaluation of the composition of protein corona of intravenously injected superparamagnetic nanoparticles in rats. Nanoscale, Aug. 2014; 6:11439-11450.

Sakulkhu et al.: Protein corona composition of superparamagnetic iron oxide nanoparticles with various physico-chemical properties and coatings. Sci Rep. 4:5020:1-9 doi: 10.1038/srep05020 (2014).

Sakulkhu, et al. Significance of surface charge and shell material of superparamagnetic iron oxide nanoparticle SPION) based core/shell nanoparticles on the composition of the protein corona. Biomater. Sci., Jan. 20, 2015; vol. 3, 265-278.

Salehi-Reyhani, A., "Evaluating single molecule detection methods for microarrays with high dynamic range for quantitative single cell analysis." Scientific Reports, Dec. 20, 2017, vol. 7, No. 17957, pp. 1-12.

Salvador-Morales, C., Zhang, L., Langer, R. & Farokhzad, O.C. Immunocompatibility properties of lipid-polymer hybrid nanoparticles with heterogeneous surface functional groups. Biomaterials 30, 2231-2240 (2009).

Salvati, A. et al. Transferrin-functionalized nanoparticles lose their targeting capabilities when a biomolecule corona adsorbs on the surface. Nature nanotechnology 8, 137-143 (2013).

Saveliev et al., Promega. Trypsin/Lys-C protease mix for enhanced protein mass spectrometry analysis. Nature Methods, Nov. 2013 (2 pages).

Schindelin, et al. Fiji: an open-source platform for biological-image analysis. Nat Methods. Jun. 28, 2012;9(7):676-682. doi: 10.1038/nmeth.2019.

Schottler, S., et al. Protein adsorption is required for stealth effect of poly(ethylene glycol)- and poly(phosphoester)-coated nanocarriers. Nat Nanotechnol 11, 372-377 (2016).

Schrittwieser, S. et al. Direct protein quantification in complex sample solutions by surface-engineered nanorod probes. Scientific Reports, 2017, 7(4752): https://doi.org/10.1038/s41598-017-04970-5.

Schroder, et al. Screening and prostate-cancer mortality in a randomized European study. N Engl J Med. Mar. 26, 2009;360(13):1320-8. doi: 10.1056/NEJMoa0810084. Epub Mar. 18, 2009.

Schwamborn et al.: Serum proteomic profiling in patients with bladder cancer. Eur Urol. 56(6):989-997 doi:10.1016/j.eururo.2009.02.031 (2009).

Seer, Inc. A New Gateway to the Proteome—Unbiased, Deep, Rapid Proteomics at Scale, YouTube, Mar. 20, 2021 URL: https://www.youtube.com/watch?v=dDe--0QMAX8.

Seer, Inc. A New Gateway to the Proteome, YouTube, Mar. 20, 2021, https://www.youtube.com/watch?v=O-goKi6_1P8.

Seer, Inc. Comparison Of Proteograph Product Suite to Peptide Fractionation, YouTube, Mar. 2021, https://www.youtube.com/watch?v=eUliHi7FB_I.

Seer, Inc. Customer Stories—Mark Flory Ph.D., OHSU/Knight Cancer Research Institute/CEDAR, YouTube, Apr. 30, 2021, https://www.youtube.com/watch?v=C3BTvhOzx0M.

Seer, Inc. Initialize and Prepare the SP100, YouTube, May 25, 2021 URL: https://www.youtube.com/watch?v=alD-8qhC9hY.

Seer, Inc. Loading Reagents and Plasticware onto the SP100 Work Deck, YouTube, May 25, 2021 URL: https://www.youtube.com/watch?v=ND3QYKvGub8.

Seer, Inc. Performing SP100 Clean-up and the Sample Plate Layout, YouTube, May 25, 2021 URL: https://www.youtube.com/watch?v=S070uN-KgTs.

Seer, Inc. Plasma Protein Profiling of Alzheimer's and Mild Cognitive Impairment, YouTube, Mar. 20, 2021 URL: https://www.youtube.com/watch?v=YLEa_7pfDuQ.

Seer, Inc. Preparing and Loading the Nanoparticles, Samples, and Controls, YouTube, May 25, 2021 URL: https://www.youtube.com/watch?v=l2MTSxjMaF4.

Seer, Inc.: Press release PPT, with online publications (published Sep. 2022).

Seer Inc., Proteograph Assay quick reference work deck layout [retrieved online Jan. 2022].

Seer, Inc. Proteograph Product Suite—Detailed 10 Minute Overview, YouTube, Mar. 20, 2021, https://www.youtube.com/watch?v=jWPKiL9fsBw.

Seer, Inc. Proteograph Product Suite—Short 3 Minute Overview, YouTube, Mar. 20, 2021, https://www.youtube.com/watch?v=u0cWT-FeEl4.

Seer, Inc. Proteograph Product Suite with the Bruker tims TOF Platform, YouTube, Apr. 10, 2021, https://www.youtube.com/watch?v=upzRuK3OAbc.

Seer, Inc. Proteograph Safety Data Sheet. URL: https://seer.bio/wp-content/uploads/2021/12/Proteograph-Assay-SDS.pdf Published Nov. 2021 (retrieved online Feb. 2022) 122 Pages.

Seer, Inc., Proteograph Training Series: Initialize and prepare the SP100, YouTube, Jan. 4, 2022, https://www.youtube.com/watch?v=jUzl-VSD23k.

Seer, Inc. Proteograph™ Training Series: Loading Reagents and Plasticware onto the SP100 Work Deck, YouTube, Jan. 4, 2022, https://www.youtube.com/watch?v=gAYy7Usa0XI.

Seer, Inc. Proteograph Training Series: Preparing and Loading the nanoparticles, samples, and controls, YouTube, Jan. 4, 2022, https://www.youtube.com/watch?v=GYnleXjmDml.

Seer, Inc., Proteograph Training Series: Preparing Materials. YouTube, Jan. 4, 2022, https://www.youtube.com/watch?v=vHld2oQRavA.

Seer, Inc., Proteograph Training Series: SP100 automation instrument [Functions & Components], YouTube, Jan. 4, 2022, https://www.youtube.com/watch?v =-8v2_Bqoi4Y.

Seer, Inc. Proteograph Training Series: SP100 Clean-up & Sample Plate Layout, YouTube, Jan. 4, 2022, https://www.youtube.com/watch?v=noXIYMZc0FI.

Seer, Inc. Proteograph Training Series: Starting the proteograph assay method, YouTube, Jan. 4, 2022, https://www.youtube.com/watch?v=nLqZT623u1M.

Seer, Inc., Proteograph Traning Series: Setting up the proteograph method, YouTube, Jan. 4, 2022, https://www.youtube.com/watch?v=XastVfF_wls.

Seer, Inc. Proteograph™ Analysis Suite User Guide. URL: https://seer.bio/wp-content/uploads/2021/12/PAS_User_Guide_CF-1003-B.pdf Published Oct. 2021 (retrieved online Feb. 2022) 103 Pages.

Seer, Inc. Proteograph™ Assay Quick Reference Work Deck Layout. CF-1020 Rev A URL: https://seer.bio/wp-content/uploads/2021/12/Seer_ProteographAssay_Quick_Reference_RevA.pdf (retrieved online Feb. 2022) 2 Pages.

Seer, Inc. Proteograph™ Product Suite: An automated workflow that scales with your studies, YouTube, Jan. 4, 2022 URL: https://www.youtube.com/watch?v=hb16g8JfWnU.

Seer, Inc. Proteograph™ Quickstart Series: How to Load Plastics and Reagents onto the SP100, YouTube, Jan. 7, 2022 URL: https://www.youtube.com/watch?v=ay4LDy5J0uw.

Seer, Inc. Proteograph™ Quickstart Series: How to Prepare and Load the Nanoparticles, Samples & Controls, YouTube, Jan. 7, 2022 URL: https://www.youtube.com/watch?v=oP40VjQ8yoE.

Seer, Inc. Proteograph™ Quickstart Series: Initialize and Prepare the SP100, YouTube, Jan. 7, 2022 URL: https://www.youtube.com/watch?v=qmvy7QKbjRI.

Seer, Inc. Proteograph™ Quickstart Series: SP100 Clean-up & Sample Plate Layout, YouTube, Jan. 7, 2022 URL: https://www.youtube.com/watch?v=HSnXFkxq-Fw.

Seer, Inc. Proteograph™ Quickstart Series: Starting the Proteograph Assay Method, YouTube, Jan. 7, 2022 URL: https://www.youtube.com/watch?v=aoJoWMDSWjg.

Seer, Inc. Proteograph™ Quickstart Series: Step-by-Step on Preparing Materials, YouTube, Jan. 7, 2022 URL:https://www.youtube.com/watch?v=UVIt4AcjsSg.

Seer, Inc. Proteograph™ Quickstart Series: Step-by-Step on SP100 Automation Instrument, YouTube, Jan. 7, 2022 URL: https://www.youtube.com/watch?v=zBrCzhmLiJU.

Seer, Inc.: Release Notes, Proteograph™ Analysis Suite v2.0, pp. 1-2 (published Aug. 3, 2022).

Seer, Inc.: Safety Data Sheet. Nov. 2021. Available at: https://seer.bio/wp-content/uploads/2021/12/Proteograph-Assay-SDS.pdf.

Seer, Inc. Seer's Nanoparticle Approach: A Novel Approach to Unbiased, Deep, Rapid and Scalable Proteomics, YouTube, Mar. 20, 2021, https://www.youtube.com/watch?v=ArvpW3IPfA0.

(56) References Cited

OTHER PUBLICATIONS

Seer, Inc. SP100 Automation Instrument Site Preparation Guide (CF-1017 B). URL: https://seer.bio/wp-content/uploads/2022/02/SP100_Site_Prep_Guide_CF_1017_B-1.pdf Published Jun. 2021 (retrieved online Feb. 2022) 15 Pages.

Seer, Inc. SP100 Automation Instrument Site Preparation Guide (Int. CF-1014 A). URL: https://seer.bio/wp-content/uploads/2022/02/SP100_Site_Prep_Guide_International_CF_1015_A.pdf Published Dec. 2021 (retrieved online Feb. 2022) 15 Pages.

Seer, Inc. Starting the Proteograph Assay Method, YouTube, May 25, 2021 URL: https://www.youtube.com/watch?v=R94DH7OAOKA.

Seer, Inc. Support Frequently Asked Questions. URL: https://seer.bio/support/faq/ (retrieved online Feb. 2022) 6 Pages.

Seer, Inc. The Challenge in Proteomics Today: Why We Need Unbiased, Deep, Rapid and Scalable Proteomics, YouTube, Mar. 20, 2021, https://www.youtube.com/watch?v=Pq8qbict1dl.

Seer Inc., The proteograph product suite: See the proteome in a way that has never been possible before. Seer.bio. Mar. 2021. Available at: https://seer.bio/resources/document-library/.

Seer, Inc. Unbiased Biomarker Discovery Research with the Porteograph Product Suite, YouTube, Jul. 23, 2021, https://www.youtube.com/watch?v=AodyEDMIdmk.

SEER: Large-scale plasma proteomics with the ProteographTM XT workflow. Seer, Inc., Technical Note (CF-1059 REV A), pp. 1-8 (2023).

Seer Nanoparticle Technology—Brief 1 Minute Overview, YouTube, Mar. 20, 2021, https://www.youtube.com/watch?v=qYFmTuz84IA.

Seer: Proteograph Product Suite: An Automated Workflow that scales with your studies. Seer, Inc., online video presentation available at https://seer.bio/resources/video-gallery/?tx_category=publications&wchannelid=dfl89n6go7&wmediaid=7ac7qj2qpi (2022).

Semb, K. A., Aamdal, S. & Oian, P. Capillary protein leak syndrome appears to explain fluid retention in cancer patients who receive docetaxel treatment. Journal of Clinical Oncology 16, 3426-3432 (1998).

Senyo, S.E et al. Mammalian heart renewal by pre-existing cardiomyocytes. Nature 493, 433-436 (2013).

Shakeri, R. et al. Multiplex H. pylori serology and risk of gastric cardia and noncardia adenocarcinomas. Cancer research 75, 4876-4883 (2015).

Sharma, S., Ray, S., Moiyadi, A., Sridhar, E. & Srivastava, S. Quantitative proteomic analysis of meningiomas for the identification of surrogate protein markers. Scientific reports 4, 7140 (2014).

Shi, J., Kantoff, P.W., Wooster, R. & Farokhzad, O.C. Cancer nanomedicine: progress, challenges and opportunities. Nat Rev Cancer 17, 20-37 (2017).

Shi, T. et al. IgY14 and SuperMix immunoaffinity separations coupled with liquid chromatography-mass spectrometry for human plasma proteomics biomarker discovery. Methods 56, 246-253 (2012).

Shoji, M. et al. Activation of coagulation and angiogenesis in cancer: immunohistochemical localization in situ of clotting proteins and vascular endothelial growth factor in human cancer. The American journal of pathology 152, 399 (1998).

Siddiqui et al., Application of the Proteograph™ Product Suite to the Identification of Differential Protein Isoform Plasma Abundance in Early Lung Cancer vs. Healthy Controls. Seer, Inc. Mar. 2021. 1 Page.

Siddiqui et al.: Deep and Unbiased Plasma Protein Profiling of Alzheimer's and Mild Cognitive Impairment Subjects with a Novel Multi-nanoparticle Approach. Seer, Inc. (Mar. 2022).

Siddiqui et al.: Deep plasma protein profiling in Alzheimer's subjects with a novel unbiased and scalable proteogenomics approach. Seer Inc., Redwood City, CA USA, poster 1 page (2022).

Siddiqui et al.: Large-scale, deep plasma proteomics: An 1800 sample study of Alzheimer's disease. 1. Seer, Inc., Redwood City, CA, USA; and 2. Massachusetts General Hospital, Boston, MA, USA, poster 1 page (2023).

Siddiqui, et al., Plasma protein-protein interactome (PPI) maps derived from the protein corona captured at the nano-bio interface of nanoparticles reveal differential networks for non-small cell lung cancer (NSCLC) and control subjects. Seer, Inc. Apr. 2020. 1 Page.

Siddiqui, et al., Plasma Proteomics at Scale Enabling Lung Cancer, Alzheimer's Disease and Proteogenomics Studies with the Proteograph™ Product Suite. Seer, Inc. Mar. 2021. 1 Page.

Siegel et al. Cancer statistics, 2015. CA Cancer J Clin 65:5-29 (2015).

Siegel et al. Cancer statistics, 2016. CA Cancer J Clin 66:7-30 (2016).

Sielaff, Malte et al. Evaluation of Fasp, SP3, and iST Protocols for Proteomic Sample Preparation in the Low Microgram Range. Journal of proteome research vol. 16,11 (2017): 4060-4072. doi:10.1021/acs.jproteome.7b00433.

Sigdel et al., Optimization for peptide sample preparation for urine peptidomics. Clin Proteomics, Feb. 25, 2014;11(1):7 (8 pages).

Simberg, et al. Differential proteomics analysis of the surface heterogeneity of dextran iron oxide nanoparticles and the implications for their in vivo clearance. Biomaterials. Aug. 2009; 30(23-24): 3926-3933.

Singh, et al. Drug delivery: advancements and challenges. Nanostructures for Drug Delivery. Elsevier, 2017. 865-886.

Smith, R. A. et al. American Cancer Society guidelines for the early detection of cancer. CA: a cancer journal for clinicians 52, 8-22 (2002).

Smith, R., Mathis, A.D., Ventura, D. & Prince, J.T. Proteomics, lipidomics, metabolomics: a mass spectrometry tutorial from a computer scientist's point of view. BMC Bioinformatics 15, S9 (2014).

Snider, et al., Fundamentals of protein interaction network mapping. Mol Syst Biol. Dec. 2015; 11(848):1-20.

Song et al. Ascertaining effects of nanoscale polymeric interfaces on competitive protein adsorption at the individual protein level. Nanoscale, 2016; 8:3496-3509.

Sparano et al.: Prospective Validation of a 21-Gene Expression Assay in Breast Cancer. N Engl J Med. 373(21):2005-2014 doi: 10.1056/NEJMoa1510764 (2015).

Star, A., Joshi, V., Skarupo, S., Thomas, D., Gabriel, J.-C. P. Gas Sensor Array Based on Metal-Decorated Carbon Nanotubes. The Journal of Physical Chemistry B 2006, 110, 21014-21020.

Staton, C.A., Brown, N.J. & Lewis, C.E. The role of fibrinogen and related fragments in tumour angiogenesis and metastasis. Expert opinion on biological therapy 3, 1105-1120 (2003).

Strehlitz, et al., Protein detection with aptamer biosensors, sensors, Jul. 23, 2008. vol. 8, No. 7 p. 4296-4307.

Strojan, K. et al. Dispersion of nanoparticles in different media importantly determines the composition of their protein corona. PloS one 12, e0169552 (2017).

Stukalov et al.: Dissecting the dynamics of protein corona formation on nanoparticles allows reconstructing deep plasma protein concentrations and discovering novel proteoforms. Seer, Inc., Redwood City, CA, poster 1 page (2023).

Stukalov et al.: Experimental & Computational Approach to Profile Nanoparticle-Protein Interactions for Deep Plasma Proteomics. Seer Inc., Redwood City, CA USA, poster 1 page (2022).

Suhre et al.: Nanoparticle Enrichment Mass-Spectrometry Proteomics Identifies Protein Altering Variants for Precise pQTL Mapping. Cold Spring Harbor Laboratory, bioRxiv pre-print, pp. 1-28. doi:10.1101/2023.04.20.537640 (2023).

Sun, C., Rosendahl, A.H., Ansari, D. & Andersson, R. Proteome-based biomarkers in pancreatic cancer. World J Gastroenterol 17, 4845-4852 (2011).

Sun, Z.-L. et al. Serum proteomic-based analysis of pancreatic carcinoma for the identification of potential cancer biomarkers. Biochimica et Biophysica Acta (BBA)-Proteins and Proteomics 1774, 764-771 (2007).

Sung, H.J., et al. Identification and validation of SAA as a potential lung cancer biomarker and its involvement in metastatic pathogenesis of lung cancer. J Proteome Res 10, 1383-1395 (2011).

Suslick, B.A., Feng, L. & Suslick, K.S. Discrimination of complex mixtures by a colorimetric sensor array: coffee aromas. Analytical chemistry 82, 2067-2073 (2010).

Swaminathan, J., et al. Highly parallel single-molecule identification of proteins in zeptomole-scale mixtures. Nat Biotechnol (2018).

(56) References Cited

OTHER PUBLICATIONS

Szala, A. et al. Ficolin-2 and ficolin-3 in women with malignant and benign ovarian tumours. Cancer Immunology, Immunotherapy 62, 1411-1419 (2013).
Tan et al.: Multi-dimensional on-particle detection technology for multi-category disease classification. Chem Commun (Camb). 52(17):3490-3493 doi:10.1039/c5cc09419d (2016).
Tan, H. T., Low, J., Lim, S. G. & Chung, M. Serum autoantibodies as biomarkers for early cancer detection. FEBS journal 276, 6880-6904 (2009).
Teng, Z.G., et al. Superparamagnetic high-magnetization composite spheres with highly aminated ordered mesoporous silica shell for biomedical applications. J Mater Chem B 1, 4684-4691 (2013).
Tenzer, S. et al. Nanoparticle size is a critical physicochemical determinant of the human blood plasma corona: a comprehensive quantitative proteomic analysis. ACS Nano 5, 7155-7167 (2011).
Tenzer, S., et al. Rapid formation of plasma protein corona critically affects nanoparticle pathophysiology. Nat Nanotechnol 8, 772-781 (2013).
Terracciano et al.: Peptidome profiling of induced sputum by mesoporous silica beads and MALDI-TOF MS for non-invasive biomarker discovery of chronic inflammatory lung diseases. Proteomics 11(16):3402-3414 doi:10.1002/pmic.201000828 (2011).
Thermo Fisher Scientific "Orbitrap Velos Pro Hardware Manual, Revision A-1288290", Jun. 2011, 202 pages.
Tirtaatmadja, N. et al. Nanoparticles-induced inflammatory cytokines in human plasma concentration manner: an ignored factor at the nanobio-interface. Journal of the Iranian Chemical Society 12, 317-323 (2015).
Tiss et al.: Serum peptide profiling using MALDI mass spectrometry: avoiding the pitfalls of coated magnetic beads using well-established ZipTip technology. Proteomics 7 Suppl 1:77-89 doi:10.1002/pmic.200700746 (2007).
Tousoulis, D., Charakida, M., Stefanadis, C. Endothelial Function and Inflammation in Coronary Artery Disease. Heart 2006, 92, 441-444.
Trendspotting: Top Diagnostics Issues in 2023. Diagnostics World, pp. 1-4 [retrieved online Jan. 18, 2023 from https://www.diagnosticsworldnews.com/news/2023/01/05/trendspotting-top-diagnostics-issues-in-2023] 2023.
Trinkle-Mulcahy, et al., Identifying specific protein interaction partners using quantitative mass spectrometry and bead proteomes. J Cell Biol. Oct. 20, 2008; 183(2): 223-239.
Troiano et al, A Quality by Design Approach to Developing and Manufacturing Polymeric Nanoparticle Drug Products, The AAPS Journal, 2016, 18, 6, 1354-1365.
Tuli et al.: LC-MS Based Detection of Differential Protein Expression. J Proteomics Bioinform. 2:416-438 doi:10.4172/jpb.1000102 (2009).
Turner, A. P., Chen, B., Piletsky, S. A. In Vitro Diagnostics in Diabetes: Meeting the Challenge. Clinical chemistry 1999, 45, 1596-1601.
Ueda, K., et al. A comprehensive peptidome profiling technology for the identification of early detection biomarkers for lung adenocarcinoma. PLoS One 6, e18567 (2011).
U.S. Appl. No. 17/215,923 Non-Final Office Action dated Feb. 10, 2022.
U.S. Appl. No. 17/215,923 Notice of Allowance dated May 26, 2022.
U.S. Appl. No. 17/215,952 Non-Final Office Action dated May 12, 2022.
U.S. Appl. No. 17/215,978 Final Office Action dated Feb. 22, 2022.
U.S. Appl. No. 17/215,978 Final Office Action dated Jan. 26, 2023.
U.S. Appl. No. 17/216,520 Final Office Action dated Nov. 15, 2021.
U.S. Appl. No. 17/216,520 Notice of Allowance dated Apr. 21, 2022.
U.S. Appl. No. 15/880,627 Notice of Allowance dated Sep. 18, 2020.
U.S. Appl. No. 15/880,627 Office Action dated Dec. 18, 2018.
U.S. Appl. No. 15/880,627 Office Action dated Jan. 30, 2020.
U.S. Appl. No. 15/880,627 Office Action dated Jun. 18, 2019.
U.S. Appl. No. 15/880,627 Office Action dated Jun. 20, 2018.
U.S. Appl. No. 17/099,331 Office Action dated Apr. 20, 2021.
U.S. Appl. No. 17/099,331Office Action dated Aug. 17, 2021.
U.S. Appl. No. 17/215,923 Office Action dated Sep. 22, 2021.
U.S. Appl. No. 17/215,952 Office Action dated Jun. 10, 2021.
U.S. Appl. No. 17/215,952 Office Action dated Sep. 17, 2021.
U.S. Appl. No. 17/215,966 Office Action dated Jun. 3, 2021.
U.S. Appl. No. 17/215,966 Office Action Sep. 23, 2021.
U.S. Appl. No. 17/215,978 Office Action dated Jun. 10, 2021.
U.S. Appl. No. 17/215,978 Office Action dated Oct. 8, 2021.
U.S. Appl. No. 17/216,520 Office Action dated Aug. 6, 2021.
U.S. Appl. No. 17/216,523 Office Action dated Aug. 17, 2021.
U.S. Appl. No. 18/460,474 Office Action dated Nov. 7, 2023.
User Guide: Proteograph Product Suite. Seer, Inc. 2021. Available at: https://seer.bio/wp-content/uploads/2021/12/Proteograph_User_Guide_CF-1016-B.pdf.
Vadapalli, et al., Proteograph™ Analysis Suite: A cloud-scalable software suite for proteogenomics data analysis and visualization. Seer, Inc. Nov. 2021. 1 Page.
Valko et al.: Learning predictive models for combinations of heterogeneous proteomic data sources. AMIA Summit on Translational Bioinformatics, 5 pages. HAL0064339 URL: https://hal.inria.fr/hal-00643349 (2008).
Van Holten et al.: Circulating biomarkers for predicting cardiovascular disease risk; a systematic review and comprehensive overview of meta-analyses. PLoS One 8(4):e62080:1-8 doi:10.1371/journal.pone.0062080 (2013).
Van Hong Nguyen, et al. Protein corona: a new approach for nanomedicine design. International journal of nanomedicine 12 (Apr. 18, 2017): 3137-3151.
Vasti, et al., Relevance of protein-protein interactions on the biological identity of nanoparticles. Colloids and surfaces B: Biointerfaces, Jun. 1, 2018; 166: 330-338.
Velstra et al.: Improved classification of breast cancer peptide and protein profiles by combining two serum workup procedures. J Cancer Res Clin Oncol. 138(12):1983-1992 doi:10.1007/s00432-012-1273-4 (2012).
Venkataraman et al.: Assessment of pQTL method performance reveals optimal proteogenomic approach to assess the impact of genetic variation on plasma protein levels. Seer, Inc., Redwood City, CA; and Massachusetts General Hospital, Boston, MA. poster 1 page (2023).
Vilanova, O., et al. Understanding the Kinetics of Protein-Nanoparticle Corona Formation. ACS Nano 10, 10842-10850 (2016).
Villanueva et al.: Automated serum peptide profiling. Nat Protoc. 1(2):880-891 doi:10.1038/nprot.2006.128 (2006).
Villanueva et al.: Differential exoprotease activities confer tumor-specific serum peptidome patterns. J Clin Invest. 116(1):271-284 doi:10.1172/JCI26022 (2006).
Villanueva, Josep et al., "Serum peptide profiling by magnetic particle-assisted, automated sample processing and MALDI-TOF mass spectrometry". Anal. Chern. (Mar. 15, 2004), 76(6): 1560-1570.
Vogt et al.: Proteomics Analysis Reveals Distinct Corona Composition on Magnetic Nanoparticles with Different Surface Coatings: Implications for Interactions with Primary Human Macrophages. PLoS One 10(10):e0129008:1-20 doi:10.1371/journal.pone.0129008 (2015).
Vollmers, H. P. & Brandlein, S. Natural human immunoglobulins in cancer immunotherapy. (2009).
Vroman, L., Adams, A.L., Fischer, G.C. & Munoz, P.C. Interaction of high molecular weight kininogen, factor XII, and fibrinogen in plasma at interfaces. Blood 55, 156-159 (1980).
Walkey, Carl D, and Warren C W Chan. Understanding and controlling the interaction of nanomaterials with proteins in a physiological environment. Chemical Society reviews vol. 41,7 (2012): 2780-99. doi:10.1039/c1cs15233e.
Walkey, et al. Protein corona fingerprinting predicts the cellular interaction of gold and silver nanoparticles. ACS Nano 8,3 (2014): 2439-2455.

(56) References Cited

OTHER PUBLICATIONS

Wang, et al., A magnetic nanoparticles relaxation sensor for protein-protein interaction detection at ultra-low magnetic field. Biosens Bioelectron. Jun. 15, 2016. 80:661-665. doi: 10.1016/j.bios.2016.02.037.

Wang et al.: Building Spectral Libraries for Large-Scale Quantitative Proteomic Studies in Human Plasma. 1. Seer, Inc., Redwood City, CA; and 2. Weill Cornell Medicine-Qatar, Doha, State of Qatar, poster 1 page (2023).

Wang, H., Li, L., Ding, L., Zhang, Z. & Pu, C. Association of genetic polymorphisms in the paraoxonase 1 gene with the risk and prognosis of non-small cell lung cancer in Chinese Han population. J Investig Med 60, 592-597 (2012).

Wang, J. et al. Cancer-derived immunoglobulin G promotes tumor cell growth and proliferation through inducing production of reactive oxygen species. Cell death & disease 4, e945 (2013).

Wang, Y. et al. Proteomic differential display identifies upregulated vinculin as a possible biomarker of pancreatic cancer. Oncology reports 28, 1845-1850 (2012).

Ward, D. et al. Identification of serum biomarkers for colon cancer by proteomic analysis. British journal of cancer 94, 1898 (2006).

Welter, D. et al. The NHGRI GWAS Catalog, a curated resource of SNP-trait associations. Nucleic acids research 42, D1001-D1006 (2013).

Westmeier et al.: The bio-corona and its impact on nanomaterial toxicity. European Journal of Nanomedicine 7(3):153-168 https://doi.org/10.1515/ejnm-2015-0018 (2015).

Whelan, S.A. et al. Mass spectrometry (LC-MS/MS) identified proteomic biosignatures of breast cancer in proximal fluid. Journal of proteome research 11, 5034-5045 (2012).

Wilcox et al.: A large scale multi-cancer, multi-omics biomarker study of 1,800 subjects incorporating deep unbiased plasma proteomics. PrognomiQ Inc. San Mateo, CA, poster 1 page (2022).

Wilcox et al.: Deep, unbiased multi-omics approach for the identification of pancreatic cancer biomarkers from blood. PrognomiQ, San Mateo, California, USA, poster 1 page (2022).

Wilcox et al.: Incorporation Of Glycoproteome Detection Into Large Scale Unbiased Proteomics Studies Utilizing Nanoparticles. PrognomiQ Inc. (Mar. 2022).

Wildes, D. & Wells, J.A. Sampling the N-terminal proteome of human blood. Proceedings of the National Academy of Sciences 107, 4561-4566 (2010).

Williams, et al., Proteominer facilitates high-throughput proteomic analysis of low abundance proteins in the cartilage secretome (LB39). The Faseb journal, Apr. 2014; 28(S1), Abstract. https://doi.org/10.1096/fasebj.28.1_supplement.lb39 (2014).

Wilson, et al., The utility of nanoparticle protein coronas for studying the plasma glycoproteome. Seer, Inc. Nov. 2021. 1 Page.

Wright, C.F. et al. Genetic diagnosis of developmental disorders in the DOD study: a scalable analysis of genome-wide research data. The Lancet 385, 1305-1314 (2015).

Wulfkuhle, J. D., Liotta, L. A. & Petricoin, E. F. Proteomic applications for the early detection of cancer. Nature reviews cancer 3, 267-275 (2003).

Xia, X.-R., Monteiro-Riviere, N.A. & Riviere, J.E. An index for characterization of nanomaterials in biological systems. Nature nanotechnology 5, 671-675 (2010).

Xu, et al., Streptavidin Bead Pulldown Assay to Determine Protein Homooligomerization. Bio Protoc. Nov. 20, 2017; 7(22): e2901, pp. 1-11.

Xu, M., et al. How Entanglement of Different Physicochemical Properties Complicates the Prediction of in Vitro and in Vivo Interactions of Gold Nanoparticles. ACS Nano 12, 10104-10113 (2018).

Xu, S., et al. Toward designer magnetite/polystyrene colloidal composite microspheres with controllable nanostructures and desirable surface functionalities. Langmuir 28, 3271-3278 (2012).

Xue et al.: Quantifying thiol-gold interactions towards the efficient strength control. Nat Commun 5:4348:1-8 doi:10.1038/ncomms5348 (2014).

Yan, L. et al. Confounding effect of obstructive jaundice in the interpretation of proteomic plasma profiling data for pancreatic cancer. Journal of proteome research 8, 142-148 (2008).

Yang et al.: Proteomic Profiling of Invasive Ductal Carcinoma (IDC) using Magnetic Beads-based Serum Fractionation and MALDI-TOF MS. J Clin Lab Anal. 29(4):321-327 doi:10.1002/jcla.21773 (2015).

Yang et al.: Serum peptidome profiling in patients with gastric cancer. Clin Exp Med. 12(2):79-87 doi:10.1007/s10238-011-0149-2 (2012).

Yates, J.R., Ruse, C.I. & Nakorchevsky, A. Proteomics by mass spectrometry: approaches, advances, and applications. Annual review of biomedical engineering 11, 49-79 (2009).

Yigitbasi, Turkan: "Multiplex Immunoassay and Bead Based Multiplex", Apr. 27, 2012, Trends in Immunolabelled and Related Techniques. 22:351-360, XP0556537 41, Retrieved from the Internet: URL: https://www.researchgate.net/profile/Ravichandran_Panchanathan/post/What_are_differences_of_different_types_of_multiplex_cytokine_ELISA/attachment/59d61ddf79197b807797b6fb/AS:273775503839238@144228457 4432/download/36219.pdf[retrieved on Dec. 17, 2019] (2012).

Yoneyama, T. et al. Identification of IGFBP2 and IGFBP3 As Compensatory Biomarkers for CA 19-9 in Early-Stage Pancreatic Cancer Using a Combination of Antibody-Based and LC-MS/MS-Based Proteomics. PloS one 11, e0161009 (2016).

Yusuf et al., Global Burden of Cardiovascular Diseases. Circulation, Dec. 4, 2001; 104(23):2855-64.

Zaccaria, et al. Accessing to the minor proteome of red blood cells through the influence of the nanoparticle surface properties on the corona composition. International journal of nanomedicine 10 (Mar. 9, 2015): 1869-1883.

Zakynthinos, E., Pappa, N. Inflammatory Biomarkers in Coronary Artery Disease. Journal of cardiology 2009, 53, 317-333.

Zamanighomi et al.: Deep and Untargeted Plasma Protein Profiling of Alzheimer's Subjects with a Novel Multi-nanoparticle Approach. Seer, Inc., Redwood City, CA, online video available at URL: https://seer.bio/resources/video-gallery/?tx_category=publications&wchannelid=dfl89n6go7&wmediaid=64xoqf4r2m (2022).

Zamanighomi et al.: Deep Plasma Proteomics at Scale Enabling Precision Analyses in a Lung Cancer (NSCLC) Study. Seer, Inc., Redwood City, CA, poster 1 page (2022).

Zanganeh, et al. Protein corona: opportunities and challenges. The international journal of biochemistry & cell biology 75 (Jun. 2016): 143-147.

Zhang, C. & Suslick, K. S. Colorimetric sensor array for soft drink analysis. Journal of agricultural and food chemistry 55, 237-242 (2007).

Zhang et al.: Evaluation of a novel, integrated approach using functionalized magnetic beads, bench-top MALDI-TOF-MS with prestructured sample supports, and pattern recognition software for profiling potential biomarkers in human plasma. J Biomol Tech. 15(3):167-175 (2004).

Zhang et al.: Integrated Proteogenomic Characterization of Human High-Grade Serous Ovarian Cancer. Cell 166(3):755-765 doi:10.1016/j.cell.2016.05.069 (2016).

Zhang et al.: Proteomic profiling of protein corona formed on the surface of nanomaterial. Science China Chemistry 58(5):780-792 doi:10.1007/s11426-015-5395-9 (2015).

Zhang, et al. Quantitative proteomics analysis of adsorbed plasma proteins classifies nanoparticles with different surface properties and size. Proteomics. Dec. 2011; 11 (23): pp. 4569-4577.

Zhang, X. et al., Preparation and characterization of superparamagnetic Fe3O4/CNTs nanocomposites Dual-drug carrier, Journal of Wuhan University of Technology-Mater. Sci. Ed., 32(1), 42-46. (Year: 2017).

Zhang, Y., Askim, J.R., Zhong, W., Orlean, P. & Suslick, K.S. Identification of pathogenic fungi with an optoelectronic nose. Analyst 139, 1922-1928 (2014).

Zhao, et al., Evaluation of Cell-Free DNA blood plasma for unbiased, deep, and rapid proteomics analysis enabling large-scale studies. Seer, Inc. Mar. 2021. 1 Page.

(56) References Cited

OTHER PUBLICATIONS

Zheng, et al., Gold Nanoparticle-enabled blood test for early stage cancer detection and risk assessment. ACS Appl. Mater. Interfaces 2015; 7: 6819-6827.
Zheng, et al. Multiplexed electrical detection of cancer markers with nanowire sensor arrays. Nat Biotechnol. Oct. 2005;23(10):1294-301. Epub Sep. 18, 2005.
Zheng, T. et al. A Rapid Blood Test To Determine the Active Status and Duration of Acute Viral Infection. ACS Infectious Diseases (2017).
Zhi et al. Multianalyte Immunoassay with Self-Assembled Addressable Microparticle Array on a Chip. Analytical Biochemistry 318:236-243 (2003).
Zhou et al.: Multi-omics data integration reveals clinically relevant biomolecules associated with type 2 diabetes. 1. Seer, Inc., Redwood City, CA; and 2. Weill Cornell Medicine-Qatar, Doha, State of Qatar, poster 1 page (2022).
Zou et al.: Synthesis and evaluation of superparamagnetic silica particles for extraction of glycopeptides in the microtiter plate format. Anal Chem. 80(4):1228-1234 doi:10.1021/ac701950h (2008).
Zupancic, K. et al. Identification of plasma biomarker candidates in glioblastoma using an antibody-array-based proteomic approach. Radiology and oncology 48, 257-266 (2014).
Zwicker, J. I., Furie, B. C. & Furie, B. Cancer-associated thrombosis. Critical reviews in oncology/hematology 62, 126-136 (2007).
Chen, Shao-Yung (Eric), et al., Comprehensive and automated profiling of host cell proteins using the Proteograph™ XT workflow. 8 pages. (2023). Accessed online Jan. 8, 2024. URL: https://media.seer.bio/uploads/2023/10/comprehensiveAutomatedProfilingHCP-proteographXT.pdf.
Chen, Shao-Yung (Eric), et al., Unbiased and deep proteomic analysis of secretome samples using the Proteograph™ XT workflow. 7 pages. (2023). Accessed online Jan. 8, 2024. URL: https://media.seer.bio/uploads/2023/12/Secretome-ProteographXT_AppNote_Seer.pdf.
Huang, Ting, et al., Deep, unbiased and quantitative mass spectrometry-based plasma proteome analyses of adaptive response to COVID-19 vaccine. 1 page. (2023) Accessed online Jan. 8, 2024. URL: https://media.seer.bio/uploads/2023/06/2023_Poster_ASMS_THuang.pdf.
Huang, Ting, et al., Protein Coronas on Functionalized Nanoparticles Enable Quantitative and Precise Large-Scale Deep Plasma Proteomics. 1 page. (2023). Accessed online Jan. 8, 2024. URL: https://media.seer.bio/uploads/2023/09/2023_Poster_Cantrell.pdf.
Jiang, Wei, et al., Human biofluids analysis using a scalable, deep, unbiased, automated, nanoparticle-based proteomics platform. 1 page. (2023). Accessed online Jan. 8, 2024. URL: https://media.seer.bio/uploads/2023/03/2023_Poster_USHUPO_Gajadhar.pdf.
Motamedchaboki, Khatereh, et al., Plasma Proteomic Landscape of Alzheimer's Disease: An 1800-Sample Cohort Study. 1 page. (2023). Accessed online Jan. 8, 2024. URL: https://media.seer.bio/uploads/2023/09/2023_Poster_Siddiqui.pdf.
U.S. Appl. No. 18/088,946 Notice of Allowance dated Jan. 25, 2024.
U.S. Appl. No. 18/460,221 Office Action dated Dec. 21, 2023.
U.S. Appl. No. 18/460,254 Office Action dated Dec. 22, 2023.
Bertoli, Filippo, et al., Magnetic Nanoparticles to Recover Cellular Organelles and Study the Time Resolved Nanoparticle-cell Interactome Throughout Uptake. Small 10(16):3307-3315 (2014).
Conzone, et al. Glass slides to DNA microarrays. Materials Today. 2004, vol. 7, No. 3, p. 20-26, doi: 10.1016/S1369-7021(04)00122-1.
Giri, K. Engineered gold nanoparticles for identification of novel ovarian biomarkers. Mayo Clinic College of Medicine Thesis. Jan. 2016. 142 pages.
Hamad-Schifferli, K. Exploiting the novel properties of protein coronas: emerging applications in nanomedicine. Nanomedicine (Lond). May 2015;10(10):1663-74. doi: 10.2217/nnm.15.6.
Kaufmann, Anton, et al., Comparison of Linear Intrascan and Interscan Dynamic Ranges of Orbitrap and Ion-mobility Time-of-flight Mass Spectrometers. Rapid Communications in Mass Spectrometry 31(22):1915-1926 (2017).
Khoo, et al. 3D printing of smart materials: A review on recent progresses in 4D printing. Virtual and Physical Prototyping. 2015, vol. 10, No. 3, p. 103-122, doi: 10.1080/17452759.2015.1097054.
Lee, G. Cancerous Immunoglobulins in Cancer Immunology. J Clin Cell Immunol 2014, vol. 5, Issue 6. 8 pages. DOI: 10.4172/2155-9899.1000279.
Li, et al. An array-based approach to determine different subtype and differentiation of non-small cell lung cancer. Theranostics. Jan. 1, 2015;5(1):62-70. doi: 10.7150/thno.10145. eCollection 2015.
Li, et al. Conjugation of Graphene Oxide with DNA-Modified Gold Nanoparticles to Develop a Novel Colorimetric Sensing Platform. Part. Syst. Charact. 2014, vol. 31, No. 2, p. 201-208, DOI: 10.1002/ppsc.201300200.
Maiolo, et al. Nanomedicine delivery: does protein corona route to the target or off road? Nanomedicine (Lond). 2015;10(21):3231-47. doi: 10.2217/nnm.15.163. Epub Oct. 16, 2015.
Milani, et al. Reversible versus irreversible binding of transferrin to polystyrene nanoparticles: soft and hard corona. ACS Nano. Mar. 27, 2012;6(3):2532-2541. doi: 10.1021/nn204951s. Epub Feb. 28, 2012. Supplementary Information. pp. S1-S7.
Milani, Silvia et al. Reversible versus irreversible binding of transferrin to polystyrene nanoparticles: soft and hard corona. ACS Nano vol. 6,3: pp. 2532-2541 (2012).
U.S. Appl. No. 17/901,294 Office Action dated Mar. 28, 2024.
U.S. Appl. No. 18/088,946 Notice of Allowance dated May 3, 2024.
U.S. Appl. No. 18/460,221 Notice of Allowance dated Mar. 20, 2024.
U.S. Appl. No. 18/460,254 Office Action dated Mar. 21, 2024.
DE202017007363U1 Cancellation Proceeding filed Jan. 13, 2025 (Machine Translation).
DE202017007363U1 Feature Structure of claims 1 and 7 issued Feb. 16, 2021 (Machine Translation).
DE602017053049.2 DPMAregister. Register extract for File No. 602017053049.2. Status on May 21, 2024. Last update in DPMAregister on May 2, 2024. (English Translation).
DE602017053049.2 Feature analysis of claim 1 of EP3554681B1 issued Feb. 2, 2022. (English Translation).
DE602017053049.2 USPTO File Wrapper for U.S. Appl. No. 62/435,409, filed Dec. 16, 2016. (priority document).
EP 3554681 UPC Opt Out. Extract from the register of the Unified Patent Court. Date of lodging: May 26, 2023. Document signed Nov. 18, 2024. 1 page.
EP17881767.2 Submission of the applicant dated Jun. 11, 2021 in the examination procedure. (EP3544681).
German Federal Patent Court. Letter of Service. The complaint for a declaration of invalidity of the patent EP3554681B1 (DE602017053049.2) dated Jan. 8, 2025. (Machine Translation).
German Federal Patent Court. Nullity complaint concerning the German part DE602017053049.2 of the European patent EP3554681B1 dated Nov. 18, 2024. (Machine Translation).

\* cited by examiner

FIG. 1

| Particle type | | Surface functionalization |
|---|---|---|
| Iron oxide (Superparamagnetic) | ○ | *anionic, cationic, neutral polymeric, lipidic, glass organic, inorganic high or low ligand density ...* |
| Silica | ○ | |
| Polymeric | ◍ | |
| Gold | ◍ | |
| Liposomes | ◍ | |

| Attribute | Methods | Description |
|---|---|---|
| Size/Geometry | DLS | Size distributions |
| | TEM | Size confirmation and indication of shape |
| | Other (A4F, LD, NTA, etc.) | Orthogonal methods for size distribution |
| Charge | Zeta potential | Surface charge in environments of interest |
| Surface Functionality | XPS | Surface chemistry (outer 10 nm) |
| | SIMS | Surface expression (outer 1 nm) |
| | Other (FTIR, Raman, etc.) | Orthogonal methods for composition |
| Magnetism | SQUID | Response to magnetic fields |
| Other | A variety of composition tests, microbial tests, and other properties | Full specification sheet to be developed prior to reagent kit distribution |

FIG. 6

Nanoparticle Panel Results- 1 hr Run

| Particle | Total MS1 Features | Filtered Features[1] | Significant Hits |
|---|---|---|---|
| SP 339 | 19042 | 2162 | 69 |
| HX 74 | 19255 | 2222 | 26 |
| SP 356 | 19754 | 1634 | 10 |
| SP 333 | 24703 | 2184 | 7 |
| HX 20 | 17789 | 1871 | 4 |
| SP 374 | 21504 | 2044 | 4 |
| HX 42 | 23278 | 2364 | 0 |
| Panel Total | 145325 | 14481 | 120 |

[1] Filtered features are detected in at 50% of the samples from at least one of the study groups (diseased and/or control)

FIG. 16A

Classification Scores from 1000-fold Cross-Validation

| Array Size | Accuracy | Glioblastoma | | Lung | | Meningioma | | Myeloma | | Pancreatic | |
|---|---|---|---|---|---|---|---|---|---|---|---|
| | | Sens. | Spec. | Sens. | Spec. | Sens. | Spec. | Sens. | Spec. | Sens. | Spec. |
| One | 84.4 | 77.4 | 95.2 | 88.9 | 98.1 | 77.3 | 95.1 | 95.7 | 96.1 | 88.4 | 97.6 |
| Two | 91.0 | 79.2 | 96.6 | 94.1 | 99.7 | 87.4 | 95.0 | 100.0 | 98.8 | 91.3 | 99.9 |
| Three | 95.0 | 88.1 | 98.5 | 94.0 | 100.0 | 95.6 | 96.1 | 100.0 | 99.4 | 95.5 | 99.9 |

*Mean test set values from the 1000 rounds of cross-validation are shown*

Increasing panel size →

| P# | Description |
|---|---|
| HX-13 or SP-001 | Carboxylate (Citrate) |
| HX-19 or SP-002 | Phenol-formaldehyde resin coated |
| HX-31 or SP-004 | Polystyrene coated |
| HX-38 or SP-005 | Carboxylated Poly(styrene-co-methacrylic acid), P(St-co-MAA) |
| HX-42 or SP-006 | N-(3-Trimethoxysilylpropyl)diethylenetriamine coated |
| HX-57 or SP-008 | 1,2,4,5-Benzenetetracarboxylic acid coated |
| HX-58 or SP-009 | Vinylbenzyltrimethylammonium chloride (PVBTMAC) coated |
| HX-59 or SP-010 | Carboxylated, Poly(acrylic acid), PAA |
| SP-333 | Carboxylate microparticle, surfactant free |
| SP-339 | Polystyrene carboxyl functionalized |
| SP-341 | Carboxylic acid, 150 nm |
| SP-347 | Silica coated, 200 nm |
| SP-348 | Carboxylic acid |
| SP-353 | Amino surface microparticle, 0.4-0.6 µm |
| SP-356 | Silica amino functionalized microparticle, 0.1- 0.39 µm |
| SP-363 | Jeffamine surface, 0.1-0.39 µm |
| SP-364 | Polystyrene microparticle, 2.0-2.9 µm |
| SP-365 | Silica |
| SP-369 | Carboxylated Original coating, 50 nm |
| SP-373 | Dextran based coating, 0.13 µm |
| SP-374 | Silica Silanol coated with lower acidity |
| HX-20 or SP-003 | Silica-coated superparamagnetic iron oxide NPs (SPION) |
| HX-56 or SP-007 | poly(N-(3-(dimethylamino)propyl) methacrylamide) (PDMAPMA)-coated SPION |
| HX-86 or SP-011 | poly(oligo(ethylene glycol) methyl ether methacrylate) (POEGMA)-coated SPION |

FIG. 21

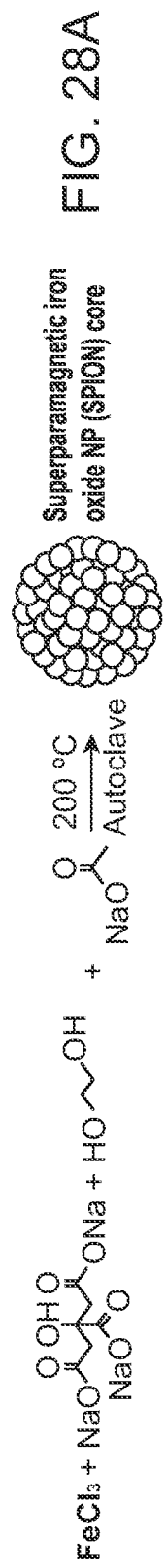
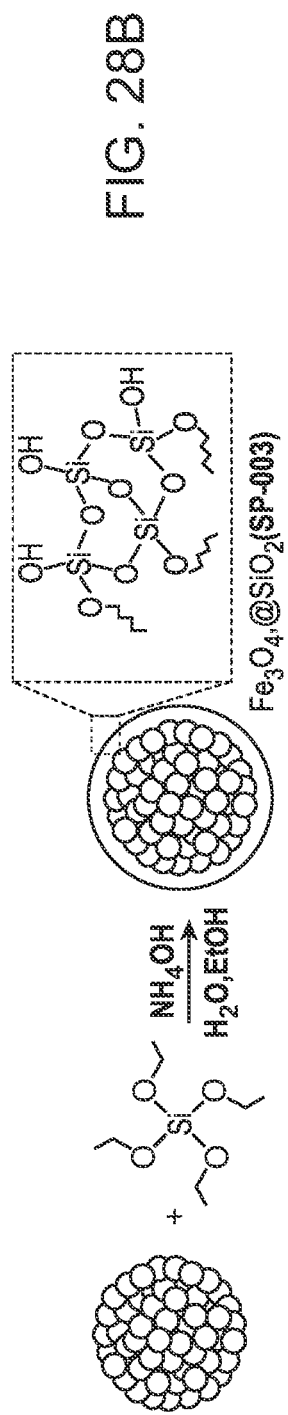
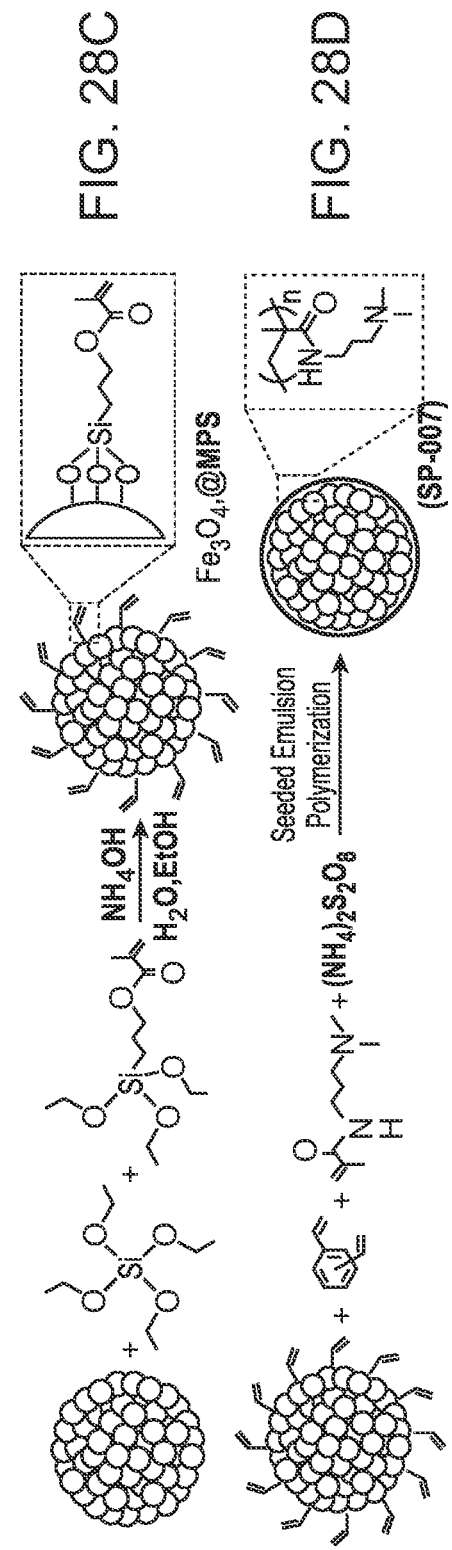
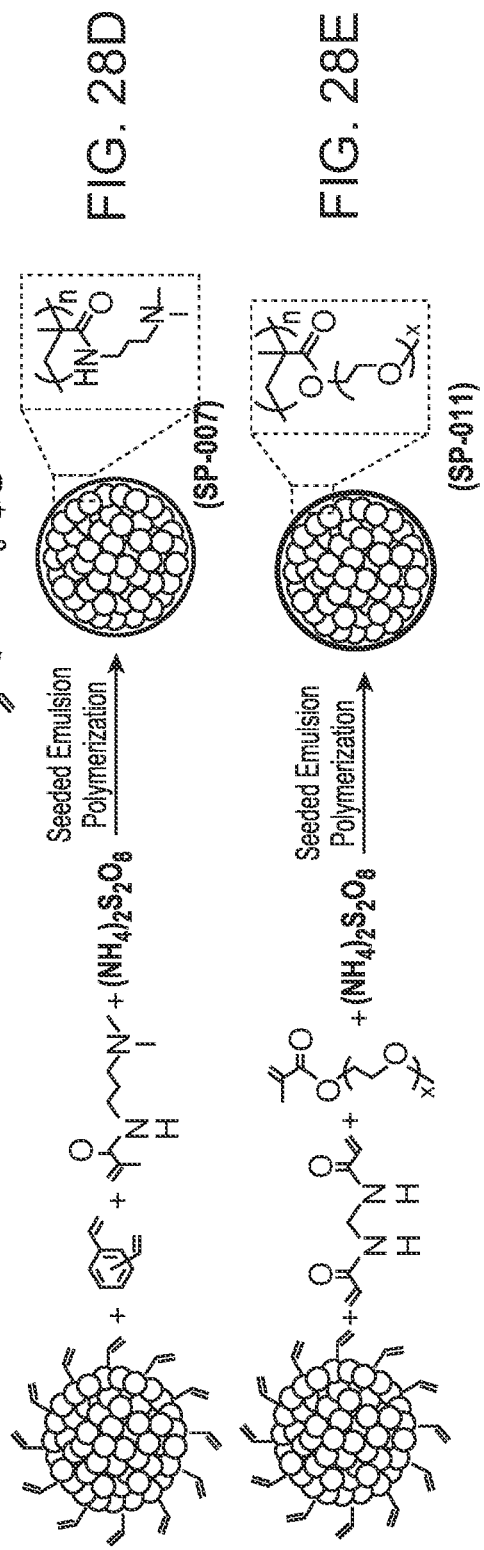
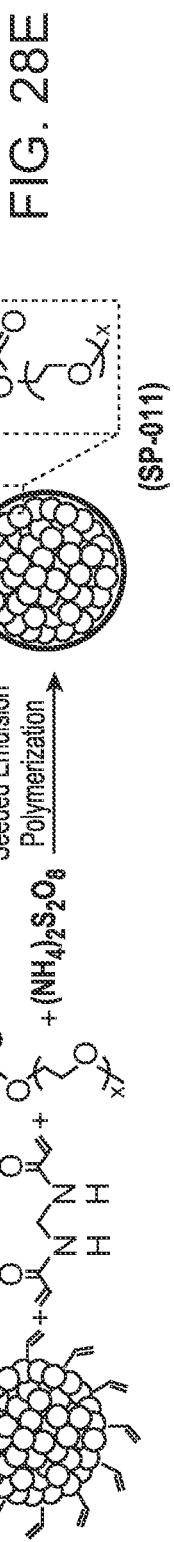
FIG. 28A
FIG. 28B
FIG. 28C
FIG. 28D
FIG. 28E

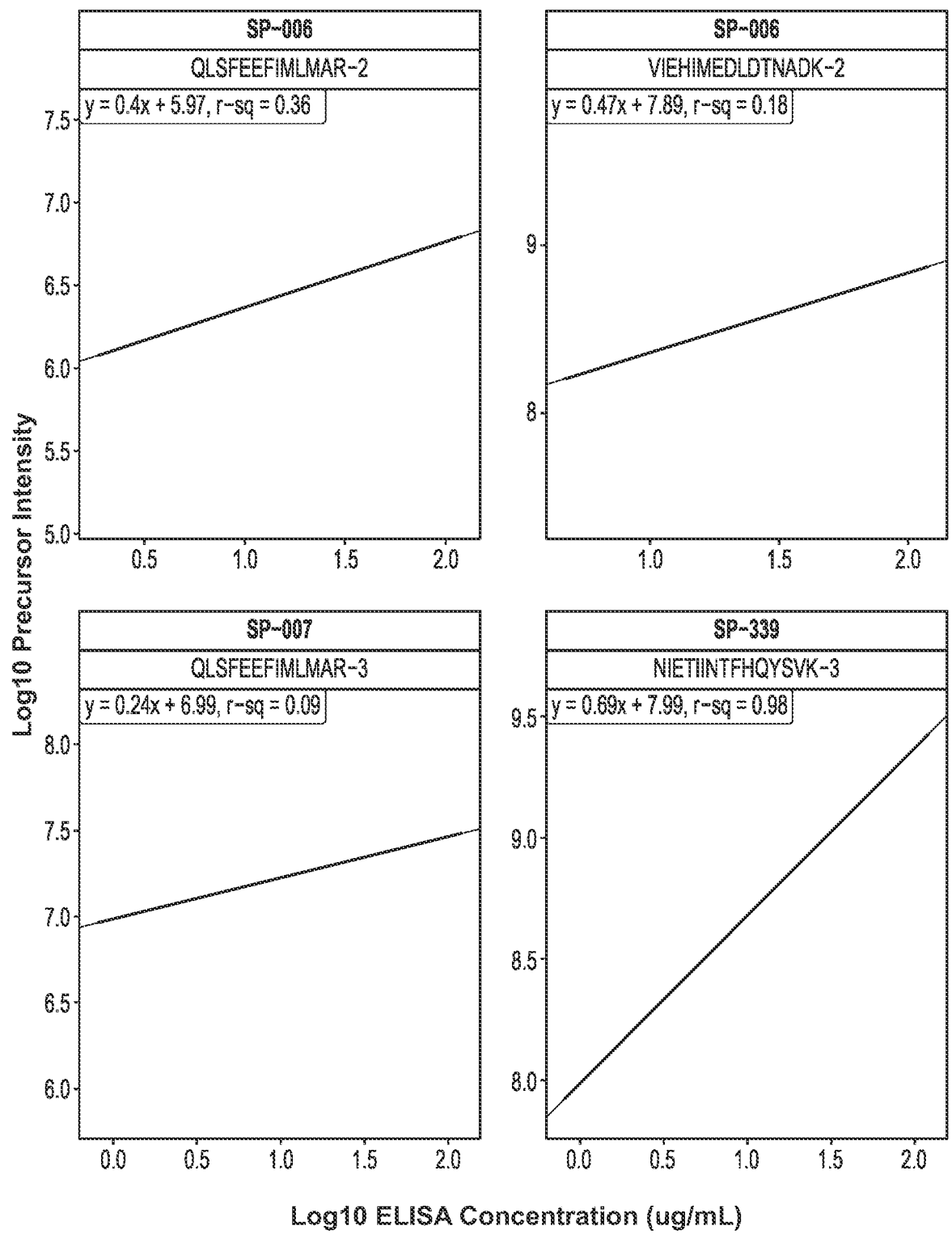
FIG. 33 (Cont. 1)

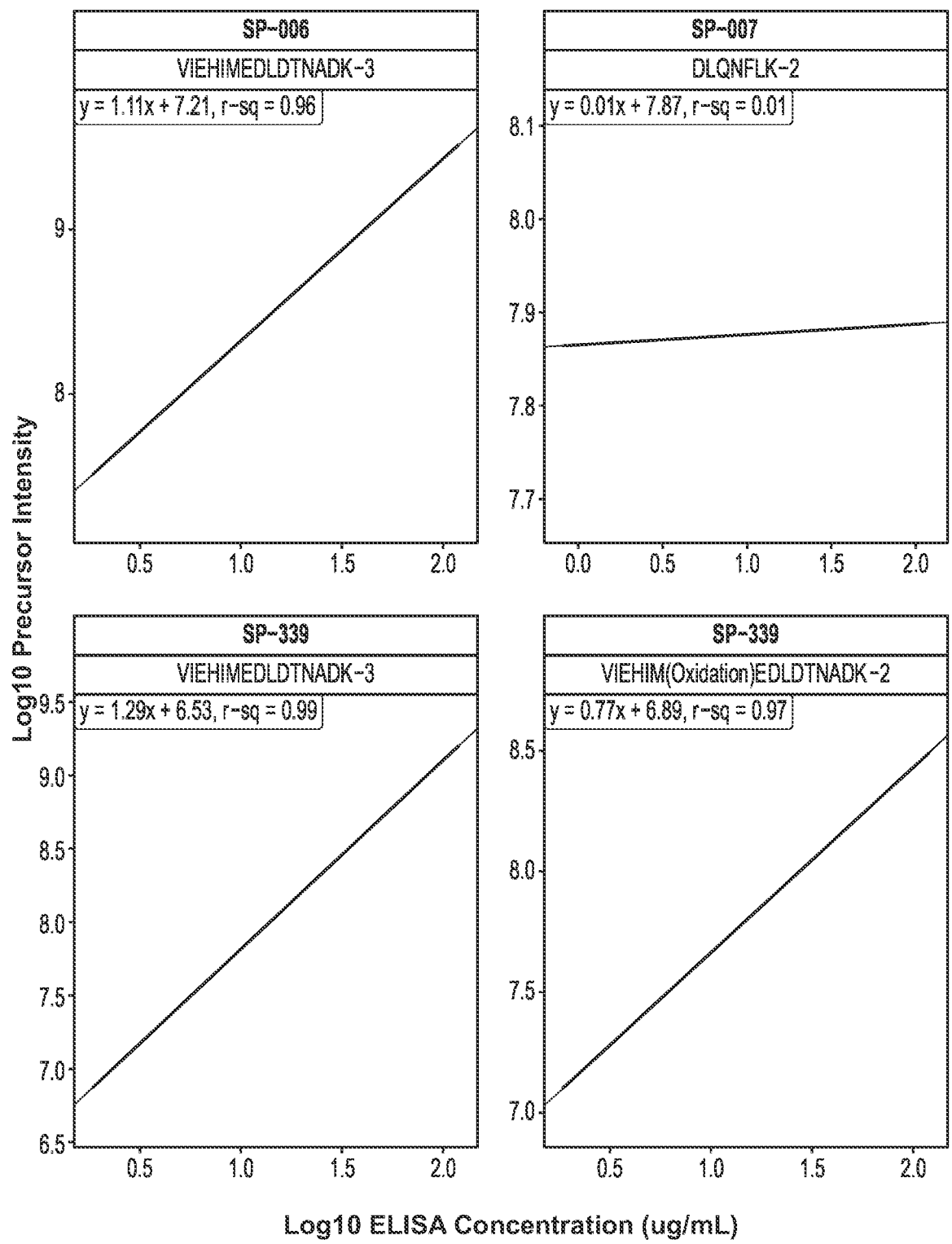
FIG. 33 (Cont. 2)

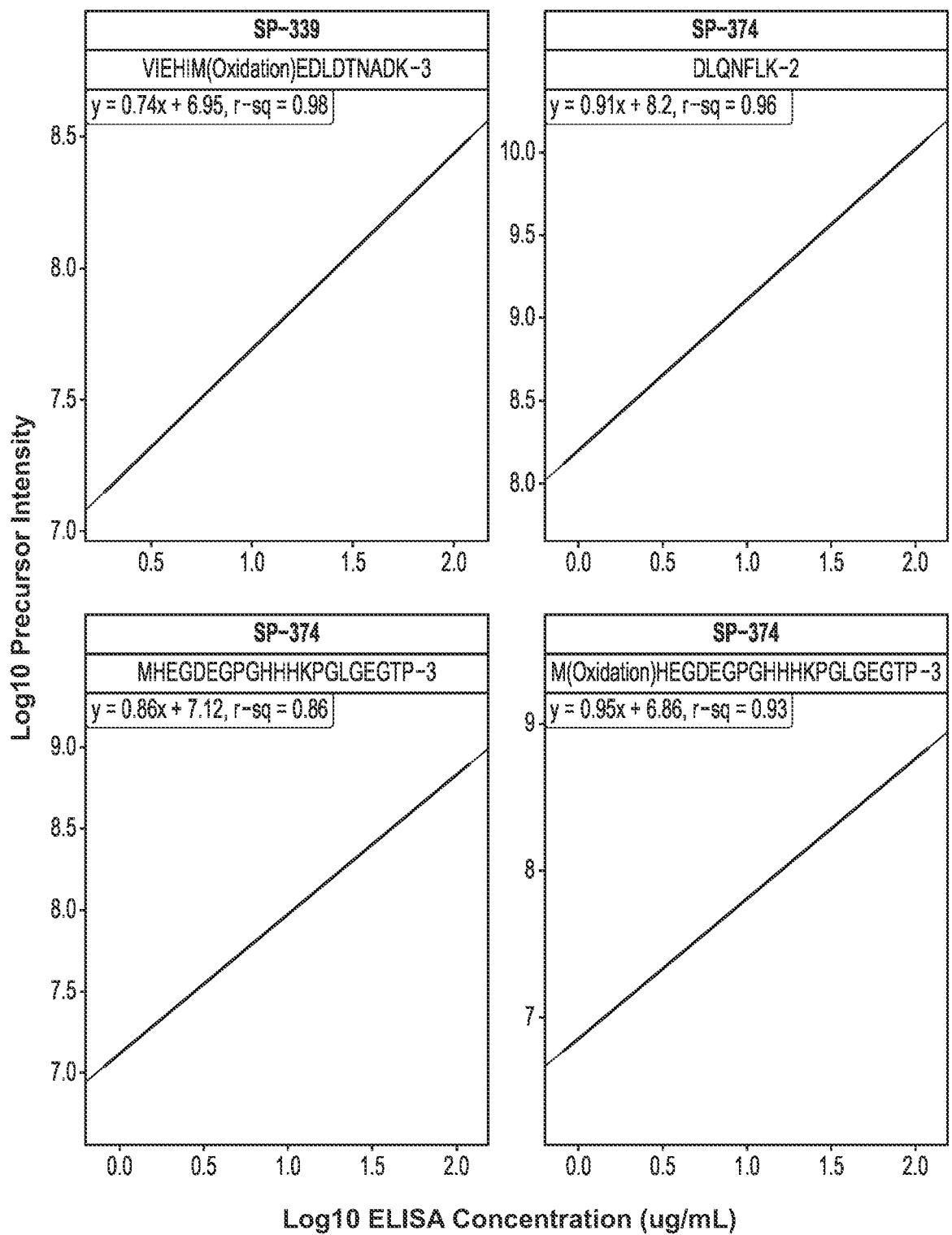
FIG. 33 (Cont. 3)

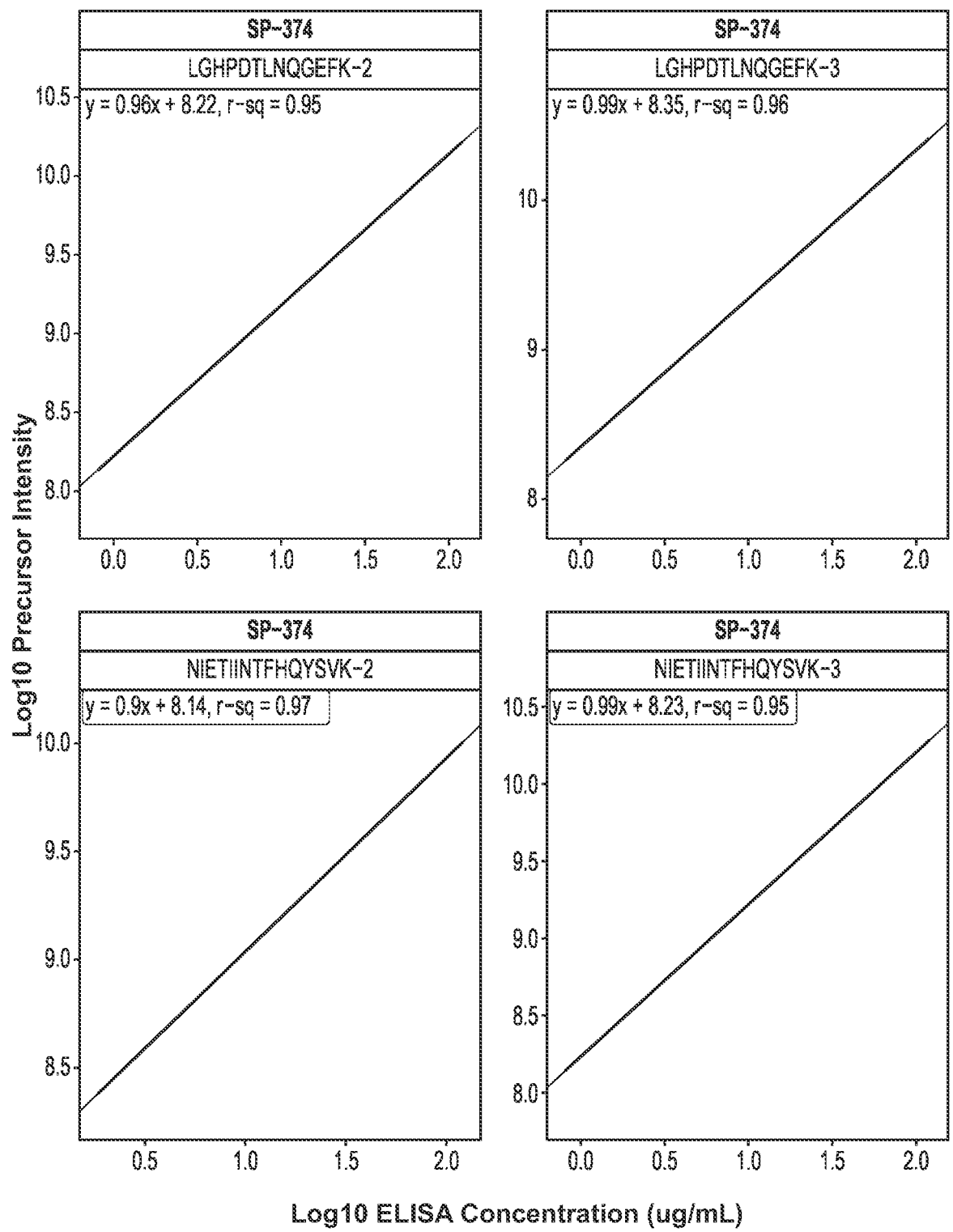
FIG. 33 (Cont. 4)

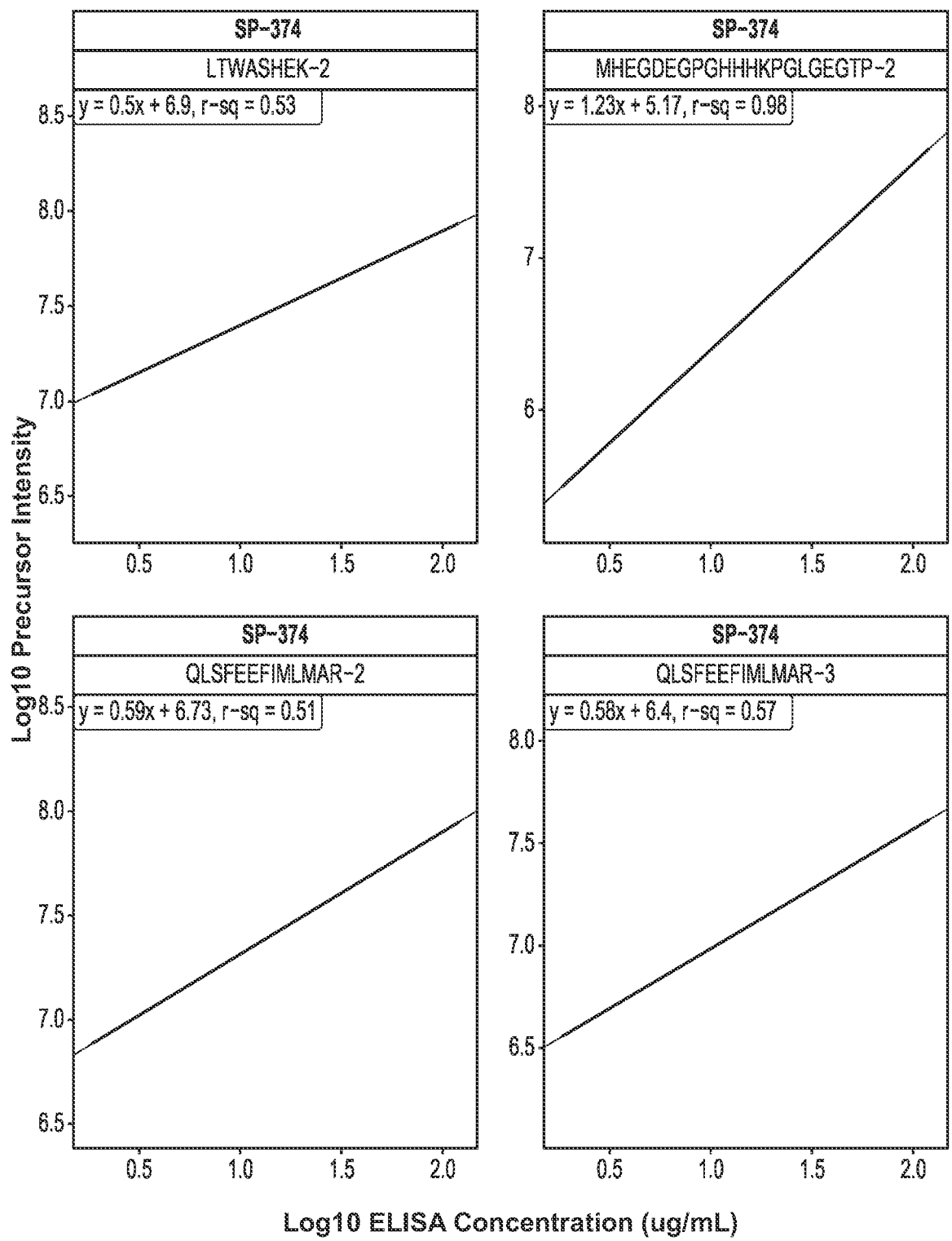
FIG. 33 (Cont. 5)

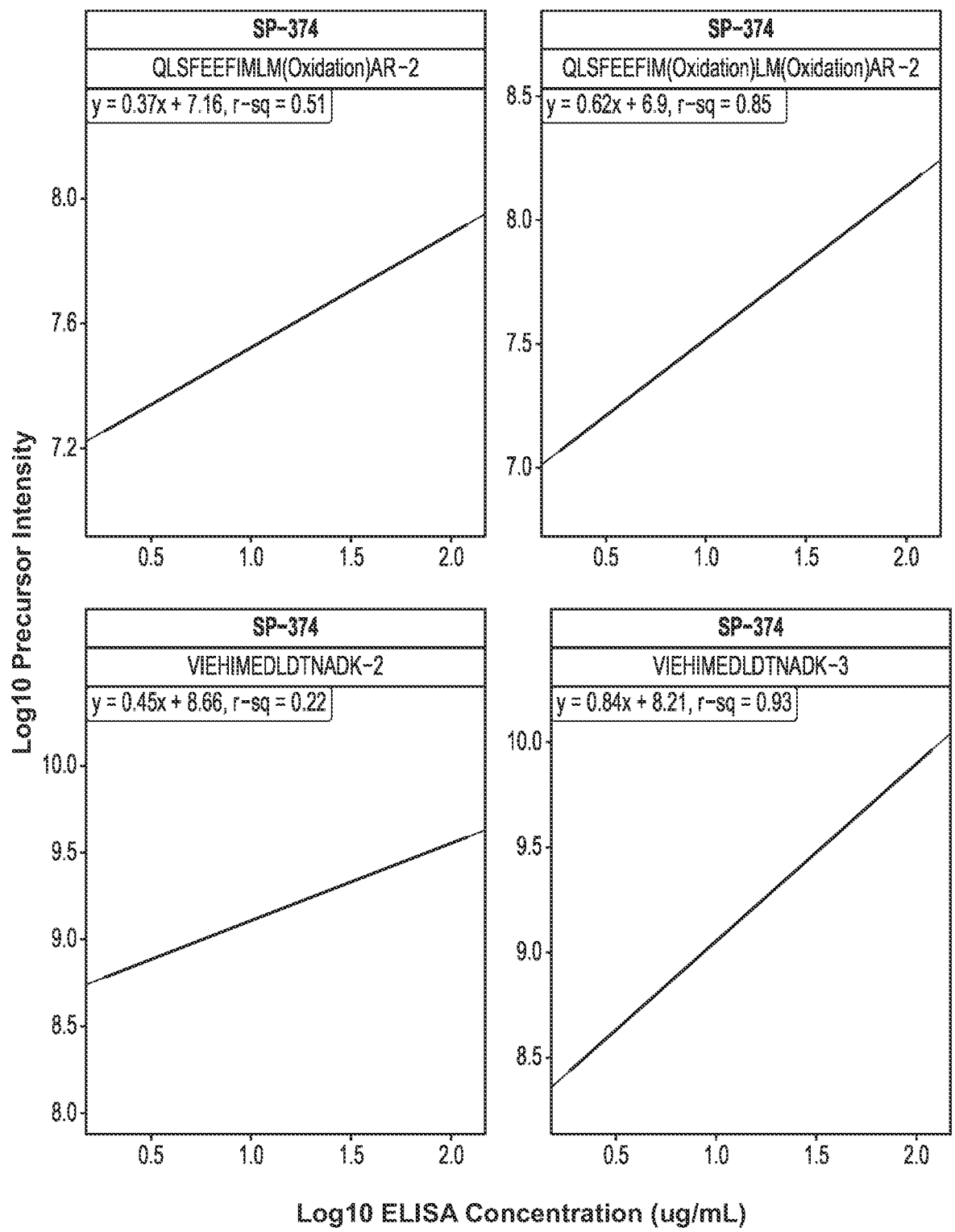
FIG. 33 (Cont. 6)

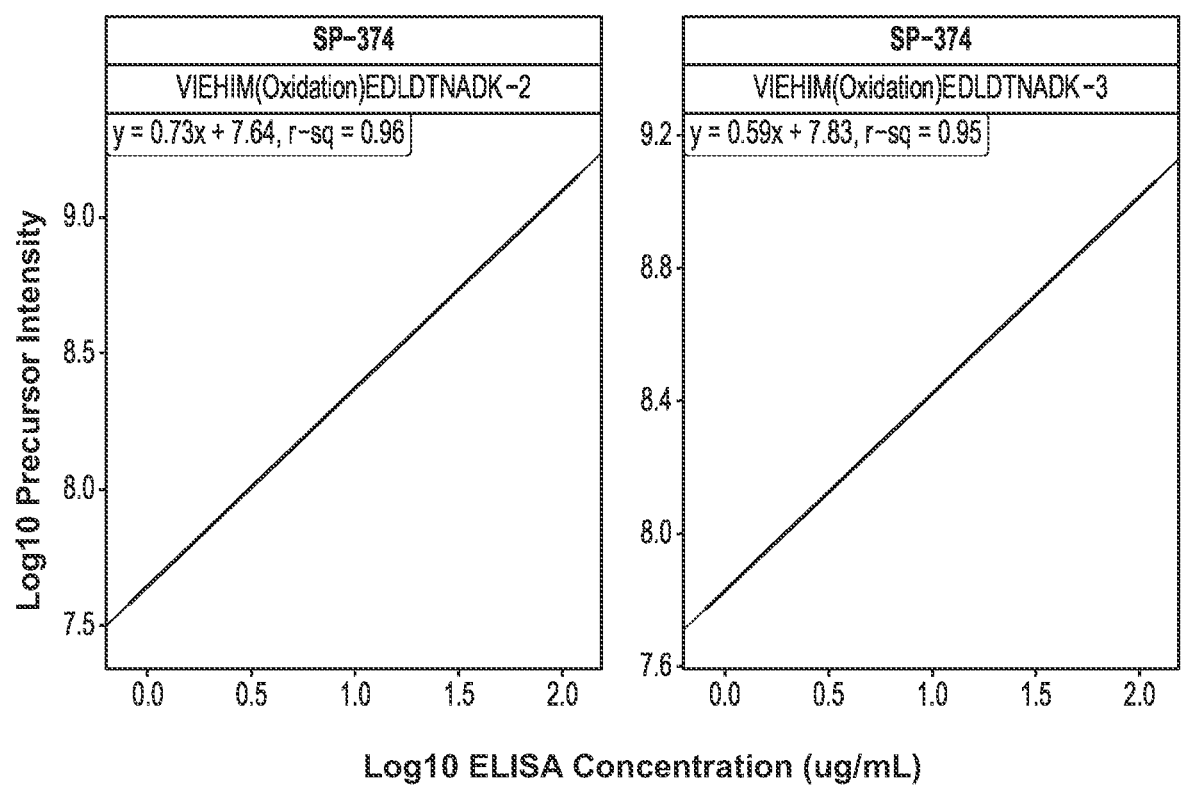
FIG. 33 (Cont. 7)

COMPOSITIONS, METHODS AND SYSTEMS FOR PROTEIN CORONA ANALYSIS AND USES THEREOF

CROSS-REFERENCE TO RELATED APPLICATIONS

The present application is a continuation of U.S. patent application Ser. No. 17/216,514, filed Mar. 29, 2021, which is a continuation of International Patent Application No. PCT/US2019/000061, filed Nov. 7, 2019, which claims the benefit of U.S. Provisional Patent Application No. 62/756,960, filed Nov. 7, 2018, U.S. Patent Application No. 62/824,278, filed Mar. 26, 2019 and U.S. Patent Application No. 62/874,862, filed Jul. 16, 2019, each of which is incorporated herein by reference in its entirety.

BACKGROUND

Broad scale implementation of proteomic information in science and medicine has lagged behind genomics in large part because of complexities inherent in protein molecules themselves, necessitating complex workflows that limit the scalability of such analyses. Disclosed herein are compositions and methods for rapid processing of proteomic data and identification of key biomarkers associated with disease.

SUMMARY

The present invention provides a panel of nanoparticles for the detection of a wide range of diseases and disorders and determination of disease states in a subject.

Creating and characterizing protein coronas has also been performed in the field; however, most of the experimentation has been done on non-magnetic particles, such as liposomes and polymeric nanoparticles, or other particle types that may be used for targeted drug delivery.

The problem with the current (typically academic) assays for protein corona formation and characterization is that they are not amenable to high-throughput and/or automated formats, as the particles used in the assay need to be isolated for corona collection. The advantage of SPMNPs used for protein coronas is their quick magnetic response that can be easily separated from the suspension mixture by applying an external magnetic field. This type of magnetic particle is a good platform for further chemical modification with different functional groups which can help fine tune the interaction between particles and plasma proteins.

In some aspects, the present disclosure provides a method of identifying proteins in a sample, the method comprising: incubating a particle panel with the sample to form a plurality of distinct biomolecule coronas corresponding to distinct particle types of the particle panel; magnetically isolating the particle panel from unbound protein in the sample to enrich proteins in the plurality of distinct biomolecule coronas; and assaying the plurality of distinct biomolecule coronas to identify the enriched proteins.

In some aspects, the assaying is capable of identifying from 1 to 20,000 protein groups. In further aspects, the assaying is capable of identifying from 1000 to 10,000 protein groups. In further aspects, the assaying is capable of identifying from 1,000 to 5,000 protein groups. In still further aspects, the assaying is capable of identifying from 1,200 to 2,200 protein groups. In some aspects, the protein group comprises a peptide sequence having a minimum length of 7 amino acid residues. In some further, the assaying is capable of identifying from 1,000 to 10,000 proteins. In some still further, the assaying is capable of identifying from 1,800 to 5,000 proteins.

In some embodiments, the sample comprises a plurality of samples. In some embodiments, the plurality of samples comprises at least two or more spatially isolated samples. In further embodiments, the incubating comprises contacting the at least two or more spatially isolated samples with the particle panel at the same time. In further embodiments, the magnetically isolating comprises magnetically isolating the particle panel from unbound protein in the at least two or more spatially isolated samples of the plurality of samples at the same time. In further embodiments, the assaying comprises assaying the plurality of distinct biomolecule coronas to identify proteins in the at least two or more spatially isolated samples at the same time.

In some embodiments, the method further comprises repeating the methods described herein, wherein, when repeated, the incubating, isolating, and assaying yields a percent quantile normalized coefficient (QNCV) of variation of 20% or less, as determined by comparing a peptide mass spectrometry feature from at least three full-assay replicates for each particle type in the particle panel. In some embodiments, when repeated, the incubating, isolating, and assaying yields a percent quantile normalized coefficient (QNCV) of variation of 10% or less, as determined by comparing a peptide mass spectrometry feature from at least three full-assay replicates for each particle type in the particle panel. In some embodiments, the assaying is capable of identifying proteins over a dynamic range of at least 7, at least 8, at least 9, or at least 10.

In some embodiments, the method further comprises washing the particle panel at least one time or at least two times after magnetically isolating the particle panel from the unbound protein. In some embodiments, after the assaying the method further comprises lysing the proteins in the plurality of distinct biomolecule coronas.

In some embodiments, the method further comprises digesting the proteins in the plurality of distinct biomolecule coronas to generate digested peptides.

In some embodiments, the method further comprises purifying the digested peptides.

In some embodiments, the assaying comprises using mass spectrometry to identify proteins in the sample. In some embodiments, the assaying is performed in about 2 to about 4 hours. In some embodiments, the method is performed in about 1 to about 20 hours. In some embodiments, the method is performed in about 2 to about 10 hours. In some embodiments, the method is performed in about 4 to about 6 hours. In some embodiments, the isolating takes no more than about 30 minutes, no more than about 15 minutes, no more than about 10 minutes, no more than about 5 minutes, or no more than about 2 minutes. In some embodiments, the plurality of samples comprises at least 10 spatially isolated samples, at least 50 spatially isolated samples, at least 100 spatially isolated samples, at least 150 spatially isolated samples, at least 200 spatially isolated samples, at least 250 spatially isolated samples, or at least 300 spatially isolated samples. In further embodiments, the plurality of samples comprises at least 96 samples.

In some embodiments, the particle panel comprises at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 particle types, or at least 30 distinct particle types. In further embodiments, the particle panel comprises at least 10 distinct particle types. In further embodiments, the at least two spatially isolated samples differ by at least one physicochemical property.

In some embodiments, the particle panel comprises a first distinct particle type and a second distinct particle type, wherein the first distinct particle type and the second distinct particle type share at least one physicochemical property and differ by at least one physicochemical property, such that the first distinct particle type and the second distinct particle type are different. In some embodiments, the particle panel comprises a first distinct particle type and a second distinct particle type, wherein the first distinct particle type and the second distinct particle type share at least two physicochemical properties and differ by at least two physicochemical properties, such that the first distinct particle type and the second distinct particle type are different. In some embodiments, the particle panel comprises a first distinct particle type and a second distinct particle type, wherein the first distinct particle type and the second distinct particle type share at least one physicochemical property and differ by at least two physicochemical properties, such that the first distinct particle type and the second distinct particle type are different.

In some embodiments, the particle panel comprises a first distinct particle type and a second distinct particle type, wherein the first distinct particle type and the second distinct particle type share at least two physicochemical properties and differ by at least one physicochemical property, such that the first distinct particle type and the second distinct particle type are different. In further embodiments, the physicochemical property comprises size, charge, core material, shell material, porosity, or surface hydrophobicity. In further embodiments, size is diameter or radius, as measured by dynamic light scattering, SEM, TEM, or any combination thereof.

In some embodiments, the particle panel comprises a first distinct particle type and a second distinct particle type, wherein the first distinct particle type and the second distinct particle type comprise a carboxylate material, wherein the first distinct particle is a microparticle, and wherein the second distinct particle type is a nanoparticle. In some embodiments, the particle panel comprises a first distinct particle type and a second distinct particle type, wherein the first distinct particle type and the second distinct particle type comprise a surface charge of from 0 mV and −50 mV, wherein the first distinct particle type has a diameter of less than 200 nm, and wherein the second distinct particle type has a diameter of greater than 200 nm.

In some embodiments, the particle panel comprises a first distinct particle type and a second distinct particle type, wherein the first distinct particle type and the second distinct particle type comprise a diameter of 100 to 400 nm, wherein the first distinct particle type has a positive surface change, and wherein the second distinct particle type has a neutral surface charge. In some embodiments, the particle panel comprises a first distinct particle type and a second distinct particle type, wherein the first distinct particle type and the second distinct particle type are nanoparticles, wherein the first distinct particle type has a surface change less than −20 mV and the second distinct particle type has a surface charge greater than −20 mV.

In some embodiments, the particle panel comprises a first distinct particle type and a second distinct particle type, wherein the first distinct particle type and the second distinct particle type are microparticles, wherein the first distinct particle type has a negative surface charge, and wherein the second distinct particle type has a positive surface charge. In some embodiments, the particle panel comprises a subset of negatively charged nanoparticles, wherein each particle of the subset differ by at least one surface chemical group. In some embodiments, the particle panel comprises a first distinct particle type, a second particle, and a third distinct particle type, wherein the first distinct particle type, the second distinct particle type, and the third distinct particle type comprise iron oxide cores, polymer shells, and are less than about 500 nm in diameter and wherein the first distinct particle type comprises a negative charge, the second distinct particle type comprises a positive charge, and the third distinct particle type comprises a neutral charge, wherein the diameter is a mean diameter as measured by dynamic light scattering. In further embodiments, the first distinct particle type comprises a silica coating, the second distinct particle type comprises a poly(N-(3-(dimethylamino)propyl) methacrylamide) (PDMAPMA), and the third distinct particle type comprises a poly(oligo(ethylene glycol) methyl ether methacrylate) (POEGMA) coating.

In some embodiments, at least one distinct particle type of the particle panel is a nanoparticle. In some embodiments, at least one distinct particle type of the particle panel is a microparticle. In some embodiments, at least one distinct particle type of the particle panel is a superparamagnetic iron oxide particle. In some embodiments, each particle of the particle panel comprise an iron oxide material. In some embodiments, at least one distinct particle type of the particle panel has an iron oxide core. In some embodiments, at least one distinct particle type of the particle panel has iron oxide crystals embedded in a polystyrene core. In some embodiments, each distinct particle type of the particle panel is a superparamagnetic iron oxide particle. In some embodiments, each distinct particle type of the particle panel comprises an iron oxide core. In some embodiments, each one distinct particle type of the particle panel has iron oxide crystals embedded in a polystyrene core. In some embodiments, at least one distinct particle type of particle panel comprises a carboxylated polymer, an aminated polymer, a zwitterionic polymer, or any combination thereof. In some embodiments, at least one particle type of the particle panel comprises an iron oxide core with a silica shell coating. In some embodiments, at least one particle type of the particle panel comprises an iron oxide core with a poly(N-(3-(dimethylamino)propyl) methacrylamide) (PDMAPMA) coating. In some embodiments, at least one particle type of the particle panel comprises an iron oxide core with a poly(oligo(ethylene glycol) methyl ether methacrylate) (POEGMA) coating.

In some embodiments, at least one distinct particle type of the particle panel comprises a negative surface charge. In some embodiments, at least one distinct particle type of the particle panel comprises a positive surface charge. In some embodiments, at least one distinct particle type of the particle panel comprises a neutral surface charge. In some embodiments, the particle panel comprises one or more distinct particle types selected from TABLE 10. In some embodiments, the particle panel comprises two or more distinct particle types, three or more distinct particle types, four or more distinct particle types, five or more distinct particle types, six or more distinct particle types, seven or more distinct particle types, eight or more distinct particle types, nine or more distinct particle types, or all ten distinct particle types selected from TABLE 10. In some embodiments, the particle panel comprises one or more distinct particle types selected from TABLE 12. In some embodiments, the particle panel comprises two or more distinct particle types, three or more distinct particle types, four or more distinct particle types, five or more distinct particle types, six or more distinct particle types, seven or more distinct particle types, eight or more distinct particle types, nine or more distinct particle types, or all ten distinct particle types selected from TABLE 12.

In various aspects, the present disclosure provides a composition comprising three or more distinct magnetic particle types that differ by two or more physicochemical properties, wherein a subset of the three or more distinct magnetic particle types share a physicochemical property of the two or more physicochemical properties and wherein such particle types of the subset bind different proteins.

In some embodiments, the three or more distinct magnetic particle types adsorb proteins from a biological sample over a dynamic range of at least 7, at least 8, at least 9, or at least 10. In some embodiments, the three or more distinct magnetic particle types are capable of adsorbing from 1 to 20,000 proteins groups from a biological sample. In some aspects, the three or more distinct magnetic particle types are capable of adsorbing from 1,000 to 10,000 protein groups from a biological sample. In further aspects, the three or more distinct magnetic particle types are capable of adsorbing from 1,000 to 5,000 protein groups from a biological sample. In further aspects, the three or more distinct magnetic particle types are capable of adsorbing from 1,200 to 2,200 protein groups from a biological sample. In still further aspects, wherein the protein group comprises a peptide sequence having a minimum length of 7 amino acid residues. In some aspects, the three or more distinct magnetic particle types are capable of adsorbing from 1 to 20,000 proteins from a biological sample. In further aspects, the three or more distinct magnetic particle types are capable of adsorbing from 1,000 to 10,000 proteins from a biological sample. In still further aspects, the three or more distinct magnetic particle types are capable of adsorbing from 1,800 to 5,000 proteins from a biological sample.

In some embodiments, the composition comprises at least 4 distinct magnetic particle types, at least 5 distinct magnetic particle types, at least 6 distinct magnetic particle types, at least 7 distinct magnetic particle types, at least 8 distinct magnetic particle types, at least 9 distinct magnetic particle types, at least 10 distinct magnetic particle types, at least 11 distinct magnetic particle types, at least 12 distinct magnetic particle types, at least 13 distinct magnetic particle types, at least 14 distinct magnetic particle types, at least 15 distinct magnetic particle types, at least 20 distinct magnetic particle types, or at least 30 distinct magnetic particle types. In some embodiments, the composition comprises at least 10 distinct magnetic particle types. In some embodiments, the composition comprises a first distinct particle type and a second distinct particle type, wherein the first distinct particle type and the second distinct particle type share at least two physicochemical properties and differ by at least two physicochemical properties, such that the first distinct particle type and the second distinct particle type are different.

In some embodiments, the composition comprises a first distinct particle type and a second distinct particle type, wherein the first distinct particle type and the second distinct particle type share at least two physicochemical properties and differ by at least one physicochemical property, such that the first distinct particle type and the second distinct particle type are different. In some embodiments, the physicochemical property comprises size, charge, core material, shell material, porosity, or surface hydrophobicity. In further embodiments, the size is diameter or radius, as measured by dynamic light scattering, SEM, TEM, or any combination thereof.

In some embodiments, the composition comprises a first distinct particle type and a second distinct particle type, wherein the first distinct particle type and the second distinct particle type comprise a carboxylate material, wherein the first distinct particle is a microparticle, and wherein the second distinct particle type is a nanoparticle. In some embodiments, the particle panel comprises a first distinct particle type and a second distinct particle type, wherein the first distinct particle type and the second distinct particle type comprise a surface charge of from 0 mV and −50 mV, wherein the first distinct particle type has a diameter of less than 200 nm, and wherein the second distinct particle type has a diameter of greater than 200 nm. In some embodiments, the particle panel comprises a first distinct particle type and a second distinct particle type, wherein the first distinct particle type and the second distinct particle type comprise a diameter of 100 to 400 nm, wherein the first distinct particle type has a positive surface change, and wherein the second distinct particle type has a neutral surface charge.

In some embodiments, the particle panel comprises a first distinct particle type and a second distinct particle type, wherein the first distinct particle type and the second distinct particle type are nanoparticles, wherein the first distinct particle type has a surface change less than −20 mV and the second distinct particle type has a surface charge greater than −20 mV. In some embodiments, the particle panel comprises a first distinct particle type and a second distinct particle type, wherein the first distinct particle type and the second distinct particle type are microparticles, wherein the first distinct particle type has a negative surface charge, and wherein the second distinct particle type has a positive surface charge. In some embodiments, the composition comprises a subset of negatively charged nanoparticles, wherein each particle type of the subset differ by at least one surface chemical group. In some embodiments, the composition comprises a first distinct particle type, a second distinct particle type, and a third distinct particle type, wherein the first distinct particle type, the second distinct particle type, and the third distinct particle type comprise iron oxide cores, polymer shells, and are less than about 500 nm in diameter and wherein the first distinct particle type comprises a negative charge, the second distinct particle type comprises a positive charge, and the third distinct particle type comprises a neutral charge, wherein the diameter is a mean diameter as measured by dynamic light scattering. In further embodiments, the first distinct particle type comprises a silica coating, the second distinct particle type comprises a poly(N-(3-(dimethylamino)propyl) methacrylamide) (PDMAPMA), and the third distinct particle type comprises a poly(oligo(ethylene glycol) methyl ether methacrylate) (POEGMA) coating.

In some embodiments, the three or more distinct magnetic particle types comprise a nanoparticle. In some embodiments, the three or more distinct magnetic particle types comprises a microparticle. In some embodiments, at least one distinct particle type of the three or more distinct magnetic particle types is a superparamagnetic iron oxide particle. In some embodiments, at least one distinct particle type of the three or more distinct magnetic particle types comprise an iron oxide material. In some embodiments, at least one distinct particle type of the three or more distinct magnetic particle types has an iron oxide core. In some embodiments, at least one distinct particle type of the three or more distinct magnetic particle types has iron oxide crystals embedded in a polystyrene core.

In some embodiments, each distinct particle type of the three or more distinct magnetic particle types is a superparamagnetic iron oxide particle. In some embodiments, each distinct particle type of the three or more distinct magnetic particle types comprise an iron oxide core. In some embodiments, each one distinct particle type of the three or more distinct magnetic particle types has iron oxide crystals embedded in a polystyrene core. In some embodiments, at least one particle type of the three or more distinct magnetic particle types comprises a polymer coating.

In some embodiments, the three or more distinct magnetic particle types comprise a carboxylated polymer, an aminated polymer, a zwitterionic polymer, or any combination thereof. In some embodiments, at least one particle type of the three or more distinct magnetic particle types comprises an iron oxide core with a silica shell coating. In some embodiments, at least one particle type of the three or more distinct magnetic particle types comprises an iron oxide core with a poly(N-(3-(dimethylamino)propyl) methacrylamide) (PDMAPMA) coating. In some embodiments, at least one particle type of the three or more distinct magnetic particle types comprises an iron oxide core with a poly(oligo(ethylene glycol) methyl ether methacrylate) (POEGMA) coating.

In some embodiments, at least one particle type of the three or more distinct magnetic particle types comprises a negative surface charge. In some embodiments, at least one particle type of the three or more distinct magnetic particle types comprises a positive surface charge. In some embodiments, at least one particle type of the three or more distinct magnetic particle types comprises a neutral surface charge.

In some embodiments, the three or more distinct magnetic particle types comprise one or more particle types of TABLE 10. In some embodiments, the particle panel comprises two or more distinct particle types, three or more distinct particle types, four or more distinct particle types, five or more distinct particle types, six or more distinct particle types, seven or more distinct particle types, eight or more distinct particle types, nine or more distinct particle types, or all ten distinct particle types selected from TABLE 10. In some embodiments, the three or more distinct magnetic particle types comprise one or more particle types of TABLE 12. In some embodiments, the particle panel comprises two or more distinct particle types, three or more distinct particle types, four or more distinct particle types, five or more distinct particle types, six or more distinct particle types, seven or more distinct particle types, eight or more distinct particle types, nine or more distinct particle types, or all ten distinct particle types selected from TABLE 12.

In some aspects, the present disclosure provides a method of determining the biological state of a sample from a subject, comprising: exposing a biological sample to a panel comprising a plurality of nanoparticles, thereby generating a plurality of protein coronas; generating proteomic data from the plurality of protein coronas; determining a protein profile of the plurality of protein coronas; and associating the protein profile to a biological state, wherein the panel comprises at least two different nanoparticles.

In some embodiments, the panel comprises at least three different nanoparticles. In some embodiments, the method associates the protein profile to the biological state with at least 90% accuracy. In some embodiments, the plurality of nanoparticles comprises at least one iron oxide nanoparticle.

In some aspects, the present disclosure provides, a method of selecting a panel for protein corona analysis, comprising selecting a plurality of nanoparticles with at least three different physicochemical properties.

In some embodiments, the different physicochemical properties is selected from a group consisting of surface charge, surface chemistry, size, and morphology. In some embodiments, the different physicochemical properties comprise surface charge.

In various embodiments, the present disclosure provides a method of identifying proteins in a sample, the method comprising: incubating a panel comprising a plurality of particle types with the sample to form a plurality of protein corona; digesting the plurality of protein coronas to generate proteomic data; and identifying proteins in the sample by quantifying the proteomic data. In some embodiments, the sample is from a subject.

In some embodiments, the method further comprises determining a protein profile of the sample from the identifying step and associating the protein profile with a biological state of the subject. In some embodiments, the method further comprises determining a biological state of the sample from the subject by: generating proteomic data by digesting the plurality of protein coronas; determining a protein profile of the plurality of protein coronas; and associating the protein profile with the biological state, wherein the panel comprises at least two different nanoparticles. In some embodiments, the associating is performed by a trained classifier.

In some embodiments, the panel comprises at least three different particle types, at least four different particle types, at least five different particle types, at least six different particle types, at least seven different particle types, at least eight different particle types, at least nine different particle types, at least 10 different particle types, at least 11 different particle types, at least 12 different particle types, at least 13 different particle types, at least 14 different particle types, at least 15 different particles, or at least 20 different particle types. In some embodiments, the panel comprises at least four different particle types. In some embodiments, at least one particle type of the panel comprises a physical feature that is different from a second particle type of the panel. In some embodiments, the physical feature is size, polydispersity index, surface charge, or morphology. In some embodiments, the size of at least one particle type of the plurality of particle types in the panel is from 10 nm to 500 nm.

In some embodiments, the polydispersity index of at least one particle type of the plurality of particle types in the panel is from 0.01 to 0.25. In some embodiments, the morphology of at least one particle type of the plurality of particle types comprises spherical, colloidal, square shaped, rods, wires, cones, pyramids, or oblong. In some embodiments, the surface charge of at least one particle type of the plurality of particle types comprises a positive surface charge. In some embodiments, the surface charge of at least one particle type of the plurality of particle types comprises a negative surface charge.

In some embodiments, the surface charge of at least one particle type of the plurality of particle types comprises a neutral surface charge. In some embodiments, at least one particle type of the plurality of particle types comprises a chemical feature that is different from a second particle type of the panel. In some embodiments, the chemical feature is a surface functional chemical group. In some embodiments, the functional chemical group is an amine or a carboxylate. In some embodiments, at least one particle type of the plurality of particle types is made of a material comprising a polymer, a lipid, or a metal.

In further embodiments, the polymer comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), or a copolymer of two or more polymers.

In further embodiments, the lipid comprises dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, or cholesterol.

In some embodiments, the metal comprises gold, silver, copper, nickel, cobalt, palladium, platinum, iridium, osmium, rhodium, ruthenium, rhenium, vanadium, chromium, manganese, niobium, molybdenum, tungsten, tantalum, iron, or cadmium. In some embodiments, at least one particle type of the plurality of particle types is surface functionalized with polyethylene glycol. In some embodiments, the method associates the protein profile to the biological state with at least 70% accuracy, at least 75% accuracy, at least 80% accuracy, at least 85% accuracy, at least 90% accuracy, at least 92% accuracy, at least 95% accuracy, at least 96% accuracy, at least 97% accuracy, at least 98% accuracy, at least 99% accuracy, or 100% accuracy. In some embodiments, the method associates the protein profile to the biological state with at least 70% sensitivity, at least 75% sensitivity, at least 80% sensitivity, at least 85% sensitivity, at least 90% sensitivity, at least 92% sensitivity, at least 95% sensitivity, at least 96% sensitivity, at least 97% sensitivity, at least 98% sensitivity, at least 99% sensitivity, or 100% sensitivity.

In some embodiments, the method associates the protein profile to the biological state with at least 70% specificity, at least 75% specificity, at least 80% specificity, at least 85% specificity, at least 90% specificity, at least 92% specificity, at least 95% specificity, at least 96% specificity, at least 97% specificity, at least 98% specificity, at least 99% specificity, or 100% specificity. In some embodiments, wherein the method identifies at least 100 unique proteins, at least 200 unique proteins, at least 300 unique proteins, at least 400 unique proteins, at least 500 unique proteins, at least 600 unique proteins, at least 700 unique proteins, at least 800 unique proteins, at least 900 unique proteins, at least 1000 unique proteins, at least 1100 unique proteins, at least 1200 unique proteins, at least 1300 unique proteins, at least 1400 unique proteins, at least 1500 unique proteins, at least 1600 unique proteins, at least 1700 unique proteins, at least 1800 unique proteins, at least 1900 unique proteins, or at least 2000 unique proteins. In some embodiments, at least one particle type of the plurality of particle types comprises an iron oxide nanoparticle. In further embodiments, the sample is a biofluid. In still further embodiments, the biofluid comprises plasma, serum, CSF, urine, tear, or saliva In various embodiments, the present disclosure provides a method of selecting a panel for protein corona analysis, comprising selecting a plurality of particle types with at least three different physicochemical properties. In some embodiments, the different physicochemical properties is selected from a group consisting of surface charge, surface chemistry, size, and morphology. In further embodiments, the different physicochemical properties comprises surface charge.

In various embodiments, the present disclosure provides a composition comprising a panel of particles, wherein the panel comprises a plurality of particle types and wherein the plurality of particle types comprises at least three different physicochemical properties. In some embodiments, the different physicochemical properties is selected from a group consisting of surface charge, surface chemistry, size, and morphology. In further embodiments, the different physicochemical properties comprises surface charge.

In various embodiments, the present disclosure provides a system of comprising any one of the above described panels.

In various embodiments, the present disclosure provides a system comprising a panel, wherein the panel comprises a plurality of particle types. In some embodiments, the plurality of particle types comprises at least three different physicochemical properties. In some embodiments, the panel comprises at least 3, at least 4, at least 5, at least 6, at least 7, at least 8, at least 9, at least 10, at least 11, or at least 12 different particle types. In some embodiments, the plurality of particle types are capable of adsorbing a plurality of proteins from a sample to form a plurality of protein coronas. In some embodiments, the plurality of protein coronas are digested to determine a protein profile. In some embodiments, the protein profile is associated with a biological state using a trained classifier.

In some aspects, wherein the sample is a biological sample. In further aspects, the biological sample is plasma, serum, CSF, urine, tear, cell lysates, tissue lysates, cell homogenates, tissue homogenates, nipple aspirates, fecal samples, synovial fluid and whole blood, or saliva. In some aspects, wherein the sample is a non-biological sample. In further aspects, the non-biological sample is water, milk, solvents, or a homogenized sample.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
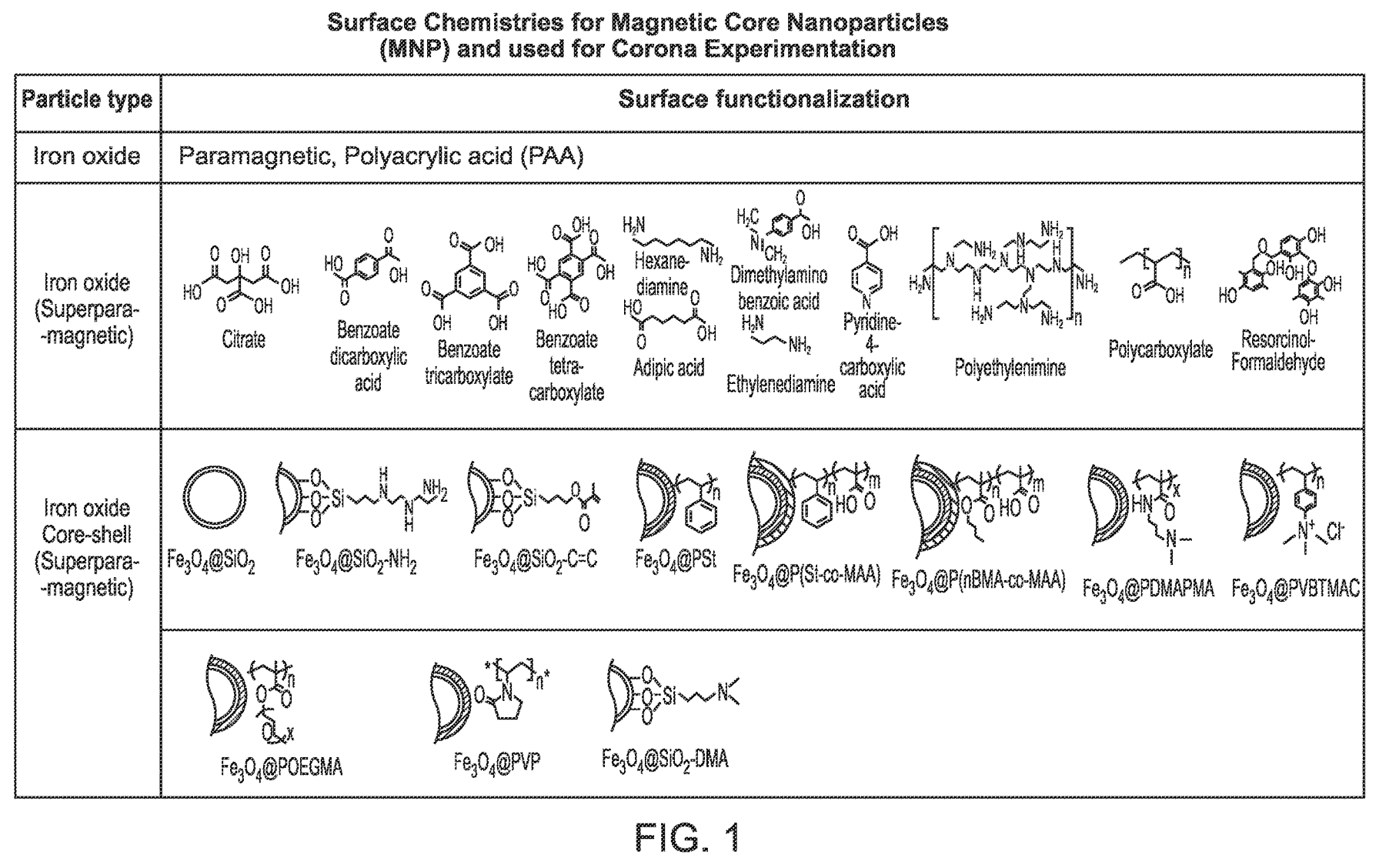

FIG. 1 shows examples of surface chemistries for magnetic particles (MPs). In some cases, the magnetic particles may be magnetic core nanoparticles (MNP).

FIG. 6 shows several examples of different attributes of particles and methods of characterizing the particles.

FIG. 7 shows a dynamic light scattering overlay of two particle types: SP-002 (phenol-formaldehyde coated particles) and SP-010 (carboxylate, PAA coated particles), both of which have iron oxide cores. Dynamic light scattering can also be used to measure a size distribution of particles of larger sizes, including microparticles.

FIG. 8A shows the transmission electron microscopy (TEM) of SP-002 (phenol-formaldehyde coated particles). FIG. 8B shows the TEM of SP-339 (polystyrene carboxyl particles). TEM can also be used to characterize particles of larger sizes, including microparticles.

FIG. 14A shows data from spike recovery experiments of CRP. The protein was spiked at 4 levels: 2×, 5×, 10×, and 100×. HX-42 (SP-006) (left) and HX-97 (right, same as SP-007) were used. FIG. 14B shows the response slopes for spikes and controls. The slopes from the regression models fit to MS~enzyme-linked immunosorbent assay (ELISA) data.

FIG. 16A shows a comparison of samples (28 diseased vs. 28 controls) using a panel of seven particle types, including SP-339, HX74 (SP-007), SP-356, SP-333, HX20 (SP-003), SP-364, and HX42 (SP-006). 14,481 filtered MS features were compared and 120 (0.8%) were different.

As shown in FIG. 18A, banked plasma from enrollment was tested. 8 years after enrollment, approximately 1000 patients developed cancers. FIG. 18B shows the classification of the banked plasma from FIG. 18A. Corona analysis of banked plasma from enrollment date accurately classified cancers for 15 out of 15 subjects examined (5 patients each for 3 cancers).

FIG. 21 illustrates an example of particle types of the present disclosure. The particle types may include nanoparticles (NPs) and microparticles.

FIG. 22A show three distinct particle types (depicted in the center of the figure, with the top, middle, and bottom spheres representing the three distinct particle types), each different from the other by at least one physicochemical property, which leads to the formation of different protein corona compositions on the particle surfaces. FIG. 22B shows the corona analysis workflow with Proteograph, which includes: (1) particle-plasma incubation and protein corona formation; (2) particle protein corona purification by a magnet; (3) digestion of corona proteins; and (4) mass spectrometry analysis.

FIG. 28A shows a schematic for synthesis of SPION core.

FIG. 28B shows a schematic for synthesis of silica-coated SPION (SP-003).

FIG. 28C shows a schematic for synthesis of vinyl group functionalized SPION.

FIG. 28D shows a schematic for synthesis of poly(N-(3-(dimethylamino)propyl) methacrylamide) (PDMAPMA)-coated SPION (SP-007).

FIG. 28E shows a schematic for synthesis of poly(oligo (ethylene glycol) methyl ether methacrylate) (POEGMA)-coated SPION (SP-011).

FIG. 37A shows a schematic of a hollow magnetic particle.

FIG. 37B shows a schematic of a particle with hydrophobic pockets.

FIG. 37C shows a schematic of a shell-yolk SPION microgel hybrid particle.

DETAILED DESCRIPTION

Figure 2A:
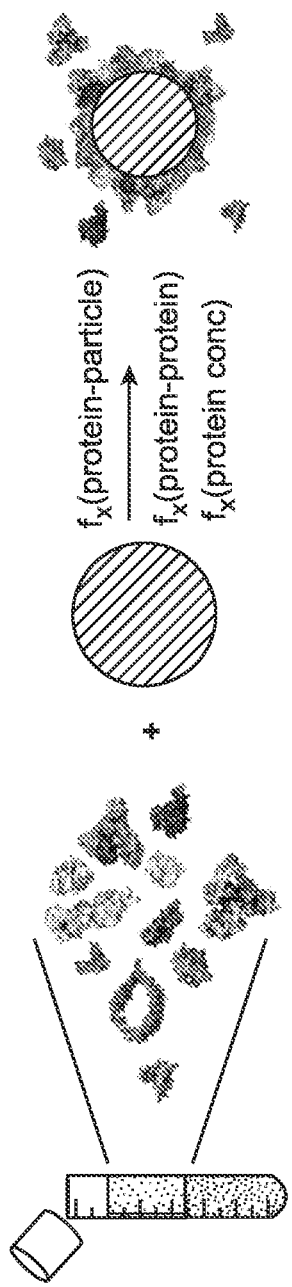
FIG. 2A shows the formation of protein corona on a particle. The profile of the protein corona depends on protein-particle, protein-protein, and protein concentration factors.
Figure 2B:
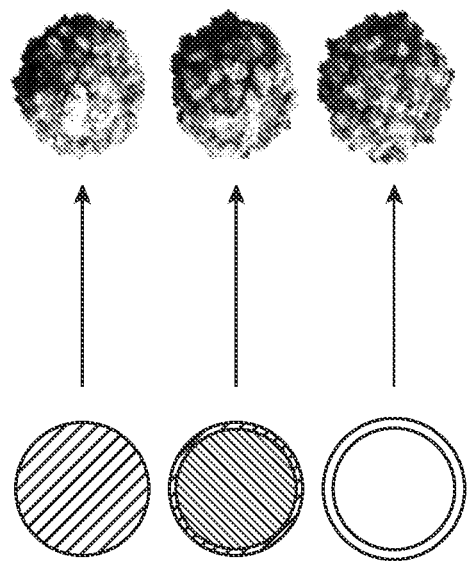
FIG. 2B shows the formation of protein corona on three different particles. In some cases, the particles may be nanoparticles. The properties of the particles result in different protein corona profiles.

Disclosed herein are compositions and methods of use thereof for assaying peptides and proteins in a sample in a simple and high throughput manner. The present disclosure provides particle panels of multiple distinct particle types, which enrich proteins from a sample onto distinct biomolecule coronas formed on the surface of the distinct particle types. The particle panels disclosed herein can be used in methods of corona analysis to detect thousands of proteins across a wide dynamic range in the span of hours.

Currently, there are a small number of protein-based biomarkers in use today for clinical diagnosis, and in spite of extensive efforts to analyze the plasma proteome for the expansion of markers, relatively few new candidates have been accepted as clinically useful tests. The plasma proteome contains >10,000 proteins and potentially an order of magnitude more protein isoforms with a concentration range spanning over 10 orders of magnitude (from mg/mL to pg/mL). These attributes, combined with a lack of convenient molecular tools for protein analytical work (such as copy- or amplification-mechanisms), make comprehensive studies of the plasma proteome exceptionally challenging. Approaches to overcome the broad dynamic range of proteins in biological samples are still for robust identification and quantification against a background of thousands of unique proteins and even more protein variants. However, there are no existing technologies that are capable of simultaneous measurement of proteins across the entire plasma concentration range in a format with a sufficient throughput and with a practical cost profile to allow for appropriately-sized studies with robust prospects for validation and replication. These challenges not only limit the discovery of protein-based biomarkers of disease but have been a bottleneck for the faster adoption of proteogenomics and protein annotation of genomic variants. Advances in mass spectrometry (MS) approaches along with development of improved data analytics have offered tools for deep and broad proteomic analysis. Several attempts have been made to substantially improve the detection of low abundance proteins, such as depletion of highly abundant proteins, plasma fractionation, peptide fractionation, and isobaric labeling. However, current approaches are fairly complex and time-consuming (days to weeks), and thus require a tradeoff between depth of protein coverage and sample throughput. Consequently, a simple and robust strategy for comprehensive and rapid analysis of the available body of information in the proteome remains an unmet need.

Additionally, the earlier a disease is diagnosed, the more likely that the disease can be cured or successfully managed leading to a better prognosis for the patient. When a disease is treated early, it may be possible to prevent or delay problems from the disease and may improve the outcomes for the patient, including extending the patient's life and/or quality of life. Early diagnosis of cancer is crucial, as many types of cancers can be successfully treated in their early stages. For example, five-year survival after early diagnosis and treatment of breast, ovarian, and lung cancers is 90%, 90%, and 70%, respectively, compared to 15%, 5%, and 10% for patients diagnosed at the most advanced stage of disease. Once cancer cells leave their tissue of origin, successful treatment using available established therapeutics becomes very unlikely. Although recognizing the warning signs of cancers and taking prompt action may lead to early diagnosis, the majority of cancers (e.g., lung) show symptoms only after cancer cells have already invaded the surrounding tissues and metastasized throughout the body. For example, more than 60% of patients with breast, lung, colon, and ovarian cancer have concealed or even metastatic colonies by the time their cancers are detected. Therefore, there is an urgent need for development of an effective approach for early detection of cancer. Such an approach should have the sensitivity to identify a cancer at various stages and the specificity to give a negative result when the person being tested is free of the cancer. There have been extensive efforts to develop methods for early detection of cancers; although huge numbers of risk factors and biomarkers have been introduced, a broadly relevant platform for early detection of a wide range of cancers remains elusive. As various types of cancers can change the composition of blood plasma—even in their early stages—one promising approach for early detection is molecular blood analysis for biomarkers. Although this strategy has already worked for a few cancers (like PSA for prostate cancer), there are not yet specific biomarkers for early detection of the majority of cancers. For such cancers (e.g., lung), none of the defined candidate circulating biomarkers has been clinically validated, and very few have reached late-stage clinical development. Therefore, there is an urgent need for novel approaches to improve our ability to detect cancer, as well as other diseases, at very early stages.

To meet the need for high throughput, simple assays for detecting proteins in a sample, which can be used to detect proteins associated a particular disease at very early stages—the present disclosure provides particle panels and methods for using said particle panels to assay for peptides and proteins in a sample (e.g., a complex, biological sample such as plasma) in a simple, rapid, and high throughput manner. In particular, the present disclosure provides particle panels of multiple distinct particle types, which enrich proteins from a sample onto distinct biomolecule coronas formed on the surface of the distinct particle types. The particle types included in the particle panels disclosed herein are particularly well suited to enriching for a high number of proteins across a wide dynamic range in an unbiased fashion. The combinations of particle types selected for inclusion in a particle panel of the present disclosure are varied in their physicochemical properties (e.g., size, surface charge, core material, shell material, surface chemistry, porosity, morphology, and other properties). However, particle types may also share several of said physicochemical properties. For example, a particle panel disclosed herein can include a first particle type and a second particle type, wherein the first particle type and the second particle type share at least two physicochemical properties and differ by at least two physicochemical properties, such that the first particle type and the second particle type are different. Importantly, the variation in at least one physicochemical property between a first particle type and a second particle type of the particle panel can lead to the formation of distinct coronas, which form on the corresponding distinct particle types. Thus, the selection of particle types for inclusion in a particle panel for use in the methods disclosed herein enables the high number of proteins that can be enriched across a wide dynamic range in a sample (e.g., plasma).

The particle panels of the present disclosure can include particle types that have magnetic properties, which allow for them to be easily separated after incubation in a complex biological sample. For example, the present disclosure provides superparamagnetic iron oxide nanoparticles (SPIONs), which have unique magnetic properties and can rapidly separate biomolecules, drug delivery and contrast agents in magnetic resonance imaging (MRI). Superparamagnetic particles can have a core of solely iron oxide (e.g., an iron oxide core) or can have small iron oxide crystals embedded in a polystyrene core.

The present disclosure provides methods that have been developed for synthesis of SPIONs. In an example, a thermal decomposition of iron oleate in a nonpolar solvent can be used to synthesize small size (usually <30 nm) monodisperse magnetic nanocrystals with high crystallinity. Those nanocrystals are hydrophobic and need to transfer to aqueous phase through the ligand exchange or chemical modifications. SPIONs generated using this method can meet requirement(s) for biomedical use. A solvothermal method is another way to synthesize SPIONs by reduction of iron (III) chloride with ethylene glycol. Highly water dispersible SPMNPs can be synthesized by a modified solvothermal approach using hydrophilic ligands such as citrate, polyacrylic acid (PAA) and polyvinylpyrrolidone (PVP). The particle surfaces can be further modified with different silanes which have functional groups via a Stöber process. The surface functionalities can also be achieved by a facile method through a surfactant-free seeded emulsion polymerization to form SPMNP@polymer composite particles.

Figure 22A:
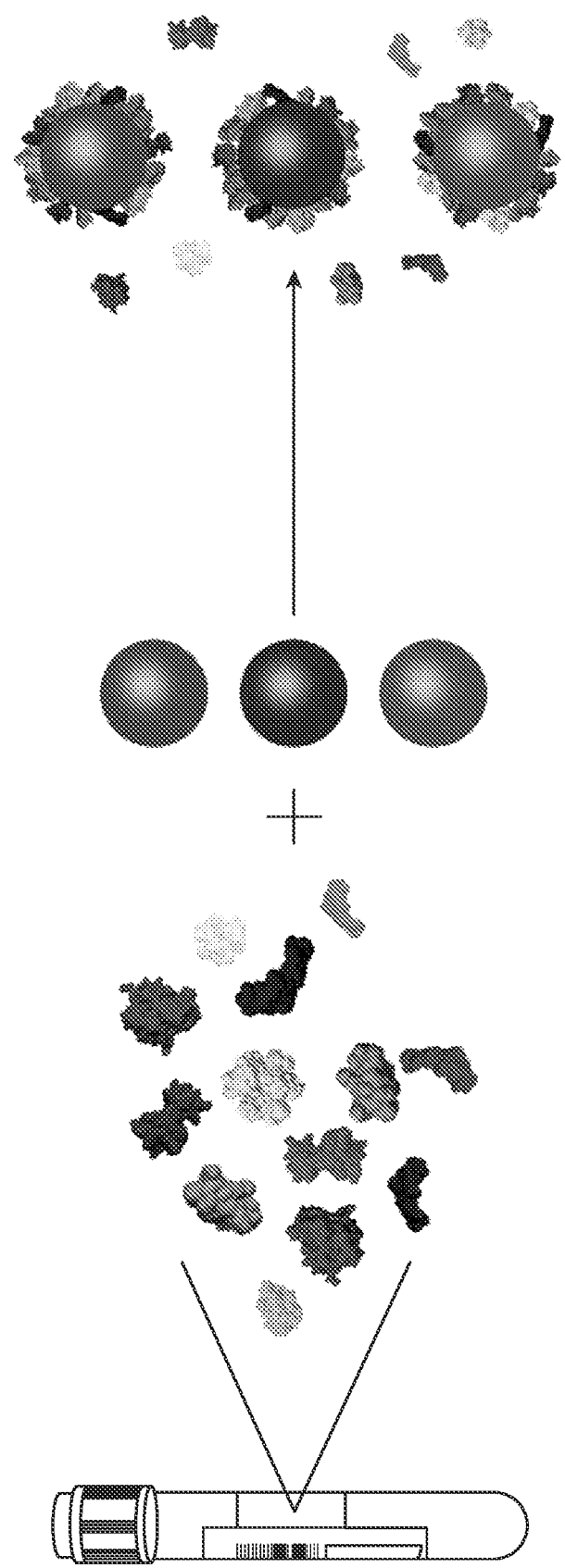
FIG. 22A-B illustrate a schematic of the formation of particle protein corona (FIG. 22A), and an embodiment of the present disclosure, the Proteograph platform workflow, based on multi-particle type protein corona approach and mass spectrometry for plasma proteome analysis (FIG. 22B).
Figure 22B:
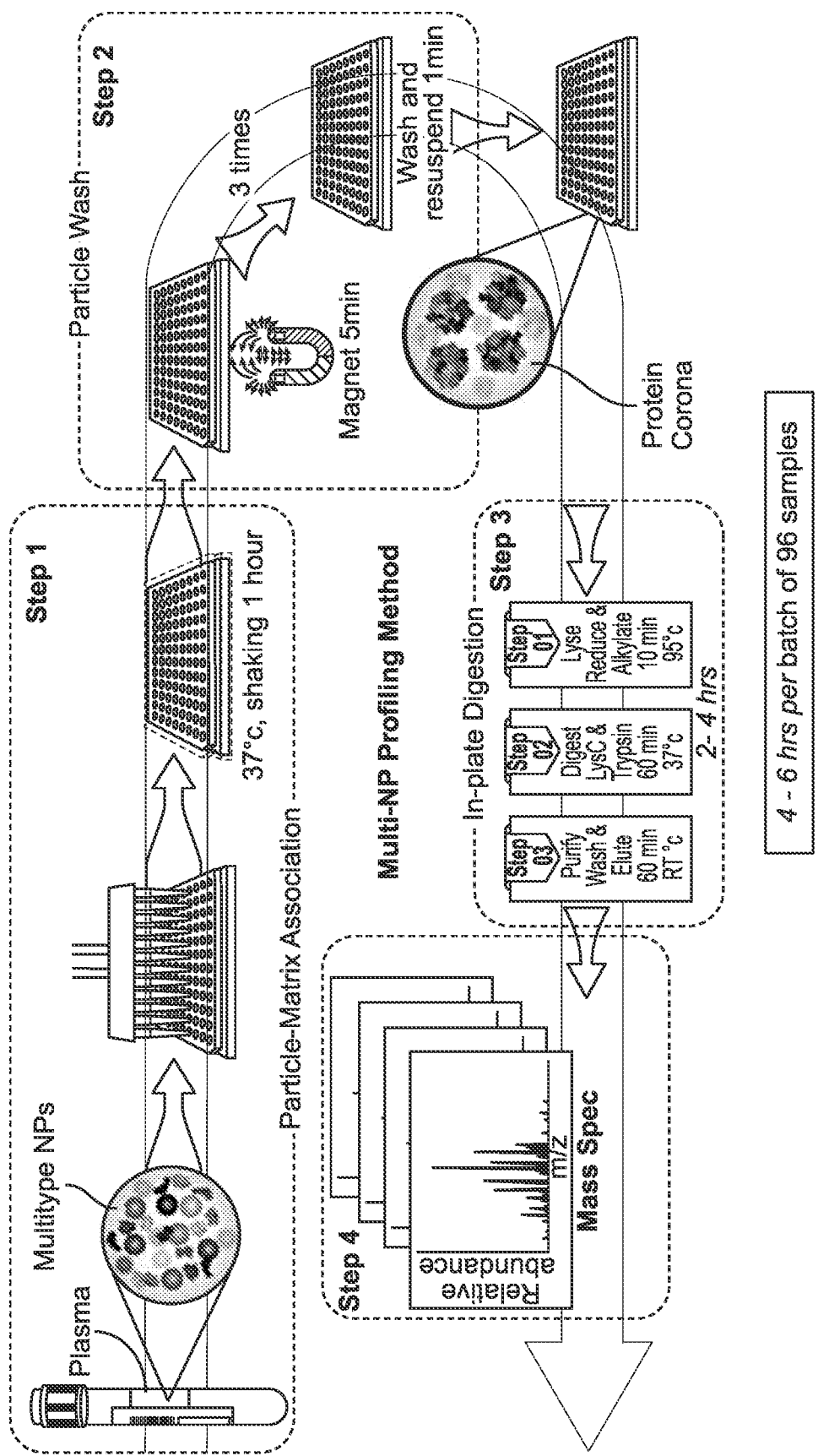

The present disclosure provides compositions, systems, and methods of use thereof for large-scale, high-throughput, efficient, and cost-effective proteomic profiling and machine learning. Disclosed herein is a scalable parallel protein identification and quantification technology for assaying proteins in a sample using a particle panel with distinct particle types to enrich proteins in distinct biomolecule coronas formed on the distinct particle types. "Biomolecule corona" as used herein can be used referred to interchangeably with the term "protein corona," and refers to the formation of a layer of proteins on the surface of a particle after the particle has been contacted with a sample (e.g., plasma). This method may be referred to interchangeably as corona analysis or, in some examples, "Proteograph" analysis (depicted in FIG. 22), which combines a multi-particle type protein corona strategy with mass spectrometry (MS). Particle types included in the particle panels disclosed herein can be superparamagnetic and are, thus, rapidly separated or isolated from unbound protein (proteins that have not adsorbed onto the surface of a particle to form the corona) in a sample, after incubation of the particle in the sample.

To date, particles have been poorly characterized for high-throughput translation proteomic analysis, due to steps in processing the proteins in the protein corona (e.g., centrifugation or membrane filtration to separate corona proteins from free plasma proteins and washing to remove loosely attached proteins from particles), which confound data and lack reproducibility and accuracy. The corona analysis (e.g., "Proteograph") methods disclosed herein can integrate overlapping but distinct particle type protein coronas with, for example, liquid chromatography-mass spectrometry (LC-MS) for potential use in large-scale efficient proteomic profiling and machine learning. The particle type platform can be unbiased (e.g., not limited to a predetermined analyte), and the MS data acquisition platform can be unbiased in terms of analyte measurement, both of which can be amenable to automation. The formation of a layer of proteins on the surface of particles upon their contact with plasma, which is referred to as protein corona (FIG. 22A) is disclosed herein as a method for identifying proteins. The composition and quantity of the corona proteins can depend on the physiochemical properties of the particle type, and changes in these engineered properties can result in reproducibly different proteins in the corona in terms of identity and/or quantity.

In some embodiments, the particles disclosed herein can be superparamagnetic iron oxide nanoparticles (SPIONS). SPIONs can be distinct from one another by being synthesized to have distinct surface chemistries. In some embodiments, SPIONs of different surface chemistries can be combined in analysis of proteins formed on their protein coronas. SPIONs, other particle types, or a combination thereof can be combined into panels of particle types that can be used for proteomic analysis of a sample.

In some embodiments, disclosed herein is a panel of three particle types with distinct surface chemistries, synthesized and used for the formation of protein corona, which can be rapidly separated by magnet from unbound proteins. Each particle type can reproducibly generate a unique protein corona pattern by capture of both high and low abundance proteins. For instance, by integrating the distinct proteomic profiles generated from at least three particle types, greater than 1,500 proteins of a single pooled colorectal cancer (CRC) plasma sample can be identified of which many can be FDA-cleared/approved biomarkers. For example, in some embodiments a screen of three particle types can detect over 1,500 proteins, of which 65 are FDA-cleared/approved biomarkers.

In some embodiments, the corona analysis workflow with Proteograph (FIG. 22B) can take ~4-6 hours to prepare a batch of 96 corona samples for MS analysis. The protein identification in the CRC pool can be done using just three total MS fractions analyzed in about one hour runs each, hence a total of about 3 hours MS time.

In some embodiments, three distinct particle types can be used identify greater than 1,500 proteins from a single pooled plasma within 8 hours including sample preparation and LC-MS, in contrast to less than 500 proteins without using the compositions, systems, and methods disclosed herein for using particle type corona strategy.

The corona analysis technology can be used to identify a disease. For example, the particles and methods of use thereof disclosed herein can be used to analyze serum samples from patients with non-small cell lung cancer (NSCLC) and age- and gender-matched healthy subjects. MS features can be discovered using this platform, including known and novel features that can distinguish between NSCLC and control samples. Thus, the corona analysis platform technology is capable of larger and more robust validation and replication studies. Moreover, the unique properties of the corona analysis for high-throughput and unbiased proteomic sampling can enable annotation of genomic data and application of machine learning classification methods. The multi-particle type protein corona-based platform technology described herein can facilitate efficient and comprehensive proteomics profiling, enabling larger-sized studies for biomarker discovery and validation.

In some embodiments, the compositions and methods of use thereof disclosed herein exhibit high assay accuracy, as demonstrated by addition of an increasing concentration of a reference, C-reactive protein (CRP), to plasma samples, and subsequent detection of CRP levels in the protein coronas, showing a slope of 0.9 (95% CI 0.81-0.98) for CRP levels in particle corona versus spiked plasma. In some embodiments, the median precision of the platform in assay replicates can be ~24 CV % across 8,738 measured MS features taken from three distinct particle type protein coronas.

SPIONs with distinct surface chemistries can be applied for protein corona analysis of a single pooled plasma sample. For instance, as down in the present disclosure, the resulting proteomic data demonstrates that increasing the number of particle types in a particle panel can result in the identification of more proteins (particularly low abundance proteins). The addition of more distinct particle types can lead to even broader and deeper proteome profiling. The compositions of particles disclosed herein and the panels of particle types comprising said different particle types can be tailored to profile the proteome at different levels of depth and breadth by varying the number and type of particles in the panels—analogous to different levels of coverage in gene sequencing.

The multi-particle type protein corona-based assay disclosed herein has shown several equally important features for plasma proteome analysis. As compared to conventional proteomic techniques that usually involve time-consuming depletion and fractionation workflows, the compositions and methods of use disclosed herein can avoid those complicated workflows and can be much faster. Notably, the corona analysis assay can be robustly automated, thus further increasing precision and reducing the amount of time required for sample analysis in, for example, a 96-well plate format. The corona analysis platform can sensitively measure differences between samples, while reducing the dynamic range of those comparisons, thus enabling more comparisons to be observed. The corona analysis technology can identify new biomarkers without targeting a pre-determined set of proteins. The scalability and efficiency of the corona analysis platform can be used for large proteomics studies, which can lead to deeper understanding of disease and biological mechanisms. For example, by adding proteomic data to multiomic data sets, and performing machine learning analyses, novel classifications can be generated and put into context genomic disease information that is not well-understood today, such as single nucleotide polymorphism (SNP) variants, changes in DNA methylation patterns and splice variants. Additionally, the technology can be extended to other biological fluids such as cerebrospinal fluid, cell lysate, and even tissue homogenate for rapid, accurate and precise profiling of proteomes, which can facilitate the discovery of new biomarkers for different diseases.

Methods for making superparamagnetic nanoparticles (SPMNPs) or superparamagnetic iron oxide particles (SPIONs) are disclosed herein. These particles and embodiments thereof can be used in a protein corona assay.

The methods and systems of the present disclosure improve proteomic analysis by simplifying sample preparation and MS data acquisition. The methods and systems perform sample preparation in about 5 steps in about 0.25 days and acquire MS data for about 12 fractions in about 0.5 days per sample.

The present disclosure provides compositions and methods of use thereof for assaying a sample for proteins. Compositions described herein include particle panels comprising one or more than one distinct particle types. Particle panels described herein can vary in the number of particle types and the diversity of particle types in a single panel. For example, particles in a panel may vary based on size, polydispersity, shape and morphology, surface charge, surface chemistry and functionalization, and base material. Panels may be incubated with a sample to be analyzed for proteins and protein concentrations. Proteins in the sample adsorb to the surface of the different particle types in the particle panel to form a protein corona. The exact protein and the concentration of protein that adsorbs to a certain particle type in the particle panel may depend on the composition, size, and surface charge of said particle type. Thus, each particle type in a panel may have different protein coronas due to adsorbing a different set of proteins, different concentrations of a particular protein, or a combination thereof. Each particle type in a panel may have mutually exclusive protein coronas or may have overlapping protein coronas. Overlapping protein coronas can overlap in protein identity, in protein concentration, or both.

The present disclosure also provides methods for selecting a particle types for inclusion in a panel depending on the sample type. Particle types included in a panel may be a combination of particles that are optimized for removal of highly abundant proteins. Particle types also consistent for inclusion in a panel are those selected for adsorbing particular proteins of interest. The particles can be nanoparticles. The particles can be microparticles. The particles can be a combination of nanoparticles and microparticles.

The present disclosure provides a method for selecting particle panels that exhibit broad coverage of proteins in a biological sample (e.g., a plasma sample). Particles are selected for inclusion in a particle panel using a combinatorial approach. Particles with a wide range of physicochemical properties are selected, for example, particles may vary by size, surface charge, core material, shell material, surface chemistry, porosity, morphology, and other properties. However, particles may also share several of said physicochemical properties. For example, a particle panel disclosed herein can include a first particle type and a second particle type, wherein the first particle type and the second particle type share at least two physicochemical properties and differ by at least two physicochemical properties, such that the first particle type and the second particle type are different. A particle panel disclosed herein can include a first particle type and a second particle type, wherein the first particle type and the second particle type share at least one physicochemical property and differ by at least two physicochemical properties, such that the first particle type and the second particle type are different. A particle panel disclosed herein can include a first particle type and a second particle type, wherein the first particle type and the second particle type share at least two physicochemical properties and differ by at least one physicochemical property, such that the first particle type and the second particle type are different. Non-limiting examples of physicochemical properties can include size, charge, core material, shell material, porosity, or surface hydrophobicity. Importantly, the variation in at least one physicochemical property between a first particle type and a second particle type of the particle panel can lead to the formation of distinct coronas, which form on the corresponding distinct particle types. For example, a first particle type and a second particle type, which vary in charge may each adsorb different proteins, different concentrations of the same proteins, or both different proteins and different concentrations of the same proteins. Thus, the first particle type and the second particle type would have distinct biomolecule coronas. Size is one example of a physicochemical property that may vary to yield this result. One or more than one physicochemical properties (e.g., size, charge, core material, shell material, porosity, or surface hydrophobicity, or any combination thereof) can vary to yield distinct biomolecule coronas. Other optimization parameters for selection of particle types for a panel may include any particular annotation set, for example interactome, secretome, FDA markers, proteins with clinically relevant genetic polymorphisms. As seen in TABLE 10 and TABLE 12, more than one of these particles are nanoparticles, but are made of different polymer coatings. As another example, more than one particle of TABLE 10 and TABLE 12 share similar surface charge and similar size but are made of different materials. As another example, more than one particle of TABLE 10 and TABLE 12_exhibit a porous surface. As another example, more than one particle of TABLE 10 and TABLE 12 exhibit a non-porous surface. As another example, more than one particle of TABLE 10 and TABLE 12 exhibit a carboxylate coated surface. As another example, more than one particle of TABLE 10 and TABLE 12 exhibit an amine coated surface. With all the many combinations of particles and particle types that can be in a particle panel, it is surprising and unexpected that the particle panels disclosed herein were capable of identifying a large number of proteins (e.g., plasma proteins) in a sample (e.g., a plasma sample) over a wide dynamic range in an unbiased manner, and were able to be used in a method of assaying proteins in a sample with a high level of reproducibility (e.g., quantile normalized coefficient of variation <20%).

The present disclosure provides over 200 distinct particle types, with over 100 different surface chemistries and over 50 diverse physical properties. In particular, over 23 particle types have been characterized for use in a method of assaying proteins in a sample. Each of these particle types can be combined with other particle types in panels that are designed to optimally assay a particular protein of interest or to optimally identify biomarkers for a disease of interest. Panels can include any number of these particle types or any combination of particle types, and the variety of particle types disclosed herein can enable assaying and detection of a wide range of proteins with varying physicochemical properties.

In some embodiments, the present disclosure provides method of identifying proteins in a sample, the method comprising: incubating a panel comprising a plurality of particle types with the sample to form a plurality of protein corona; digesting the plurality of protein coronas to generate proteomic data; and identifying proteins in the sample by quantifying the proteomic data.

Particle Materials

The particle panels disclosed herein may comprise particle types made of a variety of different materials. Panels can be assembled with specific types of particles to identify a broad range of proteins in the sample, or to selectively assay for a particular protein or set of proteins of interest. The particle types may include, for example, nanoparticles (NPs), microparticles, magnetic particles (MPs), magnetic nanoparticles (MNPs), superparamagnetic iron oxide nanoparticles (SPIONs), or superparamagnetic nanoparticles (SPMNPs). Particles described herein may be magnetic particles. Magnetic particles herein may be superparamagnetic particles (SPMP), superparamagnetic nanoparticles (SPMNP), superparamagnetic iron oxide particles (SPIOP), or superparamagnetic iron oxide nanoparticles (SPION). In some cases, a SPMNP may be a SPION. Magnetism can be conferred via iron oxide core or iron oxide crystals grafted to particle. In some cases, we refer herein to SPMNP, which is a magnetic particle. SPMNP can also be synthesized to be a SPMP.

Particles can be made from various materials. For example, particles may be made of a polymer, a lipid, a metal, silica, a protein, a nucleic acid, a small molecule, or a large molecule. For example, particle materials consistent with the present disclosure include metals, metal oxides, magnetic materials, polymers, and lipids. Examples of metal materials include any one of or any combination of gold, silver, copper, nickel, cobalt, palladium, platinum, iridium, osmium, rhodium, ruthenium, rhenium, vanadium, chromium, manganese, niobium, molybdenum, tungsten, tantalum, iron and cadmium, or any other material described in U.S. Pat. No. 7,749,299. Metal oxide particles may be iron oxide particles or titanium oxide particles. Magnetic particles may be iron oxide nanoparticles.

Examples of polymers include any one of or any combination of polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), polystyrene, or a copolymer of two or more polymers, such as a copolymer of a polyalkylene glycol (e.g., PEG) and a polyester (e.g., PLGA). In some embodiments, the polymer is a lipid-terminated polyalkylene glycol and a polyester, or any other material disclosed in U.S. Pat. No. 9,549,901, which is incorporated by reference in its entirety herein.

Examples of lipids that can be used to form the particles of the present disclosure include cationic, anionic, and neutrally charged lipids. For example, particles can be made of any one of or any combination of dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleoylphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, and cholesterol, or any other material listed in U.S. Pat. No. 9,445,994, which is incorporated by reference in its entirety herein.

Figure 37A:
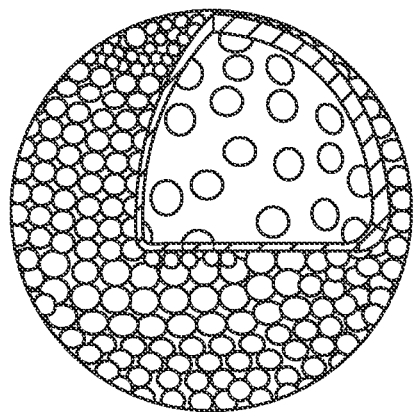
FIGS. 37A-37C show various particle types that may be included in panels disclosed herein.

The particle panels disclosed herein may include specific particle types having structures that are particularly amenable to sampling proteins of a specific size, which are present in a sample. For example, the particle panel may include a hollow magnetic particle, as shown in FIG. 37A. The hollow magnetic particle comprises a nanoparticle with a hollow core, wherein the nanoparticle shell is made of smaller primary iron oxide crystals. Hollow magnetic particles may be synthesized by an autoclave reaction based on hydrothermal treatment of $FeCl_3$, citrate, polyacrylamide or sodium polyacrylate, and urea as described in Cheng, Wei, et al. ("One-step synthesis of superparamagnetic monodisperse porous $Fe_3O_4$ hollow and core-shell spheres." Journal of Materials Chemistry 20.9 (2010): 1799-1805), which is incorporated herein by reference in its entirety. The nanoparticle shell made of the smaller primary iron oxide crystals is porous, allowing the generation of protein coronas on the surface of the nanoparticle via size exclusive effects. Binding surfaces can be primarily inside pores, thus preventing large proteins from diffusing into the particle and binding. In some cases, large proteins may still bind to the outside and included in the overall corona, but these hollow particles can enrich smaller proteins over larger ones. These hollow magnetic particles may be included in any particle panel described herein and is still easily separated from unbound protein using a magnet.

Figure 37B:
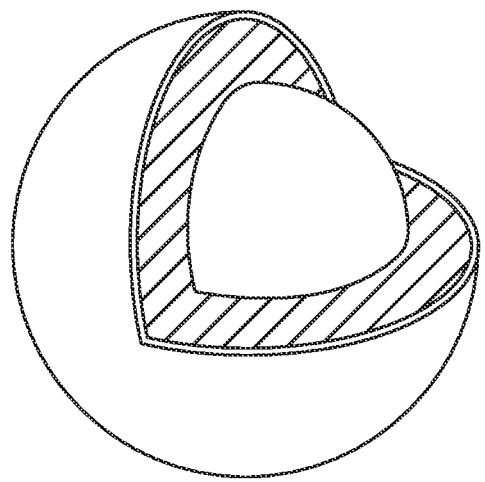

As another example, the particle panel may include a nanoparticle with a hydrophobic pocket as shown in FIG. 37B. The nanoparticle with a hydrophobic pocket is particularly amenable for sampling a molecule or protein of a specific solubility (e.g., a poorly soluble protein), which are present in a sample. A nanoparticle with a hydrophobic pocket has a structure of a superparamagnetic iron oxide core and additionally has a polymeric coating. Nanoparticles with hydrophobic pockets can be synthesized using an autoclave reaction for SPION core synthesis, as described elsewhere herein, followed by a free radical polymerization for synthesizing a poly(glycidyl methacrylate) coating. This may be further followed by post-synthetic modification of the surface with hydrophobic amines, such as a benzyl amine moiety. These nanoparticles with a hydrophobic pocket are particularly well suited to capturing small molecules for metabolomics. The pore size of the nanoparticle can be modulated to exclude proteins to that only small molecules interact with the hydrophobic pockets. In some embodiments, pore size can be tuned during synthesis. For example, the synthesis may include swelling the particle to create porosity and the degree of swelling can impact the pore size. As another example, an erosion technique can be used to carve out different pores in a particle type with a more solid surface. Protein targets may also be sampled using the nanoparticles with a hydrophobic pocket.

Figure 37C:
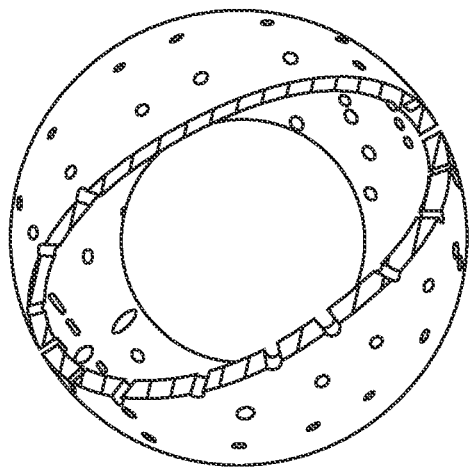

In another example, the particle panel may include a shell-yolk SPION microgel hybrid nanoparticle, as shown in FIG. 37C. A shell-yolk SPION microgel hybrid nanoparticle has a structure of a SPION exterior and a microgel interior. Shell-yolk SPION microgel hybrid nanoparticles can be synthesized using an autoclave reaction based on hydrothermal treatment of $FeCl_3$, citrate, polyacrylamide or sodium polyacrylate, and urea as described in Cheng et al. ("One-step synthesis of superparamagnetic monodisperse porous $Fe_3O_4$ hollow and core-shell spheres." Journal of Materials Chemistry 20.9 (2010): 1799-1805) and Zou et al. ("Facile synthesis of highly water-dispersible and monodispersed $Fe_3O_4$ hollow microspheres and their application in water treatment." RSC Advances 3.45 (2013): 23327-23334). In a second step of the synthesis, a hydrogel is formed inside the hollow nanoparticle.

Figure 38:
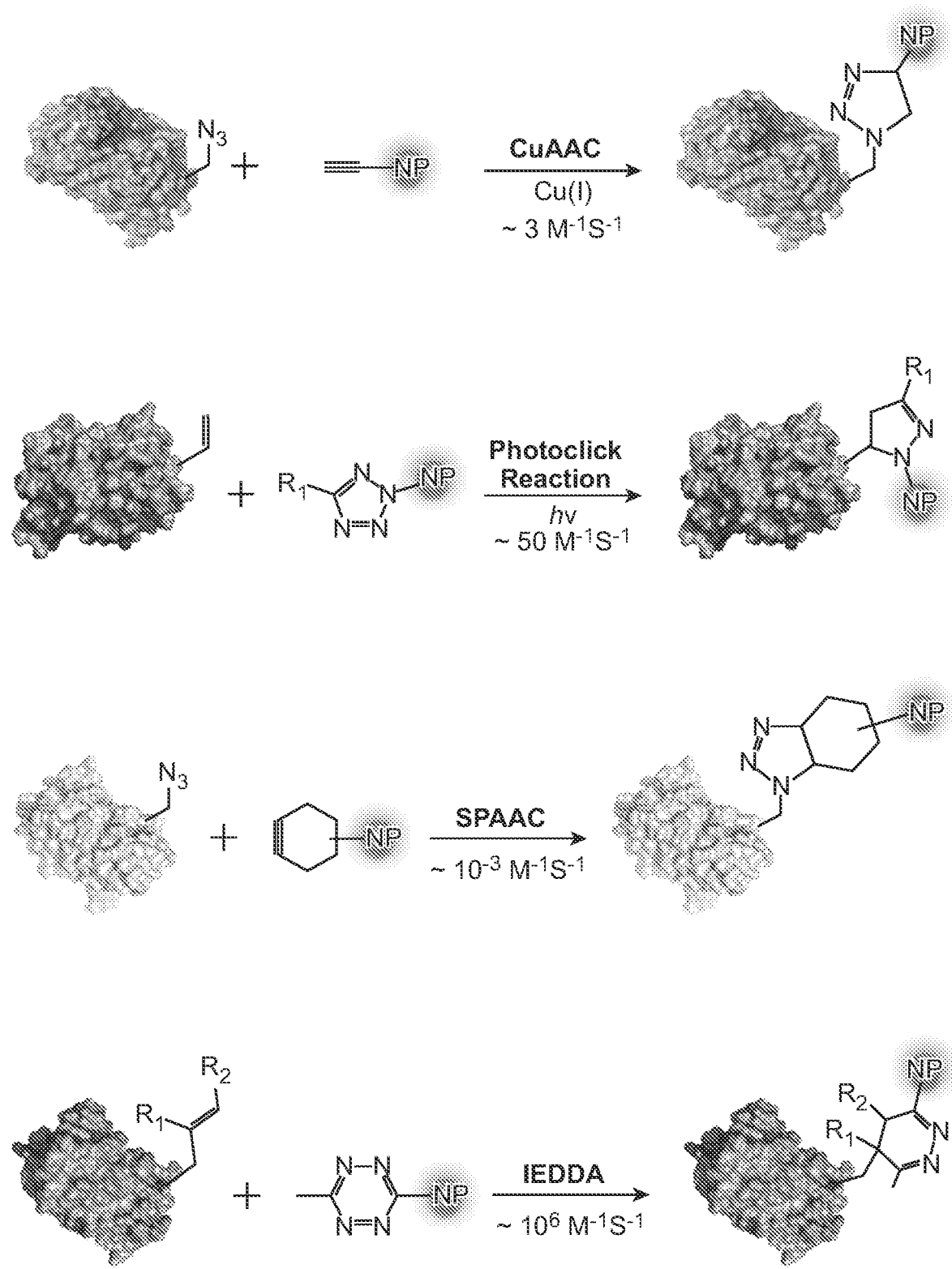
FIG. 38 shows a schematic of particle surfaces engineered to capture proteins and/or peptides, adapted from Mol. Cells 2019, 42(5), 386-396.

In another example, the particle panel may include a particle surface that is engineered to capture proteins and/or peptides. A primary layer of proteins may form an initial corona on the particle surface either non-covalently or covalently. Direct non-covalent interactions with the particle surface may include ionic bonds, hydrophobic bonds, and hydrogen bonds. Additionally, these particles, which can be initially modified with small chemical entities, can bind other proteins in the plasma after formation of a primary protein corona. Modulating the chemical modifications present at the surface of the particle can be employed to tune the non-covalent interactions between the particle surface and peptides and/or proteins in a sample. Alternatively, or additionally, the solution phase composition (e.g., pH) can be modulated to tune the non-covalent interactions between the particles and peptides and/or proteins in a sample. Covalent coupling of proteins and/or peptides to the surface of particles may be performed by introducing a reactive group (e.g., an NHS ester, a maleimide, a carboxylate, etc.) to the surface of the particle. Thus, an NHS-ester bearing particle may be particularly amenable to sampling one or more proteins in solution. Alternatively, a coupling reagent that can sample and bind proteins out of a complex mixture may be a photoinitiated reactant group, which can react with proteins only after exposure to photons of a given wavelength (e.g., UV) and intensity. Advantages of utilizing particles functionalized with said photoinitiated reactive group can include, but are not limited to: (1) locking in the primary protein corona without loss of proteins during the step of washing the particles and/or loss of proteins due to displacement by higher affinity proteins, (2) capturing proteins with intermediate binding affinities because the covalent linkage can be established at any time during the binding process, (3) generating a wider range of surfaces than would result at equilibrium, and (4) generating surfaces with certain protein stoichiometry by use of defined protein mixtures (instead of plasma) for binding. A defined protein mixture can be any synthetically-derived or purified mixture of proteins, obtained or made recombinantly or isolated and then mixed with a defined stoichiometry. For example, for a particular protein of interest for protein-protein interactions (e.g., ubiquitin), the defined protein mixture may be a simple solution of that protein. As another example, the defined protein mixture can be a purified or enriched set of proteins from a certain class of interest (e.g., glycosylated proteins). Particles may also be modified to be functionalized with one half of a click-chemistry reaction pair and unnatural point mutated proteins in a sample contain an amino acid with the other half of the click-chemistry reaction pair. Particles and other proteins in a sample can be functionalized with one half of a click-chemistry reaction pair and unnatural point mutated proteins in a sample contain an amino acid with the other half of the click-chemistry reaction pair. In the presence of a chemical catalyst (e.g., copper) or light (e.g., a photoinitiated click chemistry reagent), the reaction is carried out leading to linkage of particles to the unnatural point mutated proteins in the sample and/or linkage of the unnatural point mutated proteins in the sample and other proteins in the samples. For example, the method may start with a simple solution of proteins that may contain a mutated protein that is enriched in the sample. The main advantage of these systems is that the surface of the particles can be engineered with respect to stoichiometry, protein/surface orientation, and protein/protein orientation. This allows for engineering of durable surfaces that can withstand assay steps described elsewhere herein (e.g., extensive washing). For example, proteins with specific unnatural amino acids at a location of interest in the protein sequence can be introduced as described in Lee et al. (Mol Cells. 2019 May 31; 42(5):386-396. doi: 10.14348/molcells.2019.0078.). The unnatural amino acid that is introduced into the protein can have one half of the click-chemistry pair that can react to the other half of the click-chemistry pair on the surface of the particle. In this manner, the rather than random adsorption of proteins to the surface of a particle to form the corona, these modified proteins can bind to the surface of the particle in a particular orientation. The result is that the corona that forms on the surface of a particle type can be tuned with the proteins engineered in a specific 3-D orientation that is controlled. This same general methodology can be used to link protein complexes to the surface of the particle type. Here, one or more subunits of the complex can be modified to be covalently linked together then linked to the surface of a particle type either in a second step of the synthesis or using a different chemistry, which can be performed later in the particle surface modification process. A schematic is shown in FIG. 38. Particles that have a surface engineered to non-covalently or covalently capture proteins and/or peptides may still be SPION or polymer-modified SPION particles, which can be synthesized in a variety of ways including standard SPION synthesis via solvothermal methods, ligand exchange processes, silica coating processes, and/or activation or installation of a specific reagent coupling strategy. Advantages of these systems include biosurface generation, exploitation of interactome, and directed corona assembly.

As another example, the particle panel may include functionalized particles for histone capture. For example, these particles may be anionic. Additionally, or alternatively, the assay conditions may be optimized to enrich for histones in a sample and labeling techniques may be optimized to improve mass spectrometry detection for histones and post translational modifications. These functionalized particles for histone capture may be made of polymers, silica, target ligand, and or any combination thereof. Functionalized particles can be synthesized using a variety of approaches including standard SPION synthesis via solvothermal methods, ligand exchange processes, surface-initiated polymerization. Anionic particles surfaces can be synthesized by functionalizing the surfaces with polymers such as polycarboxylate, various ligand such as dendrimers, branched ligand, or carboxylate derivatives, and/or sulfanilamide acids. Optimization of assay conditions may include buffering the binding solution to a pH of about 9. While many proteins would exhibit diminished binding to an anionic surface at this pH, histones are basic proteins with a primary sequence having a pI~11 (e.g., H4_Human pI~11.3, H3_Human pI~11) and, this, will remain almost entirely positively charged. As a result, under basic pH conditions, histones can strongly interact with particle surfaces via ionic bonds and can, thus, be selectively enriched on particle surfaces. Additionally, histones may be selectively enriched on particle surfaces by modifying particle surfaces with histone binding proteins. Thus, a histone protein corona can be obtained using the particles disclosed herein. Optimizing labeling methodologies can help simplify the interpretation of mass spectrometry data and allow for improvements in post-translational modification (PTM) identification and assignment. As the type, location, and occupancy of a post-translational modification on a histone can be different and can help regulate gene expression, these particles can be useful for selectively enriching histones in a sample and interrogate the PTM, thus providing information about the how genes in a sample are being regulated. This may in turn help inform various disease conditions in which regulation of gene expression is aberrant.

Examples of particle types consistent with the present disclosure are shown in FIG. 21 and in TABLE 1 below.

TABLE 1

Particle Types

| P# | Description |
| --- | --- |
| HX-13 or SP-001 | Carboxylate (Citrate) |
| HX-19 or SP-002 | Phenol-formaldehyde resin coated |
| HX-31 or SP-004 | Polystyrene coated |
| HX-38 or SP-005 | Carboxylated Poly(styrene-co-methacrylic acid), P(St-co-MAA) |
| HX-42 or SP-006 | N-(3-Trimethoxysilylpropyl)diethylenetriamine coated |
| HX-57 or SP-008 | 1,2,4,5-Benzenetetracarboxylic acid coated |
| HX-58 or SP-009 | Vinylbenzyltrimethylammonium chloride (PVBTMAC) coated |
| HX-59 or SP-010 | Carboxylated, Poly(acrylic acid), PAA |
| SP-333 | Carboxylate microparticle, surfactant free |
| SP-339 | Polystyrene carboxyl functionalized |
| SP-341 | Carboxylic acid, 150 nm |
| SP-347 | Silica coated, 200 nm |
| SP-348 | Carboxylic acid |
| SP-353 | Amino surface microparticle, 0.4-0.6 μm |
| SP-356 | Silica amino functionalized microparticle, 0.1-0.39 μm |
| SP-363 | Jeffamine surface, 0.1-0.39 μm |
| SP-364 | Polystyrene microparticle, 2.0-2.9 μm |
| SP-365 | Silica |
| SP-369 | Carboxylated Original coating, 50 nm |
| SP-373 | Dextran based coating, 0.13 μm |
| SP-374 | Silica Silanol coated with lower acidity |

TABLE 1-continued

Particle Types

| P# | Description |
|---|---|
| HX-20 or SP-003 | Silica-coated superparamagnetic iron oxide NPs (SPION) |
| HX-56 or SP-007 | poly(N-(3-(dimethylamino)propyl) methacrylamide) (PDMAPMA)-coated SPION |
| HX-86 or SP-011 | poly(oligo(ethylene glycol) methyl ether methacrylate) (POEGMA)-coated SPION |

Properties of Particles

Particles that are consistent with the present disclosure can be made and used in methods of forming protein coronas after incubation in a biofluid at a wide range of sizes. For example, the particles disclosed herein can have a diameter of at least 10 nm, at least 100 nm, at least 200 nm, at least 300 nm, at least 400 nm, at least 500 nm, at least 600 nm, at least 700 nm, at least 800 nm, at least 900 nm, at least 1000 nm, at least 1100 nm, at least 1200 nm, at least 1300 nm, at least 1400 nm, at least 1500 nm, at least 1600 nm, at least 1700 nm, at least 1800 nm, at least 1900 nm, at least 2000 nm, at least 2100 nm, at least 2200 nm, at least 2300 nm, at least 2400 nm, at least 2500 nm, at least 2600 nm, at least 2700 nm, at least 2800 nm, at least 2900 nm, at least 3000 nm, at least 3100 nm, at least 3200 nm, at least 3300 nm, at least 3400 nm, at least 3500 nm, at least 3600 nm, at least 3700 nm, at least 3800 nm, at least 3900 nm, at least 4000 nm, at least 4100 nm, at least 4200 nm, at least 4300 nm, at least 4400 nm, at least 4500 nm, at least 4600 nm, at least 4700 nm, at least 4800 nm, at least 4900 nm, at least 5000 nm, at least 5100 nm, at least 5200 nm, at least 5300 nm, at least 5400 nm, at least 5500 nm, at least 5600 nm, at least 5700 nm, at least 5800 nm, at least 5900 nm, at least 6000 nm, at least 6100 nm, at least 6200 nm, at least 6300 nm, at least 6400 nm, at least 6500 nm, at least 6600 nm, at least 6700 nm, at least 6800 nm, at least 6900 nm, at least 7000 nm, at least 7100 nm, at least 7200 nm, at least 7300 nm, at least 7400 nm, at least 7500 nm, at least 7600 nm, at least 7700 nm, at least 7800 nm, at least 7900 nm, at least 8000 nm, at least 8100 nm, at least 8200 nm, at least 8300 nm, at least 8400 nm, at least 8500 nm, at least 8600 nm, at least 8700 nm, at least 8800 nm, at least 8900 nm, at least 9000 nm, at least 9100 nm, at least 9200 nm, at least 9300 nm, at least 9400 nm, at least 9500 nm, at least 9600 nm, at least 9700 nm, at least 9800 nm, at least 9900 nm, at least 10000 nm or from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm, from 10 to 100 nm, from 100 to 200 nm, from 200 to 300 nm, from 300 to 400 nm, from 400 to 500 nm, from 500 to 600 nm, from 600 to 700 nm, from 700 to 800 nm, from 800 to 900 nm, from 900 to 1000 nm, from 1000 to 1100 nm, from 1100 to 1200 nm, from 1200 to 1300 nm, from 1300 to 1400 nm, from 1400 to 1500 nm, from 1500 to 1600 nm, from 1600 to 1700 nm, from 1700 to 1800 nm, from 1800 to 1900 nm, from 1900 to 2000 nm, from 2000 to 2100 nm, from 2100 to 2200 nm, from 2200 to 2300 nm, from 2300 to 2400 nm, from 2400 to 2500 nm, from 2500 to 2600 nm, from 2600 to 2700 nm, from 2700 to 2800 nm, from 2800 to 2900 nm, from 2900 to 3000 nm, from 3000 to 3100 nm, from 3100 to 3200 nm, from 3200 to 3300 nm, from 3300 to 3400 nm, from 3400 to 3500 nm, from 3500 to 3600 nm, from 3600 to 3700 nm, from 3700 to 3800 nm, from 3800 to 3900 nm, from 3900 to 4000 nm, from 4000 to 4100 nm, from 4100 to 4200 nm, from 4200 to 4300 nm, from 4300 to 4400 nm, from 4400 to 4500 nm, from 4500 to 4600 nm, from 4600 to 4700 nm, from 4700 to 4800 nm, from 4800 to 4900 nm, from 4900 to 5000 nm, from 5000 to 5100 nm, from 5100 to 5200 nm, from 5200 to 5300 nm, from 5300 to 5400 nm, from 5400 to 5500 nm, from 5500 to 5600 nm, from 5600 to 5700 nm, from 5700 to 5800 nm, from 5800 to 5900 nm, from 5900 to 6000 nm, from 6000 to 6100 nm, from 6100 to 6200 nm, from 6200 to 6300 nm, from 6300 to 6400 nm, from 6400 to 6500 nm, from 6500 to 6600 nm, from 6600 to 6700 nm, from 6700 to 6800 nm, from 6800 to 6900 nm, from 6900 to 7000 nm, from 7000 to 7100 nm, from 7100 to 7200 nm, from 7200 to 7300 nm, from 7300 to 7400 nm, from 7400 to 7500 nm, from 7500 to 7600 nm, from 7600 to 7700 nm, from 7700 to 7800 nm, from 7800 to 7900 nm, from 7900 to 8000 nm, from 8000 to 8100 nm, from 8100 to 8200 nm, from 8200 to 8300 nm, from 8300 to 8400 nm, from 8400 to 8500 nm, from 8500 to 8600 nm, from 8600 to 8700 nm, from 8700 to 8800 nm, from 8800 to 8900 nm, from 8900 to 9000 nm, from 9000 to 9100 nm, from 9100 to 9200 nm, from 9200 to 9300 nm, from 9300 to 9400 nm, from 9400 to 9500 nm, from 9500 to 9600 nm, from 9600 to 9700 nm, from 9700 to 9800 nm, from 9800 to 9900 nm, from 9900 to 10000 nm. The diameter can be measured by dynamic light scattering (DLS) as an indirect measure of size. The DLS measurement can be an 'intensity-weighted' average, which means the size distribution that the mean is calculated from can be weighted by the sixth power of radius. This can be referred to herein as 'z-average' or 'intensity-mean'.

Alternatively, particles disclosed herein can have a radius of at least 10 nm, at least 100 nm, at least 200 nm, at least 300 nm, at least 400 nm, at least 500 nm, at least 600 nm, at least 700 nm, at least 800 nm, at least 900 nm, at least 1000 nm, at least 1100 nm, at least 1200 nm, at least 1300 nm, at least 1400 nm, at least 1500 nm, at least 1600 nm, at least 1700 nm, at least 1800 nm, at least 1900 nm, at least 2000 nm, at least 2100 nm, at least 2200 nm, at least 2300 nm, at least 2400 nm, at least 2500 nm, at least 2600 nm, at least 2700 nm, at least 2800 nm, at least 2900 nm, at least 3000 nm, at least 3100 nm, at least 3200 nm, at least 3300 nm, at least 3400 nm, at least 3500 nm, at least 3600 nm, at least 3700 nm, at least 3800 nm, at least 3900 nm, at least 4000 nm, at least 4100 nm, at least 4200 nm, at least 4300 nm, at least 4400 nm, at least 4500 nm, at least 4600 nm, at least 4700 nm, at least 4800 nm, at least 4900 nm, at least 5000 nm, at least 5100 nm, at least 5200 nm, at least 5300 nm, at least 5400 nm, at least 5500 nm, at least 5600 nm, at least 5700 nm, at least 5800 nm, at least 5900 nm, at least 6000 nm, at least 6100 nm, at least 6200 nm, at least 6300 nm, at least 6400 nm, at least 6500 nm, at least 6600 nm, at least 6700 nm, at least 6800 nm, at least 6900 nm, at least 7000 nm, at least 7100 nm, at least 7200 nm, at least 7300 nm, at least 7400 nm, at least 7500 nm, at least 7600 nm, at least 7700 nm, at least 7800 nm, at least 7900 nm, at least 8000 nm, at least 8100 nm, at least 8200 nm, at least 8300 nm, at least 8400 nm, at least 8500 nm, at least 8600 nm, at least 8700 nm, at least 8800 nm, at least 8900 nm, at least 9000 nm, at least 9100 nm, at least 9200 nm, at least 9300 nm, at least 9400 nm, at least 9500 nm, at least 9600 nm, at least 9700 nm, at least 9800 nm, at least 9900 nm, at least 10000 nm or from 10 nm to 50 nm, from 50 nm to 100 nm, from 100 nm to 150 nm, from 150 nm to 200 nm, from 200 nm to 250 nm, from 250 nm to 300 nm, from 300 nm to 350 nm, from 350 nm to 400 nm, from 400 nm to 450 nm, from 450 nm to 500 nm, from 500 nm to 550 nm, from 550 nm to 600 nm, from 600 nm to 650 nm, from 650 nm to 700 nm, from 700 nm to 750 nm, from 750 nm to 800 nm, from 800 nm to 850 nm, from 850 nm to 900 nm, from 100 nm to 300 nm, from 150 nm to 350 nm, from 200 nm to 400 nm, from 250 nm to 450 nm, from 300 nm to 500 nm, from 350 nm to 550 nm, from 400 nm to 600 nm, from 450 nm to 650 nm, from 500 nm to 700 nm, from 550 nm to 750 nm, from 600 nm to 800 nm, from 650 nm to 850 nm, from 700 nm to 900 nm, or from 10 nm to 900 nm, from 10 to 100 nm, from 100 to 200 nm, from 200 to 300 nm, from 300 to 400 nm, from 400 to 500 nm, from 500 to 600 nm, from 600 to 700 nm, from 700 to 800 nm, from 800 to 900 nm, from 900 to 1000 nm, from 1000 to 1100 nm, from 1100 to 1200 nm, from 1200 to 1300 nm, from 1300 to 1400 nm, from 1400 to 1500 nm, from 1500 to 1600 nm, from 1600 to 1700 nm, from 1700 to 1800 nm, from 1800 to 1900 nm, from 1900 to 2000 nm, from 2000 to 2100 nm, from 2100 to 2200 nm, from 2200 to 2300 nm, from 2300 to 2400 nm, from 2400 to 2500 nm, from 2500 to 2600 nm, from 2600 to 2700 nm, from 2700 to 2800 nm, from 2800 to 2900 nm, from 2900 to 3000 nm, from 3000 to 3100 nm, from 3100 to 3200 nm, from 3200 to 3300 nm, from 3300 to 3400 nm, from 3400 to 3500 nm, from 3500 to 3600 nm, from 3600 to 3700 nm, from 3700 to 3800 nm, from 3800 to 3900 nm, from 3900 to 4000 nm, from 4000 to 4100 nm, from 4100 to 4200 nm, from 4200 to 4300 nm, from 4300 to 4400 nm, from 4400 to 4500 nm, from 4500 to 4600 nm, from 4600 to 4700 nm, from 4700 to 4800 nm, from 4800 to 4900 nm, from 4900 to 5000 nm, from 5000 to 5100 nm, from 5100 to 5200 nm, from 5200 to 5300 nm, from 5300 to 5400 nm, from 5400 to 5500 nm, from 5500 to 5600 nm, from 5600 to 5700 nm, from 5700 to 5800 nm, from 5800 to 5900 nm, from 5900 to 6000 nm, from 6000 to 6100 nm, from 6100 to 6200 nm, from 6200 to 6300 nm, from 6300 to 6400 nm, from 6400 to 6500 nm, from 6500 to 6600 nm, from 6600 to 6700 nm, from 6700 to 6800 nm, from 6800 to 6900 nm, from 6900 to 7000 nm, from 7000 to 7100 nm, from 7100 to 7200 nm, from 7200 to 7300 nm, from 7300 to 7400 nm, from 7400 to 7500 nm, from 7500 to 7600 nm, from 7600 to 7700 nm, from 7700 to 7800 nm, from 7800 to 7900 nm, from 7900 to 8000 nm, from 8000 to 8100 nm, from 8100 to 8200 nm, from 8200 to 8300 nm, from 8300 to 8400 nm, from 8400 to 8500 nm, from 8500 to 8600 nm, from 8600 to 8700 nm, from 8700 to 8800 nm, from 8800 to 8900 nm, from 8900 to 9000 nm, from 9000 to 9100 nm, from 9100 to 9200 nm, from 9200 to 9300 nm, from 9300 to 9400 nm, from 9400 to 9500 nm, from 9500 to 9600 nm, from 9600 to 9700 nm, from 9700 to 9800 nm, from 9800 to 9900 nm, from 9900 to 10000 nm.

In certain examples, the particles disclosed herein have a diameter of 100 nm to 400 nm. In other examples, the particles disclosed herein have a radius of 100 nm to 400 nm. Particle size can be determined by a number of techniques, such as dynamic light scattering or electron microscopy (e.g., SEM, TEM). Particles disclosed herein can be nanoparticles or microparticles.

Additionally, particles can have a homogenous size distribution or a heterogeneous size distribution. Polydispersity index (PDI), which can be measured by techniques such as dynamic light scattering, is a measure of the size distribution. A low PDI indicates a more homogeneous size distribution and a higher PDI indicates a more heterogeneous size distribution. For example, particles disclosed herein can have a PDI of less than 0.5, less than 0.4, less than 0.3, less than less than 0.15, or less than 0.1. In particular embodiments, the particles disclosed herein have a PDI of less than 0.1.

Particles disclosed herein can have a range of different surface charges. Particles can be negatively charged, positively charged, or neutral in charge. In some embodiments, particles have a surface charge of −500 mV to −450 mV, −450 mV to −400 mV, −400 mV to −350 mV, −350 mV to −300 mV, −300 mV to −250 mV, −250 mV to −200 mV, −200 mV to −150 mV, −150 mV to −100 mV, −100 mV to −90 mV, −90 mV to −80 mV, −80 mV to −70 mV, −70 mV to −60 mV, −60 mV to −50 mV, −50 mV to −40 mV, −40 mV to −30 mV, −30 mV to −20 mV, −20 mV to −10 mV, −mV to 0 mV, 0 mV to 10 mV, 10 mV to 20 mV, 20 mV to 30 mV, 30 mV to 40 mV, 40 mV to 50 mV, 50 mV to 60 mV, 60 mV to 70 mV, 70 mV to 80 mV, 80 mV to 90 mV, 90 mV to 100 mV, 100 mV to 110 mV, 110 mV to 120 mV, 120 mV to 130 mV, 130 mV to 140 mV, 140 mV to 150 mV, 150 mV to 200 mV, 200 mV to 250 mV, 250 mV to 300 mV, 300 mV to 350 mV, 350 mV to 400 mV, 400 mV to 450 mV, 450 mV to 500 mV, −500 my to −400 mV, −400 my to −300 mV, −300 my to −200 mV, −200 my to −100 mV, −100 my to 0 mV, 0 my to 100 mV, 100 my to 200 mV, 200 my to 300 mV, 300 my to 400 mV, or 400 my to 500 mV. In particular examples, particles disclosed herein have a surface charge of −60 mV to 60 mV.

Various particle morphologies are consistent with the particle types in panels of the present disclosure. For example, particles may be spherical, colloidal, cube shaped, square shaped, rods, wires, cones, pyramids, and oblong. Particles of the present disclosure may be solid particles, porous particles, or meso porous particles. Particles may have a small surface area or a large surface area. Particles may have varied magnetic properties that can be measured by SQUID, which determines magnetism in response to an external field. In some cases, particles have a core-shell or yolk-shell structure.

Particle Panels

The particle panels disclosed herein can be used to identifying a number of proteins, peptides, or protein groups using the Proteograph workflow described herein (MS analysis of distinct biomolecule coronas corresponding to distinct particle types in the particle panel). Feature intensities, as disclosed herein, refers to the intensity of a discrete spike ("feature") seen on a plot of mass to charge ratio versus intensity from a mass spectrometry run of a sample. These features can correspond to variably ionized fragments of peptides and/or proteins. Using the data analysis methods described herein, feature intensities can be sorted into protein groups. Protein groups refer to two or more proteins that are identified by a shared peptide sequence. Alternatively, a protein group can refer to one protein that is identified using a unique identifying sequence. For example, if in a sample, a peptide sequence is assayed that is shared between two proteins (Protein 1: XYZZX and Protein 2: XYZYZ), a protein group could be the "XYZ protein group" having two members (protein 1 and protein 2). Alternatively, if the peptide sequence is unique to a single protein (Protein 1), a protein group could be the "ZZX" protein group having one member (Protein 1). Each protein group can be supported by more than one peptide sequence. Protein detected or identified according to the instant disclosure can refer to a distinct protein detected in the sample (e.g., distinct relative other proteins detected using mass spectrometry). Thus, analysis of proteins present in distinct coronas corresponding to the distinct particle types in a particle panel, yields a high number of feature intensities. This number decreases as feature intensities are processed into distinct peptides, further decreases as distinct peptides are processed into distinct proteins, and further decreases as peptides are grouped into protein groups (two or more proteins that share a distinct peptide sequence).

The particle panels disclosed herein can be used to identify at least at least 100 proteins, at least 200 proteins, at least 300 proteins, at least 400 proteins, at least 500 proteins, at least 600 proteins, at least 700 proteins, at least 800 proteins, at least 900 proteins, at least 1000 proteins, at least 1100 proteins, at least 1200 proteins, at least 1300 proteins, at least 1400 proteins, at least 1500 proteins, at least 1600 proteins, at least 1700 proteins, at least 1800 proteins, at least 1900 proteins, at least 2000 proteins, at least 2100 proteins, at least 2200 proteins, at least 2300 proteins, at least 2400 proteins, at least 2500 proteins, at least 2600 proteins, at least 2700 proteins, at least 2800 proteins, at least 2900 proteins, at least 3000 proteins, at least 3100 proteins, at least 3200 proteins, at least 3300 proteins, at least 3400 proteins, at least 3500 proteins, at least 3600 proteins, at least 3700 proteins, at least 3800 proteins, at least 3900 proteins, at least 4000 proteins, at least 4100 proteins, at least 4200 proteins, at least 4300 proteins, at least 4400 proteins, at least 4500 proteins, at least 4600 proteins, at least 4700 proteins, at least 4800 proteins, at least 4900 proteins, at least 5000 proteins, at least 10000 proteins, at least 20000 proteins, at least 50000 proteins, at least 100000 proteins, from 100 to 5000 proteins, from 200 to 4700 proteins, from 300 to 4400 proteins, from 400 to 4100 proteins, from 500 to 3800 proteins, from 600 to 3500 proteins, from 700 to 3200 proteins, from 800 to 2900 proteins, from 900 to 2600 proteins, from 1000 to 2300 proteins, from 1000 to 3000 proteins, from 3000 to 4000 proteins, from 4000 to 5000 proteins, from 5000 to 6000 proteins, from 6000 to 7000 proteins, from 7000 to 8000 proteins, from 8000 to 9000 proteins, from 9000 to 10000 proteins, from 10000 to 11000 proteins, from 11000 to 12000 proteins, from 12000 to 13000 proteins, from 13000 to 14000 proteins, from 14000 to 15000 proteins, from 15000 to 16000 proteins, from 16000 to 17000 proteins, from 17000 to 18000 proteins, from 18000 to 19000 proteins, from 19000 to 20000 proteins, from 20000 to 25000 proteins, from 25000 to 30000 proteins, from 10000 to 20000 proteins, from 10000 to 50000 proteins, from 20000 to 100000 proteins, from 2000 to 20000 proteins, from 1800 to 20000 proteins, or from 10000 to 100000 proteins.

The particle panels disclosed herein can be used to identify at least at least 100 protein groups, at least 200 protein groups, at least 300 protein groups, at least 400 protein groups, at least 500 protein groups, at least 600 protein groups, at least 700 protein groups, at least 800 protein groups, at least 900 protein groups, at least 1000 protein groups, at least 1100 protein groups, at least 1200 protein groups, at least 1300 protein groups, at least 1400 protein groups, at least 1500 protein groups, at least 1600 protein groups, at least 1700 protein groups, at least 1800 protein groups, at least 1900 protein groups, at least 2000 protein groups, at least 2100 protein groups, at least 2200 protein groups, at least 2300 protein groups, at least 2400 protein groups, at least 2500 protein groups, at least 2600 protein groups, at least 2700 protein groups, at least 2800 protein groups, at least 2900 protein groups, at least 3000 protein groups, at least 3100 protein groups, at least 3200 protein groups, at least 3300 protein groups, at least 3400 protein groups, at least 3500 protein groups, at least 3600 protein groups, at least 3700 protein groups, at least 3800 protein groups, at least 3900 protein groups, at least 4000 protein groups, at least 4100 protein groups, at least 4200 protein groups, at least 4300 protein groups, at least 4400 protein groups, at least 4500 protein groups, at least 4600 protein groups, at least 4700 protein groups, at least 4800 protein groups, at least 4900 protein groups, at least 5000 protein groups, at least 10000 protein groups, at least 20000 protein groups, at least 100000 protein groups, from 100 to 5000 protein groups, from 200 to 4700 protein groups, from 300 to 4400 protein groups, from 400 to 4100 protein groups, from 500 to 3800 protein groups, from 600 to 3500 protein groups, from 700 to 3200 protein groups, from 800 to 2900 protein groups, from 900 to 2600 protein groups, from 1000 to 2300 protein groups, from 1000 to 3000 protein groups, from 3000 to 4000 protein groups, from 4000 to 5000 protein groups, from 5000 to 6000 protein groups, from 6000 to 7000 protein groups, from 7000 to 8000 protein groups, from 8000 to 9000 protein groups, from 9000 to 10000 protein groups, from 10000 to 11000 protein groups, from 11000 to 12000 protein groups, from 12000 to 13000 protein groups, from 13000 to 14000 protein groups, from 14000 to 15000 protein groups, from 15000 to 16000 protein groups, from 16000 to 17000 protein groups, from 17000 to 18000 protein groups, from 18000 to 19000 protein groups, from 19000 to 20000 protein groups, from 20000 to 25000 protein groups, from 25000 to 30000 protein groups, from 10000 to 20000 protein groups, from 10000 to 50000 protein groups, from 20000 to 100000 protein groups, from 2000 to 20000 protein groups, from 1800 to 20000 protein groups, or from 10000 to 100000 protein groups.

The particle panels disclosed herein can be used to identify the number of distinct proteins disclosed herein, and/or any of the specific proteins disclosed herein, over a wide dynamic range. For example, the particle panels disclosed herein comprising distinct particle types, can enrich for proteins in a sample, which can be identified using the Proteograph workflow, over the entire dynamic range at which proteins are present in a sample (e.g., a plasma sample). In some embodiments, a particle panel including any number of distinct particle types disclosed herein, enriches and identifies proteins over a dynamic range of at least 2. In some embodiments, a particle panel including any number of distinct particle types disclosed herein, enriches and identifies proteins over a dynamic range of at least 3. In some embodiments, a particle panel including any number of distinct particle types disclosed herein, enriches and identifies proteins over a dynamic range of at least 4. In some embodiments, a particle panel including any number of distinct particle types disclosed herein, enriches and identifies proteins over a dynamic range of at least 5. In some embodiments, a particle panel including any number of distinct particle types disclosed herein, enriches and identifies proteins over a dynamic range of at least 6. In some embodiments, a particle panel including any number of distinct particle types disclosed herein, enriches and identifies proteins over a dynamic range of at least 7. In some embodiments, a particle panel including any number of distinct particle types disclosed herein, enriches and identifies proteins over a dynamic range of at least 8. In some embodiments, a particle panel including any number of distinct particle types disclosed herein, enriches and identifies proteins over a dynamic range of at least 9. In some embodiments, a particle panel including any number of distinct particle types disclosed herein, enriches and identifies proteins over a dynamic range of at least 10. In some embodiments, a particle panel including any number of distinct particle types disclosed herein, enriches and identifies proteins over a dynamic range of at least 11. In some embodiments, a particle panel including any number of distinct particle types disclosed herein, enriches and identifies proteins over a dynamic range of at least 12. In some embodiments, a particle panel including any number of distinct particle types disclosed herein, enriches and identifies proteins over a dynamic range of at least 13. In some embodiments, a particle panel including any number of distinct particle types disclosed herein, enriches and identifies proteins over a dynamic range of at least 14. In some embodiments, a particle panel including any number of distinct particle types disclosed herein, enriches and identifies proteins over a dynamic range of at least 15. In some embodiments, a particle panel including any number of distinct particle types disclosed herein, enriches and identifies proteins over a dynamic range of at least 20. In some embodiments, a particle panel including any number of distinct particle types disclosed herein, enriches and identifies proteins over a dynamic range of from 2 to 100. In some embodiments, a particle panel including any number of distinct particle types disclosed herein, enriches and identifies proteins over a dynamic range of from 2 to 20. In some embodiments, a particle panel including any number of distinct particle types disclosed herein, enriches and identifies proteins over a dynamic range of from 2 to 10. In some embodiments, a particle panel including any number of distinct particle types disclosed herein, enriches and identifies proteins over a dynamic range of from 2 to 5. In some embodiments, a particle panel including any number of distinct particle types disclosed herein, enriches and identifies proteins over a dynamic range of from 5 to 10.

A particle panel including any number of distinct particle types disclosed herein, enriches and identifies a single protein or protein group. In some embodiments, the single protein or protein group may comprise proteins having different post-translational modifications. For example, a first particle type in the particle panel may enrich a protein or protein group having a first post-translational modification, a second particle type in the particle panel may enrich the same protein or same protein group having a second post-translational modification, and a third particle type in the particle panel may enrich the same protein or same protein group lacking a post-translational modification. In some embodiments, the particle panel including any number of distinct particle types disclosed herein, enriches and identifies a single protein or protein group by binding different domains, sequences, or epitopes of the single protein or protein group. For example, a first particle type in the particle panel may enrich a protein or protein by binding to a first domain of the protein or protein group, and a second particle type in the particle panel may enrich the same protein or same protein group by binding to a second domain of the protein or protein group.

Figure 11:
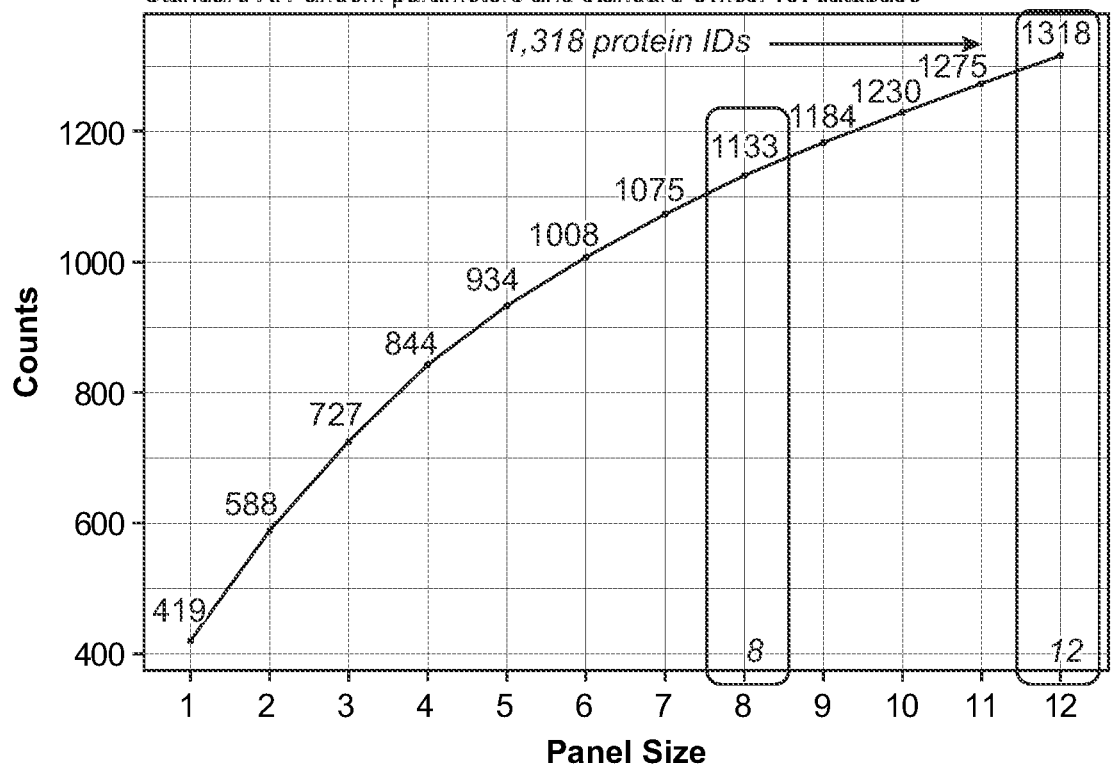
FIG. 11 shows the protein counts (number of proteins identified from corona analysis) for panel sizes ranging from 1 particle type to 12 particle types. Each particle in a panel may be unique in base material, surface functionalization, and/or physical property (e.g., size or shape). Single pooled plasma representing a pool of healthy subjects was used. Counts are the numbers of unique proteins observed across the panel of 12 particle types in about 2 hour mass spectrometry (MS) runs. 1318 proteins were identified with a panel size of 12 particle types. As used herein, a "feature" identified by mass spectrometry includes a signal at a specific combination of retention time and m/z (mass-to-charge ratio), where each feature has an associated intensity. Some features are further fragmented in a second mass spectrometry analysis (MS2) for identification.
Figure 12:
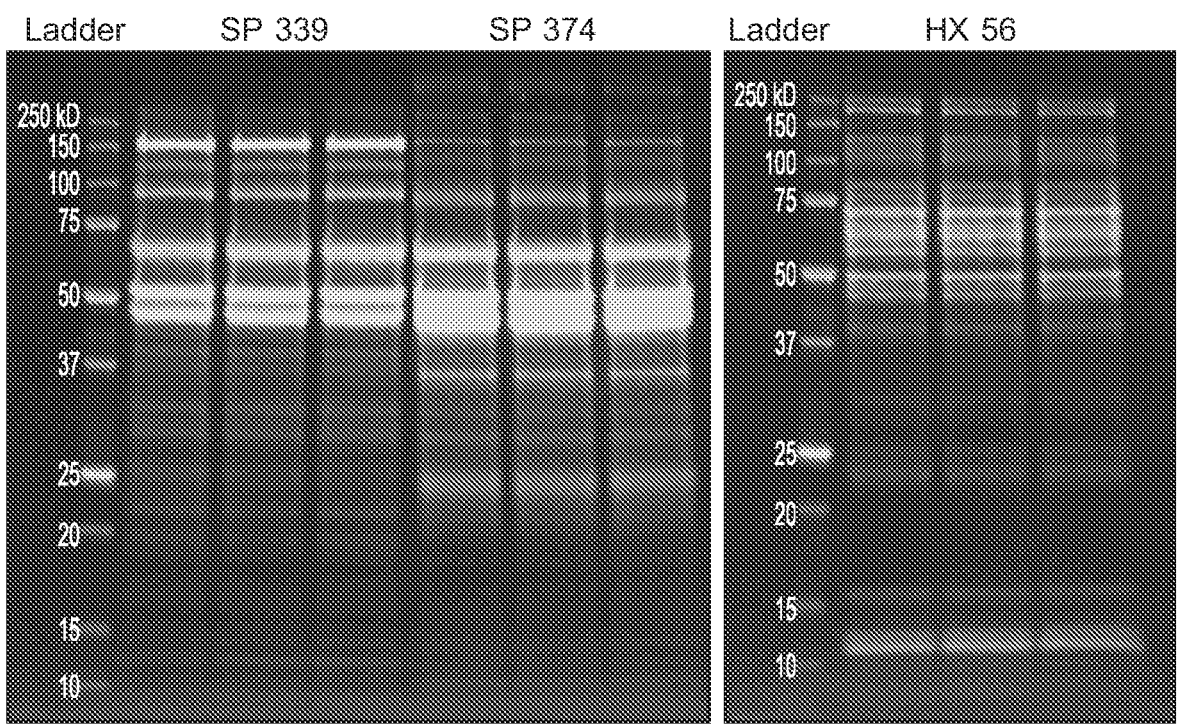
FIG. 12 represents gel electrophoresis analyses of multiple particle types after incubation in plasma across multiple days. Each individual assay typically ran for about 1 hour, but triplicate measurements were made on three different days, and by different operators, to demonstrate assay precision. From left to right, the gel shows a ladder, three consecutive columns of SP-339 (polystyrene carboxyl), three consecutive columns of SP-374 (silica silanol), a DNA ladder, and three consecutive columns of HX56 (SP-007) (silica amino).
Figure 13:
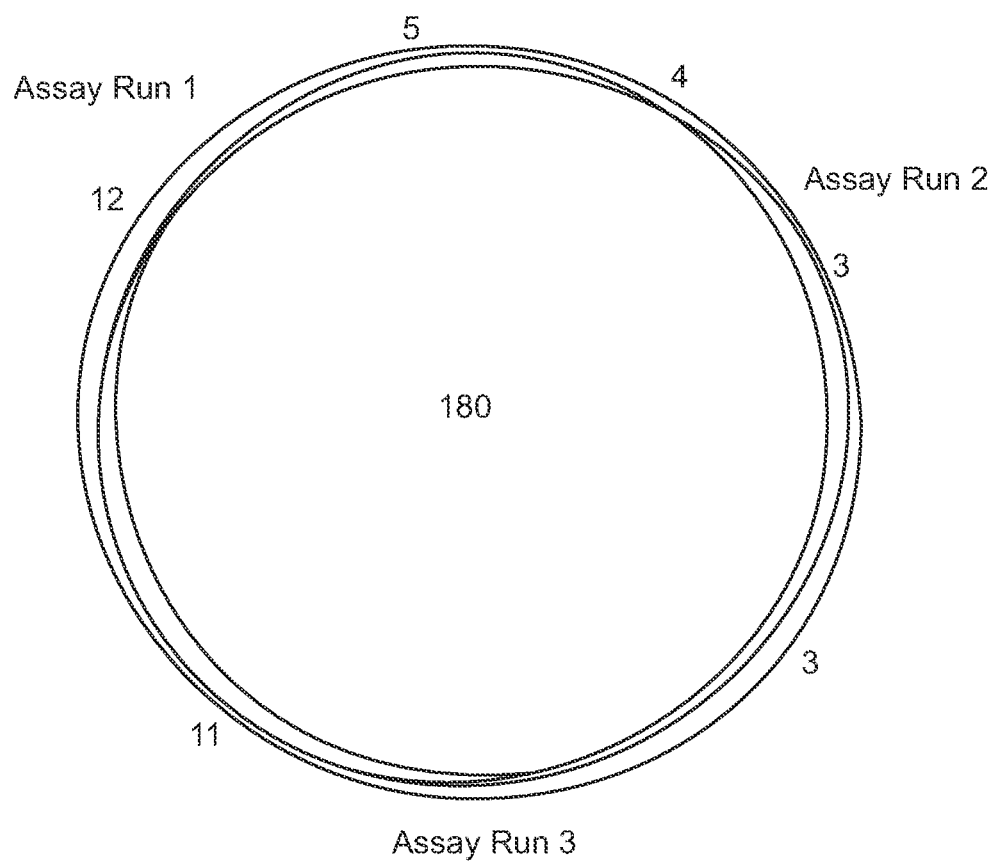
FIG. 13 shows mass spectrometry analyses for protein identification across three separate assays for one particle type (SP-339, polystyrene carboxyl). Across the three separate assays, 180 proteins were commonly identified.

In some embodiments, particle panels can have more than one particle types. Increasing the number of particle types in a panel can be a method for increasing the number of proteins that can be identified in a given sample. An example of how increasing panel size may increase the number of identified proteins is shown in FIG. 11. For example, as shown in FIG. 11, a panel size of one particle type identified 419 unique proteins, a panel size of two particle types identified 588 proteins, a panel size of three particle types identified 727 proteins, a panel size of four particle types identified 844 proteins, a panel size of five particle types identified 934 proteins, a panel size of six particle types identified 1008 proteins, a panel size of seven particle types identified 1075 proteins, a panel size of eight particle types identified 1133 proteins, a panel size of nine particle types identified 1184 proteins, a panel size of 10 particle types identified 1230 proteins, a panel size of 11 particle types identified 1275 proteins, and a panel size of 12 particle types identified 1318 proteins. The particle types may include nanoparticle types.

In some embodiments, a panel size of one particle type is capable of identifying 200 to 600 unique proteins. In some embodiments, a panel size of two particle types is capable of identifying 300 to 700 unique proteins. In some embodiments, a panel size of three particle types is capable of identifying 500 to 900 unique proteins. In some embodiments, a panel size of four particle types is capable of identifying 600 to 1000 unique proteins. In some embodiments, a panel size of five particle types is capable of identifying 700 to 1100 unique proteins. In some embodiments, a panel size of six particle types is capable of identifying 800 to 1200 unique proteins. In some embodiments, a panel size of seven particle types is capable of identifying 850 to 1250 unique proteins. In some embodiments, a panel size of eight particle types is capable of identifying 900 to 1300 unique proteins. In some embodiments, a panel size of nine particle types is capable of identifying 950 to 1350 unique proteins. In some embodiments, a panel size of 10 particle types is capable of identifying 1000 to 1400 unique proteins. In some embodiments, a panel size of 11 particle types is capable of identifying 1050 to 1450 unique proteins. In some embodiments, a panel size of 12 particle types is capable of identifying 1100 to 1500 unique proteins. The particle types may include nanoparticle types.

The present disclosure provides over 200 distinct particle types, with over 100 different surface chemistries, and over 50 diverse physical properties. Distinct particle types comprise at least one physicochemical property that differs between a first particle type and a second particle type. For example, the present disclosure provides a particle panel having at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 20 distinct particle types, at least 25 distinct particle types, at least 30 distinct particle types, at least 35 distinct particle types, at least 40 distinct particle types, at least 45 distinct particle types, at least 50 distinct particle types, at least 100 distinct particle types, at least 150 distinct particle types, at least 200 distinct particle types, at least 250 distinct particle types, at least 300 distinct particle types, at least 350 distinct particle types, at least 400 distinct particle types, at least 450 distinct particle types, at least 500 distinct particle types, from 2 to 500 distinct particle types, from 2 to 5 distinct particle types, from 5 to 10 distinct particle types, from 10 to 15 distinct particle types, from 15 to 20 distinct particle types, from 20 to 40 distinct particle types, from 40 to 60 distinct particle types, from 60 to 80 distinct particle types, from 80 to 100 distinct particle types, from 100 to 500 distinct particle types, from 4 to 15 distinct particle types, or from 2 to 20 distinct particle types. The particle types may include nanoparticle types.

In some embodiments, the present disclosure provide a panel size of at least 1 particle distinct type, at least 2 distinct particle types, at least 3 distinct particle types, at least 4 distinct particle types, at least 5 distinct particle types, at least 6 distinct particle types, at least 7 distinct particle types, at least 8 distinct particle types, at least 9 distinct particle types, at least 10 distinct particle types, at least 11 distinct particle types, at least 12 distinct particle types, at least 13 distinct particle types, at least 14 distinct particle types, at least 15 distinct particle types, at least 16 distinct particle types, at least 17 distinct particle types, at least 18 distinct particle types, at least 19 distinct particle types, at least 20 distinct particle types, at least 25 distinct particle types, at least 30 distinct particle types, at least 35 distinct particle types, at least 40 distinct particle types, at least 45 distinct particle types, at least 50 distinct particle types, at least 55 distinct particle types, at least 60 distinct particle types, at least 65 distinct particle types, at least 70 distinct particle types, at least 75 distinct particle types, at least 80 distinct particle types, at least 85 distinct particle types, at least 90 distinct particle types, at least 95 distinct particle types, at least 100 distinct particle types, from 1 to 5 distinct particle types, from 5 to 10 distinct particle types, from 10 to 15 distinct particle types, from 15 to 20 distinct particle types, from 20 to 25 distinct particle types, from 25 to 30 distinct particle types, from 30 to 35 distinct particle types, from 35 to 40 distinct particle types, from 40 to 45 distinct particle types, from 45 to 50 distinct particle types, from 50 to 55 distinct particle types, from 55 to 60 distinct particle types, from 60 to 65 distinct particle types, from 65 to 70 distinct particle types, from 70 to 75 distinct particle types, from 75 to 80 distinct particle types, from 80 to 85 distinct particle types, from 85 to 90 distinct particle types, from 90 to 95 distinct particle types, from 95 to 100 distinct particle types, from 1 to 100 distinct particle types, from 20 to 40 distinct particle types, from 5 to 10 distinct particle types, from 3 to 7 distinct particle types, from 2 to 10 distinct particle types, from 6 to 15 distinct particle types, or from 10 to 20 distinct particle types. In particular embodiments, the present disclosure provides a panel size of from 3 to 10 particle types. In particular embodiments, the present disclosure provides a panel size of from 4 to 11 distinct particle types. In particular embodiments, the present disclosure provides a panel size of from 5 to 15 distinct particle types. In particular embodiments, the present disclosure provides a panel size of from 5 to 15 distinct particle types. In particular embodiments, the present disclosure provides a panel size of from 8 to 12 distinct particle types. In particular embodiments, the present disclosure provides a panel size of from 9 to 13 distinct particle types. In particular embodiments, the present disclosure provides a panel size of 10 distinct particle types. The particle types may include nanoparticle types.

For example, the present disclosure provides a particle panel having at least 2 distinct particle types, at least 3 different surface chemistries, at least 4 different surface chemistries, at least 5 different surface chemistries, at least 6 different surface chemistries, at least 7 different surface chemistries, at least 8 different surface chemistries, at least 9 different surface chemistries, at least 10 different surface chemistries, at least 11 different surface chemistries, at least 12 different surface chemistries, at least 13 different surface chemistries, at least 14 different surface chemistries, at least 15 different surface chemistries, at least 20 different surface chemistries, at least 25 different surface chemistries, at least 30 different surface chemistries, at least 35 different surface chemistries, at least 40 different surface chemistries, at least 45 different surface chemistries, at least 50 different surface chemistries, at least 100 different surface chemistries, at least 150 different surface chemistries, at least 200 different surface chemistries, at least 250 different surface chemistries, at least 300 different surface chemistries, at least 350 different surface chemistries, at least 400 different surface chemistries, at least 450 different surface chemistries, at least 500 different surface chemistries, from 2 to 500 different surface chemistries, from 2 to 5 different surface chemistries, from 5 to 10 different surface chemistries, from 10 to 15 different surface chemistries, from 15 to 20 different surface chemistries, from 20 to 40 different surface chemistries, from 40 to 60 different surface chemistries, from 60 to 80 different surface chemistries, from 80 to 100 different surface chemistries, from 100 to 500 different surface chemistries, from 4 to 15 different surface chemistries, or from 2 to 20 different surface chemistries.

The present disclosure provides a particle panel having at least 2 different surface chemistries, at least 3 different surface chemistries, at least 4 different surface chemistries, at least 5 different surface chemistries, at least 6 different surface chemistries, at least 7 different surface chemistries, at least 8 different surface chemistries, at least 9 different surface chemistries, at least 10 different surface chemistries, at least 11 different surface chemistries, at least 12 different surface chemistries, at least 13 different surface chemistries, at least 14 different surface chemistries, at least 15 different surface chemistries, at least 20 different surface chemistries, at least 25 different surface chemistries, at least 30 different surface chemistries, at least 35 different surface chemistries, at least 40 different surface chemistries, at least 45 different surface chemistries, at least 50 different surface chemistries, at least 100 different surface chemistries, at least 150 different surface chemistries, at least 200 different surface chemistries, at least 250 different surface chemistries, at least 300 different surface chemistries, at least 350 different surface chemistries, at least 400 different surface chemistries, at least 450 different surface chemistries, at least 500 different surface chemistries, from 2 to 500 different surface chemistries, from 2 to 5 different surface chemistries, from 5 to 10 different surface chemistries, from 10 to 15 different surface chemistries, from 15 to 20 different surface chemistries, from 20 to 40 different surface chemistries, from 40 to 60 different surface chemistries, from 60 to 80 different surface chemistries, from 80 to 100 different surface chemistries, from 100 to 500 different surface chemistries, from 4 to 15 different surface chemistries, or from 2 to 20 different surface chemistries.

The present disclosure provides a particle panel having at least 2 different physical properties, at least 3 different physical properties, at least 4 different physical properties, at least 5 different physical properties, at least 6 different physical properties, at least 7 different physical properties, at least 8 different physical properties, at least 9 different physical properties, at least 10 different physical properties, at least 11 different physical properties, at least 12 different physical properties, at least 13 different physical properties, at least 14 different physical properties, at least 15 different physical properties, at least 20 different physical properties, at least 25 different physical properties, at least 30 different physical properties, at least 35 different physical properties, at least 40 different physical properties, at least 45 different physical properties, at least 50 different physical properties, at least 100 different physical properties, at least 150 different physical properties, at least 200 different physical properties, at least 250 different physical properties, at least 300 different physical properties, at least 350 different physical properties, at least 400 different physical properties, at least 450 different physical properties, at least 500 different physical properties, from 2 to 500 different physical properties, from 2 to 5 different physical properties, from 5 to 10 different physical properties, from 10 to 15 different physical properties, from 15 to 20 different physical properties, from 20 to 40 different physical properties, from 40 to 60 different physical properties, from 60 to 80 different physical properties, from 80 to 100 different physical properties, from 100 to 500 different physical properties, from 4 to 15 different physical properties, or from 2 to 20 different physical properties.

In some embodiments, panels that optimally identity proteins and associate biomarkers with diseases include panels selected from the particle types described in TABLE 1. For example, a panel that optimally identifies proteins and associate biomarkers with diseases include panels comprising SP-339, HX74, SP-356, SP-333, HX20, SP-374, HX42, SP-003, SP-007, and SP-011. Particle panels especially suitable to identifying high numbers of proteins (e.g., greater than 1500 proteins) in a sample include from 5 to 10 distinct particle types in an assay. The number of distinct particle types included in a particle panel can be tuned for a specific application (e.g., detection of a particular subset of proteins or detection of a group of markers associated with a particular disease). In some embodiments, panels with physicochemically distinct particle types that optimally identify proteins and associate biomarkers with diseases include silica-coated SPIONs, acrylamide-based SPIONs, and acrylate-based SPIONS. For example, a panel of particles disclosed herein that generates information rich proteomic data via their protein coronas, which can be associated with biomarkers and diseases with high sensitivity and specificity include silica-coated SPIONs (SP-003), poly(N-(3-(dimethylamino)propyl) methacrylamide) (PDMAPMA)-coated SPIONs (SP-007), and poly(oligo(ethylene glycol) methyl ether methacrylate) (POEGMA)-coated SPIONs (SP-011).

In some embodiments, the entire assay time from a single pooled plasma, including sample preparation and LC-MS, can be about 8 hours. In some embodiments, the entire assay time from a single pooled plasma, including sample preparation and LC-MS, can be about at least 1 hour, at least 2 hours, at least 3 hours, at least 4 hours, at least 5 hours, at least 6 hours, at least 7 hours, at least 8 hours, at least 9 hours, at least 10 hours, under 20 hours, under 19 hours, under 18 hours, under 17 hours, under 16 hours, under 15 hours, under 14 hours, under 13 hours, under 12 hours, under 11 hours, under 10 hours, under 9 hours, under 8 hours, under 7 hours, under 6 hours, under 5 hours, under 4 hours, under 3 hours, under 2 hours, under 1 hour, at least 5 min to 10 min, at least 10 min to 20 min, at least 20 min to 30 min, at least 30 min to 40 min, at least 40 min to 50 min, at least 50 min to 60 min, at least 1 hour to 1.5 hours, at least 1.5 hour to 2 hours, at least 2 hour to 2.5 hours, at least 2.5 hour to 3 hours, at least 3 hour to 3.5 hours, at least 3.5 hour to 4 hours, at least 4 hour to 4.5 hours, at least 4.5 hour to 5 hours, at least 5 hour to 5.5 hours, at least 5.5 hour to 6 hours, at least 6 hour to 6.5 hours, at least 6.5 hour to 7 hours, at least 7 hour to 7.5 hours, at least 7.5 hour to 8 hours, at least 8 hour to 8.5 hours, at least 8.5 hour to 9 hours, at least 9 hour to 9.5 hours, or at least 9.5 hour to 10 hours.

Early Stage Detection

Figure 18A:
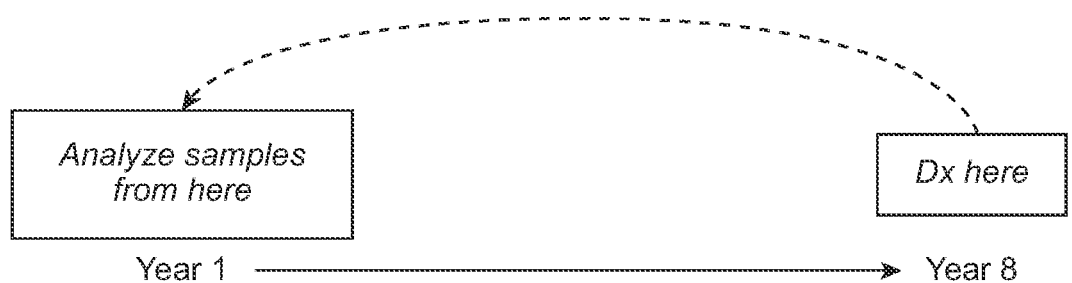
FIG. 18A and FIG. 18B show that early stage cancers can be separated up to 8 years before symptoms develop. The Golestan Cohort enrolled 50,000 healthy subjects between 2004 and 2008.
Figure 18B:
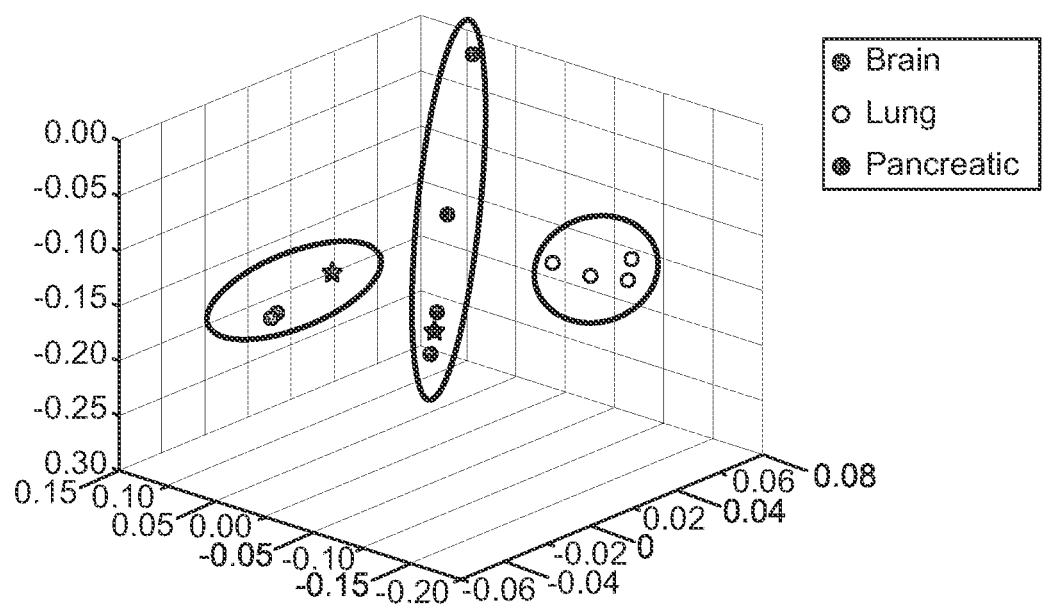

The panels and methods of use thereof described herein can be used for detection of markers in a sample from a subject, which are consistent with a particular disease state. As shown in FIG. 18A and FIG. 18B, early stage cancers can be separated up to 8 years before symptoms develop. The Golestan Cohort enrolled 50,000 healthy subjects between 2004 and 2008. As shown in FIG. 18A, banked plasma from enrollment was tested. 8 years after enrollment, approximately 1000 patients developed cancers. FIG. 18B illustrates classification of three cancers, Brain, Lung and Pancreatic from banked plasma, are classified by principle component analysis. Here, the corona results are plotted against the three principle component axes, showing three distinct statistical populations. corona analysis (involving measurement of multiple properties in order to profile a plurality of proteins) of banked plasma from enrollment date accurately classified cancers for 15 out of 15 subjects examined (5 patients each for 3 cancers). In some embodiments, the panels of the present disclosure can be used to diagnose a disease state up to one year prior, up to two years prior, up to three years prior, up to four years prior, up to five years prior, up to six years prior, up to seven years prior, up to eight years prior, up to nine years prior, up to 10 years prior, up to 15 years prior, up to 20 years prior, or up to 25 years prior to development of symptoms of that disease state.

The panels of the present disclosure can be used to detect a wide range of disease states in a given sample. For example, the panels of the present disclosure can be used to detect a cancer. The cancer may be brain cancer, lung cancer, pancreatic cancer, glioblastoma, meningioma, myeloma, or pancreatic cancer. Corona analysis signals for these cancers are shown in FIG. 17B and FIG. 18.

The panels of the present disclosure can additionally be used to detect other cancers, such as any one of the cancers listed on https://www.cancer.gov/types, including acute lymphoblastic leukemia (ALL); acute myeloid leukemia (AML); cancer in adolescents; adrenocortical carcinoma; childhood adrenocortical carcinoma; unusual cancers of childhood; AIDS-related cancers; kaposi sarcoma (soft tissue sarcoma); AIDS-related lymphoma (lymphoma); primary cns lymphoma (lymphoma); anal cancer; appendix cancer—see gastrointestinal carcinoid tumors; astrocytomas, childhood (brain cancer); atypical teratoid/rhabdoid tumor, childhood, central nervous system (brain cancer); basal cell carcinoma of the skin—see skin cancer; bile duct cancer; bladder cancer; childhood bladder cancer; bone cancer (includes ewing sarcoma and osteosarcoma and malignant fibrous histiocytoma); brain tumors; breast cancer; childhood breast cancer; bronchial tumors, childhood; burkitt lymphoma—see non-hodgkin lymphoma; carcinoid tumor (gastrointestinal); childhood carcinoid tumors; carcinoma of unknown primary; childhood carcinoma of unknown primary; cardiac (heart) tumors, childhood; central nervous system; atypical teratoid/rhabdoid tumor, childhood (brain cancer); embryonal tumors, childhood (brain cancer); germ cell tumor, childhood (brain cancer); primary cns lymphoma; cervical cancer; childhood cervical cancer; childhood cancers; cancers of childhood, unusual; cholangiocarcinoma—see bile duct cancer; chordoma, childhood; chronic lymphocytic leukemia (CLL); chronic myelogenous leukemia (CML); chronic myeloproliferative neoplasms; colorectal cancer; childhood colorectal cancer; craniopharyngioma, childhood (brain cancer); cutaneous t-cell lymphoma—see lymphoma (mycosis fungoides and sézary syndrome); ductal carcinoma in situ (DCIS)—see breast cancer; embryonal tumors, central nervous system, childhood (brain cancer); endometrial cancer (uterine cancer); ependymoma, childhood (brain cancer); esophageal cancer; childhood esophageal cancer; esthesioneuroblastoma (head and neck cancer); ewing sarcoma (bone cancer); extracranial germ cell tumor, childhood; extragonadal germ cell tumor; eye cancer; childhood intraocular melanoma; intraocular melanoma; retinoblastoma; fallopian tube cancer; fibrous histiocytoma of bone, malignant, and osteosarcoma; gallbladder cancer; gastric (stomach) cancer; childhood gastric (stomach) cancer; gastrointestinal carcinoid tumor; gastrointestinal stromal tumors (GIST) (soft tissue sarcoma); childhood gastrointestinal stromal tumors; germ cell tumors; childhood central nervous system germ cell tumors (brain cancer); childhood extracranial germ cell tumors; extragonadal germ cell tumors; ovarian germ cell tumors; testicular cancer; gestational trophoblastic disease; hairy cell leukemia; head and neck cancer; heart tumors, childhood; hepatocellular (liver) cancer; histiocytosis, langerhans cell; hodgkin lymphoma; hypopharyngeal cancer (head and neck cancer); intraocular melanoma; childhood intraocular melanoma; islet cell tumors, pancreatic neuroendocrine tumors; kaposi sarcoma (soft tissue sarcoma); kidney (renal cell) cancer; langerhans cell histiocytosis; laryngeal cancer (head and neck cancer); leukemia; lip and oral cavity cancer (head and neck cancer); liver cancer; lung cancer (non-small cell and small cell); childhood lung cancer; lymphoma; male breast cancer; malignant fibrous histiocytoma of bone and osteosarcoma; melanoma; childhood melanoma; melanoma, intraocular (eye); childhood intraocular melanoma; merkel cell carcinoma (skin cancer); mesothelioma, malignant; childhood mesothelioma; metastatic cancer; metastatic squamous neck cancer with occult primary (head and neck cancer); midline tract carcinoma with nut gene changes; mouth cancer (head and neck cancer); multiple endocrine neoplasia syndromes; multiple myeloma/plasma cell neoplasms; mycosis fungoides (lymphoma); myelodysplastic syndromes, myelodysplastic/myeloproliferative neoplasms; myelogenous leukemia, chronic (cml); myeloid leukemia, acute (AML); myeloproliferative neoplasms, chronic; nasal cavity and paranasal sinus cancer (head and neck cancer); nasopharyngeal cancer (head and neck cancer); neuroblastoma; non-hodgkin lymphoma; non-small cell lung cancer; oral cancer, lip and oral cavity cancer and oropharyngeal cancer (head and neck cancer); osteosarcoma and malignant fibrous histiocytoma of bone; ovarian cancer; childhood ovarian cancer; pancreatic cancer; childhood pancreatic cancer; pancreatic neuroendocrine tumors (islet cell tumors); papillomatosis (childhood laryngeal); paraganglioma; childhood paraganglioma; paranasal sinus and nasal cavity cancer (head and neck cancer); parathyroid cancer; penile cancer; pharyngeal cancer (head and neck cancer); pheochromocytoma; childhood pheochromocytoma; pituitary tumor; plasma cell neoplasm/multiple myeloma; pleuropulmonary blastoma; pregnancy and breast cancer; primary central nervous system (CNS) lymphoma; primary peritoneal cancer; prostate cancer; rectal cancer; recurrent cancer; renal cell (kidney) cancer; retinoblastoma; rhabdomyosarcoma, childhood (soft tissue sarcoma); salivary gland cancer (head and neck cancer); sarcoma; childhood rhabdomyosarcoma (soft tissue sarcoma); childhood vascular tumors (soft tissue sarcoma); ewing sarcoma (bone cancer); kaposi sarcoma (soft tissue sarcoma); osteosarcoma (bone cancer); soft tissue sarcoma; uterine sarcoma; sézary syndrome (lymphoma); skin cancer; childhood skin cancer; small cell lung cancer; small intestine cancer; soft tissue sarcoma; squamous cell carcinoma of the skin—see skin cancer; squamous neck cancer with occult primary, metastatic (head and neck cancer); stomach (gastric) cancer; childhood stomach (gastric) cancer; t-cell lymphoma, cutaneous—see lymphoma (mycosis fungoides and sèzary syndrome); testicular cancer; childhood testicular cancer; throat cancer (head and neck cancer); nasopharyngeal cancer; oropharyngeal cancer; hypopharyngeal cancer; thymoma and thymic carcinoma; thyroid cancer; transitional cell cancer of the renal pelvis and ureter (kidney (renal cell) cancer); carcinoma of unknown primary; childhood cancer of unknown primary; unusual cancers of childhood; ureter and renal pelvis, transitional cell cancer (kidney (renal cell) cancer; urethral cancer; uterine cancer, endometrial; uterine sarcoma; vaginal cancer; childhood vaginal cancer; vascular tumors (soft tissue sarcoma); vulvar cancer; wilms tumor and other childhood kidney tumors; or cancer in young adults. Further, the particle panels of the present disclosure can be used to detect other disease, such as Alzheimer's disease and multiple sclerosis.

Sample

The panels of the present disclosure can be used to generate proteomic data from protein coronas and subsequently associated with any of the biological states described herein. Samples consistent with the present disclosure include biological samples from a subject. The subject may be a human or a non-human animal. Biological samples may be a biofluid. For example, the biofluid may be plasma, serum, CSF, urine, tear, cell lysates, tissue lysates, cell homogenates, tissue homogenates, nipple aspirates, fecal samples, synovial fluid and whole blood, or saliva. Samples can also be non-biological samples, such as water, milk, solvents, or anything homogenized into a fluidic state. Said biological samples can contain a plurality of proteins or proteomic data, which may be analyzed after adsorption of proteins to the surface of the various particle types in a panel and subsequent digestion of protein coronas. Proteomic data can comprise nucleic acids, peptides, or proteins. Any of the samples herein can contain a number of different analytes, which can be analyzed using the compositions and methods disclosed herein. The analytes can be proteins, peptides, small molecules, nucleic acids, metabolites, lipids, or any molecule that could potentially bind or interact with the surface of a particle type.

Disclosed herein are compositions and methods for multiomic analysis. "Multi-omic(s)" or "multiomic(s)" can refer to an analytical approach for analyzing biomolecules at a large scale, wherein the data sets are multiple omes, such as proteome, genome, transcriptome, lipidome, and metabolome. Non-limiting examples of multi-omic data includes proteomic data, genomic data, lipidomic data, glycomic data, transcriptomic data, or metabolomics data. "Biomolecule" in "biomolecule corona" can refer to any molecule or biological component that can be produced by, or is present in, a biological organism. Non-limiting examples of biomolecules include proteins (protein corona), polypeptides, polysaccharides, a sugar, a lipid, a lipoprotein, a metabolite, an oligonucleotide, a nucleic acid (DNA, RNA, micro RNA, plasmid, single stranded nucleic acid, double stranded nucleic acid), metabolome, as well as small molecules such as primary metabolites, secondary metabolites, and other natural products, or any combination thereof. In some embodiments, the biomolecule is selected from the group of proteins, nucleic acids, lipids, and metabolomes.

In some embodiments, a sample of the present disclosure can be a plurality of samples. At least two samples of the plurality of samples can be spatially isolated. Spatially isolated refers to samples that are contained in separate volumes. For example, spatially isolated samples can refer to samples that are in separate wells in a plate or separate tubes. Spatially isolated samples can refer to samples that are in separate wells in a plate or separate tubes and assayed together on the same instrument. In some embodiments, the present disclosure provides particle panels and methods of use thereof that are compatible with analyzing a plurality of samples, such as at least 2 spatially isolated samples, at least 5 spatially isolated samples, at least 10 spatially isolated samples, at least 15 spatially isolated samples, at least 20 spatially isolated samples, at least 25 spatially isolated samples, at least 30 spatially isolated samples, at least 35 spatially isolated samples, at least 40 spatially isolated samples, at least 45 spatially isolated samples, at least 50 spatially isolated samples, at least 55 spatially isolated samples, at least 60 spatially isolated samples, at least 65 spatially isolated samples, at least 70 spatially isolated samples, at least 75 spatially isolated samples, at least 80 spatially isolated samples, at least 85 spatially isolated samples, at least 90 spatially isolated samples, at least 95 spatially isolated samples, at least 96 spatially isolated samples, at least 100 spatially isolated samples, at least 120 spatially isolated samples, at least 140 spatially isolated samples, at least 160 spatially isolated samples, at least 180 spatially isolated samples, at least 200 spatially isolated samples, at least 220 spatially isolated samples, at least 240 spatially isolated samples, at least 260 spatially isolated samples, at least 280 spatially isolated samples, at least 300 spatially isolated samples, at least 320 spatially isolated samples, at least 340 spatially isolated samples, at least 360 spatially isolated samples, at least 380 spatially isolated samples, at least 400 spatially isolated samples, at least 420 spatially isolated samples, at least 440 spatially isolated samples, at least 460 spatially isolated samples, at least 480 spatially isolated samples, at least 500 spatially isolated samples, at least 600 spatially isolated samples, at least 700 spatially isolated samples, at least 800 spatially isolated samples, at least 900 spatially isolated samples, at least 1000 spatially isolated samples, at least 1100 spatially isolated samples, at least 1200 spatially isolated samples, at least 1300 spatially isolated samples, at least 1400 spatially isolated samples, at least 1500 spatially isolated samples, at least 1600 spatially isolated samples, at least 1700 spatially isolated samples, at least 1800 spatially isolated samples, at least 1900 spatially isolated samples, at least 2000 spatially isolated samples, at least 5000 spatially isolated samples, at least 10000 spatially isolated samples, from 2 to 10 spatially isolated samples, from 2 to 100 spatially isolated samples, from 2 to 200 spatially isolated samples, from 2 to 300 spatially isolated samples, from 50 to 150 spatially isolated samples, from 10 to 20 spatially isolated samples, from 20 to 30 spatially isolated samples, from 30 to 40 spatially isolated samples, from 40 to 50 spatially isolated samples, from 50 to 60 spatially isolated samples, from 60 to 70 spatially isolated samples, from 70 to 80 spatially isolated samples, from 80 to 90 spatially isolated samples, from 90 to 100 spatially isolated samples, from 100 to 150 spatially isolated samples, from 150 to 200 spatially isolated samples, from 200 to 250 spatially isolated samples, from 250 to 300 spatially isolated samples, from 300 to 350 spatially isolated samples, from 350 to 400 spatially isolated samples, from 400 to 450 spatially isolated samples, from 450 to 500 spatially isolated samples, from 500 to 600 spatially isolated samples, from 600 to 700 spatially isolated samples, from 700 to 800 spatially isolated samples, from 800 to 900 spatially isolated samples, from 900 to 1000 spatially isolated samples, from 1000 to 2000 spatially isolated samples, from 2000 to 3000 spatially isolated samples, from 3000 to 4000 spatially isolated samples, from 4000 to 5000 spatially isolated samples, from 5000 to 6000 spatially isolated samples, from 6000 to 7000 spatially isolated samples, from 7000 to 8000 spatially isolated samples, from 8000 to 9000 spatially isolated samples, or from 9000 to 10000 spatially isolated samples.

The methods disclosed herein include isolating a particle panel (having a plurality of particle types) from one or more than one sample. The particle panels having particle types that are superparamagnetic can be rapidly isolated or separated from the sample using a magnetic. Moreover, multiple samples that are spatially isolated can be processed in parallel. Thus, the methods disclosed herein provide for isolating or separating a particle panel from unbound protein in a plurality of spatially isolated panels at the same time, by using a magnet. For example, particle panels may be incubated with a plurality of spatially isolated samples, wherein each spatially isolated sample is in a well in a well plate (e.g., a 96-well plate). After incubation, the particle panels in each of the wells of the well plate can be separated from unbound protein present in the spatially isolated samples by placing the entire plate on a magnet. This simultaneously pulls down the superparamagnetic particles in the particle panel. The supernatant in each well can be removed to remove the unbound protein. These steps (incubate, pull down using a magnet) can be repeated to effectively wash the particles, thus removing residual background unbound protein that may be present in a sample. This is one example, but one of skill in the art could envision numerous other scenarios in which superparamagnetic particles are rapidly isolated from one or more than one spatially isolated samples at the same time.

In some embodiments, the panels of the present disclosure provides identification and measurement of particular proteins in the biological samples by processing of the proteomic data via digestion of coronas formed on the surface of particles. Examples of proteins that can be identified and measured include highly abundant proteins, proteins of medium abundance, and low-abundance proteins. A low abundance protein may be present in a sample at concentrations at or below about 10 ng/mL. A high abundance protein may be present in a sample at concentrations at or above about 10 μg/mL. A protein of moderate abundance may be present in a sample at concentrations between about 10 ng/mL and about 10 μg/mL. Examples of proteins that are highly abundant proteins include albumin, IgG, and the top 14 proteins in abundance that contribute 95% of the mass in plasma. Additionally, any proteins that may be purified using a conventional depletion column may be directly detected in a sample using the particle panels disclosed herein. Examples of proteins may be any protein listed in published databases such as Keshishian et al. (Mol Cell Proteomics. 2015 September; 14(9):2375-93. doi: Epub 2015 Feb. 27.), Farr et al. (J Proteome Res. 2014 Jan. 3; 13(1):60-75. doi: 10.1021/pr4010037. Epub 2013 Dec. 6.), or Pernemalm et al. (Expert Rev Proteomics. 2014 August; 11(4):431-48. doi: 10.1586/14789450.2014.901157. Epub 2014 Mar. 24.).

In some embodiments, examples of proteins that can be measured and identified using the particle panels disclosed herein include albumin, IgG, lysozyme, CEA, HER-2/neu, bladder tumor antigen, thyroglobulin, alpha-fetoprotein, PSA, CA125, CA19.9, CA 15.3, leptin, prolactin, osteopontin, IGF-II, CD98, fascin, sPigR, 14-3-3 eta, troponin I, B-type natriuretic peptide, BRCA1, c-Myc, IL-6, fibrinogen. EGFR, gastrin, PH, G-CSF, desmin. NSE, FSH, VEGF, P21, PCNA, calcitonin, PR, CA125, LH, somatostatin. S100, insulin. alpha-prolactin, ACTH, Bcl-2, ER alpha, Ki-67, p53, cathepsin D, beta catenin. VWF, CD15, k-ras, caspase 3, EPN, CD10, FAS, BRCA2. CD30L, CD30, CGA, CRP, prothrombin, CD44, APEX, transferrin, GM-CSF, E-cadherin, IL-2, Bax, IFN-gamma, beta-2-MG, TNF alpha, c-erbB-2, trypsin, cyclin D1, MG B, XBP-1, HG-1, YKL-40, S-gamma, NESP-55, netrin-1, geminin, GADD45A, CDK-6, CCL21, BrMS 1, 17betaHDI, PDGFRA, Pcaf, CCLS, MMP3, claudin-4, and claudin-3. In some embodiments, other examples of proteins that can be measured and identified using the particle panels disclosed herein are any proteins or protein groups listed in the open targets database for a particular disease indication of interest (e.g., prostate cancer, lung cancer, or Alzheimer's disease).

Methods of Analysis

The proteomic data of the sample can be identified, measured, and quantified using a number of different analytical techniques. For example, proteomic data can be analyzed using SDS-PAGE or any gel-based separation technique. Peptides and proteins can also be identified, measured, and quantified using an immunoassay, such as ELISA. Alternatively, proteomic data can be identified, measured, and quantified using mass spectrometry, high performance liquid chromatography, LC-MS/MS, Edman Degradation, immunoaffinity techniques, methods disclosed in EP3548652, WO2019083856, WO2019133892, each of which is incorporated herein by reference in its entirety, and other protein separation techniques.

Computer Control Systems

The present disclosure provides computer control systems that are programmed to implement methods of the disclosure. This determination, analysis or statistical classification is done by methods known in the art, including, but not limited to, for example, a wide variety of supervised and unsupervised data analysis and clustering approaches such as hierarchical cluster analysis (HCA), principal component analysis (PCA), Partial least squares Discriminant Analysis (PLSDA), machine learning (also known as random forest), logistic regression, decision trees, support vector machine (SVM), k-nearest neighbors, naive bayes, linear regression, polynomial regression, SVM for regression, K-means clustering, and hidden Markov models, among others. The computer system can perform various aspects of analyzing the protein sets or protein corona of the present disclosure, such as, for example, comparing/analyzing the biomolecule corona of several samples to determine with statistical significance what patterns are common between the individual biomolecule coronas to determine a protein set that is associated with the biological state. The computer system can be used to develop classifiers to detect and discriminate different protein sets or protein corona (e.g., characteristic of the composition of a protein corona). Data collected from the presently disclosed sensor array can be used to train a machine learning algorithm, specifically an algorithm that receives array measurements from a patient and outputs specific biomolecule corona compositions from each patient. Before training the algorithm, raw data from the array can be first denoised to reduce variability in individual variables.

Machine learning can be generalized as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FPgrowth algorithm; Hierarchical clustering, such as Singlelinkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory. A computer system may be adapted to implement a method described herein. The system includes a central computer server that is programmed to implement the methods described herein. The server includes a central processing unit (CPU, also "processor") which can be a single core processor, a multi core processor, or plurality of processors for parallel processing. The server also includes memory (e.g., random access memory, read-only memory, flash memory); electronic storage unit (e.g. hard disk); communications interface (e.g., network adaptor) for communicating with one or more other systems; and peripheral devices which may include cache, other memory, data storage, and/or electronic display adaptors. The memory, storage unit, interface, and peripheral devices are in communication with the processor through a communications bus (solid lines), such as a motherboard. The storage unit can be a data storage unit for storing data. The server is operatively coupled to a computer network ("network") with the aid of the communications interface. The network can be the Internet, an intranet and/or an extranet, an intranet and/or extranet that is in communication with the Internet, a telecommunication or data network. The network in some cases, with the aid of the server, can implement a peer-to-peer network, which may enable devices coupled to the server to behave as a client or a server.

The storage unit can store files, such as subject reports, and/or communications with the data about individuals, or any aspect of data associated with the present disclosure.

The computer server can communicate with one or more remote computer systems through the network. The one or more remote computer systems may be, for example, personal computers, laptops, tablets, telephones, Smart phones, or personal digital assistants.

In some applications the computer system includes a single server. In other situations, the system includes multiple servers in communication with one another through an intranet, extranet and/or the internet.

The server can be adapted to store measurement data or a database as provided herein, patient information from the subject, such as, for example, medical history, family history, demographic data and/or other clinical or personal information of potential relevance to a particular application. Such information can be stored on the storage unit or the server and such data can be transmitted through a network.

Methods as described herein can be implemented by way of machine (or computer processor) executable code (or software) stored on an electronic storage location of the server, such as, for example, on the memory, or electronic storage unit. During use, the code can be executed by the processor. In some cases, the code can be retrieved from the storage unit and stored on the memory for ready access by the processor. In some situations, the electronic storage unit can be precluded, and machine-executable instructions are stored on memory. Alternatively, the code can be executed on a second computer system.

Aspects of the systems and methods provided herein, such as the server, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

The computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

Aspects of the systems and methods provided herein can be embodied in programming. Various aspects of the technology may be thought of as "products" or "articles of manufacture" typically in the form of machine (or processor) executable code and/or associated data that is carried on or embodied in a type of machine readable medium. Machine executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide nontransitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Classification of Protein Corona Using Machine Learning

The method of determining a set of proteins associated with the disease or disorder and/or disease state include the analysis of the corona of the at least two samples. This determination, analysis or statistical classification is done by methods known in the art, including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive bayes, linear regression, polynomial regression, SVM for regression, K-means clustering, and hidden Markov models, among others. In other words, the proteins in the corona of each sample are compared/analyzed with each other to determine with statistical significance what patterns are common between the individual corona to determine a set of proteins that is associated with the disease or disorder or disease state.

Generally, machine learning algorithms are used to construct models that accurately assign class labels to examples based on the input features that describe the example. In some case it may be advantageous to employ machine learning and/or deep learning approaches for the methods described herein. For example, machine learning can be used to associate the protein corona with various disease states (e.g. no disease, precursor to a disease, having early or late stage of the disease, etc.). For example, in some cases, one or more machine learning algorithms are employed in connection with a method of the invention to analyze data detected and obtained by the protein corona and sets of proteins derived therefrom. For example, in one embodiment, machine learning can be coupled with the sensor array described herein to determine not only if a subject has a pre-stage of cancer, cancer or does not have or develop cancer, but also to distinguish the type of cancer.

Numbered Embodiments

The following embodiments recite non-limiting permutations of combinations of features disclosed herein. Other permutations of combinations of features are also contemplated. In particular, each of these numbered embodiments is contemplated as depending from or relating to every previous or subsequent numbered embodiment, independent of their order as listed. 1. A method of identifying proteins in a sample, the method comprising: incubating a panel comprising a plurality of particle types with the sample to form a plurality of protein corona; digesting the plurality of protein coronas to generate proteomic data; and identifying proteins in the sample by quantifying the proteomic data. 2. The method of embodiment 1, wherein the sample is from a subject. 3. The method of embodiment 2, wherein the method further comprises determining a protein profile of the sample from the identifying step and associating the protein profile with a biological state of the subject. 4. The method of embodiment 1, wherein the method further comprises determining a biological state of the sample from the subject by: generating proteomic data by digesting the plurality of protein coronas; determining a protein profile of the plurality of protein coronas; and associating the protein profile with the biological state, wherein the panel comprises at least two different particle types. 5. The method of embodiment 4, wherein the associating is performed by a trained classifier. 6. The method of any one of embodiments 1-5, wherein the panel comprises at least three different particle types, at least four different particle types, at least five different particle types, at least six different particle types, at least seven different particle types, at least eight different particle types, at least nine different particle types, at least 10 different particle types, at least 11 different particle types, at least 12 different particle types, at least 13 different particle types, at least 14 different particle types, at least 15 different particles, or at least 20 different particle types. 7. The method of any one of embodiments 1-6, wherein the panel comprises at least four different particle types. 8. The method of any one of embodiments 1-7, wherein at least one particle type of the panel comprises a physical feature that is different from a second particle type of the panel. 9. The method of embodiment 8, wherein the physical feature is size, polydispersity index, surface charge, or morphology. 10. The method of any one of embodiments 1-9, wherein the size of at least one particle type of the plurality of particle types in the panel is from 10 nm to 500 nm. 11. The method of any one of embodiments 1-10, wherein the polydispersity index of at least one particle type of the plurality of particle types in the panel is from 0.01 to 0.25. 12. The method of any one of embodiments 1-11, wherein the morphology of at least one particle type of the plurality of particle types comprises spherical, colloidal, square shaped, rods, wires, cones, pyramids, or oblong. 13. The method of embodiment 1-12, wherein the surface charge of at least one particle type of the plurality of particle types comprises a positive surface charge. 14. The method of any one of embodiments 1-12, wherein the surface charge of at least one particle type of the plurality of particle types comprises a negative surface charge. 15. The method of any one of embodiments 1-12, wherein the surface charge of at least one particle type of the plurality of particle types comprises a neutral surface charge. 16. The method of any one of embodiments 1-15, wherein at least one particle type of the plurality of particle types comprises a chemical feature that is different from a second particle type of the panel. 17. The method of embodiment 16, wherein the chemical feature is a surface functional chemical group. 18. The method of embodiment 17, wherein the functional chemical group is an amine or a carboxylate. 19. The method of any one of embodiments 1-18, wherein at least one particle type of the plurality of particle types is made of a material comprising a polymer, a lipid, or a metal, silica, a protein, a nucleic acid, a small molecule, or a large molecule. 20. The method of embodiment 19, wherein the polymer comprises polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly(lactide-co-glycolide) (PLGA), polylactic acid, or polycaprolactone), polystyrene, or a copolymer of two or more polymers. 21. The method of embodiment 19, wherein the lipid comprises dioleoylphosphatidylglycerol (DOPG), diacylphosphatidylcholine, diacylphosphatidylethanolamine, ceramide, sphingomyelin, cephalin, cholesterol, cerebrosides and diacylglycerols, dioleoylphosphatidylcholine (DOPC), dimyristoylphosphatidylcholine (DMPC), and dioleoylphosphatidylserine (DOPS), phosphatidylglycerol, cardiolipin, diacylphosphatidylserine, diacylphosphatidic acid, N-dodecanoyl phosphatidylethanolamines, N-succinyl phosphatidylethanolamines, N-glutarylphosphatidylethanolamines, lysylphosphatidylglycerols, palmitoyloleoylphosphatidylglycerol (POPG), lecithin, lysolecithin, phosphatidylethanolamine, lysophosphatidylethanolamine, dioleoylphosphatidylethanolamine (DOPE), dipalmitoyl phosphatidyl ethanolamine (DPPE), dimyristoylphosphoethanolamine (DMPE), distearoyl-phosphatidyl-ethanolamine (DSPE), palmitoyloleoyl-phosphatidylethanolamine (POPE) palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), palmitoyloleyolphosphatidylglycerol (POPG), 16-O-monomethyl PE, 16-O-dimethyl PE, 18-1-trans PE, palmitoyloleoyl-phosphatidylethanolamine (POPE), 1-stearoyl-2-oleoyl-phosphatidyethanolamine (SOPE), phosphatidylserine, phosphatidylinositol, sphingomyelin, cephalin, cardiolipin, phosphatidic acid, cerebrosides, dicetylphosphate, or cholesterol. 22. The method of embodiment 19, wherein the metal comprises gold, silver, copper, nickel, cobalt, palladium, platinum, iridium, osmium, rhodium, ruthenium, rhenium, vanadium, chromium, manganese, niobium, molybdenum, tungsten, tantalum, iron, or cadmium, titanium, or gold. 23. The method of any one of embodiments 1-22, wherein at least one particle type of the plurality of particle types is surface functionalized with a polymer comprising polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, a polyalkylene glycol (e.g., polyethylene glycol (PEG)), a polyester (e.g., poly (lactide-co-glycolide) (PLGA), polylactic acid, or polycaprolactone), polystyrene, or a copolymer of two or more polymers polyethylene glycol. 24. The method of any one of embodiments 3-23, wherein the method associates the protein profile to the biological state with at least 70% accuracy, at least 75% accuracy, at least 80% accuracy, at least 85% accuracy, at least 90% accuracy, at least 92% accuracy, at least 95% accuracy, at least 96% accuracy, at least 97% accuracy, at least 98% accuracy, at least 99% accuracy, or 100% accuracy. 25. The method of any one of embodiments 3-24, wherein the method associates the protein profile to the biological state with at least 70% sensitivity, at least 75% sensitivity, at least 80% sensitivity, at least 85% sensitivity, at least 90% sensitivity, at least 92% sensitivity, at least 95% sensitivity, at least 96% sensitivity, at least 97% sensitivity, at least 98% sensitivity, at least 99% sensitivity, or 100% sensitivity. 26. The method of any one of embodiments 3-25, wherein the method associates the protein profile to the biological state with at least 70% specificity, at least 75% specificity, at least 80% specificity, at least 85% specificity, at least 90% specificity, at least 92% specificity, at least 95% specificity, at least 96% specificity, at least 97% specificity, at least 98% specificity, at least 99% specificity, or 100% specificity. 27. The method of any one of embodiments 1-26, wherein the method identifies at least 100 unique proteins, at least 200 unique proteins, at least 300 unique proteins, at least 400 unique proteins, at least 500 unique proteins, at least 600 unique proteins, at least 700 unique proteins, at least 800 unique proteins, at least 900 unique proteins, at least 1000 unique proteins, at least 1100 unique proteins, at least 1200 unique proteins, at least 1300 unique proteins, at least 1400 unique proteins, at least 1500 unique proteins, at least 1600 unique proteins, at least 1700 unique proteins, at least 1800 unique proteins, at least 1900 unique proteins, or at least 2000 unique proteins. 28. The method of any one of embodiments 1-27, wherein at least one particle type of the plurality of particle types comprises a superparamagnetic iron oxide nanoparticle. 29. The method of any one of embodiments 1-28, wherein the sample is a biofluid. 30. The method of embodiment 29, wherein the biofluid comprises plasma, serum, CSF, urine, tear, or saliva 31. A method of selecting a panel for protein corona analysis, comprising selecting a plurality of particle types with at least three different physicochemical properties. 32. The method of embodiment 31, wherein the different physicochemical properties is selected from a group consisting of surface charge, surface chemistry, size, and morphology. 33. The method of embodiment 32, wherein the different physicochemical properties comprises surface charge. 34. A composition comprising a panel of particles, wherein the panel comprises a plurality of particle types and wherein the plurality of particle types comprises at least three different physicochemical properties. 35. The composition of embodiment 35, wherein the different physicochemical properties is selected from a group consisting of surface charge, surface chemistry, size, and morphology. 36. The composition of embodiment 36, wherein the different physicochemical properties comprises surface charge. 37. A system of comprising the panel of any one of embodiments 1-34. 38. A system comprising a panel, wherein the panel comprises a plurality of particle types. 39. The system of embodiment 38, wherein the plurality of particle types comprises at least three different physicochemical properties. 40. The system of embodiment 38, wherein the panel comprises at least 3, at least 4, at least 5, at least 6, at least 7, at least 8, at least 9, at least 10, at least 11, or at least 12 different particle types. 41. The system of embodiment 38, wherein the plurality of particle types are capable of adsorbing a plurality of proteins from a sample to form a plurality of protein coronas. 42. The system of embodiment 41, wherein the plurality of protein coronas are digested to determine a protein profile. 43. The system of embodiment 42, wherein the protein profile is associated with a biological state using a trained classifier.

EXAMPLES

The following examples are included to further describe some aspects of the present disclosure, and should not be used to limit the scope of the invention.

Example 1

Synthesis of SPMNPs or Superparamagnetic Iron Oxide Nanoparticles (SPIONs)

SPMNPs or SPIONs were synthesized by following the method in the literature (Angew. Chem. Int. Ed. 2009, 48, 5875-5879 & Langmuir 2012, 28, 3271-3278) via solvothermal reaction at 200° C. by reduction of FeCl3 with ethylene glycol (EG) in the presence of sodium acetate (NaOAc) as an alkali source and trisodium citrate ($Na_3Cit$) as an electrostatic stabilizer. The excess EG acted as both the solvent and reductant.

Starting materials: Iron (III) chloride hexahydrate ($FeCl_3 \cdot 6H_2O$), MW 270.30, CAS #10025-77-1; Sodium acetate (NaOAc), MW 82.03, CAS #127-09-3; Trisodium citrate dihydrate ($Na_3Cit \cdot 2H_2O$), MW 294.10, CA #6132-04-3; Ethylene glycol (EG), MW 62.07, CAS #107-21-1.

Procedure for $Fe_3O_4$ nanoparticles via Solvothermal Reaction:

(1) Typically, FeCl$_3$ (0.65 g, 4.0 mmol) and sodium citrate (0.20 g, 0.68 mmol) were first dissolved in EG (20 mL), afterward, sodium acetate (1.20 g, 14.6 mmol) was added with stirring. The mixture was stirred vigorously for 30 min at 160° C. and then sealed in a Teflon-lined stainless-steel autoclave (50 mL capacity). (2) The autoclave was heated at 200° C. and maintained for 12 h, and then allowed to cool to room temperature. (3) The black products were isolated by a magnet and washed with DI water for >5 times. (4) The final Fe$_3$O$_4$ nanoparticle product was dried in vacuum at 60° C. for 12 h or freeze dried to a black powder. Fe$_3$O$_4$@SiO$_2$ core/shell colloids were prepared through a modified Stöber process by following the method in the literature (J. Am. Chem. Soc. 2008, 130, 28-29 & J. Mater. Chem. B, 2013, 1, 4684-4691)

Starting materials: Fe$_3$O$_4$ nanoparticles synthesized via the solvothermal reaction; Tetraethyl orthosilicate (TEOS), MW 208.33, CAS #78-10-4; Ammonia solution 25%; Cetrimonium bromide (CTAB), MW 364.45, CAS #57-09-0; (3-Aminopropyl)triethoxysilane (APTES), MW 221.37, CAS #919-30-2.

Procedure for Fe$_3$O$_4$@SiO$_2$ Core/Shell nanoparticles:

(1) Superparamagnetic Fe$_3$O$_4$ NPs were synthesized according to the previously reported solvothermal reaction (Angew. Chem. Int. Ed. 2009, 48, 5875-5879 & Langmuir 2012, 28, 3271-3278). Then the obtained Fe$_3$O$_4$ nanoparticles were used to prepare highly aminated superparamagnetic mesoporous composite nanoparticles through a two-step coating procedure. (2) In brief, 0.08 g of the Fe$_3$O$_4$ nanoparticles were homogeneously dispersed in the mixture of ethanol (50 mL), DI water (1 mL), and concentrated ammonia aqueous solution (1.7 mL, 25 wt %), followed by the addition of TEOS (140 µL). After stirring at 40° C. for 6 h, amorphous silica coated superparamagnetic nanoparticles (denoted as Fe$_3$O$_4$@SiO$_2$) were obtained and washed 5 times with water. (3) Then, the Fe$_3$O$_4$@SiO$_2$ nanoparticles were coated with highly aminated mesoporous silica shell via base-catalyzed sol-gel silica reactions by using CTAB as a template. Typically, the above prepared the Fe$_3$O$_4$@SiO$_2$ nanoparticles (5 mg) were dispersed in a mixed solution containing CTAB (0.08 g), ethyl acetate (0.7 mL), DI water (113 mL), and concentrated ammonia (2.42 mL, 25 wt %). TEOS (0.18 mL) and APTES (0.22 mL) were added to the dispersion with a stirring speed of 300 rpm. After reaction at room temperature for 3 h, the products were collected with a magnet and washed repeatedly with water and ethanol, respectively.

(4) To remove the pore-generating template (CTAB), the as-synthesized materials were transferred to ethanol (60 mL) with continual stirring at 60° C. for 3 h. The surfactant extraction step was repeated two times to ensure the removal of CTAB. The template-removed products were washed with ethanol twice, resulting in sandwich structured highly aminated superparamagnetic mesoporous composite nanoparticles (Fe$_3$O$_4$@SiO$_2$@mSiO$_2$—NH$_2$).

Fe$_3$O$_4$@polymer composite nanoparticles were synthesized through surfactant-free seeded emulsion polymerization (Langmuir 2012, 28, 3271-3278).

Fe$_3$O$_4$ nanoparticles synthesized via the solvothermal reaction.

Starting materials: Fe$_3$O$_4$ nanoparticles synthesized via the solvothermal reaction; Tetraethyl orthosilicate (TEOS), MW 208.33, CAS #78-10-4; 3-(trimethoxysilyl)propyl methacrylate (MPS), MW 248.35, CAS #2530-85-0; Ammonia solution 25%; Divinylbenzene (DVB), MW 130.19, CAS #1321-74-0; Styrene (St), MW 104.15, CAS #100-42-5; Methacrylic acid (MAA), MW 86.09, CAS #79-41-4; Ammonium persulfate (APS), MW 228.20, CAS #7727-54-0.

Procedure for Fe$_3$O$_4$@Polymer Core-Shell Nanoparticles:

(1) SPIONs were synthesized according to the previously reported solvothermal reaction (Angew. Chem. Int. Ed. 2009, 48, 5875-5879 & Langmuir 2012, 28, 3271-3278). (2) Fe3O4@MPS were prepared through a modified Stöber process. Typically, 1 g of Fe$_3$O$_4$ nanoparticles were homogeneously dispersed in the mixture of ethanol (50 mL), DI water (2 mL), and concentrated ammonia aqueous solution (2 mL, 25 wt %), followed by the addition of TEOS (200 µL) and MPS (2 mL). After stirring at 70° C. for 24 h, the MPS coated superparamagnetic NPs were obtained and washed 5 times with water and freeze dried to a dark brown powder and stored at −20° C. (3) Fe$_3$O$_4$@Polymer nanoparticles were synthesized through surfactant-free seeded emulsion polymerization. Typically, 100 mg of Fe$_3$O$_4$@MPS were homogeneously dispersed in 125 mL of DI water. After bubbling with N$_2$ for 30 min, 2 mL of St, 0.2 mL of DVB and 0.4 mL of MAA were added into the Fe$_3$O$_4$@MPS suspension. After addition of 5 mL of 0.2 g of NaOH and 40 mg of APS aqueous solution, the resulting mixture was heated to 75° C. overnight. (4) After cooling down, Fe$_3$O$_4$@P(St-co-MAA) were obtained and washed 5 times with water and freeze dried to a dark brown powder.

Example 2

Building Panels of Particle Types

Figure 5:
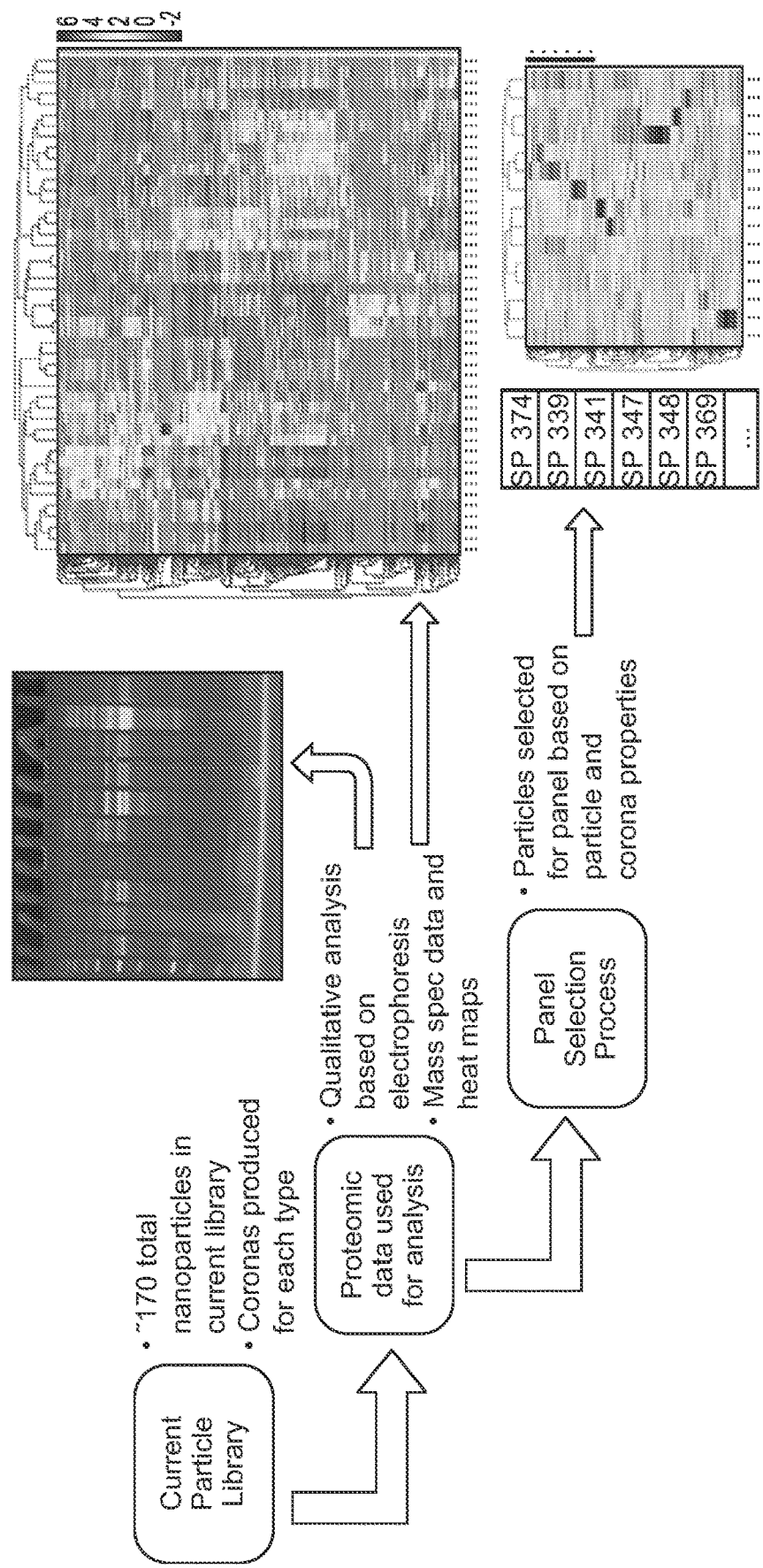
FIG. 5 provides an example of a process for generating proteomic data and a process for panel selection.
Figure 7:
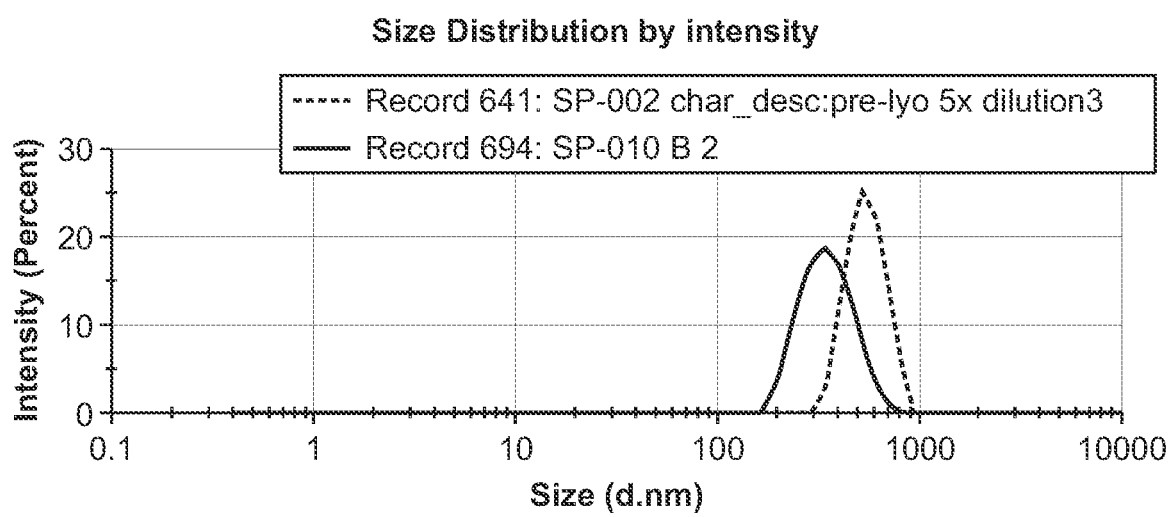
FIG. 7 is an example of size distribution of nanoparticles as characterized by dynamic light scattering.
Figure 8A:
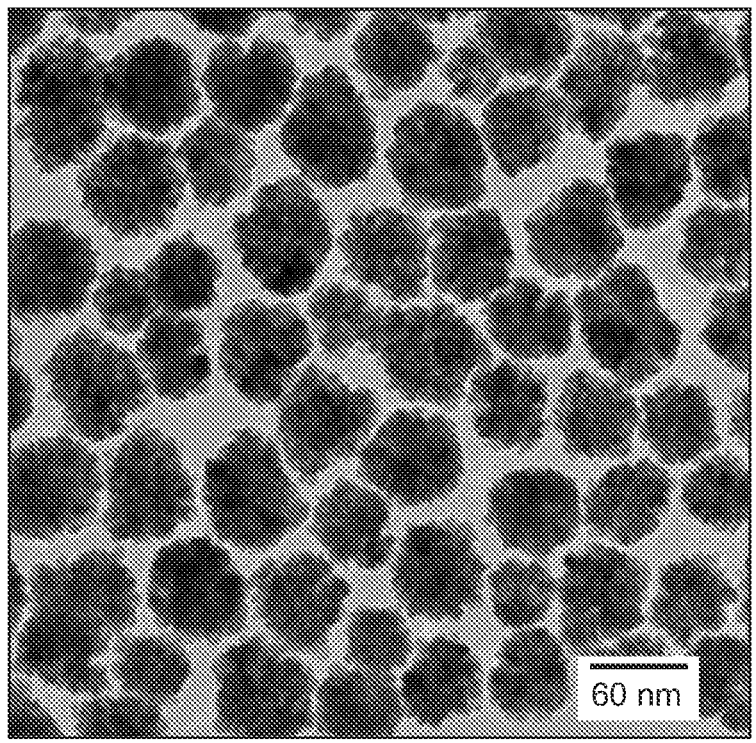
FIG. 8A and FIG. 8B show the characterization of nanoparticles with different functionalization prior to corona formation.
Figure 8B:
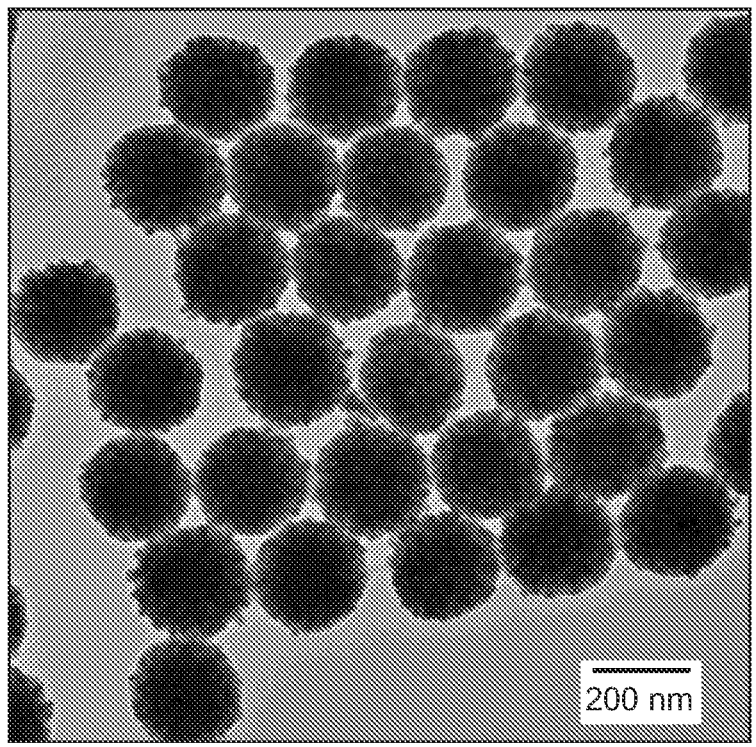
Figure 9:
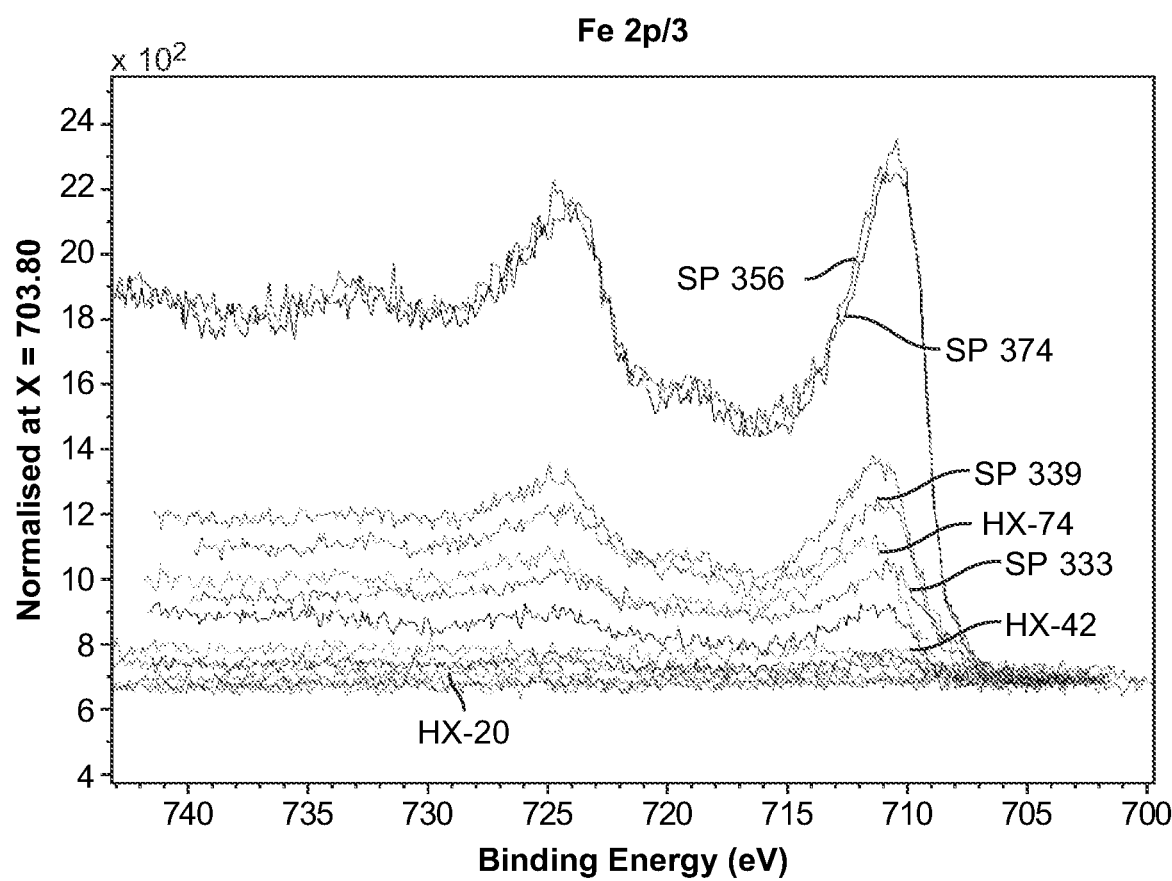
FIG. 9 shows the Fe 2p/3 spectrum for various nanoparticles including SP-333 (carboxylate), SP-339 (polystyrene carboxylate), SP-356 (silica amino), SP-374 (silica silanol), HX-20 (SP-003) (silica coated), HX-42 (SP-006) (silica coated, amine), and HX-74 (SP-007) (PDMPAPMA coated (dimethylamine). The spectrum was obtained from XPS (x-ray photoelectron spectroscopy), which provides the chemical fingerprint of the particle surfaces (measures % of various elements on the surface). XPS can also be used to measure spectra of particles of larger sizes, including microparticles.
Figure 10:
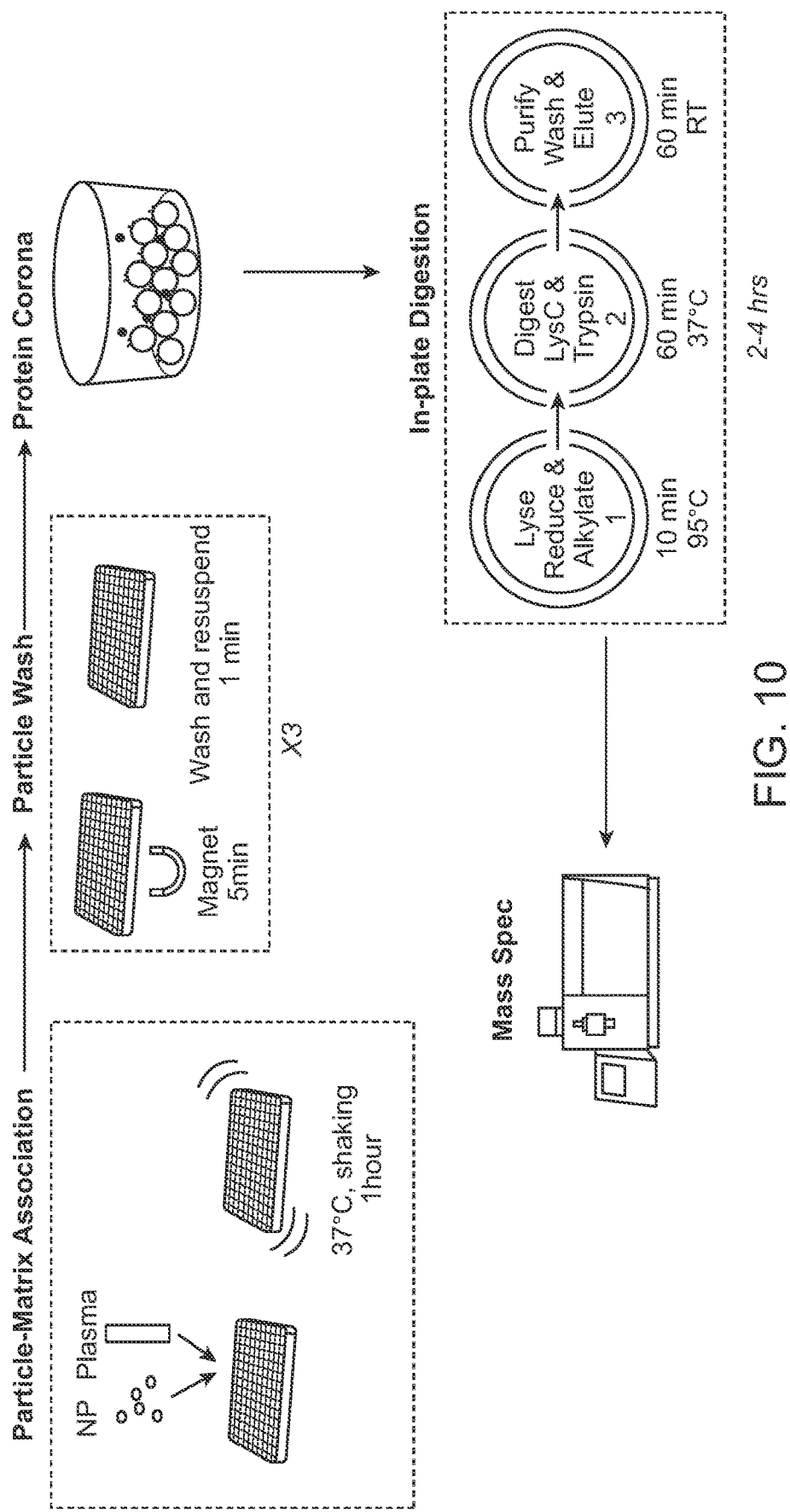
FIG. 10 shows an example of a process of the present disclosure for proteomic analysis. The process illustrated is optimized for high-throughput and automation that can be run in hours and across multiple samples in parallel. The process includes particle-matrix association, particle wash (×3), formation of the protein corona, in-plate digestion, and mass spectrometry. Using the process, it may take only 4 to 6 hours per batch of 96 samples. Typically, one particle type at a time is incubated with a sample.

This example describes building panels of particle types. A particle library was built comprising ~170 total particle types. Biomolecule coronas were produced for each particle type, by incubating each particle with a biological sample. Proteomic data from protein coronas were analyzed for each particle type, including qualitative analysis based on electrophoresis and quantitative analysis based on mass spectrometry data and heat maps. Panels were built by choosing certain particle types based on particle and corona properties. Particle types were selected for particle panels based on the broadness of coverage a particle type had for proteins in the plasma sample. FIG. 5 illustrates the process for generating proteomic data and the process for panel selection. As shown in FIG. 6, particle properties include size/geometry, charge, surface functionality, magnetism, in addition to other properties. Each of these properties can be assays by a variety of tests in fully characterizing a particle type before adding it to a panel. As shown in FIG. 7 dynamic light scattering was used to characterize the size distribution of two particle types: SP-002 (phenol-formaldehyde coated particles) and SP-010 (carboxylate, PAA coated particles). As shown in FIG. 8, TEM was used to characterize the size and morphology of two particle types including SP-002 (phenol-formaldehyde coated particles) (FIG. 8A) and SP-339 (polystyrene carboxyl particles) (FIG. 8B). As shown in FIG. 9, XPS can be used to analyze chemical groups present at the surface of various particle types including SP-333 (carboxylate), SP-339 (polystyrene carboxylate), SP-356 (silica amino), SP-374 (silica silanol), HX-20 (silica coated), HX-42 (silica coated, amine), and HX-74 (PDMPAPMA coated (dimethylamine).

Example 3

Figures 3, 4:
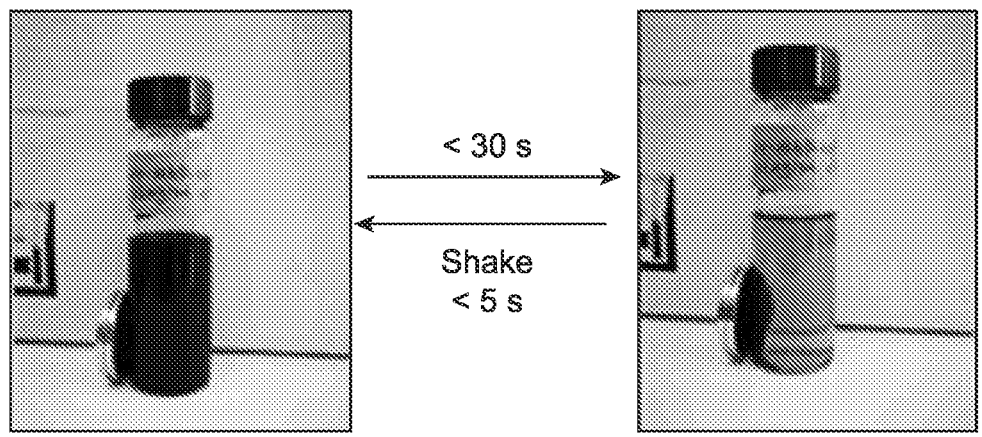
FIG. 3 shows several examples of particle types and several ways the particle surfaces can be functionalized. In some cases, the particles may be nanoparticles.
FIG. 4 shows the separation of superparamagnetic iron oxide nanoparticles (SPIONs) from the remaining solution. As illustrated in the left photo, the SPIONs are dispersed in solution, seen as a dark, opaque solution in a glass vial, prior to or concurrent with application of a magnet to the side of the vial. Within 30 seconds of applying a magnet to the side of the vial, the SPIONs are separated from the solution, as illustrated by accumulation of dark particles next to the magnet and an increase in solution transparency in the photo on the right. Upon shaking the separated solution shown in the right image, the particles return to the dispersed state shown in the left image within 5 seconds. The SPIONs have a fast response.

Synthesis and Characterization of Iron Oxide NPs with Distinct Surface Chemistries This example describes synthesis and characterization of iron oxide NPs with distinct surface chemistries. To address the need for robust particles that can be easily separated, without the need for, but which is also capable of withstanding, repeated centrifugation or membrane filtration to separate particle protein corona from free plasma proteins and to wash away loosely attached proteins from the particles, superparamagnetic iron oxide NPs (SPIONs) were developed (FIG. 23, at top) for protein corona formation. The iron oxide particle core facilitated rapid separation of the particles from plasma solution in <30 sec using a magnet (FIG. 4). This drastically reduced the time needed for extraction of particle protein corona for LC-MS/MS analysis. Moreover, SPIONs were robustly modified with different surface chemistries, which facilitated the generation of distinct patterns of protein corona for more broadly interrogating the proteome.

Three SPIONs (SP-003, SP-007, and SP-011) with different surface functionalization were synthesized (FIG. 28). SP-003 was coated with a thin layer of silica by a modified Stöber process using tetraethyl orthosilicate (TEOS). For synthesis of poly(dimethyl aminopropyl methacrylamide) (PDMAPMA)-coated SPIONs (SP-007) and poly(ethylene glycol) (PEG)-coated SPIONs (SP-011), w the iron oxide particle core was first modified with vinyl groups by a modified Stöber process using TEOS and 3-(trimethoxysilyl)propyl methacrylate. Next, the vinyl group-functionalized SPIONs were surface modified by free radical polymerization with N-[3-(dimethylamino)propyl] methacrylamide and poly(ethylene glycol) methyl ether methacrylate, respectively, to prepare SP-007 and SP-011.

Figure 23:
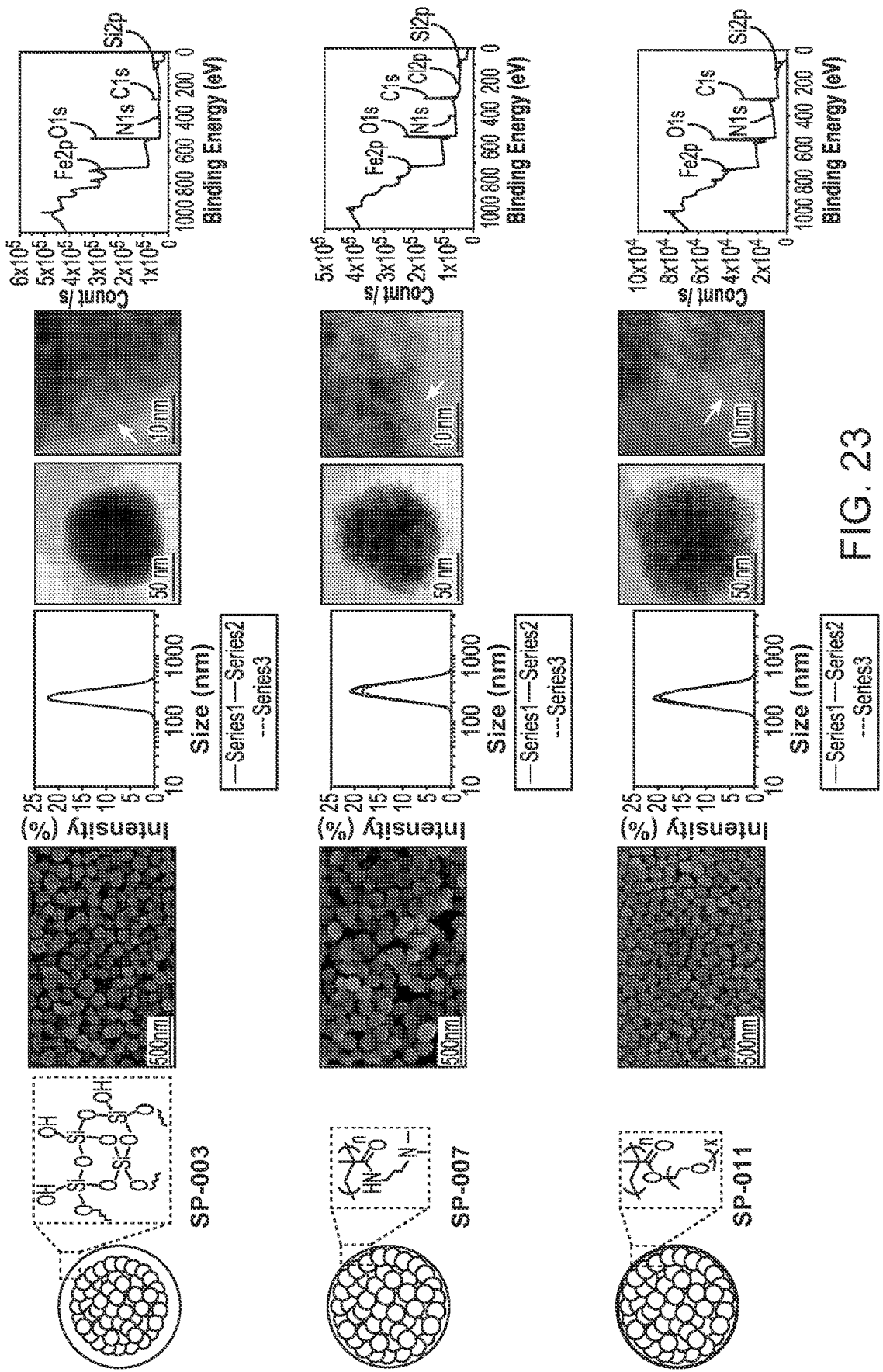
FIG. 23 illustrates characterization of the three superparamagnetic iron oxide nanoparticles (SPIONs) shown in the left-most first column, which from top to bottom, are: silica-coated SPION (SP-003), poly(N-(3-(dimethylamino) propyl) methacrylamide) (PDMAPMA)-coated SPION (SP-007), and poly(oligo(ethylene glycol) methyl ether methacrylate) (POEGMA)-coated SPION (SP-011), by the following methods: scanning electron microscopy (SEM, second columns of images), dynamic light scattering (DLS, third column of graphs), transmission electron microscopy (TEM, fourth column of images), high-resolution transmission electron microscopy (HRTEM, fifth column), and X-ray photoelectron spectroscopy (XPS, sixth column), respectively. DLS shows three replicates of each particle type. The HRTEM pictures were recorded at the surface of individual SP-003, SP-007, and SP-011 particle types, respectively, and the arrow points to the region of amorphous $SiO_2$ (top HRTEM image) coating and amorphous $SiO_2$/polymer coatings (middle and bottom HRTEM images) on the particle surface.

The three SPIONs were characterized using various techniques, including scanning electron microscopy (SEM), dynamic light scattering (DLS), transmission electron microscopy (TEM), high-resolution TEM (HRTEM), and X-ray photoelectron spectroscopy (XPS), to evaluate the size, morphology, and surface properties of SPIONs (FIG. 23). The results of DLS measurements showed that SP-003, SP-007, and SP-011 had average sizes of ~233 nm, ~283 nm, and ~238 nm, respectively. This was consistent with SEM measurements, which showed that all three SPIONs had spherical and semi-spherical morphologies with sizes ranging from 200 nm to 300 nm. The surface charge of SPIONs was evaluated by zeta potential analysis, which showed ζ-potential values of −36.9 mV, +25.8 mV, and −0.4 mV for SP-003, SP-007, and SP-011, respectively, at pH 7.4 (TABLE 2-4).

TABLE 2

Particle diameter and zeta potential of SP-003 SPION, as measured by DLS

| Measurement # | Z-average size | PDI | Zeta potential (mV) |
| --- | --- | --- | --- |
| 1 | 233.8 | 0.053 | −36.4 |
| 2 | 235.3 | 0.039 | −36.8 |
| 3 | 230.4 | 0.055 | −37.4 |
| Average | 233.2 nm | 0.05 | −36.9 mV |

TABLE 3

Particle diameter and zeta potential of SP-007 SPION, as measured by DLS

| Measurement # | Z-average size | PDI | Zeta potential (mV) |
| --- | --- | --- | --- |
| 1 | 284.4 | 0.049 | 25.7 |
| 2 | 286.1 | 0.119 | 25.9 |
| 3 | 279.7 | 0.113 | 25.9 |
| Average | 283.4 nm | 0.09 | +25.8 mV |

TABLE 4

Particle diameter and zeta potential of SP-011 SPION, as measured by DLS

| Measurement # | Z-average size | PDI | Zeta potential (mV) |
| --- | --- | --- | --- |
| 1 | 236.5 | 0.207 | 0.08 |
| 2 | 238.9 | 0.198 | −0.67 |
| 3 | 237.6 | 0.201 | −0.74 |
| Average | 237.7 nm | 0.2 | −0.4 mV |

This indicated that the SP-003, SP-007, and SP-011 had negative, positive, and neutral surfaces, which was consistent with the charge of coating functionalities used to modify the surface of each particle as shown in the schematics of FIG. 23. The thickness of the coatings was evaluated using HRTEM. For SP-003, a complete amorphous shell was observed around the iron oxide core with a thickness greater than 10 nm (FIG. 23, column 5 at top). For SP-007 and SP-011, a relatively thin (<10 nm) amorphous feature was observed at the surface of particles (arrows in FIG. 23; column 5, at middle and bottom). In addition, XPS was performed for surface analysis, which, along with HRTEM images, confirmed the successful coating of the particles with respective functional groups.

Example 4

Detection of Proteins with a Panel and Association of Protein Profiles with a Cancer This example describes detection of proteins with a panel and association of protein profiles with a cancer. The panel of particles includes three different cross-reactive liposomes with various surface charges (anionic (DOPG (1,2-dioleoyl-sn-glycero-3-phospho-fl'-rac-glycerol))), cationic (DOTAP (1,2-Dioleoyl-3-trimethylammoniumpropane)-DOPE (dioleoylphosphatidylethanolamine)), and neutral (dioleoylphosphatidylcholine (DOPC) with cholesterol).

Figure 17A:
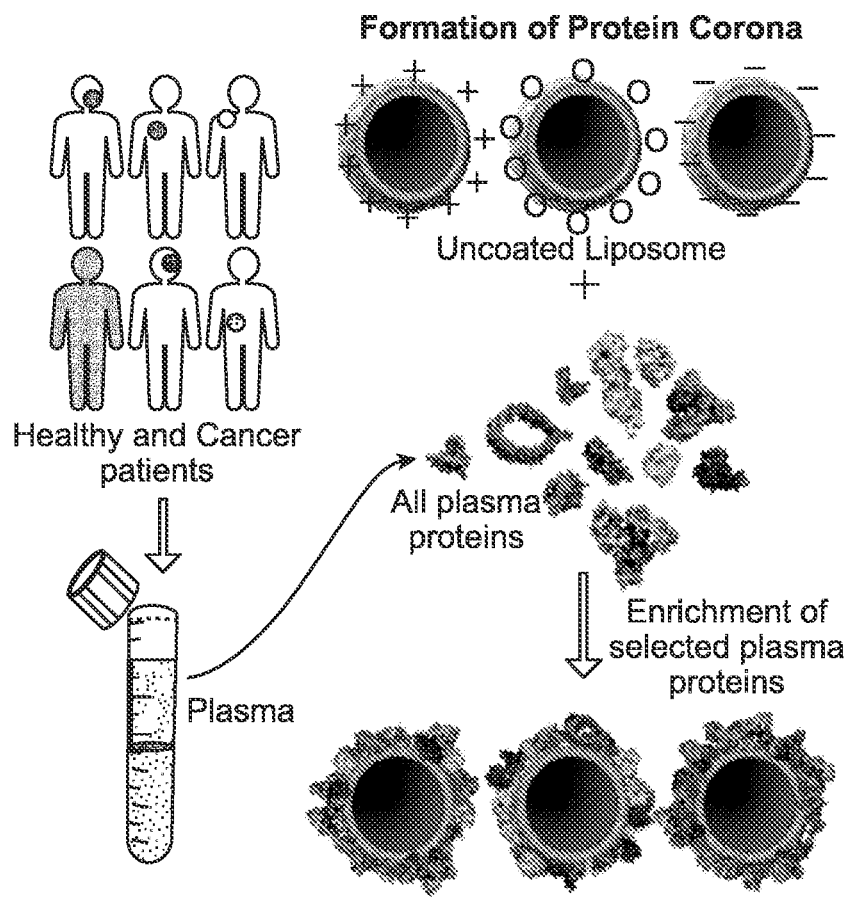
FIG. 17A shows a schematic of a process of the present application including collection of samples from healthy and cancer patients, isolation of plasma from the samples, incubation with uncoated liposomes to form protein coronas, and enrichment of select plasma proteins. Proteins in a sample were assayed using a particle-type panel with distinct particle types to enrich proteins in distinct biomolecule coronas formed on the distinct particle types. Protein corona formation is specific to the physicochemical properties of particles.
Figure 17B:
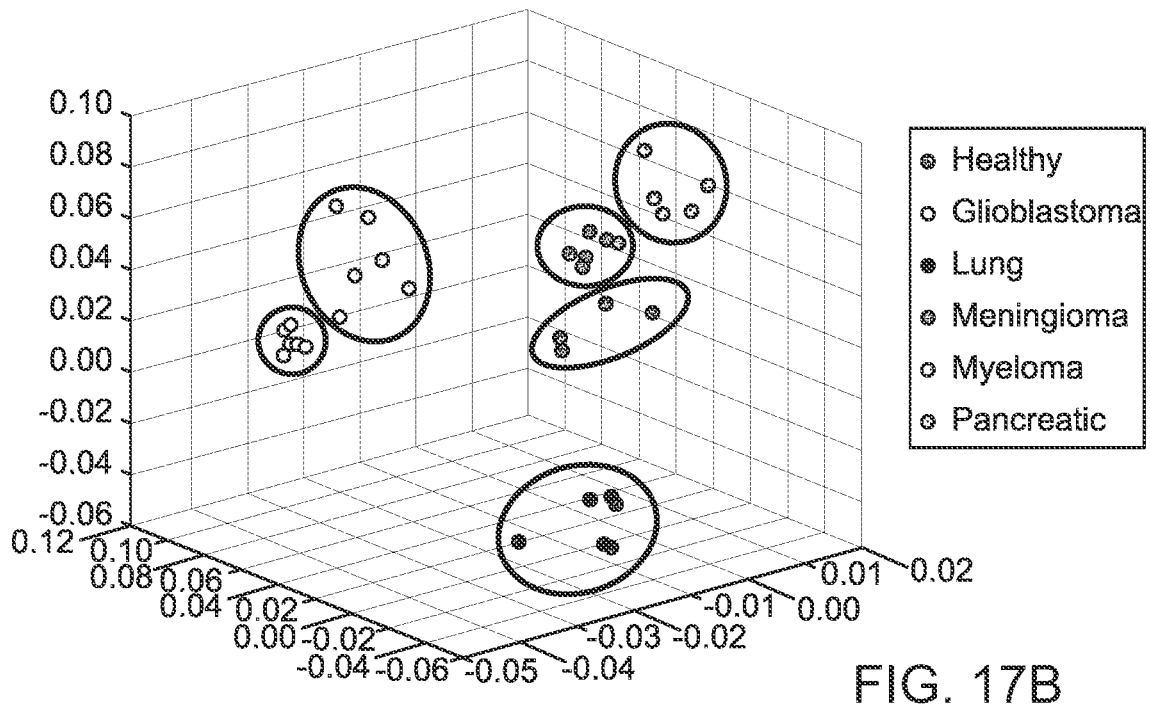
FIG. 17B shows corona analysis with an embodiment of the present disclosure, a Proteograph, for a three-particle type panel. Plasma was collected from 45 subjects (8 from each of 5 cancers, including glioblastoma, lung cancer, meningioma, myeloma, and pancreatic cancer, and 5 healthy controls). The output of the corona analysis, Proteographs, were created for each particle in the 3-particle type panel. Random forest models were built in each of 1000 rounds of cross-validation. This provided strong evidence for robust corona analysis signal. Initial exploratory analysis was done via principal component analysis (PCA) on the proteins detected from the combination of the three particles.
Figures 19, 20:
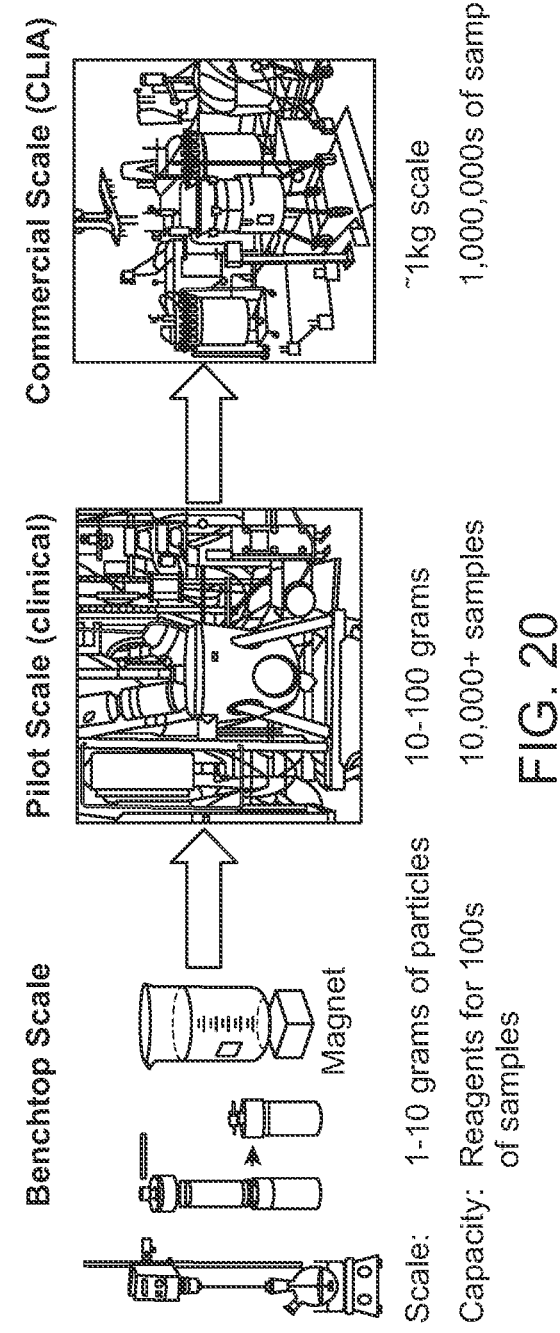
FIG. 19 shows the robust classification of five cancers using a three-particle corona analysis with Proteograph with an overall accuracy of 95%. The data shows that adding particle type diversity increases performance. Three different liposomes with negative, neutral, and positive net charge on the surfaces (at pH 7.4) were used.
FIG. 20 shows an example of scaling of particle biosensor production. The platform can be used across multiple assays and samples.

FIG. 17A shows a schematic of the processes of the present application including collection of samples from healthy and cancer patients, isolation of plasma from the samples, incubation with uncoated liposomes to form protein coronas, and enrichment of select plasma proteins. Protein corona formation can be different based on the physicochemical properties of particles. FIG. 17B shows corona analysis signals for a three-particle type panel. Plasma was collected from 45 subjects (8 from each of five cancers including glioblastoma, lung cancer, meningioma, myeloma, and pancreatic cancer and 5 healthy controls). Corona analyses were created for each particle in the three-particle type panel. Random forest models were built in each of 1000 rounds of cross-validation. There is strong evidence for robust corona analysis signal. Initial exploratory analysis was done via PCA. FIG. 18A and FIG. 18B show that early stage cancers can be separated up to 8 years before symptoms develop. The Golestan Cohort enrolled 50,000 healthy subjects between 2004 and 2008. As shown in FIG. 18A, banked plasma from enrollment was tested. 8 years after enrollment, approximately 1000 patients developed cancers. FIG. 18B shows the classification of the banked plasma. Corona analysis of banked plasma from enrollment date accurately classified cancers for 15 out of 15 subjects examined (5 patients each for 3 cancers). FIG. 19 shows the robust classification of five cancers using a three-particle type corona analysis with an overall accuracy of 95%. The data shows that adding particle type diversity increases performance. Three different liposomes with negative, neutral, and positive net charge on the surfaces (at pH 7.4) were used.

Example 5

Rapid and Deep Proteomic Analysis by the Corona Analysis Workflow

This example describes rapid and deep proteomic analysis by the corona analysis workflow. To evaluate the multi-particle type protein corona analysis platform (FIG. 22B) for analysis of plasma proteome, SPIONs were tested with a pooled plasma sample combined from eight colorectal cancer (CRC) cancer subjects. Each of these three particle types was first incubated with the plasma sample for about 1 hour at about 37° C. for protein corona formation, followed by a magnet-based purification of particles from unbound proteins (6 min per cycle for 3 times). The proteins bound onto particle were then lysed, digested, purified and eluted; these steps taking ~2-4 hours combined, before MS analysis. Notably, this preparation workflow required only ~4-6 hours in total for a batch of 96 corona samples.

Figure 24:
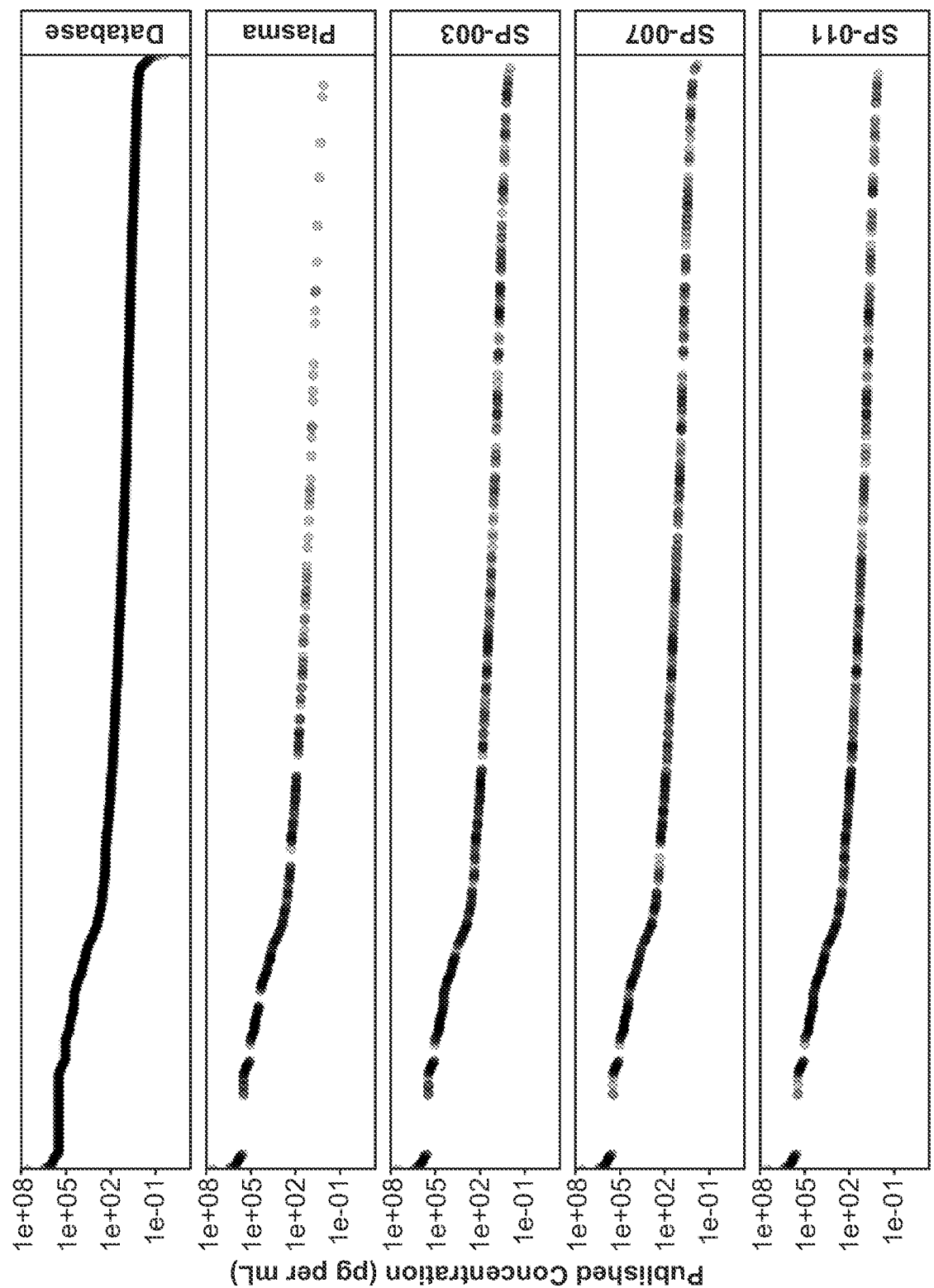
FIG. 24 shows the dynamic range for proteins observed on neat plasma vs. SP-003, SP-007, and SP-011 particles by comparison to a compiled database from Keshishian et al. (Mol Cell Proteomics. 2015 September; 14(9):2375-93. doi: 10.1074/mcp.M114.046813. Epub 2015 Feb. 27.)(top panel).

After MS analysis and data processing, the resulting MS2 peptide-spectral matches (PSM) were used to identify proteins present in each particle type corona. In parallel, proteins were also detected from a neat plasma sample directly, without particle corona formation. Comparing the identified proteins from the samples to a compiled database of MS measured or inferred plasma protein concentrations, the depth and extent of coverage by particle corona or plasma was examined by plotting observed proteins versus the database values of published protein concentrations (FIG. 24). First, the 1,255 proteins from the database covering almost 11-orders of magnitude in order from most abundant to least abundant protein were plotted. For each of the experimentally evaluated samples (neat plasma vs. SP-003/SP-007/SP-011 particle corona), the proteins matching the database were similarly plotted. As can be seen in FIG. 24, the measured plasma proteome's dynamic range as defined by the range of concentrations for database-matching proteins was 2-fold greater for particle corona (e.g., from 40 mg/mL to 0.54 ng/mL for SP-007) than it was for neat plasma (from 40 mg/mL to 1.2 ng/mL) with a 10-fold increase in the number of low abundant proteins present below 100 ng/mL (842 for particles and 84 for neat plasma). There were only 12 proteins annotated in the database with a lower concentration than the lowest protein detected on the particles. In addition, the total number of unique proteins for each of the particle type corona (1,000) is greater (>2-fold) than that observed for neat plasma (<500), as clearly demonstrated in TABLE 5.

TABLE 5

Coverage of proteins identified by SP-003, SP-007, and SP-011 particles versus neat plasma

| Group | Total Proteins | Match to Database | Fraction in Database |
|---|---|---|---|
| Plasma | 492 | 272 | 0.55 |
| SP-003 | 1062 | 387 | 0.36 |
| SP-007 | 991 | 383 | 0.39 |
| SP-011 | 1062 | 393 | 0.37 |

In addition, the fraction of proteins that were previously unobserved by comparison to the literature MS compilation was greater (61-64%) for particles as compared to neat plasma (45%). In other words, more proteins unannotated with a prior MS concentration in the published database were identified in particle corona than were observed in neat plasma. The plot of the particle protein identifications which overlap the database confirm that different particle types select differential subsets of the plasma proteins. This could be attributable to the different surface properties of the three SPION particle types, which largely determine the protein composition of corona.

Figure 25:
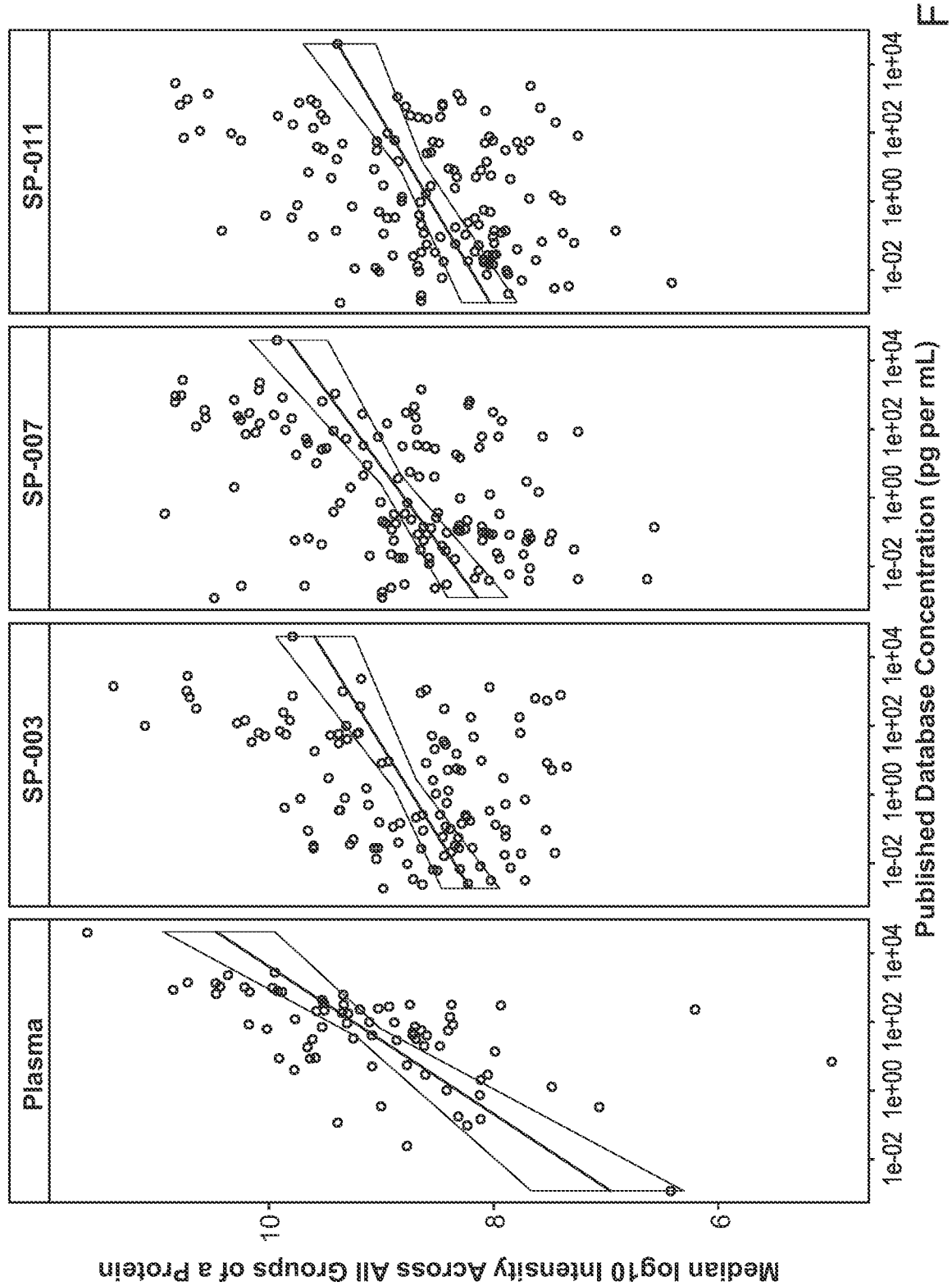
FIG. 25 shows a correlation of the maximum intensities of particle corona proteins vs. plasma proteins to the published concentration of the same proteins

In order to evaluate the ability of particles to compress the measured dynamic range, measured and identified protein feature intensities were compared to the published values for the concentration of the same protein. First, the resulting peptide features for each protein (as presented in FIG. 24) was selected with the maximum MS-determined intensity of all possible features for a protein (using the OpenMS MS data processing tools to extract monoisotopic peak values), and then the intensities were modeled against the published abundance levels for those same proteins (FIG. 25). By comparing the regression model slopes and the intensity span of the measured data, the particle coronas contain more proteins at lower abundances (measured or reported) than does plasma, similar to FIG. 24. The dynamic range of those measured values was compressed (the slope of the regression model is reduced) for particle measurements as compared to plasma measurements. This was consistent with previous observations that particle can effectively compress the measured dynamic range for abundances in the resulting corona as compared to the original dynamic range in plasma, which could be attributable to the combination of absolute concentration of a protein, its binding affinity to particles, and its interactions with neighboring proteins. All the above results indicate that the multi-particle type protein corona strategy facilitated the identification of a broad spectrum of plasma proteins, particularly those in the low abundance that are challenging for rapid detection by conventional proteomic techniques.

To evaluate the robustness of protein identification using the particle corona MS assay, full-assay triplicates were performed using the three particle type panel to create individual protein corona samples from the same pooled CRC plasma sample. For each combination of particle types ranging from any one, to all groups of two, to the single group of three, the number of unique proteins enumerated by the combination is shown in TABLE 6.

TABLE 6

Summary of the protein coverage from the combinations of SP-003, SP-007 and SP-011 Particles

| Particle Type Combination | Only One | Any One | All Three |
|---|---|---|---|
| SP-003 | 1058 ± 27.8 | 1313 | 844 |
| SP-007 | 961 ± 87.4 | 1277 | 660 |
| SP-011 | 1022 ± 37.8 | 1249 | 821 |
| SP-003:SP-007 | 1412 ± 18.9 | 1816 | 1052 |
| SP-003:SP-011 | 1272 ± 22.5 | 1595 | 973 |
| SP-007:SP-011 | 1372 ± 27.3 | 1746 | 1026 |
| SP-003:SP-007:SP-011 | 1576 ± 14.5 | 2030 | 1150 |

In the 'Only One' column, the protein counts were developed using each of the three replicates independently and then finding the mean and standard deviation for all of the combination counts. As can be seen, more proteins were discovered when increasing the number of particle types in the particle panel, with >1,500 unique proteins by the group of three particle types (65 of which are FDA-cleared/approved biomarkers, as listed in TABLE 7, below). In the 'Any One' replicate column, the protein counts were developed using the union of a particle type replicate protein lists. In the 'All Three' replicates column, the protein counts were developed using the intersection of a particle type replicate protein lists. As an additional measure of particle replicate overlap of identified proteins, the Jaccard Index, a metric for set similarity, was calculated for each pairwise-comparison. The values for SP-003, SP-007, and SP-011 were 0.74±0.018, 0.65±0.078, and 0.76±0.019 (mean±sd), respectively. Enumeration of protein content in a given MS sample is subject to the stochastic nature of MS2 data collection and may represent an undercount of the proteins represented within a sample or shared in common between samples. PSM mapping to shared MS1 features represents one approach that may alleviate this issue and will be developed for future analysis.

TABLE 7

FDA-Cleared/Approved Biomarkers

| UP_Accession | UP_Name | Class |
|---|---|---|
| P02647 | APOA1_HUMAN | Particles |
| P00747 | PLMN_HUMAN | Particles |
| P02671 | FIBA_HUMAN | Particles |
| P02675 | FIBB_HUMAN | Particles |
| P04114 | APOB_HUMAN | Particles |
| P02775 | CXCL7_HUMAN | Particles |
| P02768 | ALBU_HUMAN | Particles |
| P02679 | FIBG_HUMAN | Particles |
| P0C0L4 | CO4A_HUMAN | Particles |
| P0C0L5 | CO4B_HUMAN | Particles |
| P61626 | LYSC_HUMAN | Particles |
| P0DOY2 | IGLC2_HUMAN | Particles |
| P01024 | CO3_HUMAN | Particles |
| P08519 | APOA_HUMAN | Particles |
| P04075 | ALDOA_HUMAN | Particles |
| P00738 | HPT_HUMAN | Particles |
| P00736 | CIR_HUMAN | Particles |
| P00488 | F13A_HUMAN | Particles |
| P02765 | FETUA_HUMAN | Particles |
| P01023 | A2MG_HUMAN | Particles |
| P61769 | B2MG_HUMAN | Particles |
| P01009 | A1AT_HUMAN | Particles |
| P01834 | IGKC_HUMAN | Particles |
| P00751 | CFAB_HUMAN | Particles |
| P02746 | C1QB_HUMAN | Particles |
| P07225 | PROS_HUMAN | Particles |
| P02751 | FINC_HUMAN | Particles |
| P00450 | CERU_HUMAN | Particles |
| P02747 | C1QC_HUMAN | Particles |
| P01031 | CO5_HUMAN | Particles |
| P05155 | IC1_HUMAN | Particles |
| P09871 | C1S_HUMAN | Particles |
| P02790 | HEMO_HUMAN | Particles |
| P02745 | C1QA_HUMAN | Particles |
| P01034 | CYTC_HUMAN | Particles |
| P08697 | A2AP_HUMAN | Particles |
| P02741 | CRP_HUMAN | Particles |
| P17936 | IBP3_HUMAN | Particles |
| P01008 | ANT3_HUMAN | Particles |
| P04278 | SHBG_HUMAN | Particles |
| P19652 | A1AG2_HUMAN | Particles |
| P02787 | TRFE_HUMAN | Particles |
| P02786 | TFR1_HUMAN | Particles |
| P02763 | A1AG1_HUMAN | Particles |
| P04275 | VWF_HUMAN | Particles |
| P07195 | LDHB_HUMAN | Particles |
| P00338 | LDHA_HUMAN | Particles |
| P30613 | KPYR_HUMAN | Particles |
| P02766 | TTHY_HUMAN | Particles |
| P09972 | ALDOC_HUMAN | Particles |
| O75874 | IDHC_HUMAN | Particles |
| P06858 | LIPL_HUMAN | Particles |
| P05164 | PERM_HUMAN | Particles |
| P05121 | PAI1_HUMAN | Particles |
| P00740 | FA9_HUMAN | Particles |
| P05543 | THBG_HUMAN | Particles |
| P04070 | PROC_HUMAN | Particles |
| P08833 | IBP1_HUMAN | Particles |
| P00742 | FA10_HUMAN | Particles |
| P07477 | TRY1_HUMAN | Particles |
| P07478 | TRY2_HUMAN | Particles |
| P02753 | RET4_HUMAN | Particles |
| P43251 | BTD_HUMAN | Particles |
| P24666 | PPAC_HUMAN | Particles |
| P05160 | F13B_HUMAN | Particles |
| P01023 | A2MG_HUMAN | Plasma |
| P02768 | ALBU_HUMAN | Plasma |
| P02671 | FIBA_HUMAN | Plasma |
| P01008 | ANT3_HUMAN | Plasma |
| P01024 | CO3_HUMAN | Plasma |
| P00450 | CERU_HUMAN | Plasma |
| P02775 | CXCL7_HUMAN | Plasma |
| P02787 | TRFE_HUMAN | Plasma |
| P08697 | A2AP_HUMAN | Plasma |
| P01031 | CO5_HUMAN | Plasma |
| P0C0L4 | CO4A_HUMAN | Plasma |
| P0C0L5 | CO4B_HUMAN | Plasma |
| P01009 | A1AT_HUMAN | Plasma |
| P00736 | CIR_HUMAN | Plasma |
| P02647 | APOA1_HUMAN | Plasma |
| P02751 | FINC_HUMAN | Plasma |
| P09871 | C1S_HUMAN | Plasma |
| P00738 | HPT_HUMAN | Plasma |
| P04114 | APOB_HUMAN | Plasma |
| P00740 | FA9_HUMAN | Plasma |
| P0DOY2 | IGLC2_HUMAN | Plasma |
| P02675 | FIBB_HUMAN | Plasma |
| P00751 | CFAB_HUMAN | Plasma |
| P05543 | THBG_HUMAN | Plasma |
| P02679 | FIBG_HUMAN | Plasma |
| P02790 | HEMO_HUMAN | Plasma |
| P05155 | IC1_HUMAN | Plasma |
| P02765 | FETUA_HUMAN | Plasma |
| P61769 | B2MG_HUMAN | Plasma |
| P01834 | IGKC_HUMAN | Plasma |
| P07225 | PROS_HUMAN | Plasma |
| P00338 | LDHA_HUMAN | Plasma |
| P07195 | LDHB_HUMAN | Plasma |
| P00488 | F13A_HUMAN | Plasma |
| P19652 | A1AG2_HUMAN | Plasma |
| P00747 | PLMN_HUMAN | Plasma |
| P02747 | C1QC_HUMAN | Plasma |
| P08519 | APOA_HUMAN | Plasma |
| P43251 | BTD_HUMAN | Plasma |

TABLE 7-continued

FDA-Cleared/Approved Biomarkers

| UP_Accession | UP_Name | Class |
|---|---|---|
| P02763 | A1AG1_HUMAN | Plasma |
| P02741 | CRP_HUMAN | Plasma |
| P04275 | VWF_HUMAN | Plasma |
| P02746 | C1QB_HUMAN | Plasma |
| P17936 | IBP3_HUMAN | Plasma |
| P02745 | C1QA_HUMAN | Plasma |
| P00742 | FA10_HUMAN | Plasma |
| P04075 | ALDOA_HUMAN | Plasma |
| P01034 | CYTC_HUMAN | Plasma |
| P05160 | F13B_HUMAN | Plasma |
| P02753 | RET4_HUMAN | Plasma |
| P04070 | PROC_HUMAN | Plasma |
| P06744 | G6PI_HUMAN | Plasma |
| P02766 | TTHY_HUMAN | Plasma |
| P61626 | LYSC_HUMAN | Plasma |
| P05062 | ALDOB_HUMAN | Plasma |
| P06276 | CHLE_HUMAN | Plasma |
| P04278 | SHBG_HUMAN | Plasma |
| P02786 | TFR1_HUMAN | Plasma |

Dynamic Range. The three-particle type panel was assessed for its ability to assay proteins in a sample across a wide dynamic range of protein concentrations. Feature intensities corresponding to proteins that were identified by mass spectrometry were compared to the values determined by other assays for the same protein at the same concentration. After mass spectrometry analysis and data processing, MS2 peptide-spectral matches (PSM) were used to identify peptides and associated proteins present in the corona of the distinct particles types in the particle panel. In parallel, peptides were also directly detected in a plasma sample, without the use of the three-particle type panel for corona analysis via the Proteograph workflow. Resulting peptide features having the maximum MS-determined intensity of all observed features, as determined using the OpenMS MS data processing tools to extract monoisotopic peak values, was selected for each protein. The MS-determined intensities were then modeled against comparable published abundance levels for the same proteins. FIG. 25 shows a correlation between the maximum intensities of proteins in distinct coronas from the distinct nanoparticle types for each particle type in the three-particle type panel relative to plasma proteins and concentration of the same proteins determined using other methods. As shown by the regression model slopes and the intensity span of the measured data, the particle coronas contained more protein hits at lower abundances than does plasma. Additionally, the dynamic range of those measured values was compressed, as shown by a reduced slope of the regression models, for particle measurements as compared to plasma measurements, showing that particles effectively compressed the measured dynamic range of protein abundance in the corona as compared to in plasma. This may be attributed to a combination of absolute protein concentration, protein binding affinity to particles, and protein interactions with neighboring proteins. These results indicate that the methods disclosed herein of using a multi-particle type panel for enrichment of proteins in distinct coronas corresponding to the distinct particle types facilitated the identification of a broad spectrum of plasma proteins, particularly those in the low abundance that are challenging for rapid detection by conventional proteomic techniques.

Example 6

Precision of the Corona Analysis Assay

Figure 26:
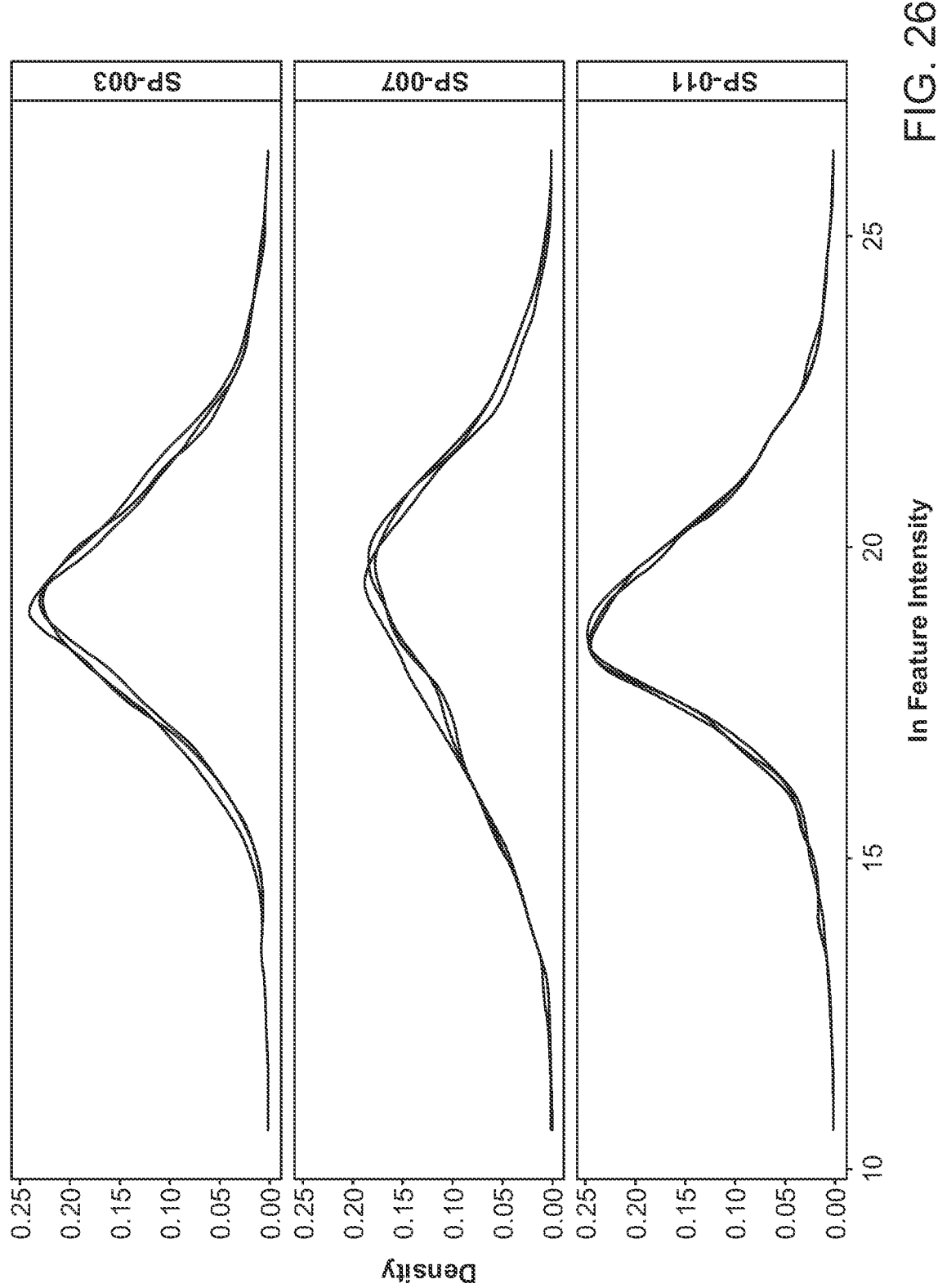
FIG. 26 shows the reproducibility of particle corona intensities for each particle type (SP-003, SP-007, and SP-011) as demonstrated by three replicates using the same plasma sample.

This example describes the precision of the coronal analysis assay. Precision, a measure of repeatability and reproducibility of an assay, was assessed by comparing multiple measurements under the same conditions and determining the variability between the individual measurements. To investigate the reproducibility of the particle protein corona analysis Proteograph workflow, the peptide MS feature intensities were extracted and compared from the three full-assay replicates for each of the three particle types. The raw MS files for each replicate were converted to mzML format, which is a standard, interchangeable MS file format, using the msconvert.exe utility from the openMS suite of programs. Also using openMS processing pipeline, MS1 features were extracted from the raw data and aligned into groups by overlapping retention time and mz value. Groups were selected which contained a feature from each of the three replicates, and filtered to remove the bottom decile based on the clustering algorithm's quality score (90% of feature groups retained for subsequent precision analysis). For the SP-003, SP-007, and SP-011 nanoparticles, a total of 2,744, 2,785, and 3,209, respectively, clustered feature groups were used for the precision analysis. The distribution of log-transformed raw intensities for each of the replicates for these feature groups were plotted in the FIG. 26 with the value of each particle type displayed in the labeled panel. As shown in FIG. 26, the feature data for each particle type was highly reproducible and this reproducibility was consistent across both high intensity and low intensity features.

For a more quantitative assessment of performance, beyond visual inspection of raw data, the overall precision of the particle coronas after quantile normalizing the group feature intensities was estimated. This normalization method was based on the assumption that all compared distributions should be identical and accordingly adjusts the intensities for each compared distribution. This assumption is reasonable given that the reproducibility of the physical characteristics of the particle types themselves and from separate analyses of these particles (e.g., with X-ray photoelectron spectroscopy, high-resolution transmission electron microscopy, and other analytical methods). With the normalized values, the standard deviations were evaluated and the coefficients of variation (CVs) were determined using the appropriate transformation of log-treated data. For each particle, the median CVs (percent of quantile normalized CV or QNCV %) are shown in TABLE 8. This result demonstrates that the particle-measured protein MS feature intensities have sufficient precision across the thousands of MS feature intensities observed to detect relatively small differences in reasonable small studies. For example, given a CV of 25%, there was approximately 100% power to detect two-fold changes with Bonferroni-corrected significance.

The overall precision of particle coronas was estimated by normalizing the group feature intensities using quantile normalization, which makes the prior assumption that all compared distributions should be identical and adjusts the intensities for each compared distribution appropriately. With the normalized values, the standard deviations were evaluated and the coefficients of variation (CVs) were determined using the appropriate transformation of log-treated data. For each particle type, the median CVs (percent of quantile normalized CV or QNCV %) are shown in TABLE 8. A low coefficient of variation (CV) was indicative of a high degree of assay precision.

TABLE 8

Median QNCV % for precision evaluation of the particle protein corona-based Proteograph workflow

| Particle | Median QNCV % | Count |
|---|---|---|
| SP-003 | 23 | 2744 |
| SP-007 | 29 | 2785 |
| SP-011 | 20 | 3209 |

This result demonstrated that the particle-measured protein MS feature intensities had sufficient precision across the thousands of MS feature intensities observed to detect relatively small differences in reasonable small studies.

Example 7

Accuracy of the Corona Analysis Assay

Figure 14A:
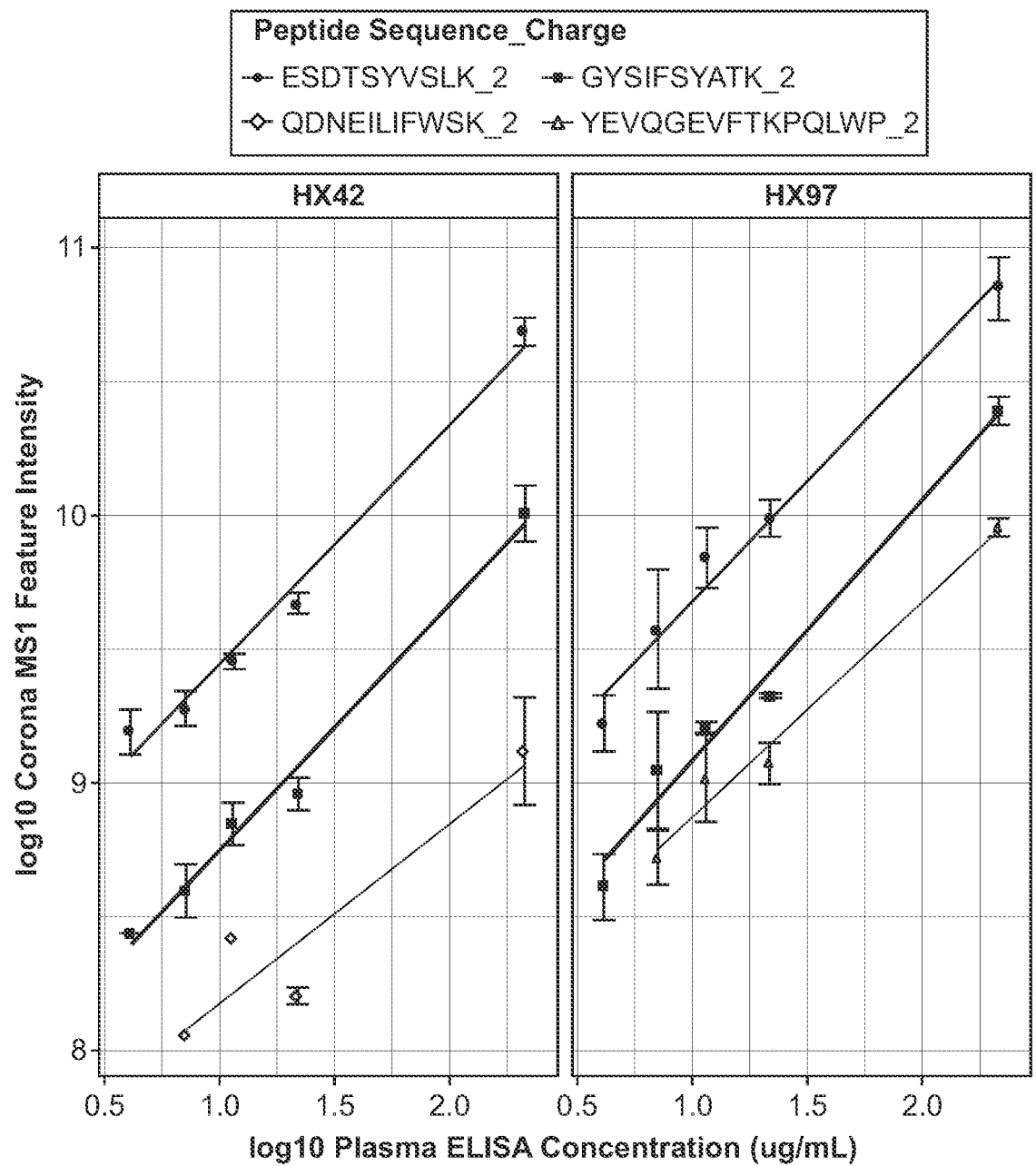
FIG. 14A and FIG. 14B show the concentration responses for spiked proteins as compared to the controls. The spikes change with concentration. Endogenous protein controls did not change with concentration.
Figure 14B:
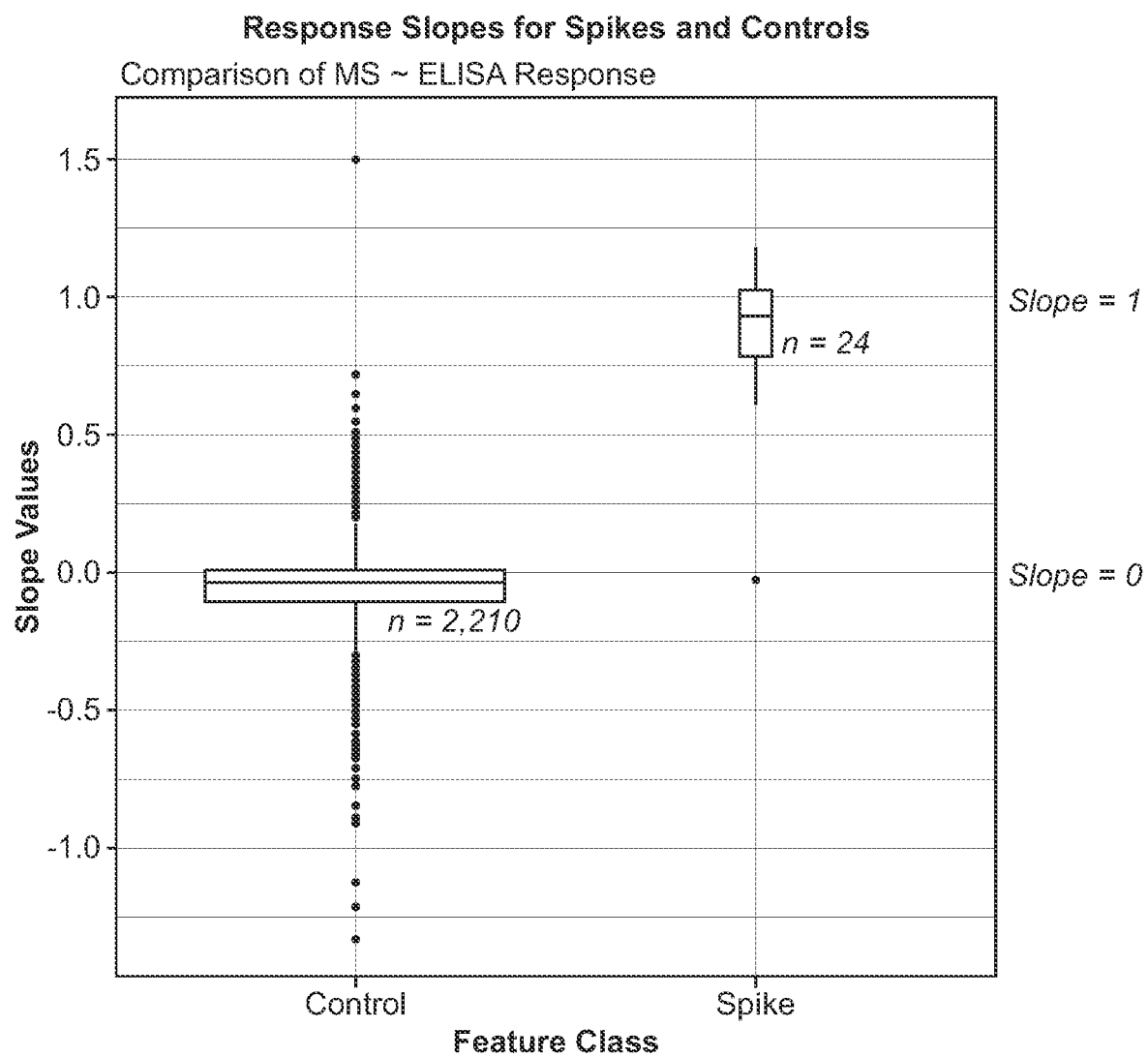
Figure 15:
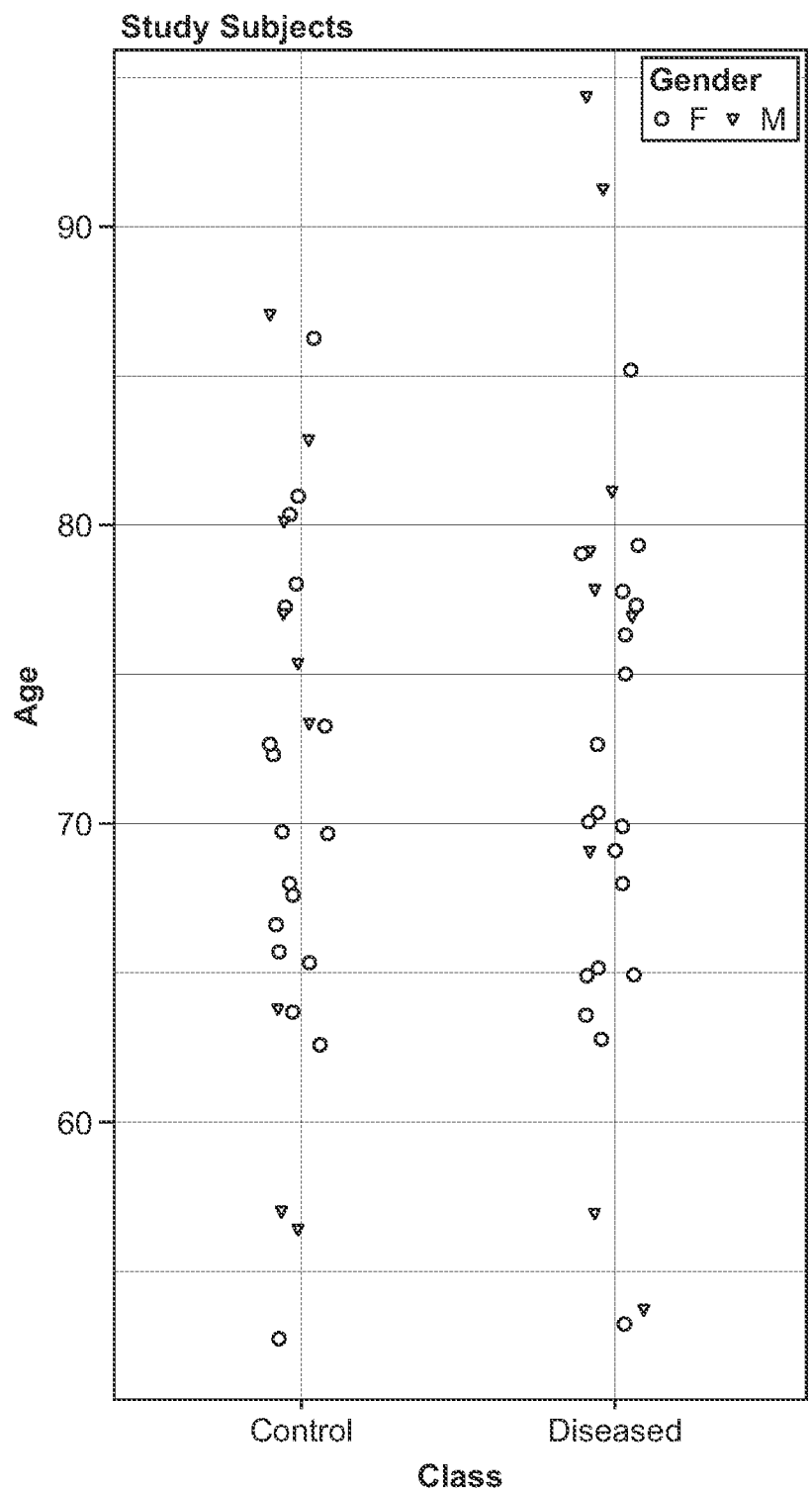
FIG. 15 shows a comparative study for evaluating particle types for panel selection. 56 serum samples were obtained from 28 diseased subjects and 28 control subjects. The diseased subjects had confirmed Stage IV non-small-cell lung carcinoma (NSCLC), comorbidities, and treatments, such as diabetes, cardiovascular disease, hypertension, and etc. The control subjects were age- and gender-matched to the diseased subjects to reduce bias. The study was used to evaluate particle types between groups with large differences, and shows they are age and gender matched. Seven particles were used for the study, as shown in FIG. 16A.
Figure 16B:
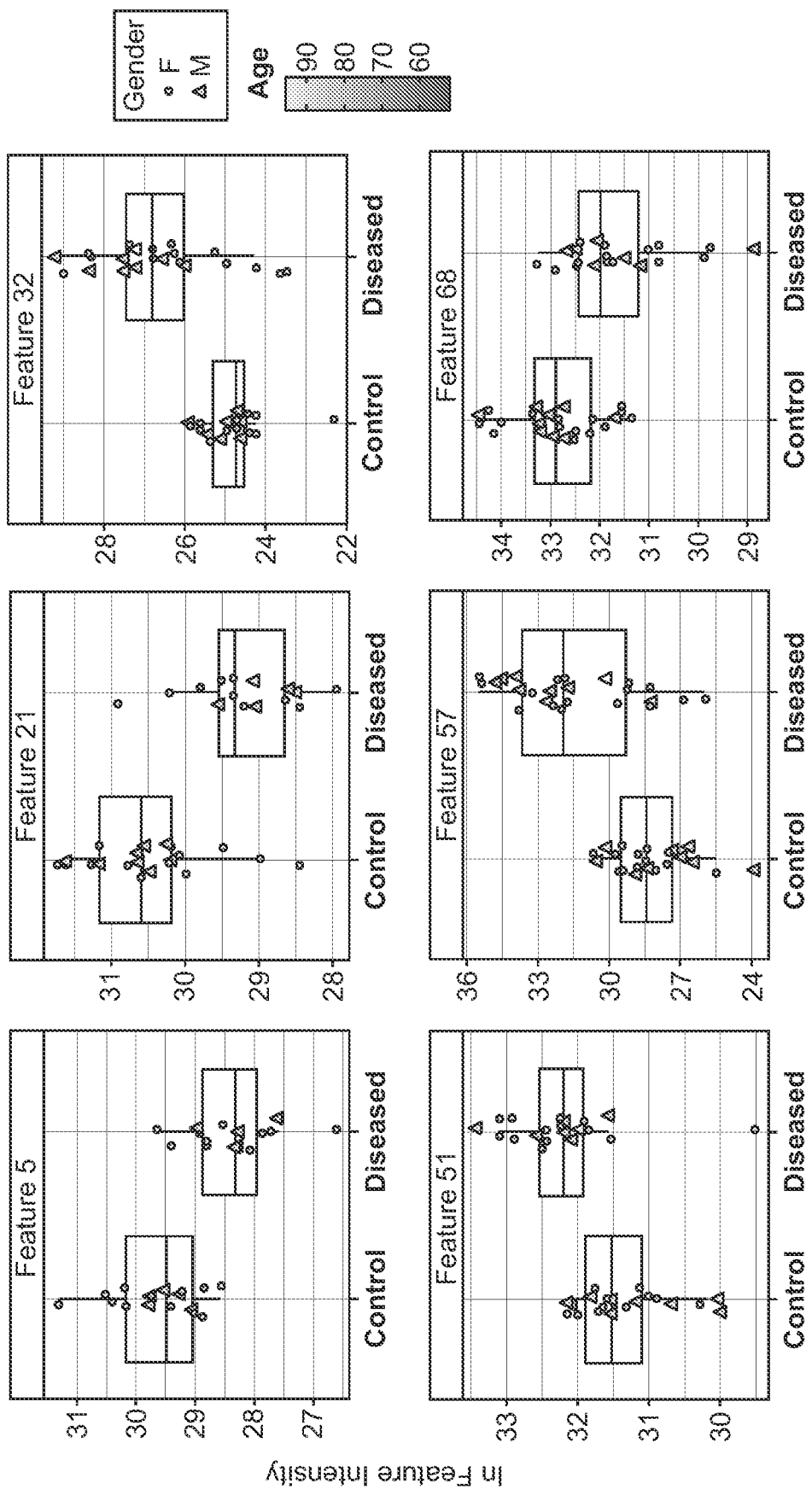
FIG. 16B shows the top hits from SP-339 of FIG. 16A. The detected differences confirm the ability of the coronas to differentiate between sample types and ultimately build classifiers to define disease vs. healthy.
Figure 30:
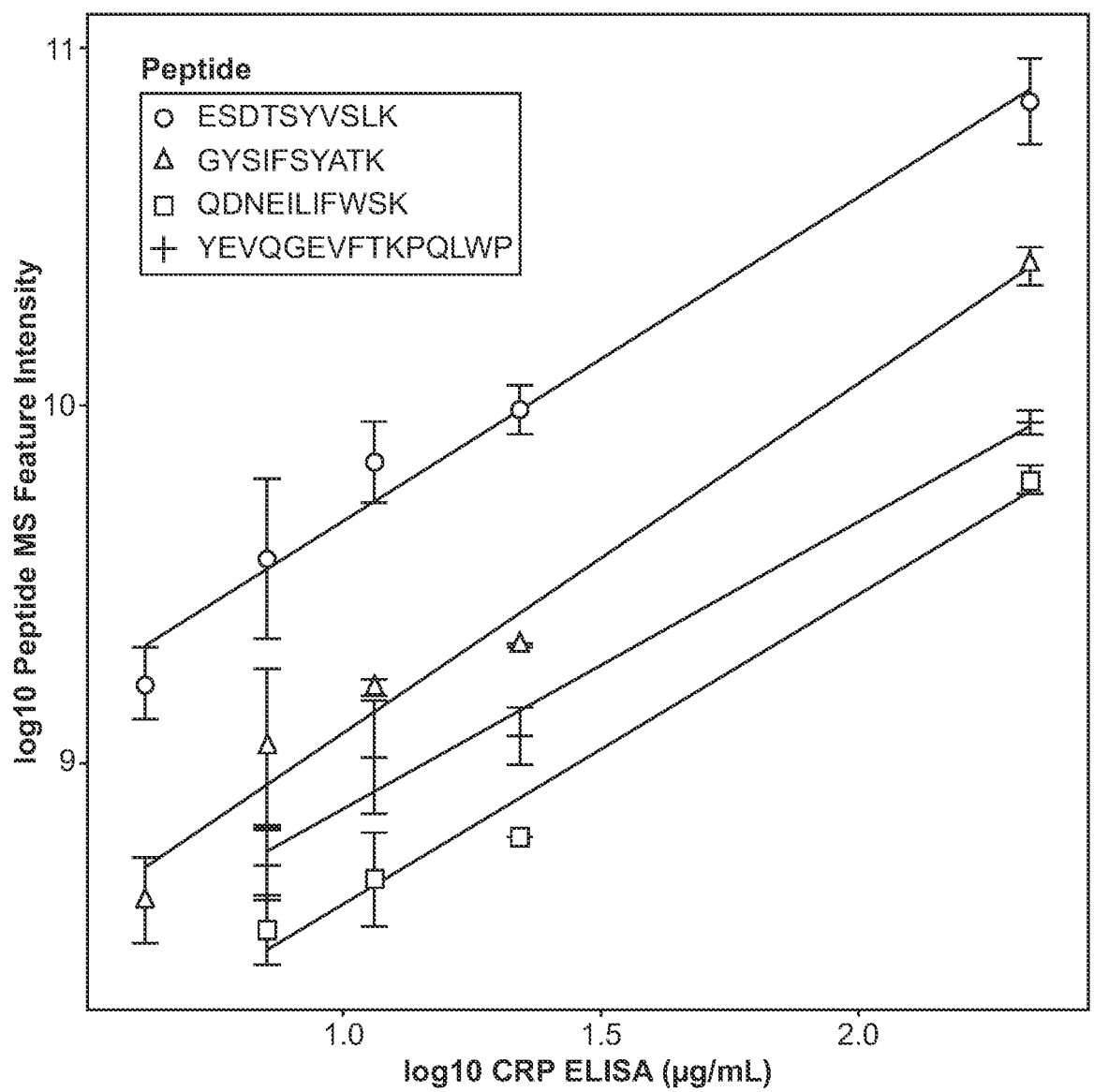
FIG. 30 shows the accuracy of measurements for C-reactive proteins (CRP) on the SP-007 nanoparticles in a spike-recovery experiment for four different peptides.

This example describes the accuracy of the corona analysis assay. The accuracy of a method should be sufficiently robust for detecting a true difference between groups of samples in biomarker discovery and validation studies. Accuracy of the corona analysis assay was determined by comparing corona analysis assay results to those obtained by other methods. To evaluate the corona analysis assay's accuracy, a spike recovery study was performed using the SP-007 nanoparticles. C-reactive protein (CRP) was selected for analysis based on the measurement of its endogenous levels. Using the enzyme-linked immunosorbent assay (ELISA)-determined endogenous plasma levels for CRP, known amounts of the purified protein (see Methods) were spiked to achieve testable multiples of the endogenous levels. The CRP levels after spiking were determined empirically by ELISA to be 4.11, 7.10, 11.5, 22.0, and 215.0 µg/mL for the 1× (unspiked), 2×, 5×, 10×, and 100× samples, respectively. The extracted MS1 feature intensities were plotted for the four indicated CRP tryptic peptides detected by MS on the SP-007 particles versus the CRP concentrations (FIG. 14A). FIG. 30 also shows the accuracy of measurements for CRP proteins on the SP-007 particles in a spike-recovery experiment for four different peptides. The MS1 feature intensity cannot be detected for two of the peptides at the unspiked 1× concentration of CRP. The fitted lines were linear models using the given feature's spike intensities.

Fitting a regression model to all 4 of the CRP tryptic peptides resulted in a slope of 0.9 (95% CI 0.81-0.98) for the response of corona MS signal intensity versus ELISA plasma level, which is close to a slope of 1 that would be considered to be perfect analytical performance. In contrast, a similar regression model fitted to 1,308 other (non-spiked) MS features identified in at least 4 of the 5 plasma samples, for whom the signals from associated MS features should not vary across the samples, had a slope of –0.086 (95% CI –0.1--0.068). These results indicated the ability of that particle type to accurately describe differences between samples will provide a useful tool to quantify potential markers in comparative studies. If a protein level changes in a sample due to some factor, the methods disclosed herein will detect a similar level change of protein bound to particle types of the particle panel, which is a critical property of the present particle type to be effective in any given assay. Moreover, the response of the spiked-protein peptide features also suggests that with appropriate calibration, the particle protein corona method could be used to determined absolute analyte levels as opposed to just relative quantitation.

Example 8

Proteomic Analysis of NSCLC Samples and Healthy Controls

This example describes proteomic analysis of NSCLC samples and healthy controls. To demonstrate the potential utility of the corona analysis platform, the platform's ability was evaluated using a single particle type, SP-007, and serum samples from 56 subjects (28 with Stage IV NSCLC and 28 age- and gender-matched controls) to observe differences between the groups. The selected subject samples represented a reasonably balanced study to identify potential MS features that are different between the groups. The age and gender characteristics of the subjects are summarized in TABLE 6 and full data on subject annotation including disease status and co-morbidities are compiled in TABLE 9.

TABLE 9

Gender and age information for the patients from whom the serum samples were obtained

| Class | Gender | Mean Age | Sd Age | Number |
|---|---|---|---|---|
| Control | F | 71.1 | 7.7 | 19 |
|  | M | 72.4 | 11.1 | 9 |
| Diseased | F | 70.7 | 7.5 | 19 |
|  | M | 15.6 | 13.6 | 9 |

After collection and filtering of the MS1 features followed by log 2 transformation of their intensity, the datasets were median scaled without respect to class.

Figure 29:
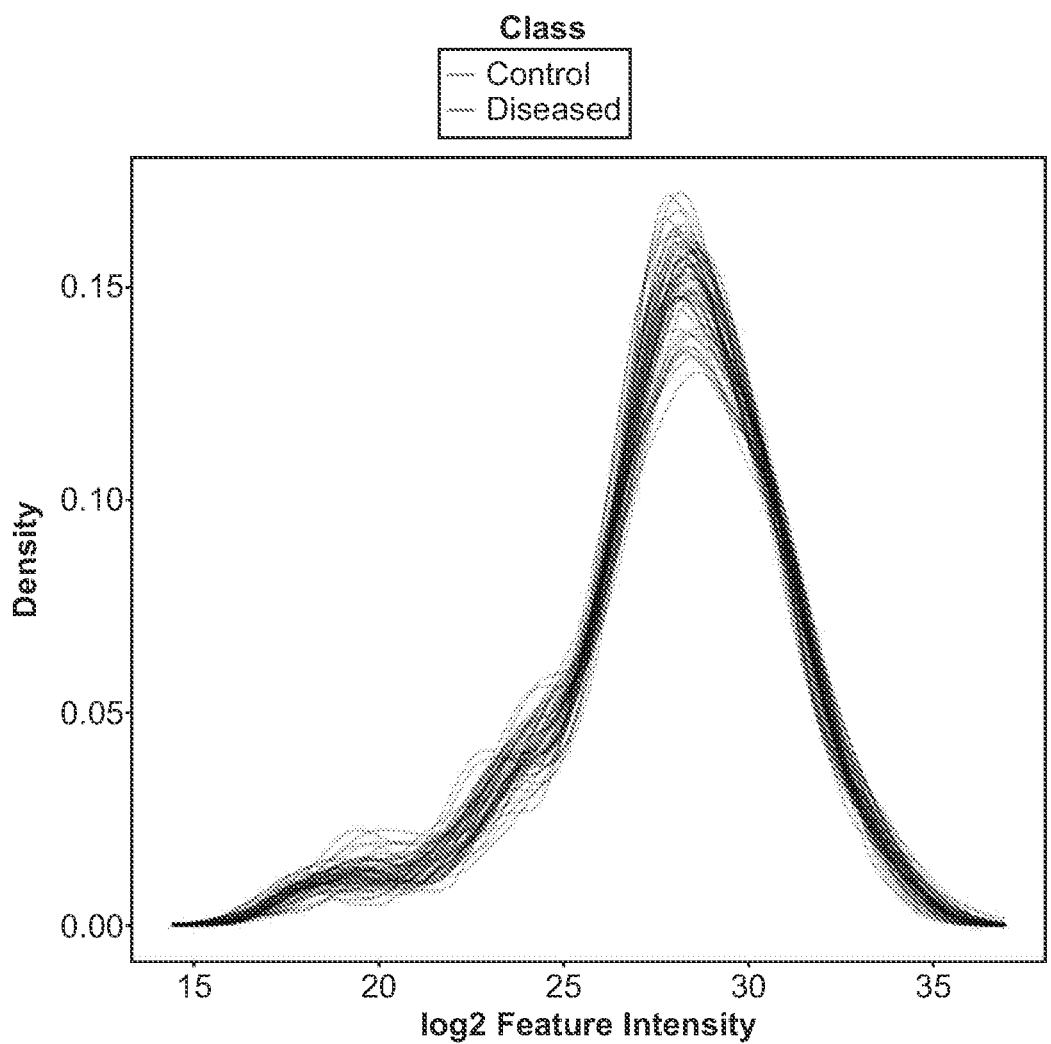
FIG. 29 shows the distribution of the presence-filtered, cluster quality-filtered, median-normalized MS feature intensities for the 56-sample NSCLC comparative study. Each line represents the density of the $\log_2$ feature intensity for either a diseased sample or a control sample. Density is plotted from 0.00 to 0.15 on the y-axis, and $\log_2$ feature intensity is plotted from 15 to 35 on the x-axis. At the highest peak located near a $\log_2$ feature intensity of about 28, with densities ranging from about 0.13 to about 0.17, the two highest traces correspond to control samples, while the lowest trace corresponds to a diseased sample. The remaining control and diseased traces are distributed between the highest and lowest traces. At the two shoulder peaks, occurring at about 20 log 2 feature intensity and about 23 $\log_2$ feature intensity, the highest two traces are control traces and the lowest two traces are control traces at the 20 log 2 feature intensity peak, and the highest traces is a diseased trace at the 23 $\log_2$ feature intensity.

FIG. 29 shows the normalized intensity distributions for all 56 subject datasets. All 56 sample MS raw data files from the NSCLC versus control study were processed by OpenMS pipeline scripts to extract MS1 features and their intensities and cluster them into feature groups based on overlapping mz and RT values within specified tolerances. Only those feature groups were retained that 1) had at least 50% presence of a feature in the group from at least one of the arms of the comparison and 2) had a feature group cluster quality above the 25th percentile. The retained features were median normalized without respect to class and used for subsequent univariate analytical comparison. There were no outliers by inspection of the distributions and all datasets were retained for the univariate analysis.

Figure 27:
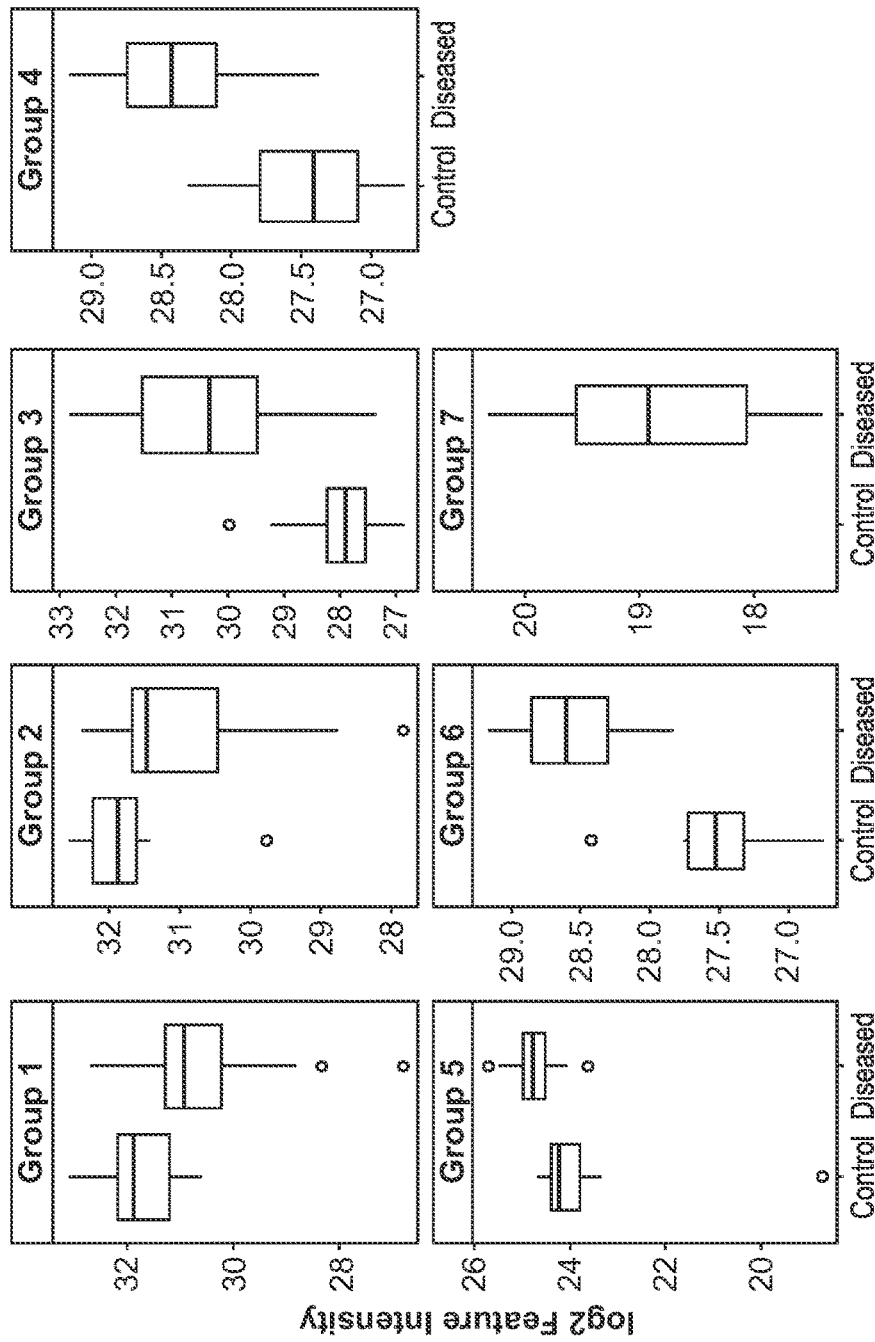
FIG. 27 shows changed features in a non-small cell lung cancer (NSCLC) pilot study using the SP-007 particles. Seven MS features were identified as statistically, significantly different between 28 subjects with Stage IV NSCLC (with associated co-morbidities and treatment effects) and 28 age- and gender-matched, apparently healthy subjects. The table at bottom is a list of the seven proteins that were significantly different, including 5 known proteins and 2 unknown proteins. If a peptide-spectrum match was made for MS2 data associated with the feature, that peptide sequence (and charge) as well as the potential parent protein are indicated; if an MS2 match was not associated with the feature, both the peptide and the protein are marked as "Unknown".

There did not appear to be any outlier datasets by inspection. Univariate comparison of feature group intensities between the classes was performed with a non-parametric, Wilcoxon Test (two-sided). The resulting p-value for the comparison was corrected for multiple testing using the method of Benjamini-Hochberg. Using an adjusted p-value cut-off of 0.05, a total of seven feature groups demonstrated statistical significance, as summarized in FIG. 27.

All five of the proteins identified as differentially abundant between the NSCLC-diseased and control groups have previously been implicated in cancer if not actually NSCLC itself. PON1, or paraoxanase-1, has a complicated pattern in lung cancer including the involvement of a relatively common minor allele variant (Q192R) as a risk factor. At the protein level, PON1 is modestly decreased in lung adenocarcinoma. SAA1 is an acute phase protein that has been shown to be overexpressed in NSCLC in MS-related studies, and the identified peptide was found to be increased 5.4-fold in diseased subjects. The matrisome factor tenascin C (TENA) has been shown to be increased in primary lung tumors and associated lymph node metastases compared with normal tissue, and the associated MS feature was found to be increased by 2-fold in this study. Neural cell adhesion molecule 1 (NCAM1) serves as a marker for diagnosing lung neuroendocrine tumors. FIBA peptides were identified by MS analysis with increased levels correlating with advancing progression of lung cancer. Of special note are the two unknown features, Group2 and Group7, which show differences between control and diseased subjects. Group2 was found in 54 out of 56 subjects and had a modest 33% decrease in diseased subjects. In contrast, Group7 was found only in diseased subjects (14 out of 28 members of the class). These results demonstrated the potential utility for the particle corona to aid in identifying known and unknown markers for different disease states.

Example 9

Particle Panel for Assaying Proteins in a Sample

This example illustrates a 10-particle type particle panel for assaying proteins in a sample. This particle panel shown in TABLE 10 includes 10 distinct particle types, which differ in size, charge, and polymer coating. All particle types in this particle panel are superparamagnetic. The panel shown in below was used to assay proteins in samples.

TABLE 10

10 Particle Type Particle Panel

| Particle ID | Particle Description | Mean DLS diameter (nm) | Mean Zeta Potential (mV) |
|---|---|---|---|
| SP-003 | Thick silica coated SPION | 262 | −36.9 |
| SP-006 | N-(3-Trimethoxysilylpropyl)diethylenetriamine coated | 232 | 20.9 |
| SP-007 | PDMAPMA-coated SPION | 259 | 25.8 |
| SP-010 | Carboxylated, PAA | 366 | −47.9 |
| SP-353 | Amino surface microparticle, 0.4-0.6 µm | 606 | 27.2 |
| SP-333 | Carboxylate microparticle, surfactant free | 1300 | −28.5 |
| SP-339 | Polystyrene carboxyl functionalized | 410 | −31.4 |
| SP-347 | Silica coated, 200 nm | 281 | −21.8 |
| SP-365 | Silica | 231 | −39.0 |
| SP-373 | Dextran based coating, 0.13 µm | 169 | −0.5 |

Protein coverage of V1 panel. To evaluate the total protein group coverage seen across multiple samples in a clinical sample set, plasma samples from 16 individuals were evaluated for a panel of ten distinct particle types shown in TABLE 10 and referred to as the V1 panel. using the sample preparation, MS data acquisition and MS data analysis methods described herein. A mix of non-small-cell lung carcinoma (NSCLC) patients and healthy individuals (n=8 for each) was used to provide a diverse set of proteins and protein groups, present in both healthy and cancer cells, for analysis and identification using the methods described herein. At the 1% FDR (protein and peptide) rate, a total of 2,009 protein groups were efficiently identified. For comparison, in the previously mentioned published study, 4,500 protein groups were detected across 16 individual plasma samples in a complex workflow comprised by more than 70 steps and more than 30 MS fractions per sample, likely taking weeks to complete.

Example 10

10-Particle Type Particle Panel for Protein Assaying

This example illustrates the development of a 10-particle type particle panel for methods of assaying proteins using biomolecule corona analysis, as described herein.

Particle Screen. To demonstrate the ability of the corona analysis platform to expand its coverage through guided particle addition, biomolecule coronas from 43 particles types with distinct physicochemical properties and screened in a similar manner to the three-particle type particle panel disclosed herein.

TABLE 11

Particles for Screening

| Particle type | Particle Description | DLS Diameter (nm) | DLS PDI | Zeta potential (mV) |
|---|---|---|---|---|
| SP-001 | Carboxylated citrate coated | 374 | 0.23 | −34.0 |
| SP-002 | Phenol-formaldehyde resin coated | 335 | 0.39 | −29.0 |
| SP-003 | Silica coated SPION | 233 | 0.05 | −36.9 |
| SP-004 | Polystyrene coated | 411 | 0.32 | −45.7 |
| SP-005 | Carboxylate Poly(styrene-co-methacrylic acid) | 247 | 0.19 | −36.5 |
| SP-006 | N-(3-Trimethoxysilylpropyl)diethylenetriamine coated | 232 | 0.30 | 20.9 |
| SP-007 | PDMAPMA-coated SPION | 283 | 0.09 | 25.8 |
| SP-008 | 1,2,4,5-Benzenetetracarboxylic acid coated | 426 | 0.43 | −34.5 |
| SP-009 | PVBTMAC coated | 229 | 0.11 | 35.9 |
| SP-010 | Carboxylated, Polyacrylic acid | 366 | 0.23 | −47.9 |
| SP-016 | Titanium(IV) oxide coated | 1623 | 0.92 | −32.1 |
| SP-019 | Phenylboronic acid coated | 305 | 0.44 | −36.4 |
| SP-047 | Poly(glycidyl methacrylate-benzylamine) coated | 1255 | 0.54 | 18.1 |
| SP-060 | Maleimide base surface | 302 | 0.15 | −40.8 |
| SP-064 | Poly(N-[3-(Dimethylamino)propyl]methacrylamide-co-[2-(methacryloyloxy)ethyl]dimethyl-(3-sulfopropyl)ammonium hydroxide, P(DMAPMA-co-SBMA) coated | 302 | 0.25 | 27.7 |

TABLE 11-continued

Particles for Screening

| Particle type | Particle Description | DLS Diameter (nm) | DLS PDI | Zeta potential (mV) |
|---|---|---|---|---|
| SP-065 | Modified Random 30 nt ssDNA | 364 | 0.21 | −43.5 |
| SP-066 | Smaller size carboxylated citrate coated | 210 | 0.25 | −35.3 |
| SP-369 | Carboxylated, Original coating, 50 nm | 104 | 0.15 | −31.5 |
| SP-373 | Dextran based coating, 0.13 μm | 169 | 0.07 | −0.6 |
| SP-374 | Silica Silanol coated with lower acidity | 225 | 0.11 | −25.6 |
| SP-389 | BioMag ®Plus Wheat Germ Agglutinin coated microparticle | 3514 | 0.97 | −21.6 |
| SP-390 | Oleic acid- Hydrophilic/hydrophobe surface | 98 | 0.10 | −38.0 |
| SP-391 | Rare earth doped phosphor particles | 130 | 0.15 | −16.0 |
| SP-392 | Gadolinium oxide nanopowder coated | 1199 | 0.82 | −4.9 |
| SP-393 | Oligonucleotide-philic Apostle MiniMax ™ Magnetic Nanoparticles | 614 | 0.23 | −41.9 |
| SP-394 | Iron Oxide Nanoparticles with Azide Groups coating, 30 nm | 64 | 0.11 | −17.0 |
| SP-397 | DEAE starch coated | 99 | 0.18 | 13.6 |
| SP-398 | Poly(maleic acid-co-olefin) amphiphilic coating | 393 | 0.31 | −27.8 |
| SP-399 | Polyvinyl alcohol coated | 163 | 0.10 | −8.9 |
| SP-300 | Poly(4-vinylpyridine) (P4VP) coated | 177 | 0.21 | −19.3 |
| SP-301 | Poly-diallyldimethylamine coated, strong anion exchanger | 114 | 0.14 | 24.6 |
| SP-305 | Amine small clusters | 75 | 0.17 | −9.5 |
| SP-406 | Boronated nanopowder surface | 491 | 0.45 | −40.7 |
| SP-413 | Nanotrap Blue VSA CS Magnetic Porous surface | 3500 | 0.77 | −3.0 |
| SP-333 | Carboxylate microparticle, surfactant free | 1348 | 0.66 | −28.5 |
| SP-339 | Polystyrene carboxyl functionalized | 410 | 0.03 | −31.4 |
| SP-341 | Carboxylic acid, 150 nm | 154 | 0.10 | −26.0 |
| SP-347 | Silica coated, 200 nm | 281 | 0.18 | −21.8 |
| SP-353 | Amino surface microparticle, 0.4-0.6 μm | 1723 | 0.75 | 31.4 |
| SP-356 | Silica amino functionalized microparticle, 0.1-0.39 μm | 2634 | 0.62 | 19.8 |
| SP-363 | Jeffamine, 0.1-0.39 μm | 253 | 0.13 | −35.4 |
| SP-364 | Polystyrene microparticle, 2.0-2.9 μm | 3176 | 0.96 | −55.9 |
| SP-365 | Silica | 231 | 0.02 | −39.0 |

The 43 particle types were evaluated using 6 conditions, as described in the methods sections, and the most optimal conditions were used in a secondary analysis to select the best combination based on total identified protein number. The 43-particle type screen was conducted using a plasma pool of healthy and lung cancer patients, different from the CRC pool used for the three-particle type particle panel, to demonstrate platform validation across biological samples. A pooled sample was used to increase protein diversity. Strict criteria were used to identify potential proteins for panel selection and optimization. For maximum potential evaluation, a protein had to be represented by at least one peptide-spectral-match (PSM; 1% false discovery rate (FDR)) in each of three full assay replicates to be counted as "identified." The panel with the largest number of individual unique Uniprot identifiers was selected for the 10-particle type particle panel.

Figure 36:
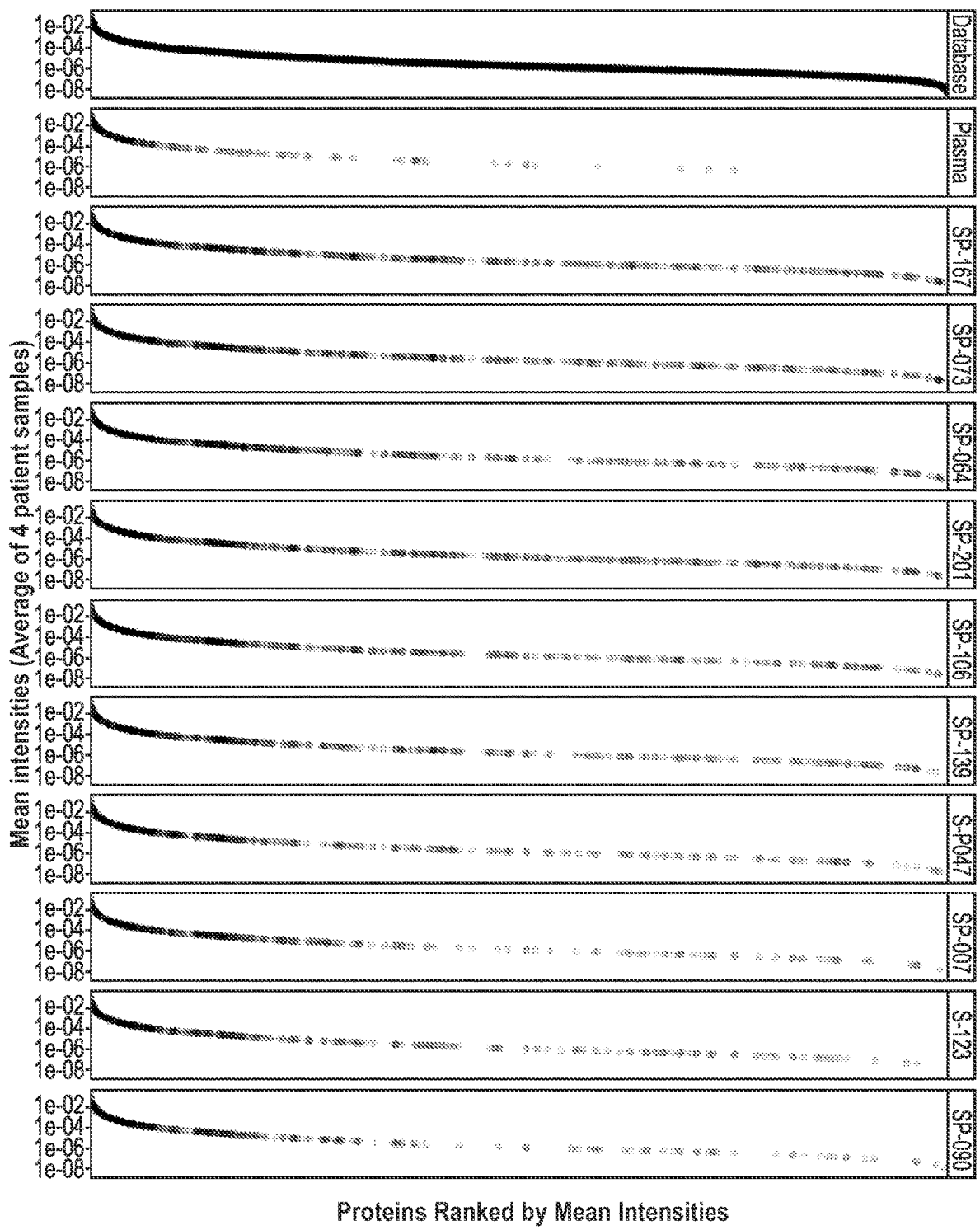
FIG. 36 shows matching and coverage of a particle panel of the 10 distinct particle types to a 5,304-plasma protein database of MS intensities. The ranked intensities for the database proteins are shown in the top panel ("Database"), the intensities for proteins from simple plasma MS evaluation are shown in the second panel ("Plasma") and the intensities for the optimal 10-particle type panel are shown in the remaining panels. The plasma protein intensities database is from Keshishian et al. (2015). Multiplexed, Quantitative Workflow for Sensitive Biomarker Discovery in Plasma Yields Novel Candidates for Early Myocardial Injury. Molecular & Cellular Proteomics, 14(9), 2375-2393.

Protein Coverage of 10-Particle Type Particle Panel. Data disclosed herein confirms that the particle panels provided can be used to determine changes in proteomic content across many biological samples. The particle panels disclosed herein have high precision and accuracy and provide methods that take an unbiased approach that doesn't require specific ligands to known proteins. Thus, these panels are particularly well suited to biomarker discovery. The breadth and depth of plasma protein coverage using the 10-particle type panel was investigated. Using a database (n=5,304) of MS-derived plasma protein intensities (a close correlate to concentration), the coverage of the 10-particle type panel was compared against the full extent of the database as well as against the coverage obtained by MS evaluation of simple plasma (direct MS analysis of the same plasma sample without particle-based sampling). FIG. 36 shows matching and coverage of a particle panel of the 10 distinct particle types to a 5,304 plasma protein database of MS intensities. The ranked intensities for the database proteins are shown in the top panel ("Database"), the intensities for proteins from simple plasma MS evaluation are shown in the second panel ("Plasma") and the intensities for the optimal 10-particle panel are shown in the remaining panels. The plasma protein intensities database is from Keshishian et al. (2015). Multiplexed, Quantitative Workflow for Sensitive Biomarker Discovery in Plasma Yields Novel Candidates for Early Myocardial Injury. Molecular & Cellular Proteomics, 14(9), 2375-2393. The results, shown in FIG. 36, confirmed and extended the results shown for the particle panel of 3 distinct particle types described above, which were used in precision experiments shown FIG. 26. The particle panel of 10 distinct particle types identified 1,598 proteins vs. 268 proteins for simple plasma. Furthermore, each individual particle type detected substantially more proteins than direct MS analysis of simple plasma. Unlike MS analysis on simple plasma, the particle panel of 10 distinct particle types interrogated the entire spectrum of the concentration of plasma proteins. Said differently, while the proteins identified from the simple plasma sample were skewed toward the higher intensity proteins (that is, higher abundance proteins), the proteins identified from the particle panel of 10 distinct particle types extended over 8 orders of magnitude in dynamic range of the concentrations in the database. Only 21 proteins in the database had intensities lower than the lowest protein matched from the particle panel of 10 distinct particle types.

As demonstrate in FIG. 36, the particle panel of 10 distinct particle types demonstrated high precision, accuracy, and broad coverage across a wide range of protein concentrations in plasma and enables broad-scale, unbiased proteomic analyses in parallel across large numbers of biological samples, and can match the cost and speed of what is possible in genomic data acquisition today.

Precision of a Particle Panel Including 10 Distinct Particle Types. This example describes reproducibility of particle corona for a particle panel including 10 distinct nanoparticle types. Particles were analyzed to determine the coefficient of variation (CV) of each feature group between the replicate runs for each particle type of the particle panel including 10 distinct nanoparticle types. A low CV indicated high precision and reproducibility between replicate runs. The data was processed using the software program OpenMS and retained feature groups which contained an observed precursor feature from each of three replicates. The bottom 5% of the data was removed to eliminate statistical outliers based on a quality score of the clustering algorithm. Group feature intensities were median normalized, and the overall precision of the coronas of each particle type was estimated. Normalization was performed such that the overall median intensity for each injection remained the same, and intensities were adjusted for each compared distribution to account for intensity shifts due to, for example, overall differences in instrument response. Differences in instrument response may arise in a variety of analysis methods, including X-ray photoelectron spectroscopy, high-resolution transmission electron microscopy, and other analytical methods. The normalized values of the coefficients of variation (CVs) of each feature group were then evaluated for each particle type of the particle panel including 10 distinct nanoparticle types. TABLE 12 shows the optimized panel of 10 distinct particle types.

TABLE 13 shows the median percent of quantile normalized CV (QNCV %) for precision evaluation of the protein corona-based Proteograph workflow for plasma and a particle panel including 10 distinct particle types for features, peptides and proteins. A 1% peptide and 1% protein false discovery rate (FDR) was applied. Data was processed using MaxLFQ analysis software, applying the condition that each protein group have at least one peptide ratio-count and detection in all replicates, which reduced the number of groups used for the precision analysis. For each particle type of the particle panel including 10 distinct nanoparticle types, the median CVs, including percent of quantile normalized CV or QNCV %, are shown in TABLE 13. A similar analysis was performed at a peptide and protein level using MaxQuant to align identifiable feature groups to features, peptides, and proteins (TABLE 13). The number of identifiable features decreases from features to peptides to proteins, as peptides can comprise multiple features and proteins can comprise multiple peptides. This nanoparticle panel detected 1,184 protein groups with a 1% false discovery rate (FDR).

TABLE 12

10 Particle Type Particle Panel

| Particle Type | Particle Description |
|---|---|
| SP-333 | Carboxylate microparticle, surfactant free |
| SP-339 | Polystyrene carboxyl functionalized |
| SP-347 | Silica coated, 200 nm |
| SP-365 | Silica |
| SP-373 | Dextran based coating, 0.13 μm |
| SP-390 | Oleic acid- Hydrophilic/hydrophobe surface |
| SP-406 | Boronated nanopowder surface |
| SP-007 | PDMAPMA-coated SPION |
| SP-047 | Poly(glycidyl methacrylate-benzylamine) coated |
| SP-064 | Poly(N-[3-(Dimethylamino)propyl]methacrylamide-co-[2-(methacryloyloxy)ethyl]dimethyl-(3-sulfopropyl)ammonium hydroxide, P(DMAPMA-co-SBMA) coated |

TABLE 13

Median QNCV % for a particle panel including 10 distinct nanoparticle types

| | Features (OpenMS) | | Peptides (MaxQuant) | | Proteins (MaxQuant) | |
|---|---|---|---|---|---|---|
| Particle | # Features | Median CV | # Peptides | Median CV | # Proteins | Median CV |
| Plasma | 2141 | 22.5 | 976 | 22.7 | 162 | 17.1 |
| SP-333 | 2163 | 17.2 | 1192 | 20.5 | 250 | 18.2 |
| SP-339 | 2330 | 19.4 | 1406 | 20.8 | 296 | 17.9 |
| SP-347 | 2792 | 15.4 | 2105 | 19.9 | 469 | 16.4 |
| SP-365 | 2322 | 17.9 | 1867 | 22.4 | 447 | 18.4 |
| SP-373 | 2796 | 27.1 | 2091 | 30.3 | 479 | 25.5 |
| SP-390 | 2267 | 29.3 | 1265 | 25.8 | 216 | 19.1 |
| SP-406 | 3823 | 28.7 | 1947 | 30.8 | 410 | 28.3 |
| SP-007 | 2351 | 21.1 | 1292 | 21.5 | 250 | 17.1 |
| SP-047 | 2233 | 36.5 | 1176 | 35.7 | 279 | 30.8 |
| SP-064 | 2984 | 20.2 | 2112 | 23.3 | 433 | 19.3 |

Coefficients of variation (CVs) were examined at the level of features, peptides and proteins independently. Analysis of feature, peptide, and protein CVs provide complementary views of assay precision. OpenMS and MaxQuant software engines were used for feature, peptide, and protein matching. MaxQuant was used to for protein grouping with FDR. OpenMS was used to perform peptide-spectrum-matching (PSM) using the X!Tandem matching tool. MaxQuant was configured to use the Andromeda algorithm. Peptide CVs and protein CVs were used to assess precision of the platform for use with biological variables. The mean CV decreased with increasing peptide size, such that the mean CV was lower for peptides than for proteins. The particles maintain a CV similar to plasma, while particles have higher occurrences of features, peptides, and proteins than plasma. In particular, the number of proteins on particles of any given particle type is higher than plasma (average: 218% higher, range: 133%-296% higher) while maintaining a comparable CV (21.1% vs 17.1% for particles and plasma, respectively). Furthermore, the panel of the particle types identified 1,184 proteins while only identifying 162 proteins for plasma alone.

Figure 31:
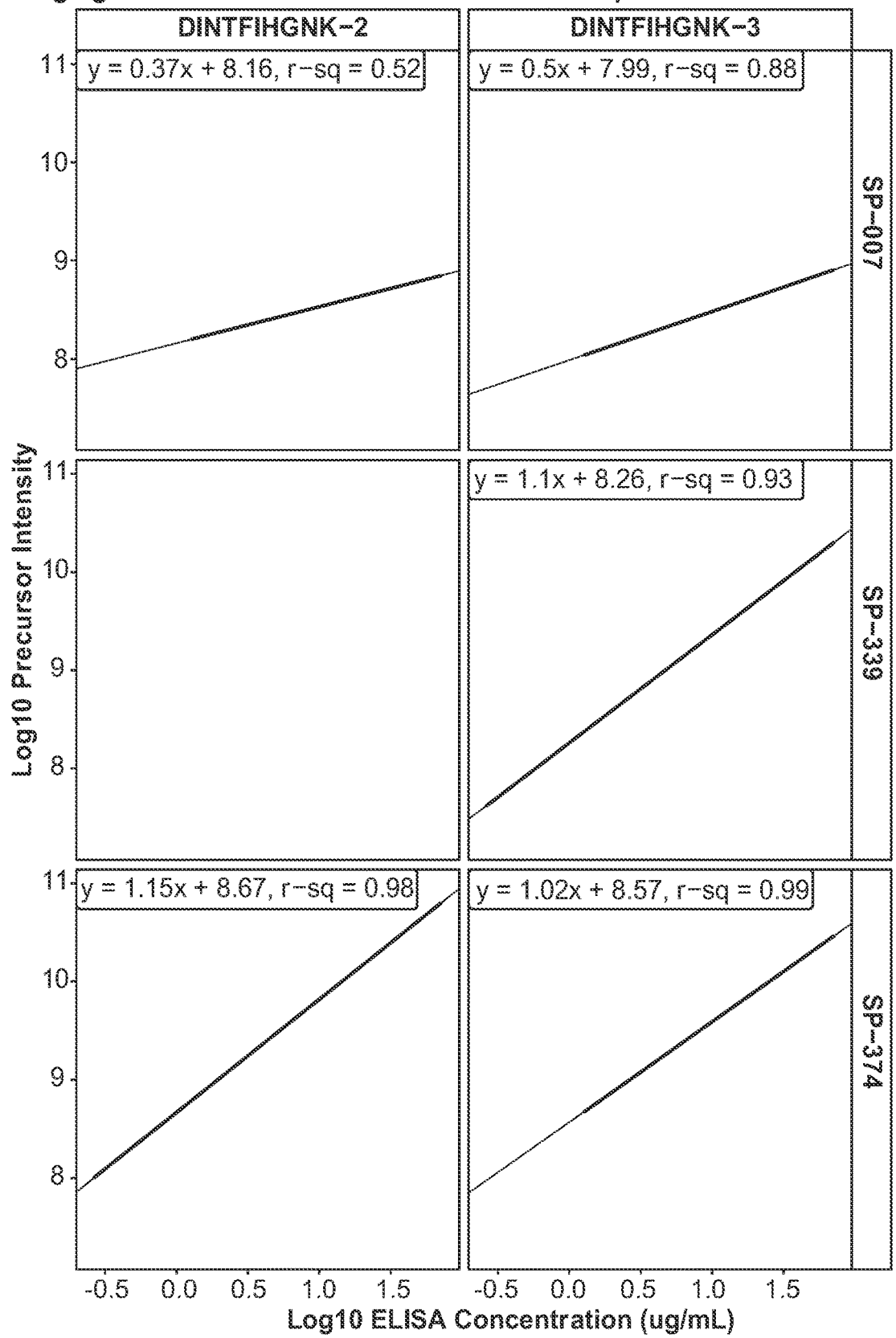
FIG. 31 shows the accuracy of measurement for peptide features of Angiogenin in a spike-recovery experiment.
Figure 32:
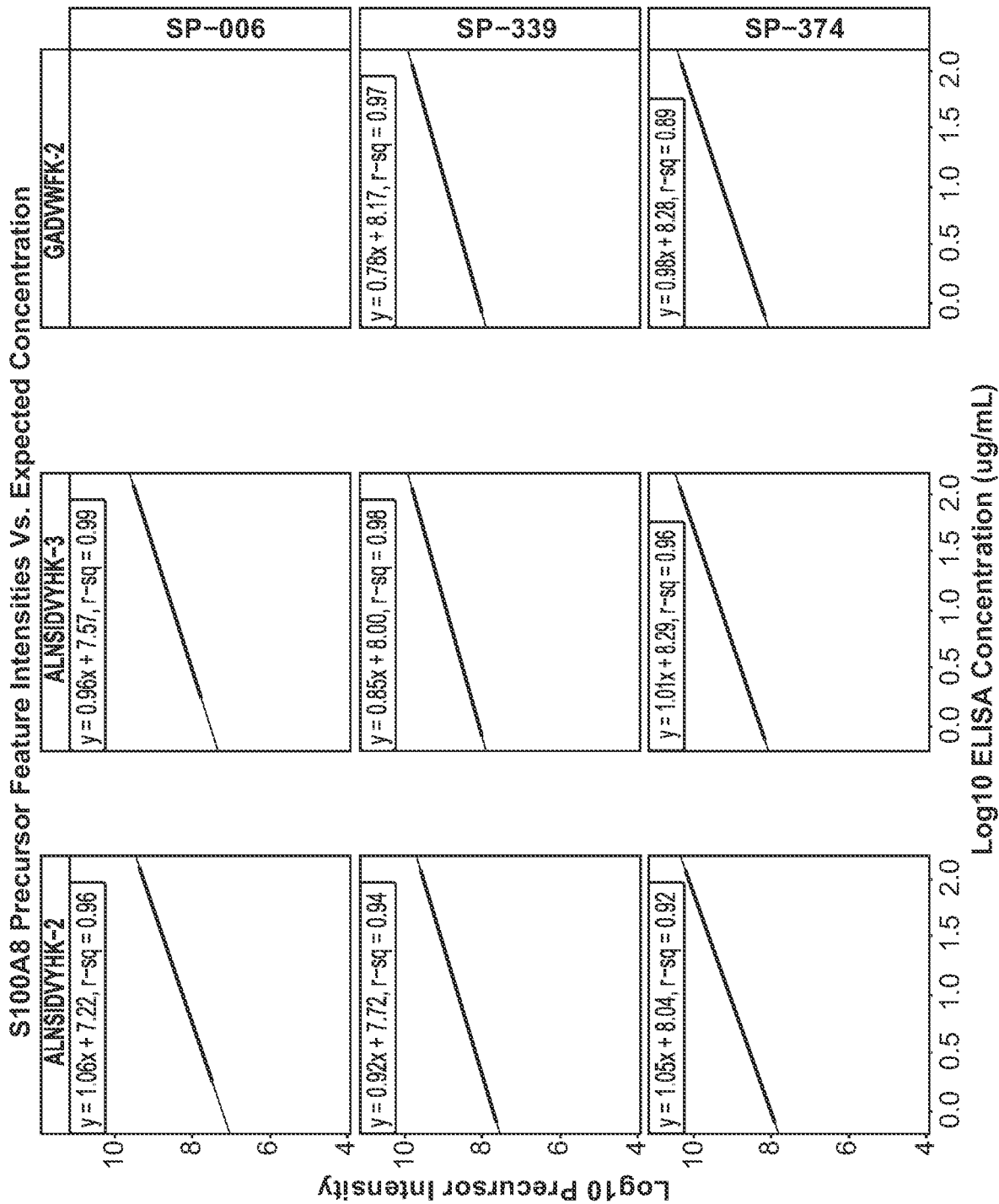
FIG. 32 shows the accuracy of measurement for peptide features of S10A8 in a spike-recovery experiment.
Figure 32:
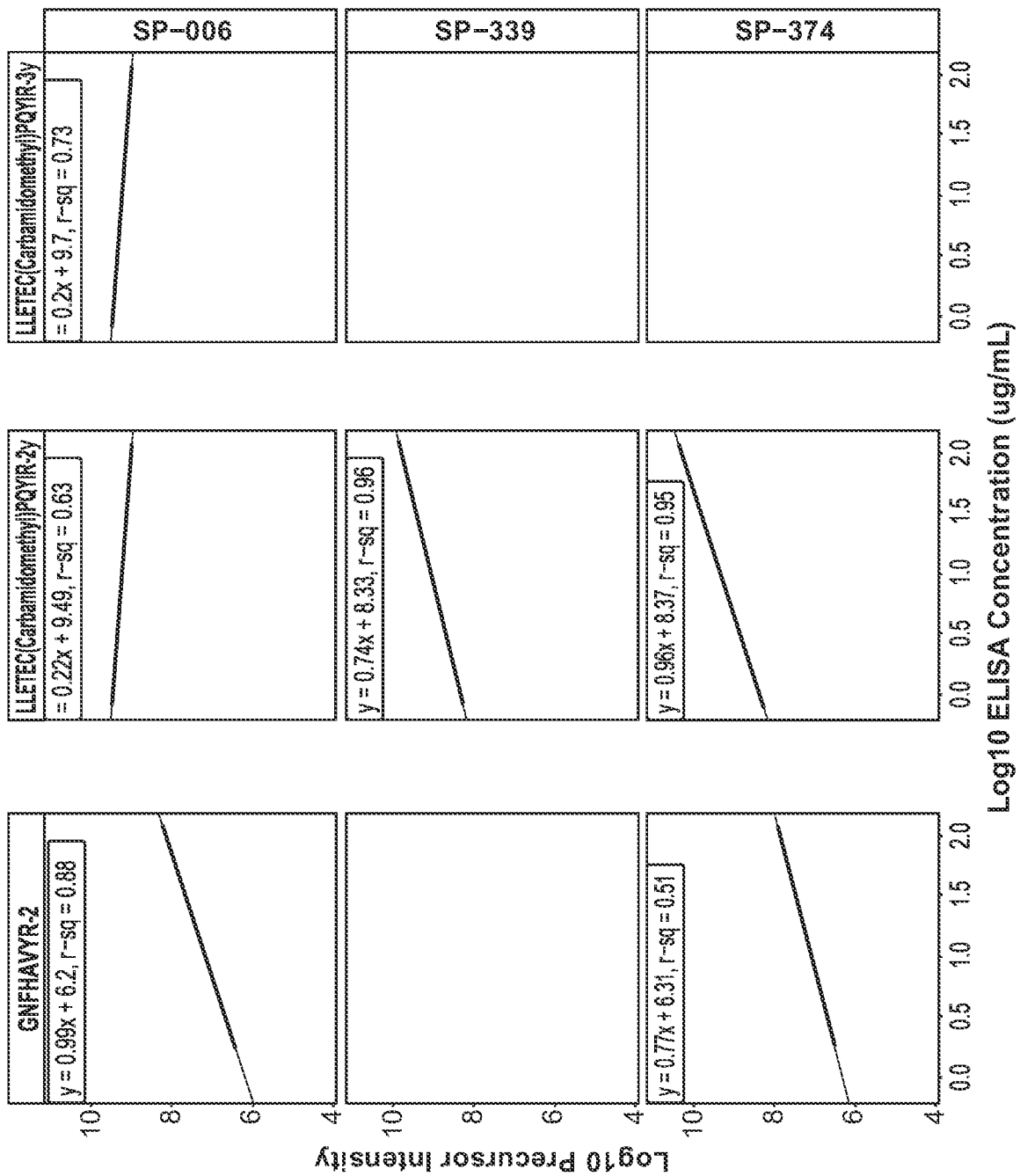
Figure 33:
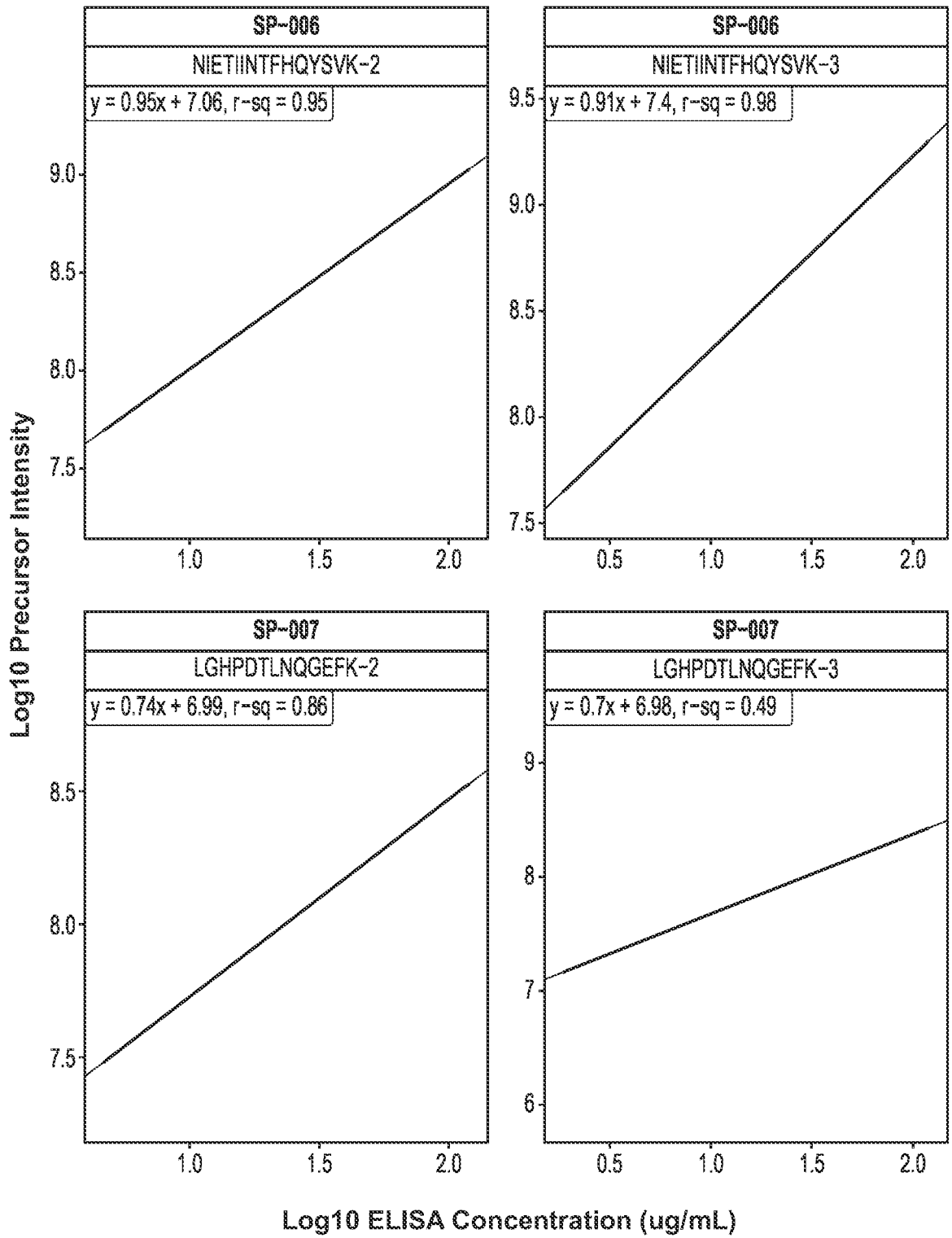
FIG. 33 shows the accuracy of measurement for peptide features of S10A9 in a spike-recovery experiment.
Figure 34:
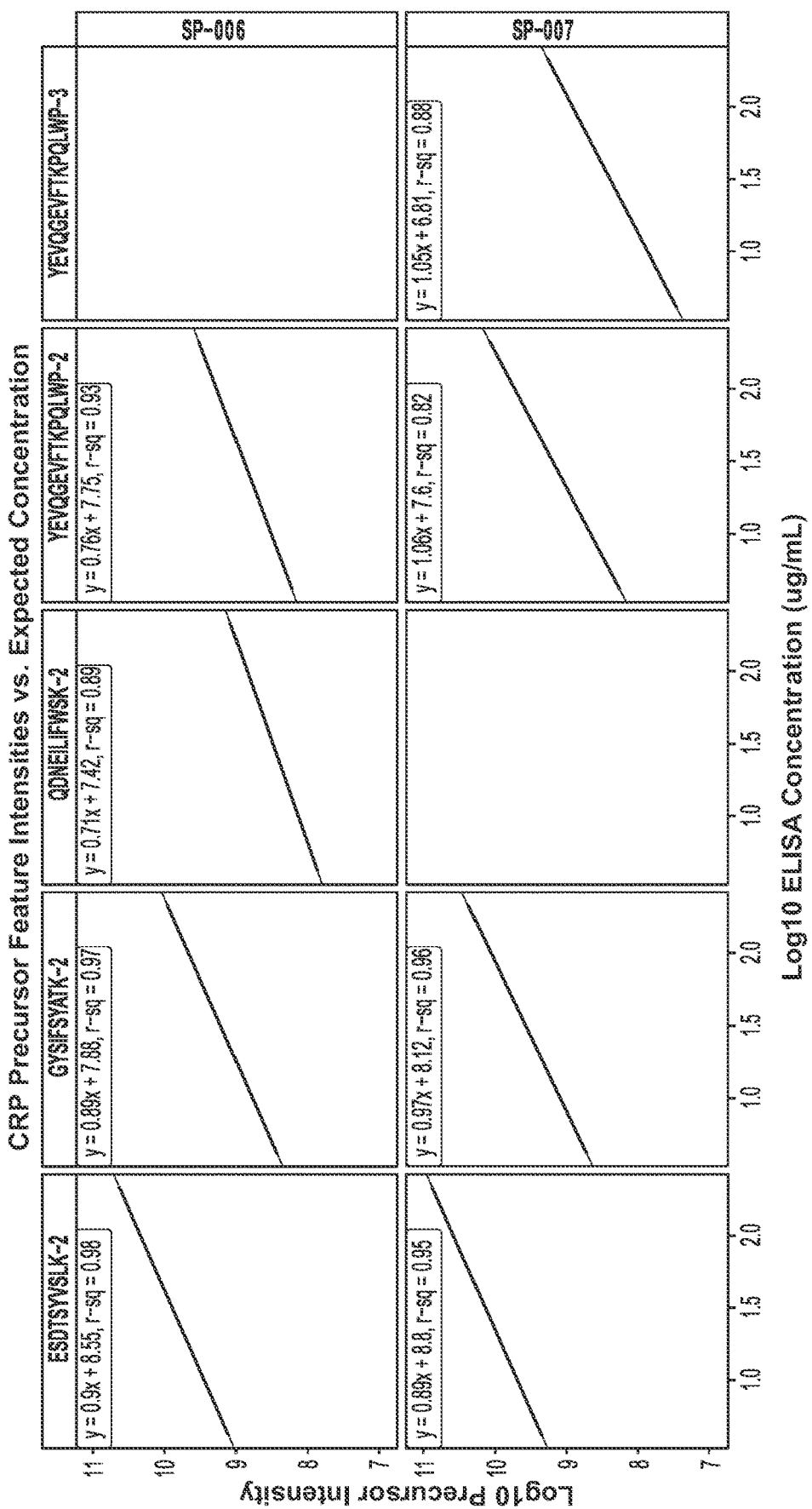
FIG. 34 shows the accuracy of measurement for peptide features of C-reactive protein (CRP) in a spike-recovery experiment.
Figure 35:
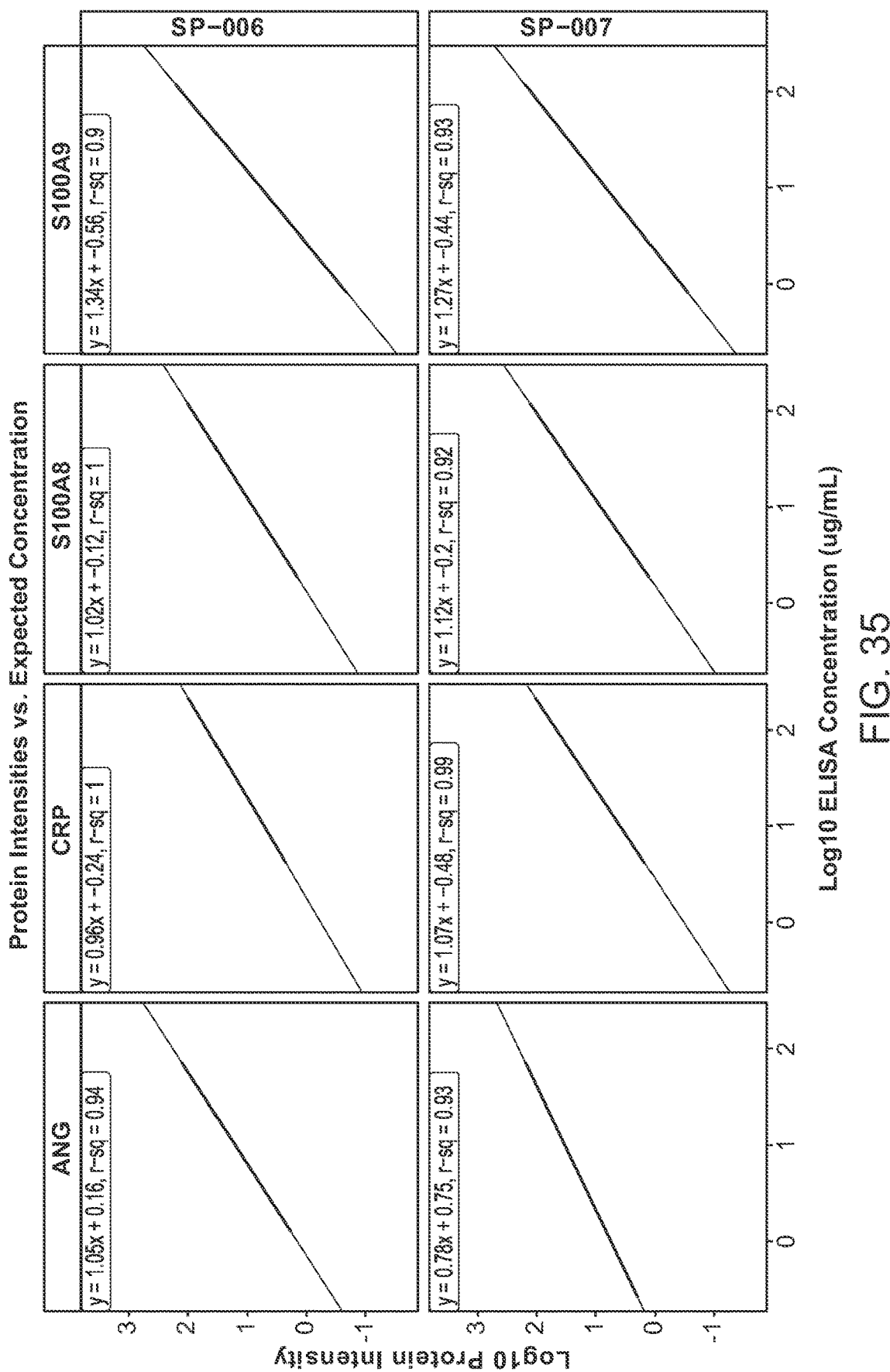
FIG. 35 shows the accuracy of measurement for protein features in a spike-recovery experiment.
Figure 35:
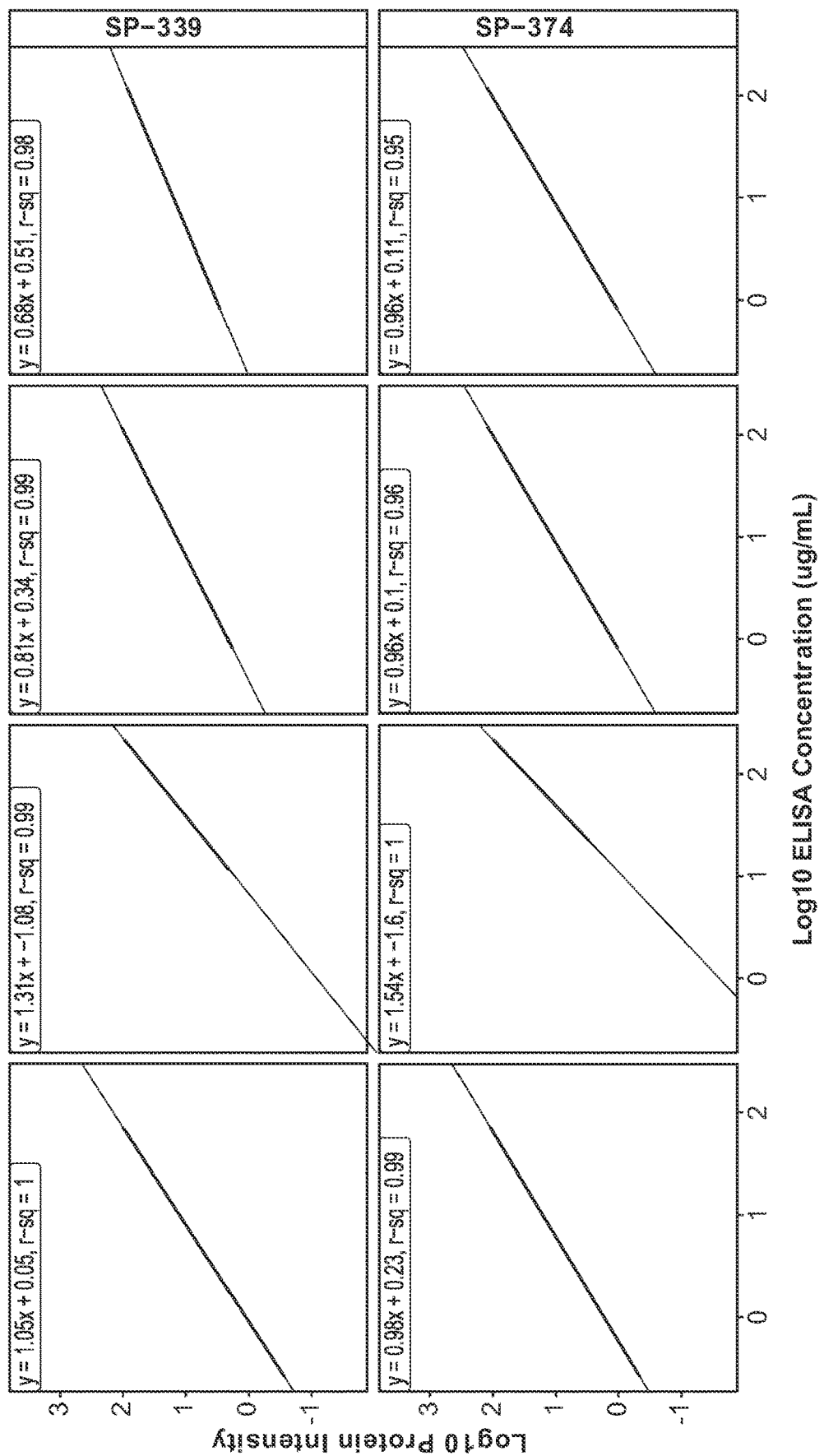

Accuracy of a Particle Panel Including 10 Distinct Nanoparticle Types. The accuracy of for the particle panel including 10 distinct nanoparticle types to detect a real difference between groups of samples in biomarker discovery and validation studies was assessed. Accuracy was determined by measuring spike recovery data in the presence a nanoparticle types SP-007, and C-reactive protein (CRP). Spike recovery data was further measured in the presence of one three additional polypeptides (S100A8/9, and Angiogenin) in combination with each of three particle types (SP-006, SP-339, SP-374). Known amounts of each polypeptide were spiked in at different concentrations, increasing by factors of 10 (e.g., 1×, 2×, 5×, 10×, and 100×). The level of each polypeptide was measured by ELISA. Derived peptide and protein intensities were plotted against the ELISA protein concentration. Peptide intensities were derived using OpenMS MS1/MS2 pipeline to find clustered feature groups that have a target protein MS2 ID assigned to at least one feature within the cluster. Only cluster groups with representation in at least one replicate for the top spike levels were used for the analysis. Protein intensities were derived using the MaxQuant software. Intensity values for each protein were summarized. and the data was scaled such that the maximal concentration was 2. MS datasets were performed in triplicate for each spike concentration (e.g., 1×, 2×, 5×, 10×, and 100×), providing 15 individual protein or peptide measurements. Not all peptides were detected in all particle types or particle type replicates. Results of the MS datasets are shown in FIG. 31-34. FIG. 31 shows the accuracy of peptide feature measurements of Angiogenin in a spike-recovery experiment. FIG. 32 shows the accuracy of peptide feature measurements of S10A8 in a spike-recovery experiment. FIG. 33 shows the accuracy of peptide feature measurements of S10A9 in a spike-recovery experiment. FIG. 34 shows the accuracy of peptide feature measurements of CRP in a spike-recovery experiment. The fitted lines are linear fits to the spike intensities of each feature.

FIG. 31-34 illustrate the results of three spike recovery experiments to determine the accuracy of peptide feature measurements of Angiogenin, S10A8, S10A9, and CRP, respectively. The data demonstrated high degrees of correlation between individual measurements for peptides (mean $r^2$ is 0.81) and proteins (mean $r^2$ is 0.97). The mean slope across all proteins is 1.06. TABLE 14 showed the $r^2$ correlation per comparison and also the mean $r^2$ correlation per protein. Out of 20 peptides, only two showed no correlation between ELISA assays on two different particles types, in which one peptide presented in two charge states. The aberrations decreased with increasing peptide size, such that the frequency of aberrations was lower for peptides than for proteins. The two peptides that showed now correlation with the ELISA on two different particles showed a high degree of correlation to ELISA in the other particle types. The offending peptide may be co-eluting with another peptide that masks its signal, for example through charge stealing.

TABLE 14 provides a summary of regression fits to protein intensity as measured by corona analysis or ELISA. Values are shown for individual particle types and averaged between four repeats per particle type. The protein concentrations, as measured by corona analysis, were consistent across a range of conditions and a range of particle types. As shown in TABLE 14, protein measurements were well correlated, as shown by high $r^2$ values (mean 0.97, range across individual particles 0.92-1.0; range averaged across particles 0.94-0.99). This consistent behavior across the four proteins as measured by an ELISA illustrates the accuracy of the corona analysis assay.

TABLE 14

Summary of protein intensity regression fit.

| Protein | Particle Type | intercept | slope | r_sq | adj_r_sq | intercept | slope | r_sq | adj_r_sq |
|---------|---------------|-----------|-------|------|----------|-----------|-------|------|----------|
| ANG | SP-006 | 0.16 | 1.05 | 0.94 | 0.91 | 0.30 | 0.96 | 0.97 | 0.95 |
| ANG | SP-007 | 0.75 | 0.78 | 0.93 | 0.90 | | | | |
| ANG | SP-339 | 0.05 | 1.05 | 1.00 | 1.00 | | | | |
| ANG | SP-374 | 0.23 | 0.98 | 0.99 | 0.99 | | | | |
| CRP | SP-006 | −0.24 | 0.96 | 1.00 | 1.00 | −0.85 | 1.22 | 0.99 | 0.99 |
| CRP | SP-007 | −0.48 | 1.07 | 0.99 | 0.99 | | | | |
| CRP | SP-339 | −1.08 | 1.31 | 0.99 | 0.98 | | | | |
| CRP | SP-374 | −1.60 | 1.54 | NA | NA | | | | |
| S100A8 | SP-006 | −0.12 | 1.02 | 1.00 | 1.00 | 0.03 | 0.98 | 0.97 | 0.95 |
| S100A8 | SP-007 | −0.20 | 1.12 | 0.92 | 0.89 | | | | |
| S100A8 | SP-339 | 0.34 | 0.81 | 0.99 | 0.98 | | | | |
| S100A8 | SP-374 | 0.10 | 0.96 | 0.96 | 0.95 | | | | |
| S100A9 | SP-006 | −0.56 | 1.34 | 0.90 | 0.87 | −0.09 | 1.06 | 0.94 | 0.92 |
| S100A9 | SP-007 | −0.44 | 1.27 | 0.93 | 0.91 | | | | |
| S100A9 | SP-339 | 0.51 | 0.68 | 0.98 | 0.97 | | | | |
| S100A9 | SP-374 | 0.11 | 0.96 | 0.95 | 0.93 | | | | |

Comparison to other platforms. The methods disclosed herein using multi-particle types panels to enrich proteins in distinct coronas corresponding to each particle type in the panel (e.g., corona analysis using the Proteograph workflow) provides wide and unbiased coverage of protein identification in the proteome. Other methods that attempt broad coverage of the proteome require multiple fractionation steps, complex workflows, and are slow in comparison to the methods presented herein. Other methods lack the breadth and impartiality of the methods disclosed herein and are compared herein to the presently disclosed methods of assaying proteins.

Geyer et al (Cell Systems 2016) utilized a rapid shotgun proteomics approach and yielded an average of 284 protein groups per assay and 321 protein groups across all replicates. The assessment utilized a slower, multi-day protocol with fractionation that yielded approximately 1,000 protein groups. No replicates were performed, likely due to prohibitive costs and time requirements, and so no variance could be determined.

Geyer used a short run to generate 321 protein groups, and the CV of each protein was determined. The 321 groups assessed by Geyer and the 1,184 protein groups identified by the 10 particle type panel comprised 88 protein groups in common between the two methods. As protein groups may comprise multiple related proteins which may be differentially combined based on the detected peptides, identification of 88 common protein groups is unexpectedly high.

For the 88 common protein groups, the data from Geyer et al. was analyzed, and a median CV of 12.1% was determined. In contrast, the same 88 common protein groups, as analyzed by Proteograph, had a lower CV of only 7.2%. Thus, the instant methods of corona analysis using multi-particle type panels and the Proteograph workflow provided improved precision over the methods of Geyer et al. Additionally, Geyer et al.'s assessment showed an $r^2$, indicative of assay accuracy, of 0.99 for 4 proteins. Similarly, the Proteograph assay showed an $r^2$ of 0.97.

Geyer et al. further assessed the number of protein groups with CVs<20%, the commonly used cutoff for in vitro diagnostic assays. The particle panel methods detected 761 protein groups with CV<20% which was 3.7 times greater than the number identified by Geyer et al. A further assessment by Dr. Mann (Niu et al, 2019) identified 272 protein groups with CV<20%, 2.8-fold lower than the number identified by the multi particle type panels and methods of use thereof disclosed herein.

Bruderer et al. assessed protein group CV's using data generated by a Biognosys platform (Bruderer et al, 2019). This assessment identified 465 proteins, wherein those 465 proteins had a median CV of 5.2% and 404 of those proteins had CVs <20%. In contrast, the best 465 proteins from the 1,184 proteins identified using the methods disclosed herein had a median CV of 4.7% and 761 of the 1,184 proteins identified by Proteograph had CV's<20%.

In comparison to the assessments of Geyer et al., Niu et al, and Bruderer et al., the instant particle panels provided improved CVs for an equivalent number of proteins as well as number of proteins meeting a CV threshold, over other identification methods. The methods disclosed herein additionally have reduced bias relative to other methods, such as targeted mass spectrometry and other analyte specific reagents (e.g., Olink). Such approaches measure a small number of pre-selected proteins, thereby introducing bias during the protein panel selection process. As a result, these approaches have low CVs and high r 2 for the proteins on their panel as compared to the proteins identified by Proteograph and are limited to detecting proteins on the panel.

Example 11

Materials and Methods for Particle Synthesis

This example describes materials and methods for particle synthesis.

Materials. Iron (III) chloride hexahydrate ACS, sodium acetate (anhydrous ACS), ethylene glycol, ammonium hydroxide 2830%, ammonium persulfate (APS) (≥98%, Pro-Pure, Proteomics Grade), ethanol (reagent alcohol ACS) and methanol (≥99.8% ACS) were purchased from VWR. N,N'-Methylenebisacrylamide (99%) was purchased from EMD Millipore. Trisodium citrate dihydrate (ACS reagent, ≥99.0%), tetraethyl orthosilicate (TEOS) (reagent grade, 98%), 3-(trimethoxysilyl)propyl methacrylate (MPS) (98%) and poly(ethylene glycol) methyl ether methacrylate (OEGMA, average Mn 500, contains 100 ppm MEHQ as inhibitor, 200 ppm BHT as inhibitor) were purchased from Sigma-Aldrich. 4,4'-Azobis(4-cyanovaleric acid) (ACVA, 98%, cont. ca 18% water) and divinylbenzene (DVB, 80%, mixture of isomers) were purchased from Alfa Aesar and purified by passing a short silica column to remove the inhibitor. N-(3-Dimethylaminopropyl)methacrylamide (DMAPMA) was purchased from TCI and purified by passing a short silica column to remove the inhibitor. The ELISA kit to measure human C-reactive protein (CRP) was purchased from R&D Systems (Minneapolis, MN). Human CRP protein purified from human serum was from Sigma Aldrich.

Synthesis of superparamagnetic iron oxide nanoparticle (SPION)-based SP-003, SP-007, and SP-011. The iron oxide core was synthesized via solvothermal reaction (FIG. 28A-E, at top (FIG. 28A)) (Liu, J., et al. Highly water-dispersible biocompatible magnetite particles with low cytotoxicity stabilized by citrate groups. Angew Chem Int Ed Engl 48, 5875-5879 (2009); Xu, S., et al. Toward designer magnetite/polystyrene colloidal composite microspheres with controllable nanostructures and desirable surface functionalities. Langmuir 28, 3271-3278 (2012)). Typically, about 26.4 g of iron (III) chloride hexahydrate was dissolved in about 220 mL of ethylene glycol at about 160° C. for −10 min under mixing. Then about 8.5 g of trisodium citrate dihydrate and about 29.6 g sodium acetate anhydrous were added and fully dissolved by mixing for about an additional 15 min at about 160° C. The solution was then sealed in a Teflon-lined stainless-steel autoclave (300 mL capacity) and heated to about 200° C. for about 12h. After cooling down to room temperature, the black paramagnetic product was isolated by a magnet and washed with DI water 3-5 times. The final product was freeze-dried to a black powder for further use.

The silica-coated iron oxide nanoparticles (SP-003) were prepared through a modified Stöber process as reported before (FIG. 28B)(Deng, Y., Qi, D., Deng, C., Zhang, X. & Zhao, D. Superparamagnetic high-magnetization microspheres with an $Fe_3O_4@SiO_2$ core and perpendicularly aligned mesoporous SiO2 shell for removal of microcystins. J Am Chem Soc 130, 28-29 (2008); Teng, Z. G., et al. Superparamagnetic high-magnetization composite spheres with highly aminated ordered mesoporous silica shell for biomedical applications. J Mater Chem B 1, 4684-4691 (2013)). Typically, about 1 g of the SPIONs were homogeneously dispersed in the mixture of ethanol (about 400 mL), DI water (about 10 mL), and concentrated ammonia aqueous solution (about 10 mL, 2830 wt %), followed by the addition of TEOS (about 2 mL). After stirring at about 70° C. for about 6 h, amorphous silica coated SPIONs (denoted as $Fe_3O_4@SiO_2$) were obtained and washed 3 times with methanol and additional 3 times with water and the final product was freeze-dried to a powder.

To prepare SP-007 (PDMAPMA-modified SPION) and SP-011 (PEG-modified SPION), vinyl group functionalized SPIONs (denoted as $Fe_3O_4@MPS$) were first prepared through a modified Stöber process as previously reported (FIG. 28C) (Crutchfield, C. A., Thomas, S. N., Sokoll, L. J. & Chan, D. W. Advances in mass spectrometry-based clinical biomarker discovery. Clin Proteomics 13, 1 (2016)). Briefly, about 1 g of the SPIONs was homogeneously dispersed under the aid of vortexing (or sonication) in the mixture of ethanol (about 400 mL), DI water (about 10 mL), and concentrated ammonia aqueous solution (about 10 mL, 2830 wt %), followed by the addition of TEOS (about 2 mL). After stirring at about 70° C. for about 6 h, about 2 mL of 3-(trimethoxysilyl)propyl methacrylate was added into the reaction mixture and stirred at about 70° C. overnight. Vinyl functionalized SPIONs were obtained and washed 3 times with methanol and additional 3 times with water and the final product was freeze-dried to a powder. Next, for synthesis of poly(dimethyl aminopropyl methacrylamide) (PDMAPMA)-coated SPIONs (denoted as $Fe_3O_4$@PDMAPMA, SP-007 in FIG. 28D), about 100 mg of $Fe_3O_4$@MPS were homogeneously dispersed in about 125 mL of DI water. After bubbling with $N_2$ for about 30 min, about 2 g of N-[3-(dimethylamino)propyl] methacrylamide (DMAPMA) and about 0.2 g of divinylbenzene (DVB) were added into the $Fe_3O_4$@MPS suspension under $N_2$ protection. After the resulting mixture was heated to about 75° C., about 40 mg of ammonium persulfate (APS) in about 5 mL DI water was added and stirred at about 75° C. overnight. After cooling down, $Fe_3O_4$@PDMAPMA were isolated with a magnet and washed 3-5 times with water. The final product was freeze-dried to a dark brown powder. For synthesis of poly(ethylene glycol) (PEG)-coated SPIONs (denoted as $Fe_3O_4$@PEGOMA, SP-011 in FIG. 28E), about 100 mg of $Fe_3O_4$@MPS were homogeneously dispersed in about 125 mL of DI water. After bubbling with $N_2$ for about 30 min, about 2 g of poly (ethylene glycol) methyl ether methacrylate (OEGMA, average Mn 500) and about 50 mg of N,N'-Methylenebisacrylamide (MBA) were added into the $Fe_3O_4$@MPS suspension under $N_2$ protection. After the resulting mixture was heated to about 75° C., about 50 mg of 4,4'-azobis(4-cyanovaleric acid) (ACVA) in about 5 mL ethanol was added and stirred at about 75° C. overnight. After cooling down, $Fe_3O_4$@POEGMA were isolated with a magnet and washed 3-5 times with water. The final product was freeze-dried to a dark brown powder.

Example 12

Patient Samples

This example describes patient samples used in the present disclosure. A set of 8 colorectal cancer (CRC) plasma samples with 8 age- and gender-matched controls was purchased from BioIVT (Westbury, NY). A set of 28 non-small cell lung cancer (NSCLC) serum samples with 28 controls matched by age and gender was also obtained from BioIVT. The detailed information regarding the CRC/NSCLC patient samples and controls are shown in TABLE 15 and TABLE 16.

TABLE 15

| NSCLC and Controls | | | | |
|---|---|---|---|---|
| Class | Age | Gender | Diagnosis | Medications |
| Diseased | 53 | Female | Non Small Cell Lung Cancer (NSCLC) | Alimta 800 mg/Carboplatin 760 mg, Advil 200 mg, Compazine 10 mg, Dexamethasone 4 mg, Diclofenac Sodium 50 mg, Dicyclomine 10 mg, Folic Acid 1 mg, Lactulose 10 g/15 ml, Lansoprazole 30 mg, Multivitamin, Oxycodone 5 mg, Reglan 10 mg, Vitamin C 1000 mg, Vitamin D2 50000 iu |
| Diseased | 64 | Female | Non Small Cell Lung Cancer (NSCLC), Vitamin B Deficiency, Hypertension (HTN), Hyperlipidemia | Opdivo, Alendronate Sodium 10 mg, Allegra Allergy 180 mg, Anoro Ellipta 62.5 mcg-25 mcg, Aspirin 81 mg, Bystolic 5 mg, Calcium and D 500 mg-200 iu, Compazine 10 mg, Crestor 40 mg, Dilaudid 1200 mg, Emla 2.5%-2.5%, Erythromycin 5 mg, Fish Oil 340 mg-1000 mg, Flonase Allergy Relief 50 mcg, Hydromorphone 4 mg, Isosorbide Mononitrate 60 mg, Levothyroxine 75 mcg, Lisinopril 20 mg, Medical Marijuana, Multivitamin 9 mg-Iron 15 ml, Neurontin 300 mg, Nitro, Oxycodone 5 mg, Plavix 75 mg, Protonix 20 mg, Unisom 25 mg, Ventolin 90 mcg, Vitamin D3 5000 iu, Xanax 1 mg |
| Diseased | 73 | Female | Non Small Cell Lung Cancer (NSCLC), Impaired Fasting Glucose (IFG), Pulmonary Nodule | Carboplatin/Paclitaxel, Acetaminophen 325 mg, Multivitamin 1000 mg, Cymbalta 60 mg, Eliquis 5 mg, Guaifenesin 100 mg/5 ml, Neurontin 300 mg, Synthroid 100 mcg, Zofran 8 mg |
| Diseased | 75 | Female | Non Small Cell Lung Cancer, Pneumothorax | Osimertinib, Colace 100 mg, Flonase 50 mcg, Zofran 8 mg, Restasis 0.05%, Norco 5 mg-325 mg, Megace 400 mg/10 ml, Tagrisso 80 mg |
| Diseased | 65 | Female | Non Small Cell Lung Cancer (NSCLC), Type 2 Diabetes, Multiple Sclerosis | Ceritinib 150 mg, Cipro 500 mg, Excedrin 500 mg, Lasix 40 mg, Glimepiride 4 mg, Lamotrigine 200 mg, Metformin 1000 mg, Naproxen 500 mg, Zofran 8 mg, Slow Release Iron 142 mg |
| Diseased | 94 | Male | Non Small Cell Lung Cancer (NSCLC), Anemia (CKD), Chronic Kidney Disease (CKD), Hyperlipidemia (HLD), Prostate Cancer | Keytruda 100 mg/4 ml, Betamethasone Dipropionate 0.05%, Eliquis 2.5 mg, Fludrocortisone 0.1 mg, Folic Acid 1 mg, Lomotil 2.5 mg-0.025 mg, Midodrine 10 mg, Omega Q, Prednisone 5 mg, Ranitidine 150 mg, Simvastatin 40 mg |

TABLE 15-continued

NSCLC and Controls

| Class | Age | Gender | Diagnosis | Medications |
|---|---|---|---|---|
| Diseased | 65 | Female | Non Small Cell Lung Cancer (NSCLC), Hypertension (HTN) | Atenolol 50 mg, Biotin 2500 mcg, Melatonin 3 mg, Mometasone 0.1%, Vitamin D3 1000 iu, Zofran 8 mg |
| Diseased | 79 | Female | Non Small Cell Lung Cancer (NSCLC), Type 2 Diabetes, Hypercholesterolemia, Emphysema | Amlodipine 5 mg, Amoxicillin 875 mg, Estradiol 0.01%, Folic Acid 1 mg, Januvia 100 mg, Lidocaine/Prilocaine 2.5%, Losartan HCL 50 mg, Nitrofurantoin 100 mg, Pantoprazole 20 mg, Simvastatin 40 mg, Urinary Pain Relief 95 mg, Zofran 8 mg, Gemcitabine, Carboplatin |
| Diseased | 57 | Male | Non Small Cell Lung Cancer (NSCLC), Lung Mass, Primary Adenocarcinoma of Lower Lobe of Right Lung, Brain Metastases, Hypokalemia | Carboplatin/Etoposide, Norvasc 10 mg, Lotensin HCT 20 mg-12.5 mg, Celexa 20 mg, Mycelex 10 mg, Lasix 20 mg, Norco 7.5 mg-325 mg, Magnesium 400 mg, Melatonin Gummies 2.5 mg, Metformin 750 mg, Mycostatin 100,000 iu/mL, Zofran 8 mg, Potassium Chloride 20 mEq, Compazine 10 mg |
| Diseased | 63 | Female | Non Small Cell Lung Cancer (NSCLC), Hypertension (HTN), Hypercholesterolemia, Gastroesophageal Reflux Disease (GERD), Diverticulitis, Disease of Thyroid, Arhropathy, Actinic Keratosis | Alimta, Carboplatin, Calcium-Vitamin D, Folvite 1 mg, Keppra 500 mg, Synthroid 125 mcg, Prilosec 20 mg, Zofran 8 mg, Compazine 10 mg, Zocor 40 mg |
| Diseased | 77 | Male | Non Small Cell Lung Cancer (NSCLC), Hypertension (HTN), Myelodysplastic Syndromes, Anemia (Iron), Hypothyroidism, Prostate Cancer, Bradycardia | Singulair 10 mg, Meclizine HCL 25 mg, Xarelto 20 mg, Synthroid 125 mcg, Miralax 17 g, Lidocaine 5%, Arnuity Ellipta 100 mcg, Medipro Vegan Chocolate 23.28 oz, Exos Catalyte, Zinc Picolinate 15 mg, Albuterol Sulfate 90 mcg, Vitamin B12/Folic Acid 500 mcg/400 mcg |
| Diseased | 70 | Female | Non Small Cell Lung Cancer (NSCLC), Hypertension (HTN), Polycythemia, Left Lower Extremity Edema, Cellulitis of Left Lower Extremity | Alimta/Carboplatin/Keytruda/Neulasta, Decadron 4 mg, Breo Ellipta 200 mcg/25 mcg, Folvite 1 mg, Lasix 40 mg, Neurontin 300 mg, Emla, Zestril 5 mg, Magic Mouthwash, Glucophage 500 mg, Aleve 220 mg, Zofran 8 mg, Potassium Chloride 10 meq, ProAir HFA 108 mcg, Spiriva 18 mcg, Valtrex 1000 mg |
| Diseased | 70 | Female | Non Small Cell Lung Cancer (NSCLC), Hypertension (HTN), Type 2 Diabetes | Taxotere 75 mg-Cyramza 10 mg-Nuelasta, Ativan 0.5 mg, Basaglar 100 iu/mL, Dexamethasone 4 mg, Eliquis 5 mg, Fentanyl 25 mcg, Folic Acid 1 mg, Glimepiride 2 mg, Hydrochlorothiazide 12.5 mg, Lorazepam 0.5 mg, Magnesium 300 mg, Metformin 1000 mg, Multivitamin 9 mg Iron/15 mL, Oxycodone 5 mg, Tramadol 50 mg, Trazodone 50 mg, Vitamin D3 2000 iu |
| Diseased | 78 | Female | Non Small Cell Lung Cancer (NSCLC), Hypothyroidism | Folic Acid 1 mg, Lasix 20 mg, Atarax 25 mg, Hydroxyzine 25 mg, Klor Con 10 meq, Emla, Methylprednisolone 4 mg, Zofran 8 mg, Synthroid 100 mcg, Kenalog 0.025% |
| Diseased | 68 | Female | Non Small Cell Lung Cancer (NSCLC), Leukocystosis, Hypercalcemia, Asthma, Major Depressive Disorder, Hypothyroidism, Hyperlipidemia, Type 2 Diabetes | Abraxane 100 mg, Procrit 40000 iu, Aspirin 325 mg, Benadryl 25 mg, Calcium 500 mg, Clopidogrel 75 mg, Codeine- Guaifenesin 10 mg-100 mg/5 ml, Imodium 2 mg, Iron 325 mg, Klor-Con 20 meq, Lasix 20 mg, Levothyroxine 50 mcg, Metformin 500 mg, Niacin 500 mg, Ondansetron 8 mg, Proventil 90 mcg, Spiriva 18 mcg, Symbicort 160 mcg-4.5 mcg, Tylenol 500 mg, Xanax 0.5 mg, Zolpidem 10 mg |
| Diseased | 78 | Male | Non Small Cell Lung Cancer (NSCLC), Lymphadenitis, Hypertension (HTN), Hyperlipidemia, Atrial | Xgeva 120 mg, Keytruda, Atorvastatin 40 mg, Digoxin 125 mcg, Furosemide 40 mg, Lexapro 20 mg, Medrol 4 mg, Metoprolol Tartrate 100 mg, Namzaric 21 mg-10 mg, Noxylane 500 mg, Vitamin D2 50000 iu, |

TABLE 15-continued

NSCLC and Controls

| Class | Age | Gender | Diagnosis | Medications |
|---|---|---|---|---|
| | | | Fibrillation (AF), Malignant Neoplasm of Left Main Bronchus | Warfarin 2 mg |
| Diseased | 79 | Female | Non Small Cell Lung Cancer (NSCLC), Pancytopenia, Liver Cirrhosis, Zoster, Neuralgia, Neuritis, Essential Primary Hypertension | Feraheme Non-ESRD, Amlodipine 5 mg, Aspirin 81 mg, Atenolol 50 mg, Bayer Aspirin 325 mg, Calcium/Vitamin D3 1250 mg, Caltrate/Vitamin D3 1500 mg, Cartia XT 180 mg, Crestor 20 mg, Duragesic 25 mcg, Eliquis 5 mg, Folic Acid 1 mg, Gabapentin 300 mg, Oxycodone/Acetaminophen 5 mg/325 mg, Percocet 5 mg/325 mg, Prednisone 1 mg, Procrit 40000 iu/ml, Tessalon Perles 100 mg, Vitamin D2 50000 iu |
| Diseased | 79 | Male | Non Small Cell Lung Cancer (NSCLC), Prostate Cancer, Immune Thrombocytopenic Purpura, HTN, Hyperlipidemia | Octagam Liquid 10%, Calcium 600 mg, Digoxin 125 mcg, Folic Acid 400 mcg, Metoprolol Tartrate 25 mg, Probiotic, Rosuvastatin 10 mg |
| Diseased | 54 | Male | Non Small Cell Lung Cancer (NSCLC), Type 2 Diabetes, Hypertension (HTN) | Pembrolizumab, Dexamethasone 4 mg, Glipizide 5 mg, Hydrocodone-Acetaminophen 10 mg-325 mg, Ipratropium Bromide 17 mcg, Lantus, Lisinopril 10 mg, Metformin 500 mg, Pravastatin Sodium 40 mg |
| Diseased | 69 | Male | Non Small Cell Lung Cancer (NSCLC), Unilateral Primary Osteoarthritis of Left Knee, Essential Primary Hypertension, Type 2 Diabetes | Aloxi 0.25 mg/5 ml, Cardizem 120 mg, Crestor 20 mg, Digoxin 250 mcg, Eliquis 5 mg, Furosemide 20 mg, Glucosamine Chondroitin PLUS 375 mg/100 mg/36 mg/54 mg, Metformin ER 750 mg, Potassium Chloride ER 10 meq, Zofran 8 mg |
| Diseased | 81 | Male | Non Small Cell Lung Cancer (NSCLC), Vascular Dementia, Hypertension (HTN), Lipid Disease | Ipratropium Albuterol 0.5 mg/3 mg, Metoprolol 50 mg, Coumadin 7.5 mg, Atorvastatin 80 mg, Lovenox 80 mg/0.8 ml, Magace ES 625 mg/5 ml, Lexapro 10 mg |
| Diseased | 70 | Female | Non Small Cell Lung Cancer (NSCLC), Anemia (Antineoplastic Chemotherapy), Idiopathic Thrombocytopenia (ITP), Malignant Neoplasm of Upper Left Lobe, Vitamin B12 Deficiency, Folic Acid Deficiency, Asthma, Type 2 Diabetes, Hyperlipidemia (HLD), Hypertension (HTN), Hypercholesterolemia | Nplate, Procrit 40,000 iu, Alimta 500 mg, Ferrous Sulfate 325 mg, Folic Acid 1 mg, Medrol 4 mg, Metformin 500 mg, Simvastatin 40 mg, Tudorza Pressair 400 mcg |
| Diseased | 76 | Female | Non Small Cell Lung Cancer (NSCLC), Anemia (Iron Deficiency), , Impaired Fasting Glucose (IFG) | Biotin 300 mcg, Cleocin 1%, Fenofibrate 160 mg, Flonase 50 mcg, Medrol 4 mg, Ranitidine 150 mg, Tagrisso 80 mg, Tarceva 150 mg, Ventolin HFA 90 mcg, Vitamin D2 50000 iu |
| Diseased | 91 | Male | Non Small Cell Lung Cancer (NSCLC), Anemia (Iron Deficiency), Hypothyroidism, HTN | Clotrimazole 1%, Dextran, Digoxin 125 mcg, Furosemide 20 mg, Hydrocodone-Homatropine 5 mg-1.5 mg/5 ml, Lasix 20 mg, Levothyroxine 25 mcg, Metoprolol Succinate 25 mg, Miracle Mouthwash, Mucinex 30 mg-600 mg, Nystatin 100000 iu, Omeprazole 20 mg, Oxycodone 20 mg, Pravastatin 10 mg, Prednisone 10 mg, Proair 90 mcg, Procto-Med 2.5%, Relistor 150 mg, Sodium Chloride 1 g |

TABLE 15-continued

| | | | NSCLC and Controls | |
|---|---|---|---|---|
| Class | Age | Gender | Diagnosis | Medications |
| Diseased | 69 | Female | Non Small Cell Lung Cancer (NSCLC), Anemia (Iron Deficiency), Vitamin B12 Deficiency, T-Cell Prolymphocytic Leukemia, Hypertension (HTN) | Ativan 0.5 mg, Trazodone 50 mg |
| Diseased | 65 | Female | Non Small Cell Lung Cancer (NSCLC), Chronic Obstructive Pulmonary Disease (Emphysema), Cardiovascular Disease, Osteoporosis | Dexamethasone 4 mg, Emla 2.5%, Loperamide 2 mg, Lorazepam 1 mg, Nystatin 100000 iu/ml, Ondansetron 4 mg, Oravig 50 mg, Symbicort 160 mcg/4.5 mcg, Ventolin HFA 90 mcg, Navelbine 30 mg |
| Diseased | 77 | Female | Non Small Cell Lung Cancer (NSCLC) | Avastin 15 mg/kg, Alimta 500 mg/Carboplatin/Neulasta then Alimta 500 mg, Aspirin 81 mg, Chantix 1 mg, Dexamethasone 4 mg, Folic Acid 1 mg, Instaflex, Metformin 500 mg, Quinapril 40 mg, Simvastatin 20 mg, Vitamin D3 2000 iu, Zofran 8 mg |
| Diseased | 85 | Female | Non Small Cell Lung Cancer (NSCLC) | Aletinib |
| Control | 53 | Female | Normal Donor | None |
| Control | 64 | Female | Normal Donor | None |
| Control | 67 | Female | Normal Donor, Hyopercholesterolemia | Atorvastatin 40 mg |
| Control | 72 | Female | Normal Donor | None |
| Control | 73 | Female | Normal Donor, Osteoarthritis (OA) | Prolia, Aciphex 20 mg |
| Control | 87 | Male | Normal Donor, Donor with Fever | Vitamin B Complex, Zinc 50 ml, Alka Seltzer, Vitamin B6, Vitamin B1, Vitamin B12, Pepsin 40 mg |
| Control | 65 | Female | Normal Donor, Hypercholesterolemia | None |
| Control | 80 | Female | Normal Donor | None |
| Control | 57 | Male | Normal Donor | Multivitamin |
| Control | 63 | Female | Normal Donor | None |
| Control | 75 | Male | Normal Donor, Hypertension (HTN) | Lisinopril 2.5 mg |
| Control | 70 | Female | Normal Donor | None |
| Control | 70 | Female | Normal Donor | Multivitamin 1000 mg |
| Control | 77 | Female | Normal Donor | Lipitor 20 mg, Prevacid 20 mg |
| Control | 68 | Female | Normal Donor, Hypertension (HTN) | Lisinopril 10 mg |
| Control | 73 | Male | Normal Donor | Tamsulosin HCL, Finasteride 5 mg |
| Control | 81 | Female | Normal Donor | Norvasc, Ditropan |
| Control | 77 | Male | Normal Donor, Cataract, Progressive Hearing Loss, Hypertension (HTN), Hypercholesterolemia | Lipitor 20 mg, Tricor 145 mg, Metoprolol 50 mg, Omeprazole 20 mg, Aspirin 80 mg |
| Control | 56 | Male | Normal Donor | Nexium 60 mg, Zocor 40 mg |
| Control | 64 | Male | Normal Donor | Protonix 40 mg, Aspirin 325 mg |
| Control | 80 | Male | Normal Donor | Vitamin D, Lipitor, Aspirin 81 mg |
| Control | 73 | Female | Normal Donor, Allergic Rhinitis | Allegra 180 mg |
| Control | 77 | Female | Normal Donor | None |
| Control | 83 | Male | Normal Donor | None |
| Control | 68 | Female | Normal Donor | Losartan 50 mg, Lipitor 20 mg |
| Control | 66 | Female | Normal Donor, Hypertension (HTN) | Lisinopril 10 mg |
| Control | 78 | Female | Normal Donor | Lipitor 10 mg, Toprol 50 mg, Ambien 10 mg |
| Control | 86 | Female | Normal Donor, Hypertension (HTN) | Amlodipine 2.5 mg, Vitamin B |

TABLE 16

CRC and Controls

| Class | Age | Gender | Diagnosis |
| --- | --- | --- | --- |
| Diseased | 74 | Female | Colorectal Cancer |
| Diseased | 41 | Male | Colorectal Cancer |
| Diseased | 57 | Male | Colorectal Cancer, Anemia (Iron Deficiency), Type 2 Diabetes |
| Diseased | 78 | Male | Colorectal Cancer, Chronic Lymphocytic Leukemia (CLL), Hypertension (HTN), Type 2 Diabetes, Arthritis |
| Diseased | 60 | Female | Colorectal Cancer, CKD, Iron Deficiency, RLS, Carcinoma of Colon, Carcinoma of Right Ovary, Anxiety |
| Diseased | 37 | Male | Colorectal Cancer, Erectile Dysfunction, Thrombocytopenia |
| Diseased | 68 | Female | Colorectal Cancer, Major Depressive Disorder (MDD), Type 2 Diabetes, Hernia with Obstruction, Ventral Hernia, Dysphonia, Hypercholesterolemia, Hyperlipidemia, Hypertension (HTN), Migraine, Obesity, Diabetic Polyneuropathy, Reflux Esophagitis, Edema, Asthma, Chronic Obstructive Pulmonary Disease (COPD), E Coil Bacteremia, Subdural Hematoma, Hepatic Abscess |
| Diseased | 60 | Female | Colorectal Cancer, Rectal Cancer, Type 1 Diabetes, Hypertension (HTN), Hypothyroidism |
| Control | 75 | Female | Normal Donor |
| Control | 42 | Male | Normal Donor |
| Control | 56 | Male | Normal Donor |
| Control | 78 | Male | Normal Donor |
| Control | 58 | Female | Normal Donor |
| Control | 36 | Male | Normal Donor |
| Control | 68 | Female | Normal Donor |
| Control | 59 | Female | Normal Donor |

Example 13

Characterization of Physicochemical Properties of Particle Types

This example describes characterization of particle physicochemical properties by various techniques. Dynamic light scattering (DLS) and zeta potential were performed on a Zetasizer Nano ZS (Malvern Instruments, Worcestershire, UK). Particles were suspended at 10 mg/mL in water with about 10 min of bath sonication prior to testing. Samples were then diluted to approximately 0.02 wt % for both DLS and zeta potential measurements in respective buffers. DLS was performed in water at about 25° C. in disposable polystyrene semi-micro cuvettes (VWR, Randor, PA, USA) with a about 1 min temperature equilibration time and consisted of the average from 3 runs of about 1 min, with a 633 nm laser in 173° backscatter mode. DLS results were analyzed using the cumulants method. Zeta potential was measured in 5% pH 7.4 PBS (Gibco, PN 10010-023, USA) in disposable folded capillary cells (Malvern Instruments, PN DTS1070) at about 25° C. with an about 1 min equilibration time. 3 measurements were performed with automatic measurement duration with a minimum of 10 runs and a maximum of 100 runs, and a 1 min hold between measurements. The Smoluchowski model was used to determine the zeta potential from the electrophoretic mobility.

Scanning electron microscopy (SEM) was performed by using a FEI Helios 600 Dual-Beam FIB-SEM. Aqueous dispersions of particles were prepared to a concentration of about 10 mg/mL from weighted particle powders re-dispersed in DI water by about 10 min sonication. Then, the samples were 4× diluted by methanol (from Fisher) to make a dispersion in water/methanol that was directly used for electron microscopy. The SEM substrates were prepared by drop-casting about 6 µL of particle samples on the Si wafer from Ted Pella, and then the droplet was completely dried in a vacuum desiccator for about 24 hours prior to measurements.

A Titan 80-300 transmission electron microscope (TEM) with an accelerating voltage of 300 kV was used for both low- and high-resolution TEM measurements. The TEM grids were prepared by drop-casting about 2 µL of the particle dispersions in water-methanol mixture (25-75 v/v %) with a final concentration of about 0.25 mg/mL and dried in a vacuum desiccator for about 24 hours prior to the TEM analysis. All measurements were performed on the lacey holey TEM grids from Ted Pella.

X-Ray Photoelectron Spectroscopy (XPS) was performed by using a PHI VersaProbe and a ThermoScientific ESCALAB 250e III. XPS analysis was performed on the particle fine powders kept sealed and stored under desiccation prior to the measurements. Materials were mounted on a carbon tape to achieve a uniform surface for analysis. A monochromatic Al K-alpha X-ray source (50 W and 15 kV) was used over a 200 µm² scan area with a pass energy of 140 eV, and all binding energies were referenced to the C-C peak at 284.8 eV. Both survey scans and high-resolution scans were performed to assess in detail elements of interest. The atomic concentration of each element was determined from integrated intensity of elemental photoemission features corrected by relative atomic sensitivity factors by averaging the results from two different locations on the sample. In some cases, four or more locations were averaged to assess uniformity.

Example 14

Protein Corona Preparation and Proteomic Analysis

This example describes protein corona preparation and proteomic analysis. Plasma and serum samples were diluted 1:5 in a dilution buffer composed of TE buffer (10 mM Tris, 1 mM disodium EDTA, 150 mM KCl) with 0.05% CHAPS. Particle powder was reconstituted by sonicating for about 10 min in DI water followed by vortexing for about 2-3 sec. To make a protein corona, about 100 µL of particle suspension (SP-003, 5 mg/ml; SP-007, 2.5 mg/ml; SP-011, 10 mg/ml) was mixed with about 100 µL of diluted biological samples in microtiter plates. The plates were sealed and incubated at 37° C. for about 1 hour with shaking at 300 rpm. After incubation, the plate was placed on top of magnetic collection for about 5 mins to pellet down the nanoparticles. Unbound proteins in supernatant were pipetted out. The protein corona was further washed with about 200 µL of dilution buffer for three times with magnetic separation. For the 10 particle type particle panel screen, the five additional assay conditions that were evaluated were identical to the description above with one of the following exceptions. First, a low concentration of particles was evaluated that was 50% the concentration of the original particle concentration (ranging from 2.5-15 mg/ml for each particle, depending on expected peptide yield). For the second and third assay variations, both low and high particle concentrations were run using an undiluted, neat plasma rather than diluting the plasma in buffer. For the fourth and fifth assay variations, both low and high particle concentrations were run using a pH 5 citrate buffer for both dilution and rinse.

To digest the proteins bound onto nanoparticles, a trypsin digestion kit (iST 96X, PreOmics, Germany) was used according to protocols provided. Briefly, about 50 µL of Lyse buffer was added to each well and heated at about 95° C. for about 10 min with agitation. After cooling down the plates to room temperature, trypsin digest buffer was added and the plate was incubated at about 37° C. for about 3 hours with shaking. The digestion process was stopped with a stop buffer. The supernatant was separated from the nanoparticles by a magnetic collector and further cleaned up by a peptide cleanup cartridge included in the kit. The peptide was eluted with about 75 µL of elution buffer twice and combined. Peptide concentration was measured by a quantitative colorimetric peptide assay kit from Thermo Fisher Scientific (Waltham, MA).

Next, the peptide eluates were lyophilized and reconstituted in 0.1% TFA. A 2 µg aliquot from each sample was analyzed by nano LC-MS/MS with a Waters NanoAcquity HPLC system interfaced to an Orbitrap Fusion Lumos Tribrid Mass Spectrometer from Thermo Fisher Scientific. Peptides were loaded on a trapping column and eluted over a 75 vim analytical column at 350 nL/min; both columns were packed with Luna C18 resin from Phenomenex (Torrance, CA). The mass spectrometer was operated in a data-dependent mode, with MS and MS/MS performed in the Orbitrap at 60,000 FWHM resolution and 15,000 FWHM resolution, respectively. The instrument was run with a 3 sec cycle for MS and MS/MS.

Example 15

Mass Spectrometry Data Analysis

This example describes mass spectrometry data analysis methods. The acquired MS data files were processed using the OpenMS suite of tools. These tools include modules and pipeline scripts for the conversion of vendor instrument raw files to mzML files, for MS1 feature identification and intensity extraction, for MS dataset run-time alignment and feature-group clustering, and for MS2 spectrum database matching with the X! Tandem search engine. During spectrum-database searching the precursor ion and fragment ion matching tolerances were set to 10 and 30 ppm, respectively. Default settings for fixed, Carbamidomethyl (C), and variable, Acetyl (N-term) and Oxidation (M), modifications were enabled. The UniProtKB/Swiss-Prot protein sequence database (accession date Jan. 27, 2019) was used for searches and peptide spectral matches (PSMs) were scored using a standard reverse-sequence decoy database strategy at 1% FDR. Using the PSMs, protein lists for each particle type replicate were compiled using a single PSM as sufficient evidence to add a protein to a given particle type replicate's enumerated protein list. In addition, a PSM that matched more than one protein added all of the possible proteins to the given particle type replicate's enumerated protein list. Although this threshold for protein enumeration is permissive, and possibly includes false-positives (higher sensitivity, lower specificity), the more stringent test of requiring 2 or more peptides (including at least one unique peptide) suffers from the opposite problem of having false-negatives (lower sensitivity, higher specificity). For quantitative analysis of known peptides, a custom R script was used to assign MS2 PSMs to MS1 feature groups based on positional overlap with 1 da and 30 sec tolerances for mz and retention time, respectively. In the event that more than one PSM initially mapped to an MS1 feature within the tolerances previously specified, the PSM which was closest to the MS1 feature (within MS datasets) or to the center of the MS1 feature cluster (between MS datasets) was used. It should be noted that not all MS2s have been assigned to MS1 feature group clusters, and not all MS1 feature group clusters have an assigned MS2; work continues in this area to improve mapping and subsequent peptide feature identification.

Example 16

Identification of Protein Groups

This example describes methods for identification of protein groups by mass spectrometry. For protein group-level analysis, the MS data at the protein group level was performed as follows. MS raw files were processed with MaxQuant (v. 1.6.7(49) and Andromeda(50), searching MS/MS spectra against the UniProtKB human FASTA database (UP000005640, 74,349 forward entries; version from August 2019) employing standard settings. Enzyme digestion specificity was set to trypsin allowing cleavage N-terminal to proline and up to 2 miscleavages. Minimum peptide length was set to 7 amino acids and maximum peptide mass was set to 4,600 Da. Methionine oxidation and protein N-terminus acetylation were configured as a variable modification, carbamidomethylation of cysteines was set as fixed modification. MaxQuant improves precursor ion mass accuracy by time-dependent recalibration algorithms and defines individual mass tolerances for each peptide. Initial maximum precursor mass tolerances allowed were 20 ppm during the first search and 4.5 ppm in the main search. The MS/MS mass tolerance was set to 20 ppm. For analysis, a false discovery rate (FDR) cutoff of 1% was applied at the peptide and protein level (in the proteinGroups.txt table, all protein groups are reported with their corresponding q-value). "Match between runs," was disabled. Number of identifications where counted based on protein intensities (counting only proteins with q-value lower than 1%) requiring at least one razor peptide. MaxLFQ normalized protein intensities (requiring at least 1 peptide ratio count) are reported in the raw output and were used only for the CV precision analysis. Peptides that could be distinguished were sorted into their own protein groups and proteins that could not be discriminated based on unique peptides were assembled in protein groups. Furthermore, proteins were filtered for a list of common contaminants included in MaxQuant. Proteins identified only by site modification were strictly excluded from analysis.

Example 17

Spike Recovery

This example describes methods for spike recovery experiments of C-reactive protein (CRP). Baseline concentration of CRP in a pooled healthy plasma sample was measured with the ELISA kit as described above (Materials) according to the manufacturer-suggested protocols. A stock solution and appropriate dilutions of CRP were prepared and spiked into the identical pooled plasma samples to make final concentrations that were 2×, 5×, 10×, and 100× of baseline, endogenous concentrations for CRP. The volume of additions to the pooled plasma was 10% of the total sample volume. A spike control was made by adding same volume of buffer to the pooled plasma sample. Concentrations of spiked samples were measured again by ELISA to confirm the CRP levels in each spiking level. The samples were used to evaluate particle corona measurement accuracy as described in the Results above.

Example 18

Proteomic Analysis of NSCLC Samples and Healthy Controls

This example describes proteomic analysis of NSCLC samples and health controls. Serum samples from 56 subjects, 28 with Stage IV NSCLC and 28 age- and gender-matched controls were purchased commercially and evaluated with SP-007 nanoparticle corona formation (see above for sample acquisition and corona formation and processing). MS spectral data for each corona were collected as described and the raw data were processed as described above (MS data analysis). 19,214 groups of features were identified and extracted across the 56 subject samples with group sizes ranging from one (singleton features in just one sample, n=6,249 or 0.29% of the data) to 56 (features present in all samples, n=450 or 12% of the data). The clustering algorithm calculates a 'group_quality' metric which is related to the spatial uniformity of grouping of features with groups between datasets. The bottom quartile of groups, partitioned by group size, was then removed from consideration due to the skewed nature of the distribution of low-quality scores leaving 15,967 groups. As an additional filter prior to analysis, only those groups with features present in at least 50% of at least one of the classes, diseased or control, were carried forward leaving a set of 2,507 feature groups for analysis.

Peptide and protein identities were assigned to the feature groups as follows. MS2 PSMs and MS1 feature groups were assigned together as described above (MS data analysis). 25% of the 19,249 original feature groups were associated with a peptide sequence using this approach. All feature groups, with or without assigned peptide sequence, were carried through the univariate statistical comparison between the groups.

Example 19

Statistical Analysis

This example describes statistical analysis of the data disclosed herein. Statistical analysis and visualization were performed using R (v3.5.2) with appropriate packages (R: A language and environment for statistical computing. R Foundation for Statistical Computing, Vienna, Austria. URL https://www.R-project.org/).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A high-throughput method of preparing to identify proteins in a biological sample, the method comprising:
   (a) incubating magnetic microparticles with the biological sample to form protein coronas comprising proteins, the magnetic microparticles comprising: (i) silica, (ii) carboxylate functional groups, (iii) negative surface charges from −30 mV to −10 mV in zeta potential, wherein the zeta potential is measurable with a concentration of 0.02 wt % in a solution in 5% pH 7.4 PBS at about 25° C. with an about 1 minute equilibration time on a Zetasizer Nano ZS (Malvern Instruments) in the absence of biological sample, and (iv) a heterogeneous distribution of sizes including from about 1 µm to about 10 µm in diameter, wherein the magnetic microparticles are configured to form protein coronas having at least 200 unique protein groups that can be identified using mass spectrometry;
   (b) magnetically isolating the magnetic microparticles, by applying an external magnetic field, from unbound protein in the biological sample to enrich the proteins in the protein coronas;
   (c) washing the enriched proteins and the magnetic microparticles after magnetically isolating the magnetic microparticles;
   (d) incubating the enriched proteins in the protein coronas by adding a denaturing reagent to the protein coronas and the magnetic microparticles;
   (e) digesting the enriched proteins in the protein coronas to generate digested peptides by adding a digestion reagent to the protein coronas and the magnetic microparticles; and
   (f) purifying the digested peptides.

2. The method of claim 1, wherein said purifying the digested peptides comprises binding the digested peptides to a solid phase, washing the bound digested peptides, and eluting the washed and bound digested peptides.

3. The method of claim 1, further comprising using a stop reagent to stop the digestion reagent.

4. The method of claim 1, wherein the digestion reagent comprises trypsin.

5. The method of claim 4, wherein the digestion reagent further comprises LysC.

6. The method of claim 1, wherein the magnetic microparticles are configured to form protein coronas having at least 500 unique protein groups that can be identified using mass spectrometry.

7. The method of claim 1, wherein the magnetic microparticles comprise a polydispersity index greater than 0.5.

8. The method of claim 1, further comprising assaying, using mass spectrometry, the purified digested peptides to identify the unique protein groups from the enriched proteins.

9. The method of claim 8, wherein the assaying yields a percent quantile normalized coefficient (QNCV) of variation of 20% or less, as determined by comparing a peptide mass spectrometry feature from at least three full-assay replicates.

10. The method of claim 1, wherein said washing the enriched proteins and the magnetic microparticles is performed at least two times.

11. The method of claim 1, wherein the biological sample comprises plasma or serum.

12. The method of claim 1, wherein the magnetic microparticles are incubated with the biological sample at a basic pH.

13. The method of claim 1, wherein (a)-(f) is performed in about 4-6 hours.

14. A high-throughput method of preparing to identify proteins in a biological sample, the method comprising:
(a) incubating magnetic particles with the biological sample to form protein coronas comprising proteins, the magnetic particles comprising at least two distinct particle types, wherein the first particle type comprises silica and having negative surface charges from −30 mV to −10 mV in zeta potential, and the second particle comprises positive surface charges, wherein the zeta potential of the magnetic microparticles is measurable with a concentration of 0.02 wt % in a solution in 5% pH 7.4 PBS at about 25° C. with an about 1 minute equilibration time on a Zetasizer Nano ZS (Malvern Instruments) in the absence of biological sample and wherein the magnetic particles are configured to form protein coronas having at least 400 unique protein groups that can be identified using mass spectrometry;
(b) magnetically isolating the magnetic particles, by applying an external magnetic field, from unbound protein in the biological sample to enrich the proteins in the protein coronas;
(c) washing the enriched proteins and the magnetic particles at least two times after the magnetically isolating of the magnetic particles;
(d) incubating the enriched proteins in the protein coronas by adding a denaturing reagent to the protein coronas and the magnetic particles;
(e) digesting the enriched proteins in the protein coronas to generate digested peptides by adding a digestion reagent to the protein coronas and the magnetic particles; and
(f) purifying the digested peptides,
wherein said purifying the digested peptides comprises binding the digested peptides to a solid phase, washing the bound digested peptides, and eluting the washed and bound digested peptides, and wherein the biological sample is plasma or serum.

15. The method of claim 14, further comprising using a stop reagent to stop the digestion reagent.

16. The method of claim 14, wherein the digestion reagent comprises trypsin.

17. The method of claim 16, wherein the digestion reagent further comprises LysC.

18. The method of claim 14, wherein the magnetic particles are configured to form protein coronas having at least 1000 unique protein groups that can be identified using mass spectrometry.

19. The method of claim 14, wherein the magnetic particles comprise a polydispersity index less than 0.5.

20. The method of claim 14, further comprising assaying, using mass spectrometry, the purified digested peptides to identify the unique protein groups from the enriched proteins.

21. The method of claim 14, wherein the magnetic particles further comprise carboxylate functional groups.

22. The method of claim 14, wherein the magnetic particles are incubated with the biological sample at a basic pH.

23. The method of claim 14, wherein (a)-(f) is performed in 4-6 hours.

24. The method of claim 14, wherein the second distinct particle type comprises a poly (N-(3-(dimethylamino) propyl) methacrylamide) (PDMAPMA) coating.

25. The method of claim 14, wherein the magnetic particles are incubated with the biological sample and a Tris buffer.

26. The method of claim 14, wherein the first distinct particle type is a nanoparticle and the second distinct particle type is a microparticle.

27. The method of claim 26, wherein the first distinct particle type comprises an iron oxide core.

28. The method of claim 27, wherein the second distinct particle type comprises a non-magnetic core.

* * * * *